(12) United States Patent
Ikeda et al.

(10) Patent No.: US 10,032,991 B2
(45) Date of Patent: Jul. 24, 2018

(54) COMPOUND, ORGANIC ELECTROLUMINESCENCE ELEMENT MATERIAL, INK COMPOSITION, ORGANIC ELECTROLUMINESCENCE ELEMENT, ELECTRONIC DEVICE, AND METHOD FOR PRODUCING COMPOUND

(71) Applicant: IDEMITSU KOSAN CO., LTD., Chiyoda-ku (JP)

(72) Inventors: Kiyoshi Ikeda, Sodegaura (JP); Hironori Kawakami, Katsushika-ku (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 253 days.

(21) Appl. No.: 14/911,606

(22) PCT Filed: Dec. 17, 2014

(86) PCT No.: PCT/JP2014/083486
§ 371 (c)(1),
(2) Date: Feb. 11, 2016

(87) PCT Pub. No.: WO2015/093551
PCT Pub. Date: Jun. 25, 2015

(65) Prior Publication Data
US 2016/0197288 A1    Jul. 7, 2016

(30) Foreign Application Priority Data
Dec. 18, 2013 (JP) .................. 2013-261799
Mar. 31, 2014 (JP) .................. 2014-074090

(51) Int. Cl.
*H01L 51/00* (2006.01)
*C09D 11/52* (2014.01)
(Continued)

(52) U.S. Cl.
CPC ........ *H01L 51/0067* (2013.01); *C07D 403/14* (2013.01); *C09D 11/037* (2013.01);
(Continued)

(58) Field of Classification Search
CPC ............. H01L 51/0067; H01L 51/0052; H01L 51/006; H01L 51/0061; H01L 51/0072;
(Continued)

(56) References Cited

U.S. PATENT DOCUMENTS

2011/0237594 A1    9/2011  Beier et al.
2011/0267729 A1    11/2011 Yeo
(Continued)

FOREIGN PATENT DOCUMENTS

JP    2010-040830 A    2/2010
JP    2010-135467 A    6/2010
(Continued)

OTHER PUBLICATIONS

International Search Report dated Mar. 31, 2015 for PCT/JP2014/083486 filed on Dec. 17, 2014.

*Primary Examiner* — Jayne L Mershon
(74) *Attorney, Agent, or Firm* — Foley & Lardner LLP

(57) ABSTRACT

A compound represented by formula (1):

$$*a-A^1 \quad *b-L^1-(L^2)_n-A^2 \tag{1}$$

(with pyrimidine ring bearing $R^1$, $X^1$, $*c1$, $*c2$)

wherein $*a$, $*b$, $R^1$, $X^1$, $L^1$, $L^2$, n, $A^1$, and $A^2$ are as defined in the description, and a production method of the compound (Continued)

represented by formula (1) are provide. In the production method, $A^1$ is introduced under a reaction condition in which the reactivity of $Hal^2$ in a compound represented by formula (I):

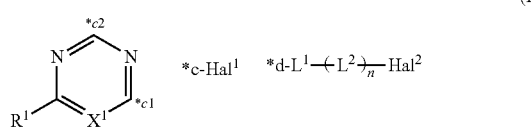

(I)

wherein *c, *d, $R^1$, $X^1$, $L^1$, $L^2$, n, $A^1$, $A^2$, $Hal^1$, and $Hal^2$ are as defined in the description,
is extremely low as compared with that of $Hal^1$ and then $A^2$ which is different from $A^1$ is introduced under a reaction condition in which the reactivity of $Hal^2$ is high. The compound represented by formula (1) is formed into a layer by a coating method and meets various performance requirements of an organic EL device.

31 Claims, 1 Drawing Sheet

(51) Int. Cl.
C07D 403/14 (2006.01)
C09K 11/02 (2006.01)
C09K 11/06 (2006.01)
C09D 11/037 (2014.01)
C09D 11/50 (2014.01)
H01L 51/50 (2006.01)

(52) U.S. Cl.
CPC ............ C09D 11/50 (2013.01); C09D 11/52 (2013.01); C09K 11/025 (2013.01); C09K 11/06 (2013.01); H01L 51/006 (2013.01); H01L 51/0052 (2013.01); H01L 51/0061 (2013.01); H01L 51/0072 (2013.01); H01L 51/0085 (2013.01); C09K 2211/1007 (2013.01); C09K 2211/1011 (2013.01); C09K 2211/1029 (2013.01); C09K 2211/1033 (2013.01); C09K 2211/1037 (2013.01); C09K 2211/1044 (2013.01); C09K 2211/1059 (2013.01); C09K 2211/1088 (2013.01); C09K 2211/1092 (2013.01); C09K 2211/185 (2013.01); H01L 51/5008 (2013.01); H01L 51/5016 (2013.01); H01L 51/5056 (2013.01); H01L 51/5072 (2013.01)

(58) Field of Classification Search
CPC ... H01L 51/0085; C07D 403/14; C09D 11/50; C09D 11/52; C09D 11/025; C09D 11/06
USPC .......................................................... 428/690
See application file for complete search history.

(56) References Cited

U.S. PATENT DOCUMENTS

2013/0306959 A1 11/2013 Ikeda et al.
2014/0114069 A1 4/2014 Kim et al.

FOREIGN PATENT DOCUMENTS

| JP | 2011-503006 A | | 1/2011 | | |
|---|---|---|---|---|---|
| JP | 2012-508718 A | | 4/2012 | | |
| KR | 10 2010 0094415 | * | 8/2010 | ........... | C07D 209/82 |
| KR | 2011-0011578 A | | 2/2011 | | |
| KR | 2012-0122812 A | | 11/2012 | | |
| KR | 2012-0122813 A | | 11/2012 | | |
| WO | 2012/077520 A1 | | 6/2012 | | |
| WO | 2012/086170 A1 | | 6/2012 | | |
| WO | 2012/134124 A1 | | 10/2012 | | |
| WO | 2013/012297 A1 | | 1/2013 | | |
| WO | 2013/081088 A1 | | 6/2013 | | |
| WO | 2013/108589 A1 | | 7/2013 | | |
| WO | 2013/165192 A1 | | 11/2013 | | |
| WO | 2015/020217 A1 | | 2/2015 | | |

* cited by examiner

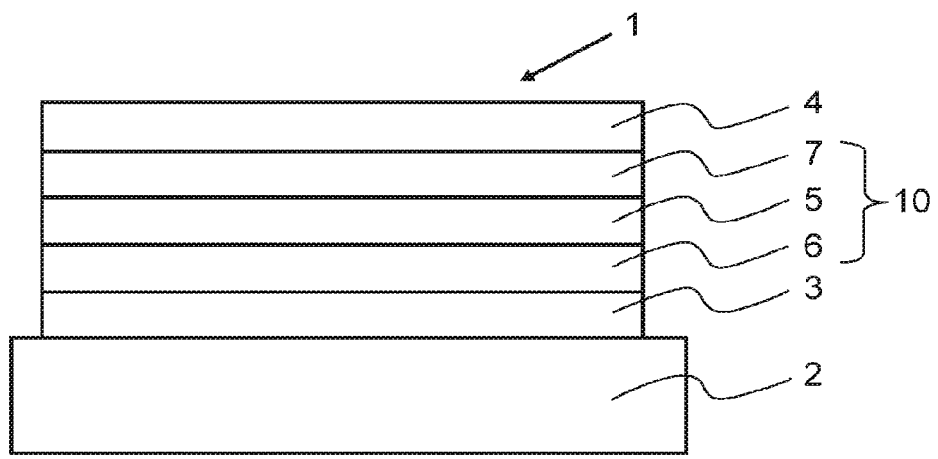

COMPOUND, ORGANIC ELECTROLUMINESCENCE ELEMENT MATERIAL, INK COMPOSITION, ORGANIC ELECTROLUMINESCENCE ELEMENT, ELECTRONIC DEVICE, AND METHOD FOR PRODUCING COMPOUND

TECHNICAL FIELD

The present invention relates to compounds, materials for organic electroluminescence devices, organic electroluminescence devices, ink compositions, electronic equipment and methods for procuring the compounds.

BACKGROUND ART

An organic electroluminescence device (hereinafter also referred to as "organic EL device") has been known, in which an organic thin film layer including a light emitting layer is disposed between an anode and a cathode, holes and electrons injected into the light emitting layer are recombined to form excitons, and the exciton energy is released as light.

Since the organic EL device is a spontaneous emitting device, it has been expected to provide, using its advantages as the spontaneous emitting device, a light emitting device having a high emission efficiency, a high image quality, a low power consumption, and a thin good design. It has been also known to make the light emitting layer into a host/dopant light emitting layer by doping a host with a light emitting material (dopant).

In the host/dopant light emitting layer, excitons can be efficiently generated from charges injected into a host material. The energy of generated excitons is transferred to the dopant, and the light emission with high efficiency from the dopant can be obtained.

To improve the performance of organic EL device, the recent study is directed also to the host/dopant system, and the search for a suitable host material and other materials for organic EL device has been continued. Patent Literatures 1 to 10 disclose various compounds wherein a carbazole structure is bonded to a non-fused or fused azine ring directly or via a linking group.

The method of forming each layer of an organic EL device is roughly classified into two, i.e., a vapor deposition method, such as a vacuum vapor deposition method and a molecular beam epitaxy method, and a coating method, such as a dipping method, a spin coating method, a casting method, a bar coating method and a roll coating method. The material to be made into a layer by a coating method is required to meet the properties not required for the material for use in a vapor deposition method, for example, the heat resistance and the solubility to a solvent. Therefore, a material useful in a vapor deposition method is not necessarily useful in a coating method. In addition, the material for use in a coating method should meet various performance requirements of organic EL device, while capable of forming a layer by a coating method.

The coating method is applicable particularly to the formation of a layer in the production of a large-sized organic EL display and lighting panel. Therefore, it has been required to develop a material for organic EL devices usable in the coating method.

Patent Literatures 1 to 8 disclose compounds in which a non-fused nitrogen-containing ring has one or more biscarbazole-containing groups or tricarbazole-containing groups. However, Patent Literature 1 to 8 fail to disclose a compound in which a fused nitrogen-containing ring has different biscarbazole-containing groups, different tricarbazole-containing groups, or both of a biscarbazole-containing group and a tricarbazole-containing group.

Patent Literature 9 discloses a compound in which a fused nitrogen-containing ring has a biscarbazole-containing group. However, a fused nitrogen-containing ring compound having two or more biscarbazole-containing groups is not disclosed therein. In addition, this document is completely silent about forming a layer by a coating method.

Patent Literature 10 teaches that a compound in which a non-fused or fused nitrogen-containing ring has more than one biscarbazole-containing group or tricarbazole-containing group is applicable to an organic EL device. It is further taught that some of the compounds are soluble in a solvent and an organic EL device is produced by forming a layer by a coating method. However, the compounds used in the production of organic EL device by forming the layer by a coating method all include the same biscarbazole-containing groups on the non-fused nitrogen-containing ring. Therefore, the properties verified in Patent Literature 10 are limited only to a compound having the same biscarbazole-containing groups on the non-fused nitrogen-containing ring, and the compound disclosed therein is still insufficient to meet the various performance requirements of an organic EL device.

CITATION LIST

Patent Literature

Patent Literature 1: WO2012/077520 A1
Patent Literature 2: WO2013/081088 A1
Patent Literature 3: WO2013/108589 A1
Patent Literature 4: KR2011-0011578A
Patent Literature 5: KR2012-0122812A
Patent Literature 6: KR2012-0122813A
Patent Literature 7: JP 2010-135467A
Patent Literature 8: JP 2010-040830A
Patent Literature 9: WO2012/134124 A1
Patent Literature 10: WO2012/086170 A1

SUMMARY OF INVENTION

Technical Problem

In an aspect of the invention, a compound which can be made into a film by a coating method and meets various properties required for EL devices is provided. In another aspect of the invention, a material for organic electroluminescence devices comprising the compound, an organic electroluminescence device employing the compound, and a ink composition comprising the compound are provided. In still another aspect of the invention, a method for producing the compound is provided.

Solution to Problem

The inventors have found a compound represented by formula (1) which has various kinds of substituents and can be made into a layer by a coating method and have further found a method of producing the compound efficiently and easily. The present invention is based on these findings.

Thus, in an aspect of the invention, a compound represented by formula (1) (hereinafter also referred to as "compound (1)") is provided:

(1)

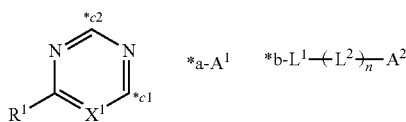

wherein one of *a and *b is bonded to a carbon atom *c1, and the other is bonded to a carbon atom *c2;

$R^1$ represents a hydrogen atom or a substituent;

$X^1$ represents N or $CR^2$, $R^2$ represents a hydrogen atom or a substituent, and $R^2$ may be bonded to $R^1$ to form a ring;

when *b is bonded to the carbon atom *c2, $X^1$ represents $CR^2$, and $R^2$ is bonded to $R^1$ to form a ring, $-R^1-R^2-$ represents $-X^a=X^b-X^c=X^d-$;

$X^a$ to $X^d$ each independently represent N or $CR^a$, $R^a$ represents a hydrogen atom or a substituent, and adjacent two groups $R^a$ may be bonded to each other to form a ring;

$L^1$ represents a linking group;

$L^2$ represents a divalent linking group;

n represents an integer of 0 to 3 and when n is 0, $L^2$ represents a single bond;

$A^1$ and $A^2$ are different from each other and each represent a group represented by any of formulae (2), (2'), (3), (3'), (3"), and (4):

(2)

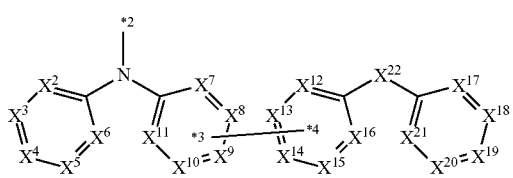

wherein *2 is bonded to the carbon atom *c1, the carbon atom *c2, $L^1$ when n is 0, or $L^2$ when n is an integer of 1 to 3, each described in formula (1);

one of $X^7$ to $X^{11}$ is a carbon atom bonded to 3;

one of $X^{14}$ to $X^{16}$ is a carbon atom bonded to *4;

the rest of $X^7$ to $X^{11}$, the rest of $X^{12}$ to $X^{16}$, $X^2$ to $X^6$, and $X^{17}$ to $X^{21}$ each independently represent N or $CR^3$;

$R^3$ represents a hydrogen atom or a substituent and groups $R^3$ may be bonded to each other to form a ring;

$X^6$ and $X^{11}$ may be carbon atoms which are bonded to each other, and $X^{16}$ and $X^{21}$ may be carbon atoms which are bonded to each other;

$X^{22}$ represents $NR^4$, $CR^5R^6$, O, S, Se, or $SiR^7R^8$; and $R^4$ to $R^8$ each independently represent a hydrogen atom or a substituent, and $R^5$ and $R^6$, and $R^7$ and $R^8$ may be bonded to each other to form a ring;

wherein *2', $X^7$ to $X^{11}$, $X^{12}$ to $X^{16}$, $X^{17}$ to $X^{21}$, and $X^{22}$ are as defined above;

one of $X^{2'}$ to $X^{6'}$ represents a carbon atom bonded to *3';

one of $X^{12'}$ to $X^{16'}$ represents a carbon atom bonded to *4';

the rest of $X^{2'}$ to $X^{16'}$, the rest of $X^{12'}$ to $X^{16'}$, and $X^{17'}$ to $X^{21'}$ each independently represent N or $CR^3$;

$R^3$ is as defined above;

$X^{6'}$ and $X^{11}$ may be carbon atoms which are bonded to each other, $X^{16}$ and $X^{21}$ may be carbon atoms which are bonded to each other, and $X^{16'}$ and $X^{21'}$ may be carbon atoms which are bonded to each other;

$X^{22'}$ represents $NR^4$, $CR^5R^6$, O, S, Se, or $SiR^7R^8$; and $R^1$ to $R^8$ are as defined above;

(3)

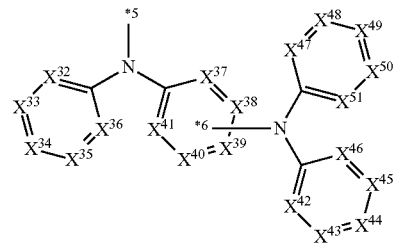

wherein *5 is bonded to the carbon atom *c1, the carbon atom *c2, $L^1$ when n is 0, or $L^2$ when n is an integer of 1 to 3, each described in formula (1);

one of $X^{37}$ to $X^{41}$ represents a carbon atom bonded to *6;

the rest of $X^{37}$ to $X^{41}$, $X^{32}$ to $X^{36}$, and $X^{42}$ to $X^{51}$ each independently represent N or $CR^9$;

$R^9$ represents a hydrogen atom or a substituent and groups $R^9$ may be bonded to each other to form a ring; and $X^{36}$ and $X^{41}$ may be carbon atoms which are bonded to each other and $X^{46}$ and $X^{51}$ may be carbon atoms which are bonded to each other;

(3')

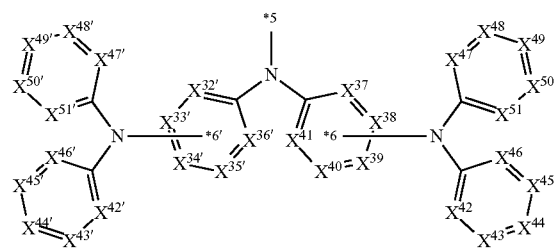

(2')

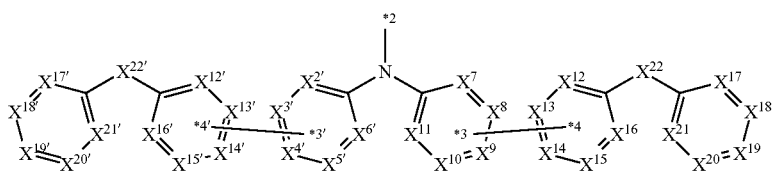

wherein *5, $X^{37}$ to $X^{41}$, and $X^{42}$ to $X^{51}$ are as defined above;
one of $X^{32'}$ to $X^{36'}$ represents a carbon atom bonded to *6'
the rest of $X^{32'}$ to $X^{36'}$ and $X^{42'}$ to $X^{51'}$ each independently represent N or $CR^9$;
$R^9$ is as defined above; and
$X^{36'}$ and $X^{41}$ may be carbon atoms which are bonded to each other, $X^{16}$ and $X^{51}$ may be carbon atoms which are bonded to each other, and $X^{46'}$ and $X^{51'}$ may be carbon atoms which are bonded to each other;

(3″)

[Chemical structure diagram]

wherein *5, $X^{37}$ to $X^{41}$, and $X^{42}$ to $X^{61}$ are as defined above;
one of $X^{32''}$ to $X^{36''}$ represents a carbon atom bonded to *3″;
one of $X^{12''}$ to $X^{16''}$ represents a carbon atom bonded to *4″;
the rest of $X^{32''}$ to $X^{36''}$, the rest of $X^{12''}$ to $X^{16''}$, and $X^{17''}$ to $X^{21''}$ each independently represent N or $CR^3$;
$R^3$ is as defined above;
$X^{36''}$ and $X^{41}$ may be carbon atoms which are bonded to each other, $X^{46}$ and $X^{51}$ may be carbon atoms which are bonded to each other, and $X^{16''}$ and $X^{21''}$ may be carbon atoms which are bonded to each other;
$X^{22''}$ represents $NR^4$, $CR^5R^6$, O, S. Se, or $SiR^7R^8$; and
$R^4$ to $R^8$ are as defined above;

(4)

[Chemical structure diagram]

wherein *7 is bonded to the carbon atom *c1, the carbon atom *c2, $L^1$ when n is 0, or $L^2$ when n is an integer of 1 to 3, each described in formula (1);

one of adjacent two selected from $X^{67}$ to $X^{71}$ represents a carbon atom bonded to *8 and the other represents a carbon atom bonded to *9;
the rest of $X^{67}$ to $X^{71}$, $X^{62}$ to $X^{66}$, and $X^{72}$ to $X^{75}$ each independently represent N or $CR^{10}$;
$R^{10}$ represents a hydrogen atom or a substituent, and groups $R^{10}$ may be bonded to each other to form a ring;
$X^{66}$ and $X^{71}$ may be carbon atoms which are bonded to each other;
$X^{76}$ represents $NR^{11}$, $CR^{12}R^{13}$, O, S, Se, or $SiR^{14}R^{15}$; and
$R^{11}$ to $R^{15}$ each independently represent a hydrogen atom or a substituent, and $R^{11}$ and $R^{12}$, and $R^{13}$ and $R^{14}$ may be bonded to each other to form a ring.

In another aspect of the invention, a material for organic electroluminescence devices comprising the compound (1) is provided.

In still another aspect of the invention, an ink composition comprising a solvent and the compound (1) is provided.

In still another aspect of the invention, an organic electroluminescence device which comprises a cathode, an anode, and at least one organic thin film layer which is disposed between the cathode and the anode, wherein the at least one organic thin film layer comprises a light emitting layer and at least one layer of the at least one organic thin film layer comprises the compound (1) is provided.

In still another aspect of the invention, an electronic equipment comprising the organic electroluminescence device is provided.

In still another aspect of the invention, a method of producing the compound (1) comprising the following coupling reaction 1 and the following coupling reaction 2 is provided,
(1) the coupling reaction 1, wherein a compound represented by formula (I):

(I)

[Chemical structure diagram]

wherein $R^1$, $X^1$, $L^1$, $L^2$, and n are as defined in formula (1);
one of *c and *d is bonded to the carbon atom *c1 and the other is bonded to the carbon atom *c2; and
$Hal^1$ and $Hal^2$ represent the same or different halogen atoms;
is allowed to react with an amine compound represented by any of formulae (II), (II'), (III), (III'), (III''), and (IV):

(II)

[Chemical structure diagram]

(II')

[Chemical structure diagram]

-continued

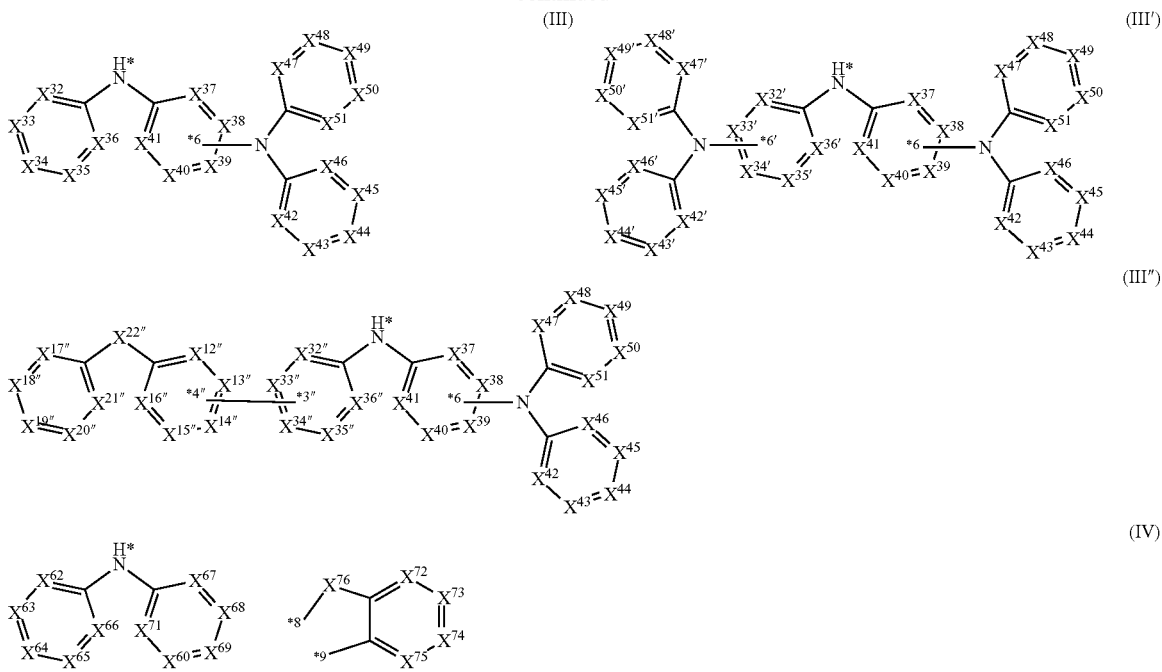

wherein $X^2$ to $X^{22}$, $X^{32}$ to $X^{51}$, $X^{62}$ to $X^{76}$, $X^{2'}$ to $X^{6'}$, $X^{12'}$ to $X^{22'}$, $X^{32'}$ to $X^{36'}$, $X^{42'}$ to $X^{51'}$, $X^{32''}$ to $X^{36''}$, and $X^{12''}$ to $X^{22''}$ are as defined in formula (1), and H* represents a hydrogen atom to be reacted with $Hal^1$ of formula (I), in an organic solvent in the presence of a basic catalyst and in the absence of a transition metal catalyst, thereby obtaining a compound represented by formula (V):

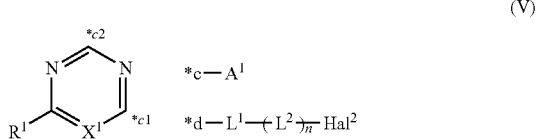

wherein *c, *d, $A^1$, $R^1$, $X^1$, $L^1$, $L^2$, and n are as defined in formula (1) and $Hal^2$ is as defined above, and (2) the coupling reaction 2, wherein the compound represented by formula (V) and an amine compound represented by any of formulae (II), (II'), (III), (III'), (III''), and (IV) which is different from the amine compound used in the coupling reaction 1 are subject to a coupling reaction by eliminating $Hal^2$ of the compound represented by formula (V) and the hydrogen atom H* of the amine compound in an organic solvent in the presence of a transition metal catalyst and a ligand and in the presence or absence of a base, thereby synthesizing the compound represented by formula (1).

Advantageous Effects of Invention

The compound (1) can be made into a layer by a coating method and meet various properties required for an organic EL device. The compound (1) is produced efficiently and easily by the synthetic method described below.

BRIEF DESCRIPTION OF DRAWINGS

FIG. 1 is a schematic illustration of the structure of an organic EL device in an aspect of the present invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The definition of "hydrogen atom" used herein includes isotopes different in the neutron numbers, i.e., light hydrogen (protium), heavy hydrogen (deuterium), and tritium.

The optional substituent referred to by "substituted or unsubstituted" used herein is, unless otherwise noted, at least one preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms which includes 1 to 5, preferably 1 to 3, more preferably 1 or 2 heteroatoms, wherein the heteroatoms are the same or different and selected from a nitrogen atom, an oxygen atom and a sulfur atom; a haloalkyl group having 1 to 50, preferably 1 to 18, more preferably 1 to 8 carbon atoms wherein one or more, preferably 1 to 15, more preferably 1 to 7 hydrogen atoms or all the hydrogen atoms are substituted with the same or different halogen atoms selected from a fluorine atom, a chlorine atom, a bromine atom, and a iodine atom; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group: an epoxy group; and an oxetanyl group.

Of the above substituents, more preferred are an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; a mono- or di-substituted amino group wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms: a halogen atom; and a cyano group.

The above optional substituent may further has the substituent mentioned above. The optional substituents may be bonded to each other to form a ring.

In an aspect of the invention, a compound represented by formula (1) (compound (1)) is provided:

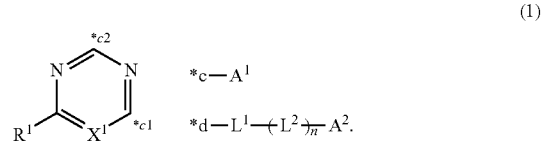
(1)

In an embodiment of the invention, the compound (1) is preferably represented by formula (1a), (1b) or (1c) and more preferably represented by formula (1a) or (1c):

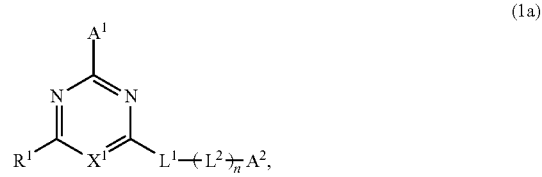
(1a)

(1b)

or

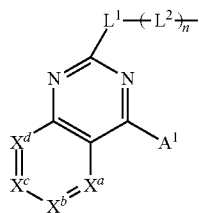

(1c)

R[1] represents a hydrogen atom or a substituent which is selected from a halogen atom, a cyano group, a nitro group, a substituted or unsubstituted alkyl group having 1 to 50, preferably 1 to 18, and more preferably 1 to 8 carbon atoms; a substituted or unsubstituted cycloalkyl group having 3 to 50, preferably 3 to 10, and more preferably 3 to 8 ring carbon atoms; a substituted or unsubstituted aryl group having 6 to 60, preferably 6 to 25, and more preferably 6 to 18 ring carbon atoms; a substituted or unsubstituted aralkyl group having 7 to 51, preferably 7 to 30, and more preferably 7 to 20 carbon atoms which includes an aryl group having 6 to 50, preferably 6 to 25, and more preferably 6 to 18 ring carbon atoms; an amino group; a mono- or di-substituted amino group wherein the substituent is selected from a substituted or unsubstituted alkyl group having 1 to 50, preferably 1 to 18, and more preferably 1 to 8 carbon atoms and a substituted or unsubstituted aryl group having 6 to 60, preferably 6 to 25, and more preferably 6 to 18 ring carbon atoms; a substituted or unsubstituted alkoxy group having 1 to 50, preferably 1 to 18, and more preferably 1 to 8 carbon atoms; a substituted or unsubstituted cycloalkoxy group having 3 to 50, preferably 3 to 10, and more preferably 3 to 8 ring carbon atoms; a substituted or unsubstituted aryloxy group having 6 to 60, preferably 6 to 25, and more preferably 6 to 18 ring carbon atoms; a substituted or unsubstituted alkylthio group having 1 to 50, preferably 1 to 18, and more preferably 1 to 8 carbon atoms; a substituted or unsubstituted arylthio group having 6 to 60, preferably 6 to 25, and more preferably 6 to 18 ring carbon atoms; a silyl group; a mono-, di- or tri-substituted silyl group, wherein the substituent is selected from a substituted or unsubstituted alkyl group having 1 to 50, preferably 1 to 18, and more preferably 1 to 8 carbon atoms and a substituted or unsubstituted aryl group having 6 to 60, preferably 6 to 25, and more preferably 6 to 18 ring carbon atoms; a substituted or unsubstituted heteroaryl group having 5 to 60, preferably 5 to 30, and more preferably 5 to 26 ring atoms; and a substituted or unsubstituted haloalkyl group having 1 to 50, preferably 1 to 18, and more preferably 1 to 8 carbon atoms.

The halogen atom is, for example, a fluorine atom, a chlorine atom, a bromine atom, or an iodine atom, with a fluorine atom being preferred.

Examples of the alkyl group include a methyl group, an ethyl group, a n-propyl group, an isopropyl group, a n-butyl group, an isobutyl group, a s-butyl group, a t-butyl group, a pentyl group, a hexyl group, a heptyl group, an octyl group, a nonyl group, a decyl group, an undecyl group, a dodecyl group, a tridecyl group, a tetradecyl group, an octadecyl group, a tetracosanyl group, and a tetracontanyl group. Each of these groups includes isomeric groups, if any.

Preferred are a methyl group, an ethyl group, a n-propyl group, an isopropyl group, a n-butyl group, an isobutyl group, a s-butyl group, a t-butyl group, a pentyl group, a hexyl group, a heptyl group, an octyl group, a nonyl group, a decyl group, an undecyl group, a dodecyl group, a tridecyl group, a tetradecyl group, and an octadecyl group, with a methyl group, an ethyl group, a n-propyl group, an isopropyl group, a n-butyl group, an isobutyl group, a s-butyl group, a t-butyl group, a pentyl group, a hexyl group, a heptyl group, and an octyl group being more preferred. Each of these groups includes isomeric groups, if any.

Examples of the cycloalkyl group include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

Examples of the aryl group include a phenyl group, a 1-naphthyl group, a 2-naphthyl group, a naphthylphenyl group, a biphenylyl group, a terphenylyl group, a quarterphenylyl group, a quinquephenylyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, a dibenzanthryl group, a 9,9-dimethylfluorenyl group, and a 9,9-diphenylfluorenyl group. Each of these groups includes isomeric groups, if any.

Preferred are a phenyl group, a 1-naphthyl group, a 2-naphthyl group, a biphenylyl group, a terphenylyl group, a phenanthryl group, a benzophenanthryl group, a fluorenyl group, a 9,9'-spirobifluorenyl group, a benzofluorenyl group, a dibenzofluorenyl group, a chrysenyl group, a benzochrysenyl group, a s-indacenyl group, an as-indacenyl group, a triphenylenyl group, a benzotriphenylenyl group, an anthryl group, a 9,9-dimethylfluorenyl group, and a 9,9-diphenylfluorenyl group. More preferred are a phenyl group, a biphenylyl group, a terphenylyl group, a 1-naphthyl group, a 2-naphthyl group, a phenanthryl group, a fluorenyl group, a 9,9'-spirobifluorenyl group, a chrysenyl group, a triphenylenyl group, a 9,9-dimethylfluorenyl group, and a 9,9-diphenylfluorenyl group.

Examples, preferred examples, and more preferred examples of the aryl portion of the aralkyl group are the same as those of the aryl group mentioned above. Examples, preferred examples, and more preferred examples of the alkyl portion of the aralkyl group are the same as those of the alkyl group mentioned above.

Examples, preferred examples, and more preferred examples of the alkyl substituent and the aryl substituent of the mono- or di-substituted amino group are respectively the same as those of the alkyl group and the aryl group each mentioned above.

Examples, preferred examples, and more preferred examples of the alkyl portion of the alkoxy group are the same as those of the alkyl group mentioned above.

Examples, preferred examples, and more preferred examples of the cycloalkyl portion of the cycloalkoxy group are the same as those of the cycloalkyl group mentioned above.

Examples, preferred examples, and more preferred examples of the aryl portion of the aryloxy group are the same as those of the aryl group mentioned above.

Examples, preferred examples, and more preferred examples of the alkyl portion of the alkylthio group are the same as those of the alkyl group mentioned above.

Examples, preferred examples, and more preferred examples of the aryl portion of the arylthio group are the same as those of the aryl group mentioned above.

The mono-, di-, or trisubstituted silyl group include a monoalkylsilyl group, a dialkylsilyl group, a trialkylsilyl group, a monoarylsilyl group, a diarylsilyl group, a triarylsilyl group, an alkyldiarylsilyl group, and a dialkylarylsilyl group, with a monoalkylsilyl group, a dialkylsilyl group, a trialkylsilyl group, a monoarylsilyl group, a diarylsilyl group, and a triarylsilyl group being preferred and a trialkylsilyl group and a triarylsilyl group being more preferred.

Examples, preferred examples, and more preferred examples of the alkyl group and the aryl group are the same as those of the alkyl group and the aryl group each mentioned above.

Examples of such a substituted silyl group include a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group. Preferred are a trimethylsilyl group, a triethylsilyl group, a triphenylsilyl group, and a phenyldimethylsilyl group, with a trimethylsilyl group and a triphenylsilyl group being more preferred.

The heteroaryl group includes at least one, preferably 1 to 5, more preferably 1 to 3, and still more preferably 1 or 2 hetero atoms which may be the same or different, for example, a nitrogen atom, a sulfur atom, an oxygen atom, and a phosphorus atom.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a biscarbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group, and a dinaphto[2',3':2,3:2',3':6,7]carbazolyl group.

Preferred are a pyridyl group, a pyridazinyl group, a pyrimidinyl group, a pyrazinyl group, a triazinyl group, an imidazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a quinazolinyl group, a quinoxalinyl group, a benzimidazolyl group, a benzoxazolyl group, a benzothiazolyl group, a benzisoxazolyl group, a benzisothiazolyl group, a dibenzofuranyl group, a dibenzothiophenyl group, a carbazolyl group, a bicarbazolyl group, a phenanthridinyl group, an acridinyl group, a phenanthrolinyl group, an azatriphenylenyl group, a diazatriphenylenyl group, a xanthenyl group, an azacarbazolyl group, an azadibenzofuranyl group, and an azadibenzothiophenyl group. More preferred are a pyridyl group, a pyrimidinyl group, a triazinyl group, a benzofuranyl group, an isobenzofuranyl group, a quinolyl group, an isoquinolyl group, a quinazolinyl group, a benzothiophenyl group, an isobenzothiophenyl group, an indolizinyl group, a dibenzofuranyl group, a dibenzothiophenyl group, a carbazolyl group, a bicarbazolyl group, an azatriphenylenyl group, a diazatriphenylenyl group, a xanthenyl group, an azacarbazolyl group, an azadibenzofuranyl group, and an azadibenzothiophenyl group.

In the present invention, the substituted or unsubstituted carbazolyl group includes the following carbazolyl group:

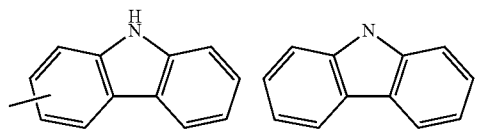

and a substituted carbazolyl group having the optional substituent mentioned above and further include, for example, the following substituted carbazolyl groups:

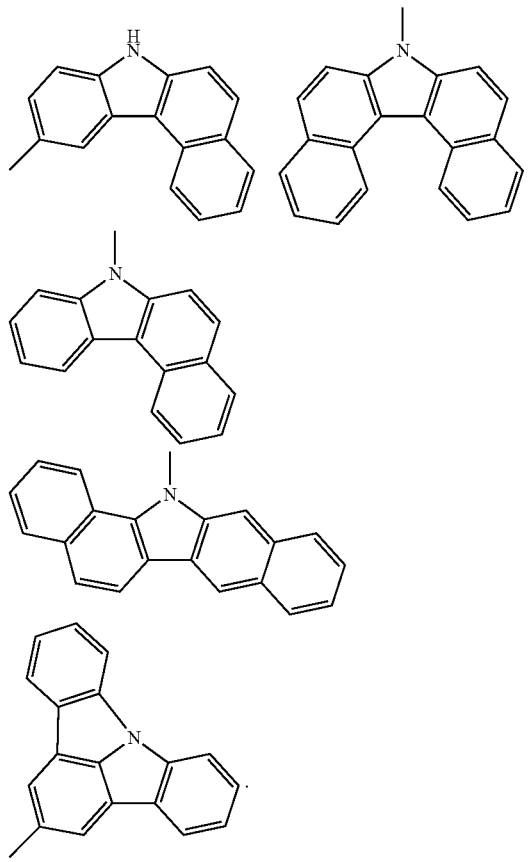

In the present invention, the substituted or unsubstituted dibenzofuranyl group and the dibenzothiophenyl group include the following dibenzofuranyl group and dibenzothiophenyl group:

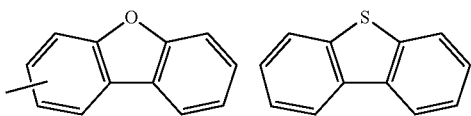

and a substituted dibenzothiophenyl group and a substituted dibenzothiophenyl group each having the optional substituent mentioned above and further include, for example, the following substituted dibenzothiophenyl groups and substituted dibenzothiophenyl groups:

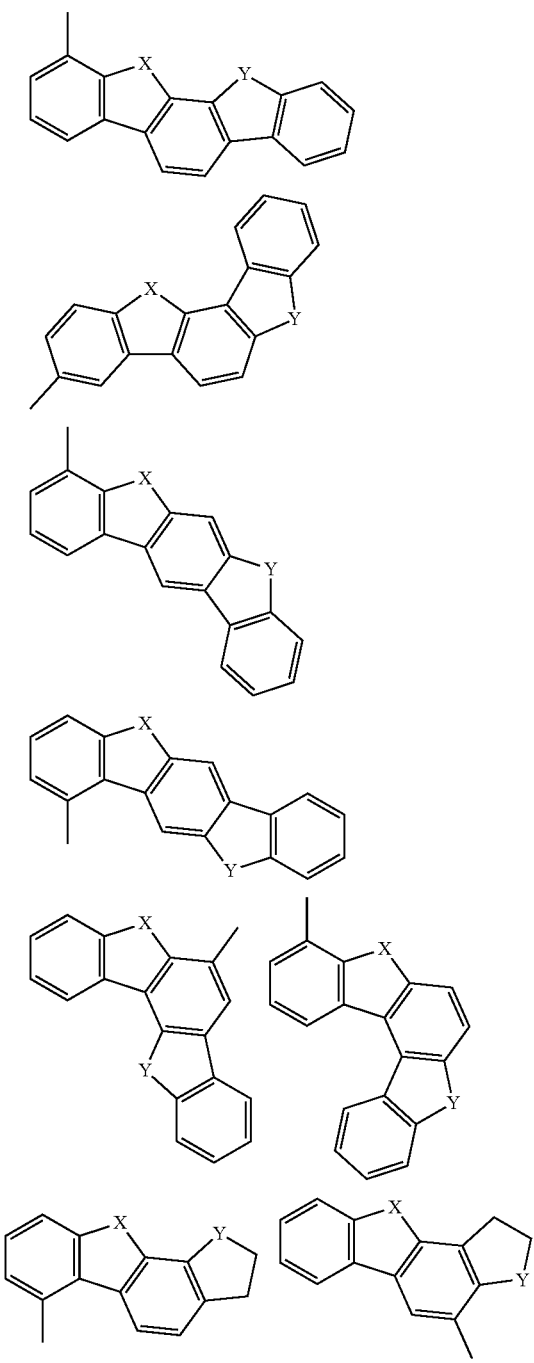

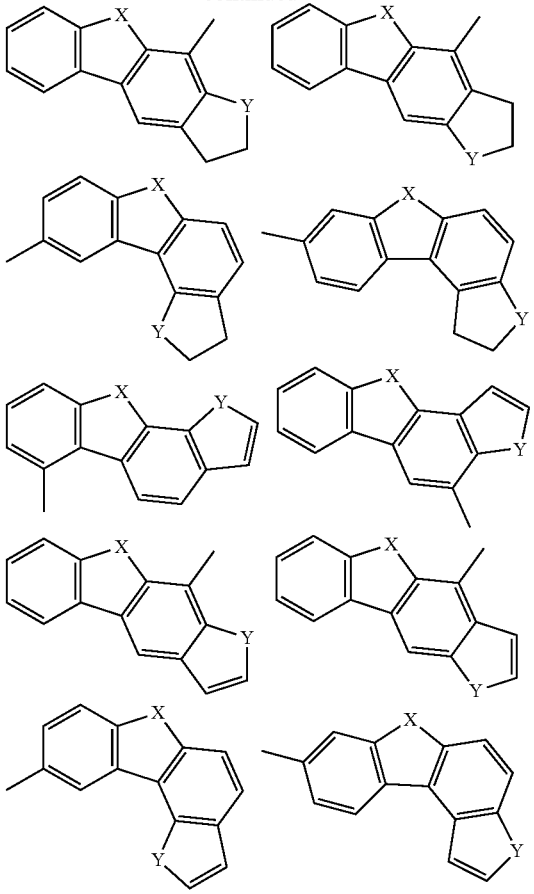

wherein X represents an oxygen atom or a sulfur atom; and Y represents an oxygen atom, a sulfur atom, NH, $NR^b$ wherein $R^b$ represents an alkyl group or an aryl group, $CH_2$, or $CR^c_2$ wherein $R^c$ represents an alkyl group or an aryl group.

The haloalkyl group is a group derived from the alkyl group by replacing at least one, preferably 1 to 15, more preferably 1 to 7 hydrogen atoms or all the hydrogen atoms with the same or different halogen atoms, such as a fluorine atom, a chlorine atom, a bromine atom, and an iodine atom. Examples, preferred examples, and more preferred examples of the alkyl group are the same as those of the alkyl group mentioned above. Examples of the haloalkyl group include a trifluoromethyl group, a pentafluoroethyl group, and a heptafluoropropyl group.

$R^1$ is preferably a hydrogen atom, the substituted or unsubstituted alkyl group, the substituted or unsubstituted aryl group, or the substituted or unsubstituted heteroaryl group, each mentioned above, more preferably a hydrogen atom, the substituted or unsubstituted aryl group, or the substituted or unsubstituted heteroaryl group, still more preferably a hydrogen atom, a phenyl group, a naphthyl group (inclusive of isomeric groups), a biphenyl group (inclusive of isomeric groups), a terphenyl group (inclusive of isomeric groups), a phenylterphenyl group (inclusive of isomeric groups), a dibenzofuranyl group (inclusive of isomeric groups), or a dibenzothiophenyl group (inclusive of isomeric groups), and particularly preferably a phenyl group.

$X^1$ represents N or $CR^2$.

$R^2$ represents a hydrogen atom or a substituent, and $R^2$ and $R^1$ may be bonded to each other to form a ring.

The substituent as $R^2$, examples, preferred examples, and more preferred examples thereof are each selected from those of the substituent described above with respect to $R^1$.

$R^2$ is preferably a hydrogen atom, the substituted or unsubstituted alkyl group, the substituted or unsubstituted aryl group, or the substituted or unsubstituted heteroaryl group, more preferably a hydrogen atom, the substituted or unsubstituted alkyl group, or the substituted or unsubstituted aryl group, and particularly preferably a hydrogen atom.

$R^2$ may be bonded to $R^1$ to form a ring, for example, a fused or non-fused aromatic ring having 6 to 50 ring carbon atoms, a partially hydrogenated fused or non-fused aromatic ring having 6 to 50 ring carbon atoms, a fused or non-fused aromatic heterocyclic ring having 5 to 50 ring atoms, and a partially hydrogenated fused or non-fused aromatic heterocyclic ring having 5 to 50 ring atoms. Preferred are a benzene ring, a naphthalene ring, an anthracene ring, a phenanthrene ring, a pyridine ring, a pyrimidine ring, a quinoline ring, a quinazoline ring, a carbazole ring, a dibenzofuran ring, and a dibenzothiophene ring, with a benzene ring, a naphthalene ring, a pyridine ring, and a pyrimidine ring being more preferred and a benzene ring being particularly preferred. These rings may have the optional substituent mentioned above.

In an embodiment of the invention, when *b is bonded to the carbon atom *c2, $X^1$ represents $CR^2$, and $R^2$ is bonded to $R^1$ to form a ring, —$R^1$—$R^2$— preferably represents —$X^a$=$X^b$—$X^c$=$X^d$—.

$X^a$ to $X^d$ each independently represent N or $CR^a$, preferably $CR^a$. $R^a$ represents a hydrogen atom or a substituent, and adjacent two groups $R^a$ may be bonded to each other to form a ring.

The substituent as $R^a$, examples, preferred examples, and more preferred examples thereof are each selected from those of the substituent described above with respect to $R^1$.

$R^a$ is preferably a hydrogen atom, the substituted or unsubstituted alkyl group, the substituted or unsubstituted aryl group, or the substituted or unsubstituted heteroaryl group, each mentioned above, more preferably a hydrogen atom, the substituted or unsubstituted aryl group, or the substituted or unsubstituted heteroaryl group, still more preferably a hydrogen atom, a phenyl group, a naphthyl group (inclusive of isomeric groups), a biphenyl group (inclusive of isomeric groups), a terphenyl group (inclusive of isomeric groups), a phenylterphenyl group (inclusive of isomeric groups), a dibenzofuranyl group (inclusive of isomeric groups), or a dibenzothiophenyl group (inclusive of isomeric groups), further preferably a hydrogen atom or a phenyl group, and particularly preferably a hydrogen atom.

Adjacent two groups $R^a$ may be bonded to each other to form a ring. Examples, preferred examples, more preferred examples, and particularly preferred examples of such a ring are as described above with respect to the ring formed when $R^1$ and $R^2$ are bonded to each other.

When *b is bonded to the carbon atom *c2, $X^1$ represents $CR^2$, and $R^2$ is bonded to $R^1$ to form a ring, the compound (1) is represented by formula (1c), wherein the structure in formula (1c) represented by the following formula:

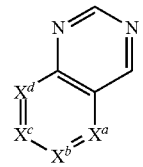

is preferably represented by any of the following formulae:

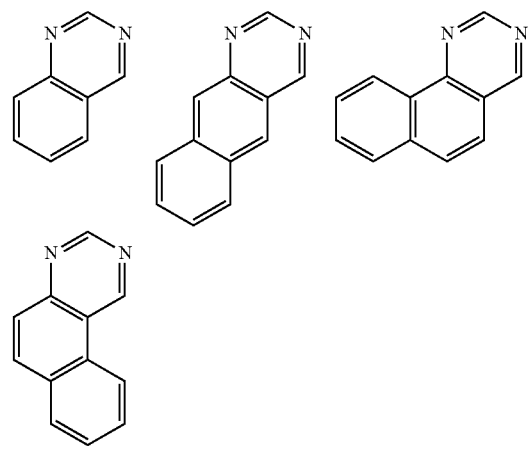

and preferably represented by the following formula:

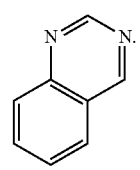

When *b is bonded to the carbon atom *c1, formula (1) is represented by formula (1a) and $L^1$ preferably represents a substituted or unsubstituted arylene group or a group of atoms which complete a ring together with $R^2$. The number of ring carbon atoms of the arylene group is preferably 6 to 50, more preferably 6 to 25, and still more preferably 6 to 18.

Examples, preferred examples, and more preferred examples of the arylene group are selected from those derived from the aryl group mentioned above with respect to $R^1$ by removing one hydrogen atom, with a phenylene group being preferred and a m-phenylene group and a p-phenylene group being particularly preferred.

When $L^1$ represents a group of atoms which complete a ring together with $R^2$, each of formulae (1) and (1a) is represented by formula (1'):

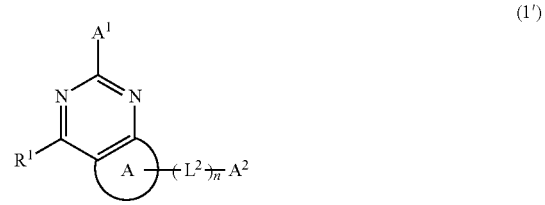

(1')

wherein $R^1$, $L^2$, and n re as defined in formula (1), the ring A is a ring formed by $L^1$ and $R^2$ in formula (1) which are bonded to each other, and $A^1$ and $A^2$ will be described below.

Examples of the ring A include a fused or non-fused aromatic ring having 6 to 50 ring carbon atoms, a partially hydrogenated fused or non-fused aromatic ring having 6 to 50 ring carbon atoms, a fused or non-fused aromatic heterocyclic ring having 5 to 50 ring atoms, and a partially hydrogenated fused or non-fused aromatic heterocyclic ring having 5 to 50 ring atoms. Preferred examples are a benzene ring, a naphthalene ring, an anthracene ring, a phenanthrene ring, a pyridine ring, a pyrimidine ring, a quinoline ring, a quinazoline ring, a carbazole ring, a dibenzofuran ring, and a dibenzothiophene ring, with a benzene ring, a naphthalene ring, a pyridine ring, and a pyrimidine ring being more preferred, and a benzene ring being particularly preferred. These ring may have the optional substituent mentioned above.

When n is an integer of 1 to 3, the position of the ring A to which $L^2$ is bonded is not particularly limited. When n is 0, i.e., $L^2$ is a single bond, the position of the ring A to which $A^2$ is bonded is also not particularly limited.

When *b is bonded to the carbon atom *c2, formula (1) is represented by formula (1b) or (1c) and $L^1$ preferably represents a divalent linking group.

The divalent linking group is selected from a substituted or unsubstituted alkylene group having 1 to 50, preferably 1 to 18, and more preferably 1 to 8 carbon atoms, a substituted or unsubstituted cycloalkylene group having 3 to 50, preferably 3 to 10, and more preferably 3 to 8 ring carbon atoms, a substituted or unsubstituted arylene group having 6 to 60, preferably 6 to 25, and more preferably 6 to 18 ring carbon atoms, and a substituted or unsubstituted heteroarylene group having 5 to 60, preferably 5 to 30, and more preferably 5 to 26 ring atoms.

Examples, preferred examples, and more preferred examples of the alkylene group, the cycloalkylene group, the arylene group, and the heteroarylene group are selected from those derived from the alkyl group, the cycloalkyl group, the aryl group, and the heteroaryl group each mentioned above with respect to $R^1$ by removing one hydrogen atom.

$L^1$ is preferably the substituted or unsubstituted alkylene group having 1 to 50 carbon atoms or the substituted or unsubstituted arylene group having 6 to 60 ring carbon atoms each mentioned above, more preferably the substituted or unsubstituted arylene group having 6 to 60 ring carbon atoms, still more preferably a phenylene group, and particularly preferably a m-phenylene group or a p-phenylene group.

The divalent linking group for $L^2$ is selected from a substituted or unsubstituted alkylene group having 1 to 50, preferably 1 to 18, and more preferably 1 to 8 carbon atoms, a substituted or unsubstituted cycloalkylene group having 3 to 50, preferably 3 to 10, and more preferably 3 to 8 ring carbon atoms, a substituted or unsubstituted arylene group having 6 to 60, preferably 6 to 25, and more preferably 6 to 18 ring carbon atoms, and a substituted or unsubstituted heteroarylene group having 5 to 60, preferably 5 to 30, and more preferably 5 to 26 ring atoms.

Examples, preferred examples, and more preferred examples of the alkylene group, the cycloalkylene group, the arylene group, and the heteroarylene group are selected from those derived from the alkyl group, the cycloalkyl group, the aryl group, and the heteroaryl group each mentioned above with respect to $R^1$ by removing one hydrogen atom.

$L^2$ is preferably a single bond, the substituted or unsubstituted alkylene group having 1 to 50 carbon atoms or the substituted or unsubstituted arylene group having 6 to 60 ring carbon atoms, more preferably the substituted or unsubstituted arylene group having 6 to 60 ring carbon atoms, still more preferably a phenylene group, and particularly preferably a m-phenylene group or a p-phenylene group.

The subscript n represents an integer of 0 to 3 and particularly preferably 0. When n is 0, $L^2$ represents a single bond.

When n is 1, $L^1$ and $L^2$ may be the same or different and $L^1$ and $L^2$ may be crosslinked together. For example, when $L^1$ is a substituted or unsubstituted arylene group having 6 to 50 ring carbon atoms and n is 1, $L^1$ and $L^2$ may be the same or different and L and $L^2$ may be crosslinked together.

When is 2 or 3, L and two or three groups $L^2$ may be the same or different, and $L^1$ and $L^2$, or two groups $L^2$ may be crosslinked together. For example, wherein L is a substituted or unsubstituted arylene group having 6 to 50 ring carbon atoms and n is 2 or 3, $L^1$ and two or three groups $L^2$ may be the same or different, and $L^1$ and $L^2$, or two groups $L^2$ may be crosslinked together.

The crosslinking group may include a methylene group, a dimethylmethylene group, a diphenylmethylene group, an imino group (>NH), a phenylimino group, —O—, and —S—.

$A^1$ and $A^2$ are different from each other and each represented by any of formulae (2), (2'), (3), (3'), (3''), and (4).

(2)

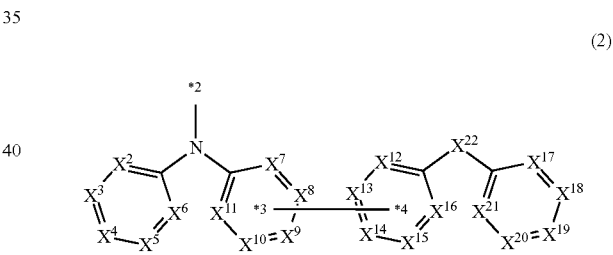

In formula (2),

*2 is bonded to the carbon atom *c1, the carbon atom *c2, $L^1$ when n is 0, or $L^2$ when n is an integer of 1 to 3;

one of $X^7$ to $X^{11}$ is a carbon atom bonded to *3;

one of $X^{12}$ to $X^{16}$ is a carbon atom bonded to *4;

the rest of $X^7$ to $X^{11}$, the rest of $X^{12}$ to $X^{16}$, $X^2$ to $X^6$, and $X^{17}$ to $X^{21}$ each independently represent N or $CR^3$, preferably $CR^3$, $X^6$ and $X^{11}$ are preferably carbon atoms which are bonded to each other, and $X^{16}$ and $X^{21}$ are preferably carbon atoms which are bonded to each other; and $R^3$ represents a hydrogen atom or a substituent and groups $R^3$ may be bonded to each other to form a ring.

The substituent as $R^3$, examples, preferred examples, and more preferred examples thereof are each selected from those of the substituent described above with respect to $R^1$.

$R^3$ is preferably a hydrogen atom.

In an embodiment of the invention, one of $X^2$ to $X^6$, preferably $X^3$ or $X^4$, represents $CR^3$ and $R^3$ represents a carbazolyl group or a N-substituted carbazolyl group, preferably a N-phenylcarbazolyl group.

$X^{22}$ represents $NR^4$, $CR^5R^6$, O, S, Se, or $SiR^7R^8$.

$R^4$ to $R^8$ each independently represent a hydrogen atom or a substituent. $R^5$ and $R^6$, or $R^7$ and $R^8$ may be bonded to each other to form a ring.

The substituent represented by $R^4$ to $R^8$ is selected from a halogen atom, a cyano group, a nitro group, a substituted or unsubstituted alkyl group having 1 to 50, preferably 1 to 18, and more preferably 1 to 8 carbon atoms; a substituted or unsubstituted cycloalkyl group having 3 to 50, preferably 3 to 10, and more preferably 3 to 8 ring carbon atoms; a substituted or unsubstituted aryl group having 6 to 60, preferably 6 to 25, and more preferably 6 to 18 ring carbon atoms; a substituted or unsubstituted aralkyl group having 7 to 51, preferably 7 to 30, and more preferably 7 to 20 carbon atoms which includes an aryl group having 6 to 50, preferably 6 to 25, and more preferably 6 to 18 ring carbon atoms; an amino group; a mono- or di-substituted amino group wherein the substituent is selected from a substituted or unsubstituted alkyl group having 1 to 50, preferably 1 to 18, and more preferably 1 to 8 carbon atoms and a substituted or unsubstituted aryl group having 6 to 60, preferably 6 to 25, and more preferably 6 to 18 ring carbon atoms; a substituted or unsubstituted alkoxy group having 1 to 50, preferably 1 to 18, and more preferably 1 to 8 carbon atoms; a substituted or unsubstituted cycloalkoxy group having 3 to 50, preferably 3 to 10, and more preferably 3 to 8 ring carbon atoms; a substituted or unsubstituted aryloxy group having 6 to 60, preferably 6 to 25, and more preferably 6 to 18 ring carbon atoms; a substituted or unsubstituted alkylthio group having 1 to 50, preferably 1 to 18, and more preferably 1 to 8 carbon atoms; a substituted or unsubstituted arylthio group having 6 to 60, preferably 6 to 25, and more preferably 6 to 18 ring carbon atoms; a silyl group; a mono-, di- or tri-substituted silyl group, wherein the substituent is selected from a substituted or unsubstituted alkyl group having 1 to 50, preferably 1 to 18, and more preferably 1 to 8 carbon atoms and a substituted or unsubstituted aryl group having 6 to 60, preferably 6 to 25, and more preferably 6 to 18 ring carbon atoms; a substituted or unsubstituted heteroaryl group having 5 to 60, preferably 5 to 30, and more preferably 5 to 26 ring atoms; and a substituted or unsubstituted haloalkyl group having 1 to 50, preferably 1 to 18, and more preferably 1 to 8 carbon atoms.

Examples, preferred examples, and more preferred examples of the substituent represented by $R^4$ to $R^8$ are each selected from those of the substituent described with respect to $R^1$.

$X^{22}$ preferably represents an imino group (>NH), a phenylimino group, a methylene group, a dimethylmethylene group, a diphenylmethylene group, a 9,9-dimethylfluorenylimino group, a biphenylimino group, a naphthylimino group, —O—, —S—, —Se—, a silylene group (>SiH$_2$), or a dimethylsilylene group, with an imino group, a phenylimino group, a dimethylmethylene group, a 9,9-dimethylfluorenylimino group, a biphenylimino group, a naphthylimino group, —O—, and —S— being more preferred.

In formula (2'),

*2, $X^7$ to $X^{11}$, $X^{12}$ to $X^{16}$, $X^{17}$ to $X^{21}$, and $X^{22}$ are as defined in formula (2);

one of $X^{2'}$ to $X^{6'}$ is a carbon atom bonded to *3';

one of $X^{12'}$ to $X^{16'}$ is a carbon atom bonded to *4';

the rest of $X^{2'}$ to $X^{6'}$, the rest of $X^{12'}$ to $X^{16'}$, and $X^{17'}$ to $X^{21'}$ each independently represent N or CR$^3$, preferably CR$^3$, $X^{6'}$ and $X^{11}$ are preferably carbon atoms which are bonded to each other, $X^{16}$ and $X^{21}$ are preferably carbon atoms which are bonded to each other, and $X^{16'}$ and $X^{21'}$ are preferably carbon atoms which are bonded to each other;

$R^3$ is as defined in formula (2), preferably a hydrogen atom;

$X^{22'}$ represents NR$^4$, CR$^5$R$^6$, O, S, Se, or SiR$^7$R$^8$; and $R^4$ to $R^8$ are as defined in formula (2).

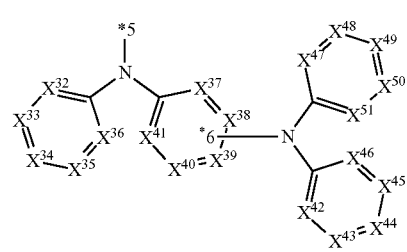

(3)

In formula (3),

*5 is bonded to the carbon atom *c1, the carbon atom *c2, L$^1$ when n is 0, or L$^2$ when n is an integer of 1 to 3, each described in formula (1);

one of $X^{37}$ to $X^{41}$ represents a carbon atom bonded to a carbon atom bonded to *6;

the rest of $X^{37}$ to $X^{41}$, $X^{32}$ to $X^{36}$, and $X^{42}$ to $X^{51}$ each independently represent N or CR$^9$, preferably CR$^9$, $X^{36}$ and $X^{41}$ are preferably carbon atoms which are bonded to each other, and $X^{46}$ and $X^{51}$ are preferably carbon atoms which are bonded to each other; and $R^9$ represents a hydrogen atom or a substituent and groups $R^9$ may be bonded to each other to form a ring.

The substituent as $R^9$, examples, preferred examples, and more preferred examples thereof are each selected from those of the substituent described above with respect to $R^1$.

Examples of the ring to be formed when groups $R^9$ are bonded to each other are the same as those described with respect to $R^1$.

$R^9$ is preferably a hydrogen atom.

In an embodiment of the invention, one of $X^{32}$ to $X^{36}$, preferably $X^{34}$ represents CR$^9$ and $R^9$ represents a N-carbazolyl group.

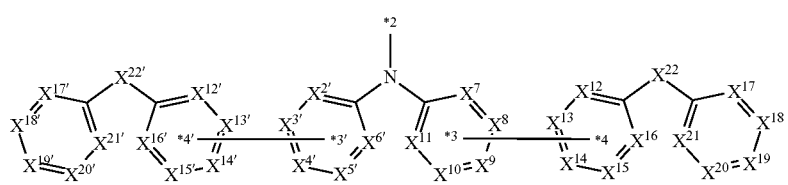

(2')

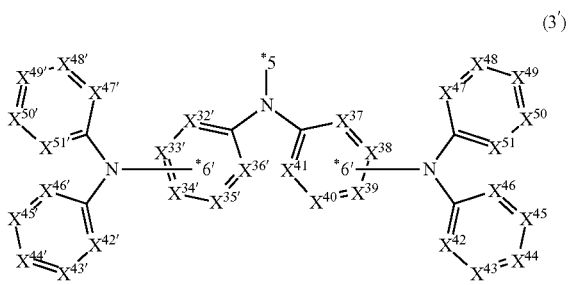

(3')

In formula (3'),
*5, $X^{37}$ to $X^{41}$, and $X^{42}$ to $X^{51}$ are as defined in formula (3);
one of $X^{32'}$ to $X^{36'}$ represents a carbon atom bonded to *6';
the rest of $X^{32'}$ to $X^{3'}$ and $X^{42'}$ to $X^{51'}$ each independently represent N or $CR^9$;
$R^9$ is as defined in formula (3), preferably a hydrogen atom; and
$X^{36'}$ and $X^{41}$ are preferably carbon atoms which are bonded to each other, $X^{46}$ and $X^{51}$ are preferably carbon atoms which are bonded to each other, and $X^{46'}$ and $X^{51''}$ are preferably carbon atoms which are bonded to each other.

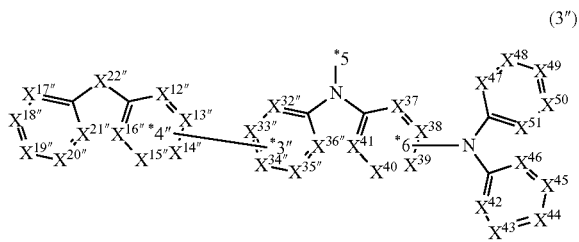

(3")

In formula (3"),
*5, $X^{37}$ to $X^{41}$, and $X^{42}$ to $X^{51}$ are as defined in formula (3);
one of $X^{32'''}$ to $X^{36'''}$ represents a carbon atom bonded to *3";
one of $X^{12'''}$ to $X^{16'''}$ represents a carbon atom bonded to *4";
the rest of $X^{12'''}$ to $X^{16'''}$ and $X^{17'''}$ to $X^{21'''}$ each independently represent N or $CR^3$, preferably $CR^3$, and the rest of $X^{32'''}$ to $X^{36'''}$ each represent N or $CR^9$, preferably $CR^9$;
$R^3$ is as defined in formula (2), preferably a hydrogen atom;
$R^9$ is as defined in formula (3), preferably a hydrogen atom;
$X^{36'''}$ and $X^{41}$ are preferably carbon atoms which are bonded to each other, $X^{46}$ and $X^{51}$ are preferably carbon atoms which are bonded to each other, and $X^{16'''}$ and $X^{21'''}$ are preferably carbon atoms which are bonded to each other;
$X^{22''}$ represents $NR^4$, $CR^5R^6$, O, S, Se, or $SiR^7R^8$; and
$R^4$ to $R^8$ are as defined in formula (2).

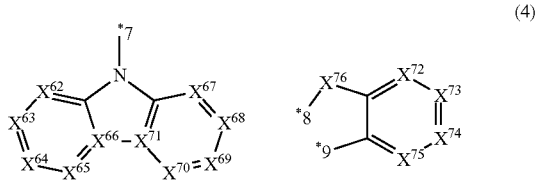

(4)

In formula (4),
*7 is bonded to the carbon atom *c1, the carbon atom *c2, $L^1$ when n is 0, or $L^2$ when n is an integer of 1 to 3, each described in formula (1);
one of adjacent two selected from $X^{67}$ to $X^{71}$ represents a carbon atom bonded to *8 and the other represents a carbon atom bonded to *9;
the rest of $X^{67}$ to $X^{71}$, $X^{62}$ to $X^{66}$, and $X^{72}$ to $X^{75}$ are each independently represent N or $CR^{10}$, preferably $CR^{10}$;
$X^{66}$ and $X^{71}$ are preferably carbon atoms which are bonded to each other;
$R^{10}$ represents a hydrogen atom or a substituent, and groups $R^{10}$ may be bonded to each other to form a ring;
the substituent as $R^{10}$, examples, preferred examples, and more preferred examples thereof are each selected from those of the substituent described above with respect to $R^1$;
examples of the ring to be formed when groups $R^{10}$ are bonded to each other are the same as those described with respect to $R^1$;
$R^{10}$ is preferably a hydrogen atom;
$X^{76}$ represents $NR^{11}$, $CR^{12}R^{13}$, O, S, Se, or $SiR^{14}R^{15}$; and
$R^{11}$ to $R^{15}$ each independently represent a hydrogen atom or a substituent, and $R^{12}$ and $R^{13}$, or $R^{14}$ and $R^{15}$ may be bonded to each other to form a ring.
The substituent as $R^{11}$ to $R^{15}$, examples, preferred examples, and more preferred examples thereof are each selected from those of the substituent described above with respect to $R^4$ to $R^8$.
$X^{76}$ preferably represents an imino group (>NH), a phenylimino group, a methylene group, a dimethylmethylene group, a diphenylmethylene group, —O—, —S—, —Se—, a silylene group (>$SiH_2$), or a dimethylsilylene group, with an imino group, a phenylimino group, a dimethylmethylene group, —O—, and —S— being more preferred.
In formula (1), the term "$A^1$ and $A^2$ are different from each other" means that:
(1) one of $A^1$ and $A^2$ is selected from one of formulae (2), (2'), (3), (3'), (3"), and (4), and the other is selected from the rest of the formulae;
(2) $A^1$ and $A^2$ are both selected from formula (2), but
  (2a) different in the bonding position of at least one selected from *3 and *4;
  (2b) different in at least one selected from $X^2$ to $X^{21}$; or
  (2c) different in $X^{22}$;
(3) $A^1$ and $A^2$ are both selected from formula (2'), but
  (3a) different in the bonding position of at least one selected from *3, *3', *4 and *4';
  (3b) different in at least one selected from $X^7$ to $X^{21}$, $X^{2'}$ to $X^{6'}$, and $X^{12'}$ to $X^{21'}$; or
  (3c) different in at lease one selected from $X^{22}$ and $X^{22'}$;
(4) $A^1$ and $A^2$ are both selected from formula (3), but
  (4a) different in the bonding position of *6; or
  (4b) different in at least one selected from $X^{32}$ to $X^{51}$;
(5) $A^1$ and $A^2$ are both selected from formula (3'), but
  (5a) different in the bonding position of at least one selected from *6 and *6'; or
  (5b) different from at least one selected from $X^{37}$ to $X^{51}$, $X^{32'}$ to $X^{36'}$, and $X^{42'}$ to $X^{51'}$;
(6) $A^1$ and A2 are both selected from formula (3"), but
  (6a) different in the bonding position of at least one selected from *6, *3" and *4";
  (6b) different in at least one selected from $X^{37}$ to $X^{51}$, $X^{32'''}$ to $X^{36'''}$, and $X^{12'''}$ to $X^{21'''}$; or
  (6c) different in $X^{22}$; and
(7) $A^1$ and $A^2$ are both selected from formula (4), but
  (7a) different in the bonding position of at least one selected from *8 and *9;

(7b) different in at least one selected from $X^{62}$ to $X^{75}$; or (7c) different in $X^{76}$.

$A^1$ and $A^2$ are preferably different by (1), (2a), (2c), (3a), (3c), (4a), (5a), (6a), (6c), (7a), or (7c) and more preferably by (1), (2a), (3a), (4a), (5a), (6a), or (7a), The group represented by formula (2) is preferably represented by any of formulae (2a) to (2c):

(2a)
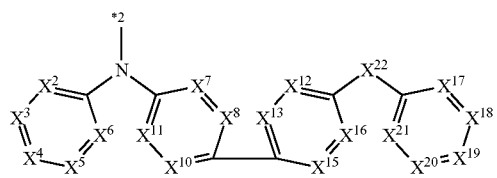

(2b)
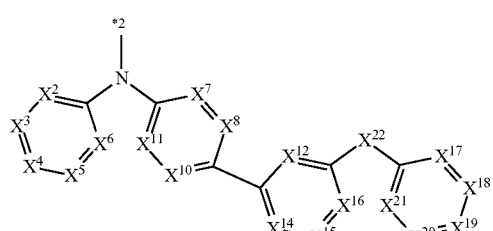

(2c)
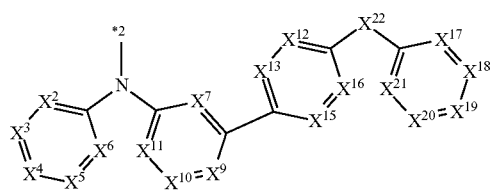

wherein 2 and $X^2$ to $X^{22}$ are as defined above.

The group represented by formula (2a) is preferably represented by any of formulae (2a-1) to (2a-3):

(2a-1)
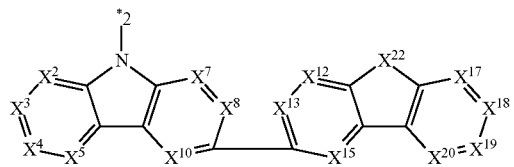

(2a-2)
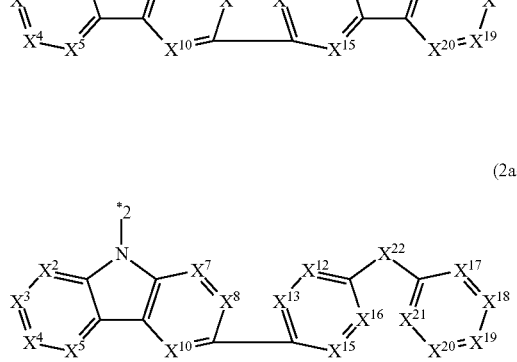

(2a-3)
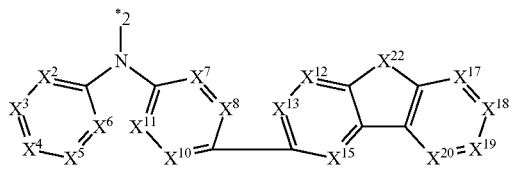

wherein *2 and each X are as defined above.

The group represented by formula (2b) is preferably represented by any of formulae (2b-1) to (2b-3):

(2b-1)
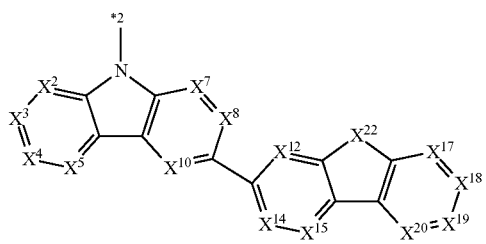

(2b-2)
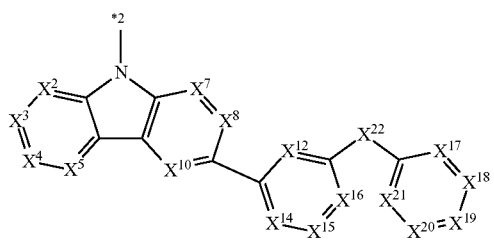

(2b-3)
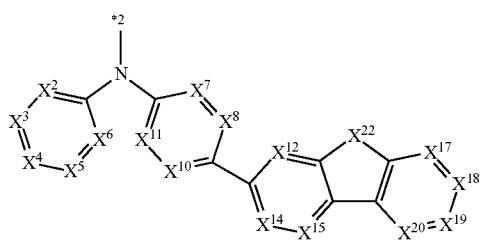

wherein *2 and each X are as defined above.

The group represented by formula (2c) is preferably represented by any of formulae (2c-1) to (2c-3).

(2c-1)
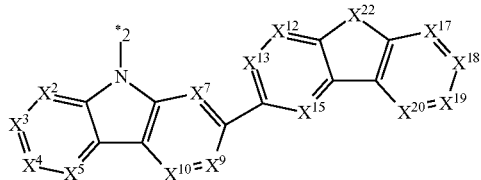

-continued
(2c-2)
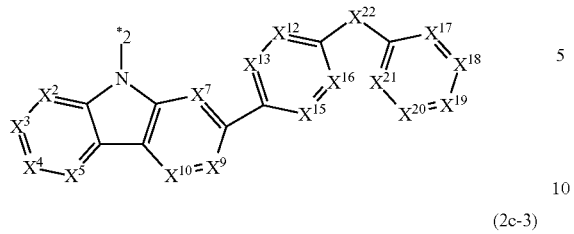
(2c-3)
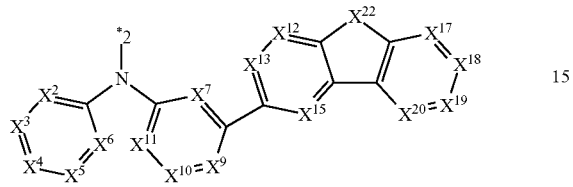
wherein *2 and each X are as defined above.
The group represented by formula (2') is preferably represented by any of formulae (2'a) to (2'i):
(2'a)
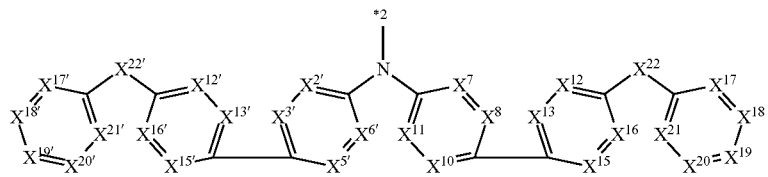
(2'b)
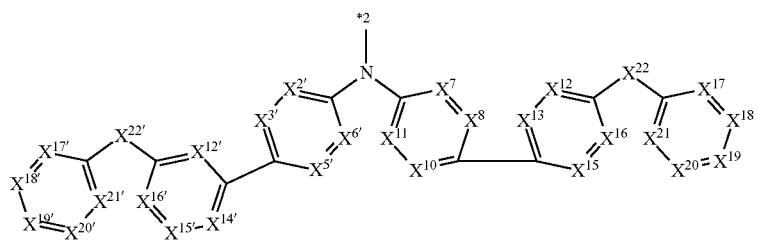
(2'c)
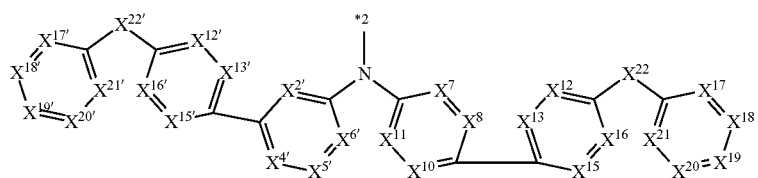
(2'd)
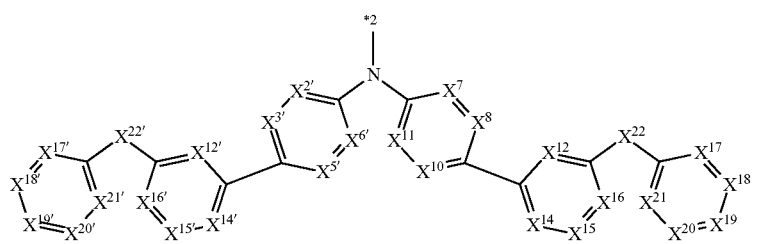

(2′e)
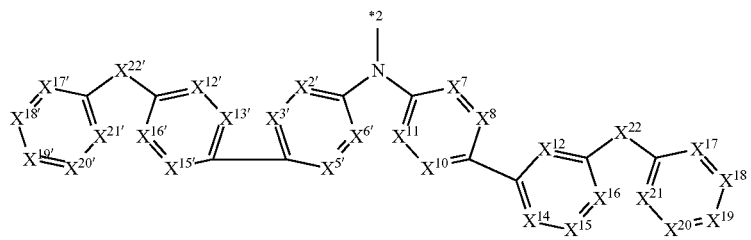
(2′f)
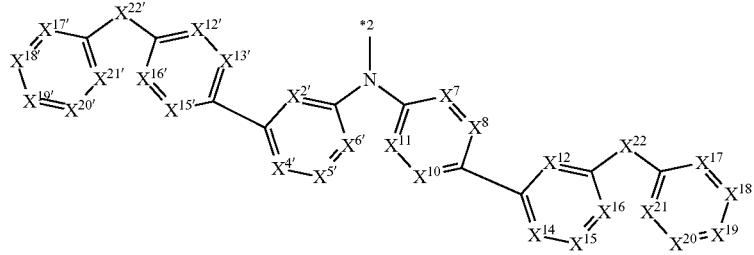
(2′g)
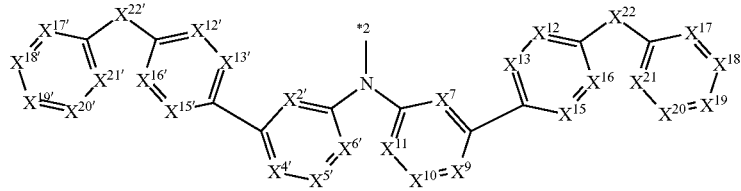
(2′h)
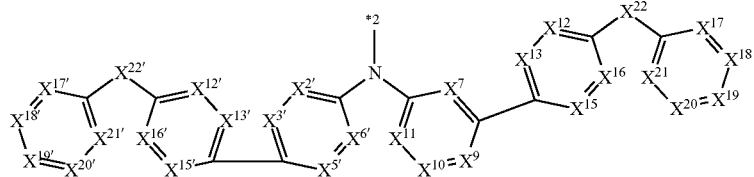
(2′i)
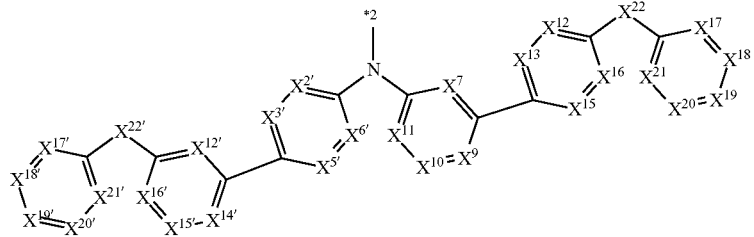
wherein *2, $X^7$ to $X^{22}$, $X^{2'}$ to $X^{6'}$, and $X^{12'}$ to $X^{22'}$ are as defined above.
The group represented by formula (2′a) is preferably represented by any of formulae (2′a-1) to (2′a-5):
(2′a-1)
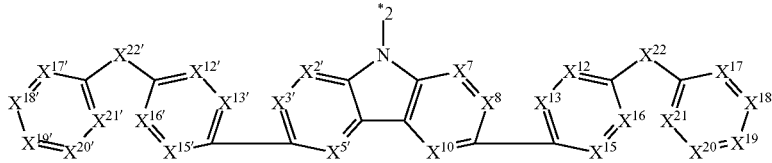

(2'a-2)
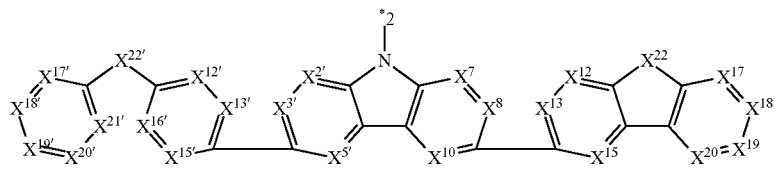
(2'a-3)
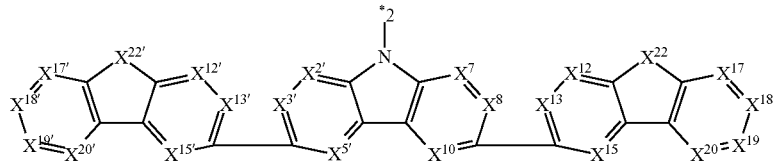
(2'a-4)
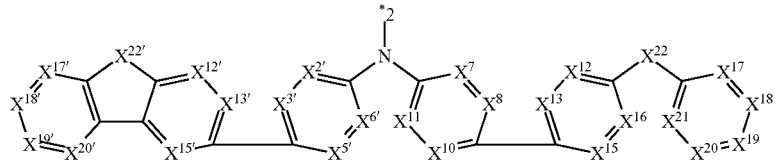
(2'a-5)
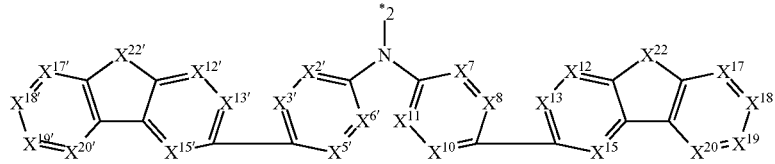
wherein *2 and each X are as defined above.
The group represented by formula (2'b) is preferably represented by any of formulae (2'b-1) to (2'b-7):
(2'b-1)
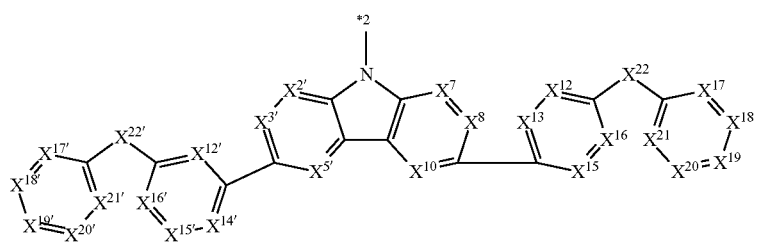
(2'b-2)
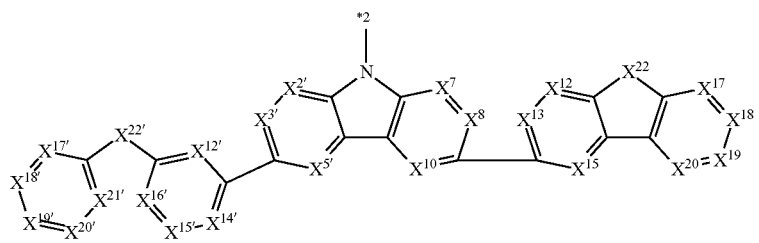

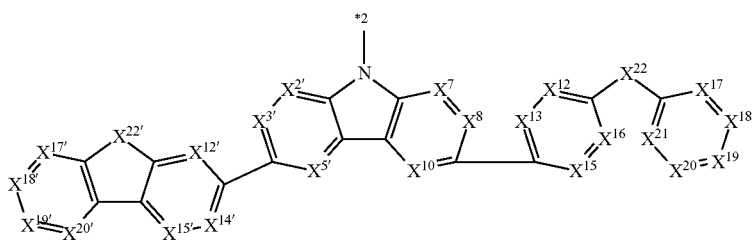
(2′b-3)
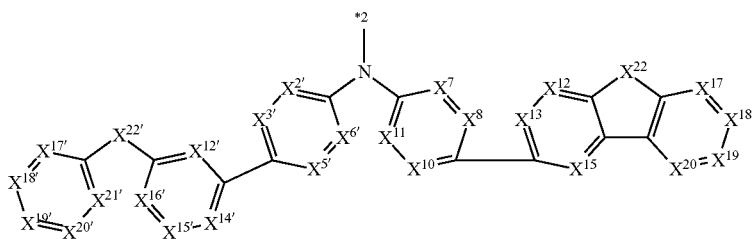
(2′b-5)
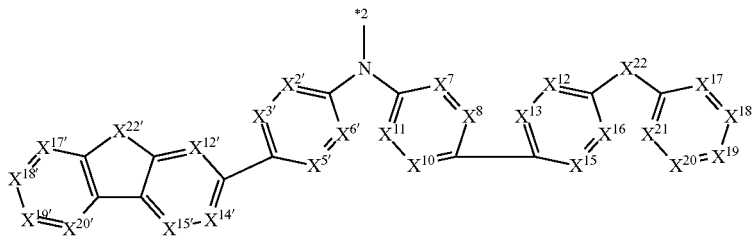
(2′b-6)
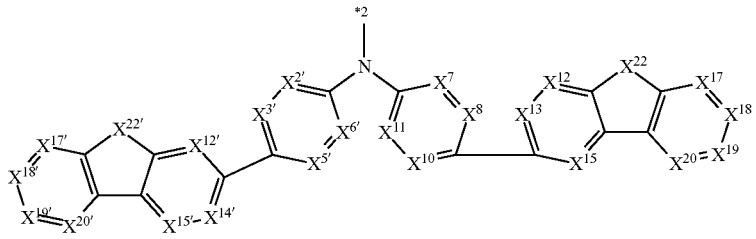
(2′b-7)
wherein *2 and each X are as defined above.
The group represented by formula (2′c) is preferably represented by any of formulae (2′c-1) to (2′c-7):
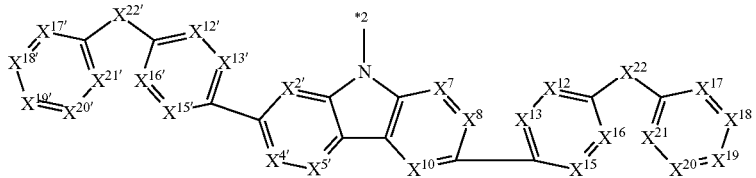
(2′c-1)
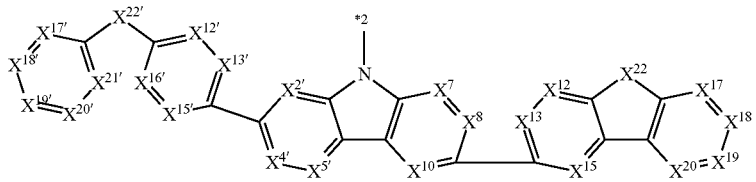
(2′c-2)

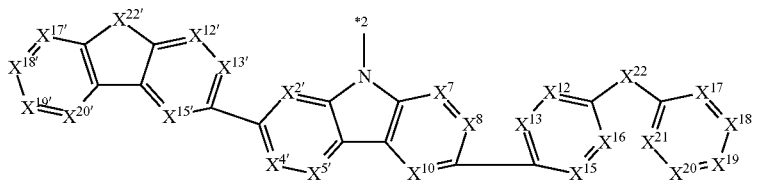
(2'c-3)
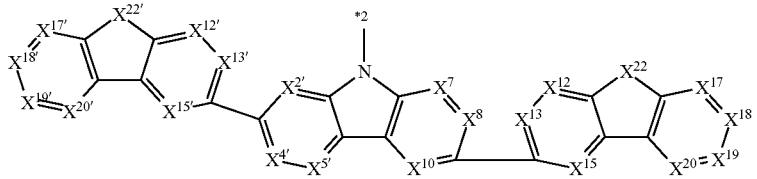
(2'c-4)
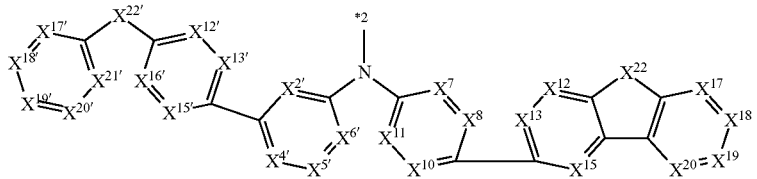
(2'c-5)
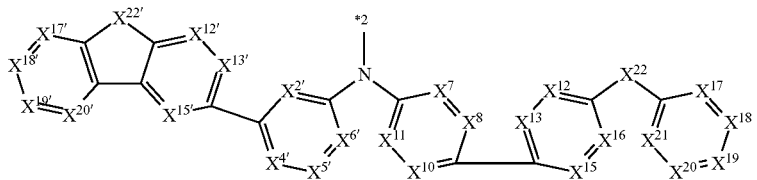
(2'c-6)
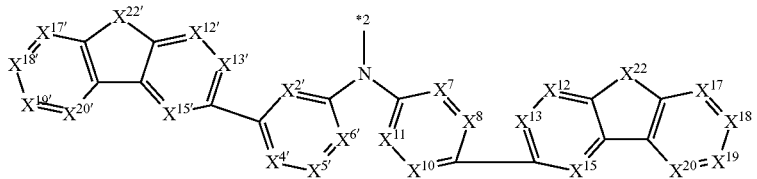
(2'c-7)
wherein *2 and each X are as defined above.
The group represented by formula (2'd) is preferably represented by any of formulae (2'd-1) to (2'd-5):
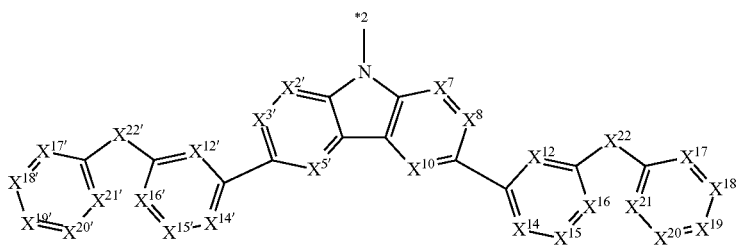
(2'd-1)

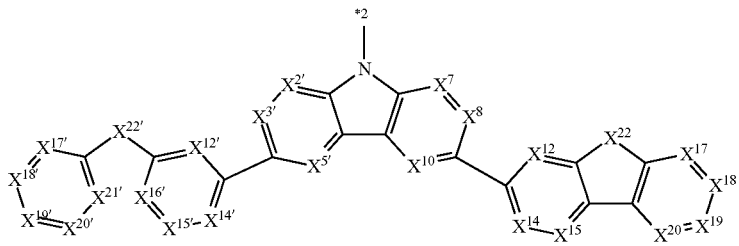
(2'd-2)
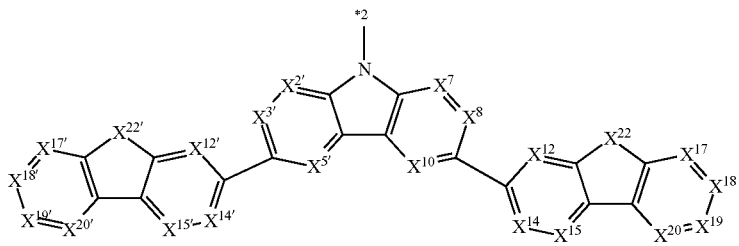
(2'd-3)
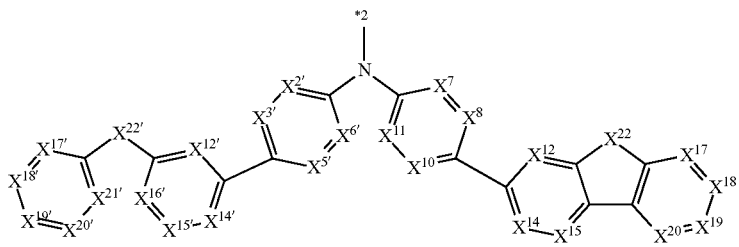
(2'd-4)
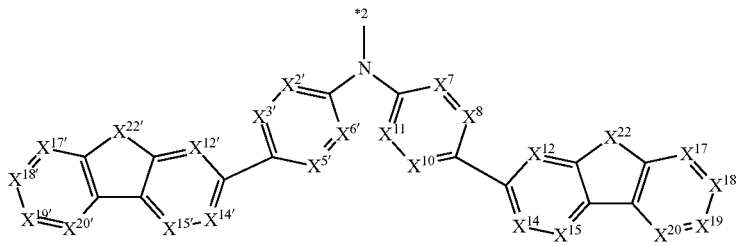
(2'd-5)
wherein *2 and each X are as defined above.
The group represented by formula (2'e) is preferably represented by any of formulae (2'e-1) to (2'e-7):
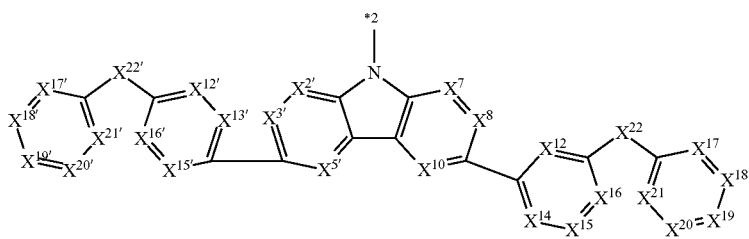
(2'e-1)

-continued
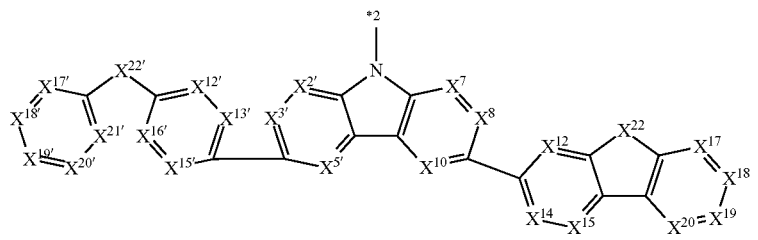
(2′e-2)
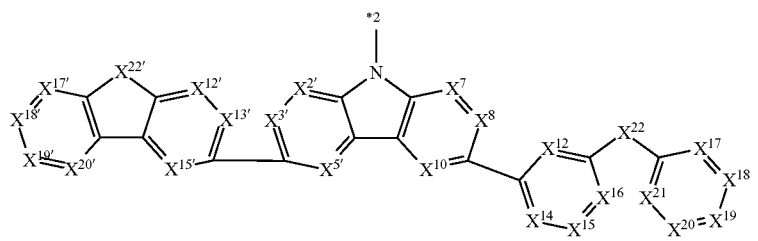
(2′e-3)
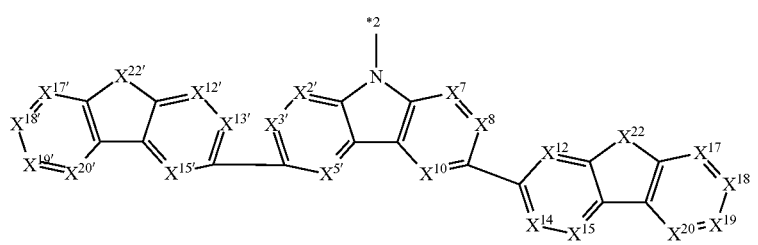
(2′e-4)
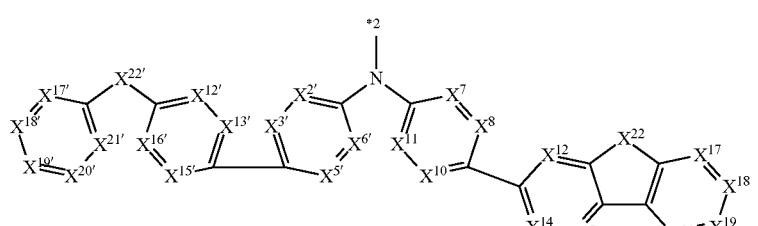
(2′e-5)
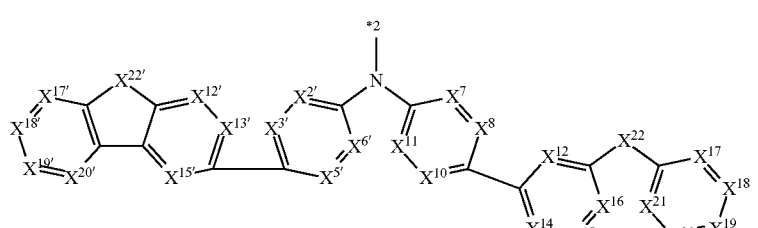
(2′e-6)
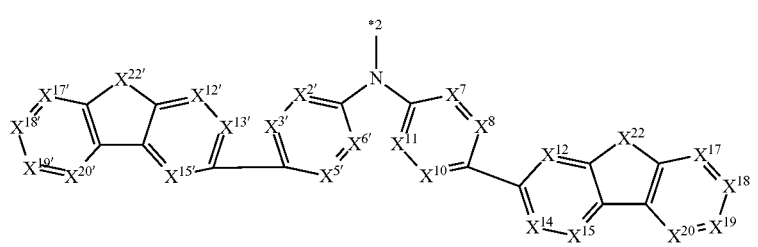
(2′e-7)
wherein *2 and each X are as defined above.

The group represented by formula (2'f) is preferably represented by any of formulae (2'f-1) to (2'f-7):
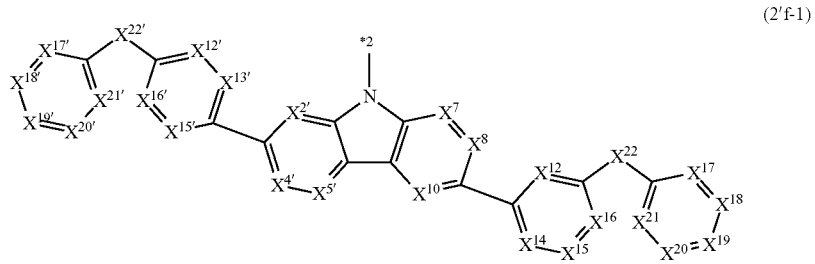
(2'f-1)
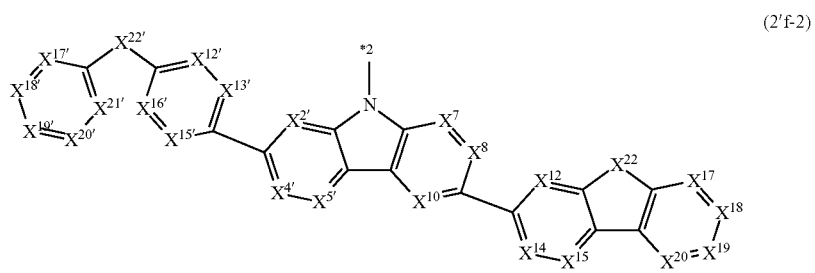
(2'f-2)
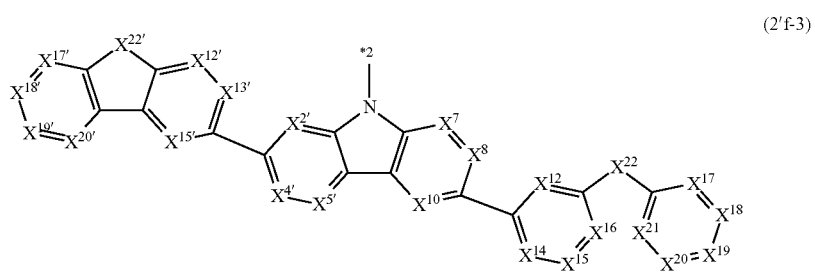
(2'f-3)
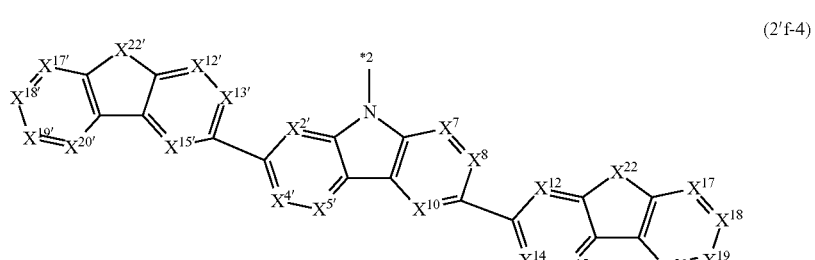
(2'f-4)
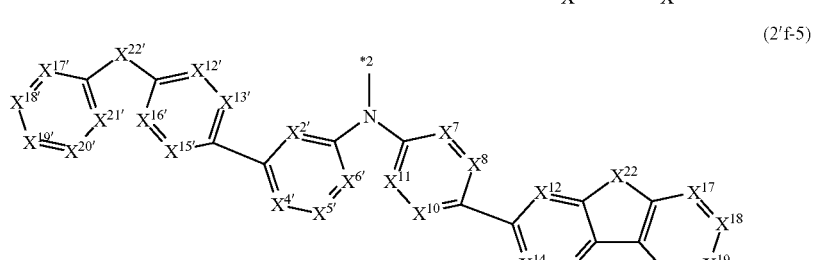
(2'f-5)
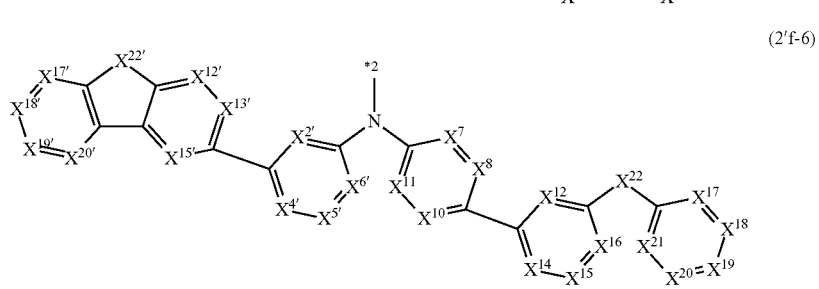
(2'f-6)

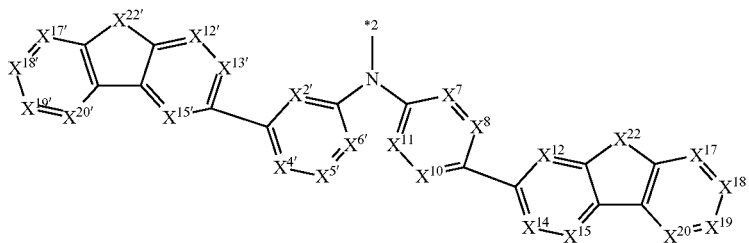
(2'f-7)
wherein 2 and each X are as defined above.
The group represented by formula (2'g) is preferably represented by any of formulae (2'g-1) to (2'g-5):
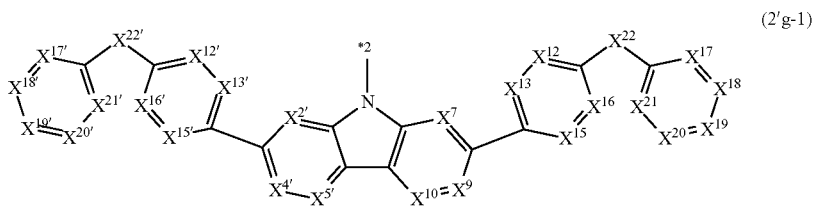
(2'g-1)
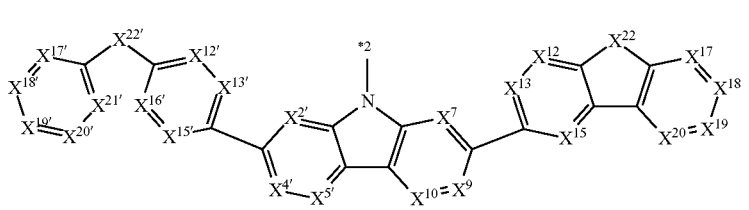
(2'g-2)
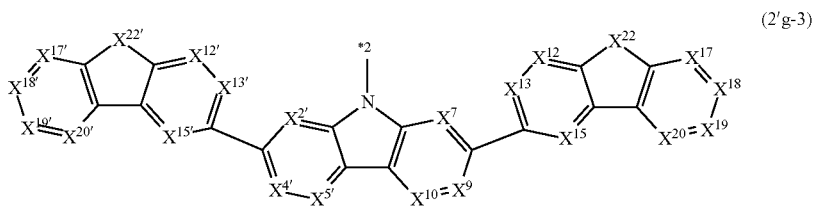
(2'g-3)
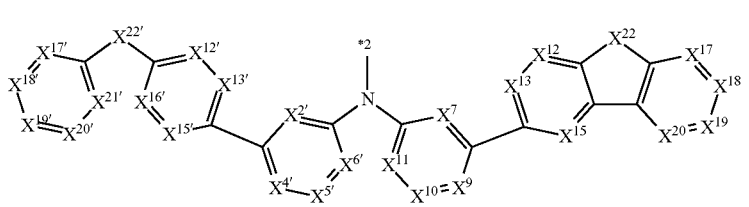
(2'g-4)
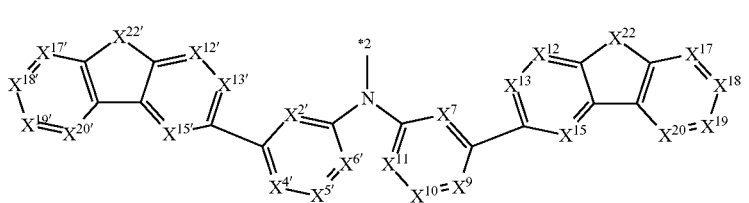
(2'g-5)
wherein *2 and each X are as defined above.

The group represented by formula (2'h) is preferably represented by any of formulae (2'h-1) to (2'h-7):
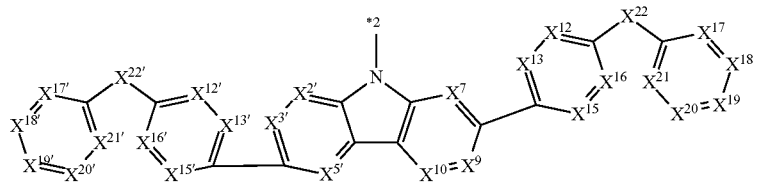
(2'h-1)
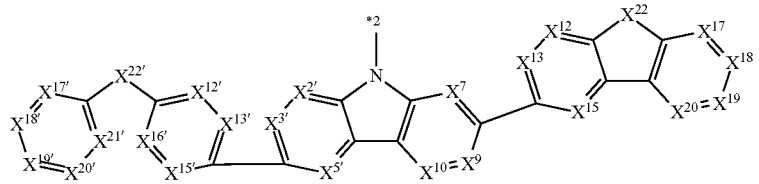
(2'h-2)
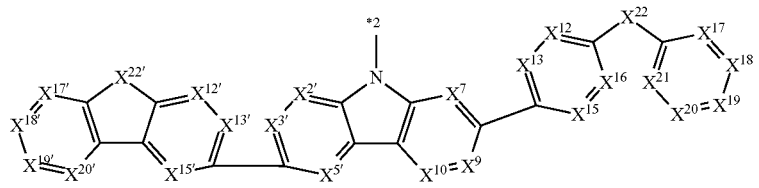
(2'h-3)
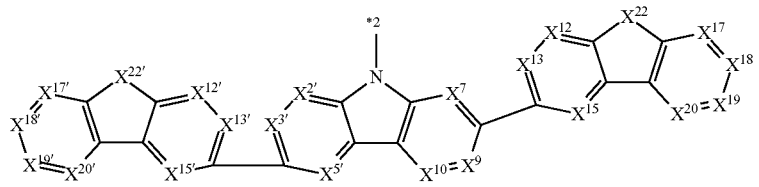
(2'h-4)
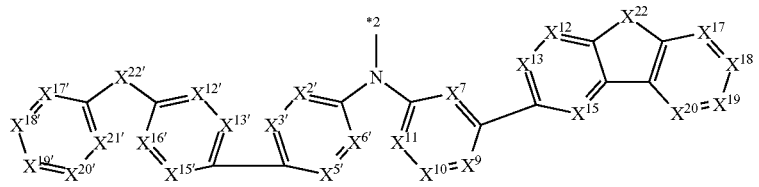
(2'h-5)
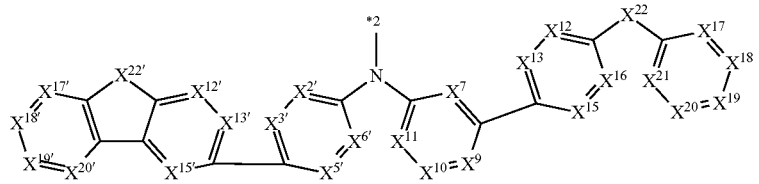
(2'h-6)
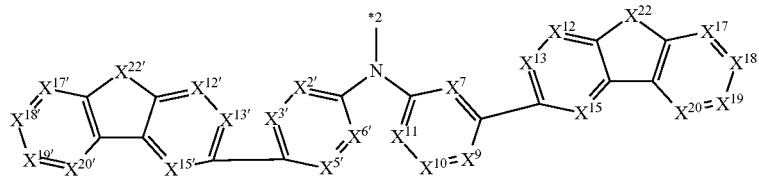
(2'h-7)
wherein *2 and each X are as defined above.

The group represented by formula (2'i) is preferably represented by any of formulae (2'i-1) to (2'i-7):
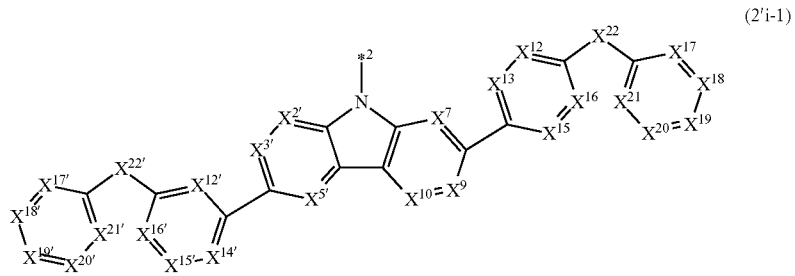
(2'i-1)
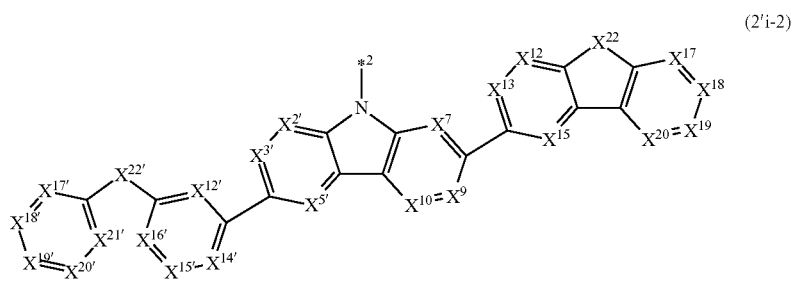
(2'i-2)
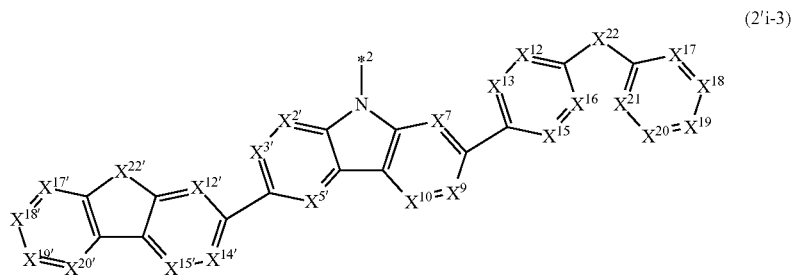
(2'i-3)
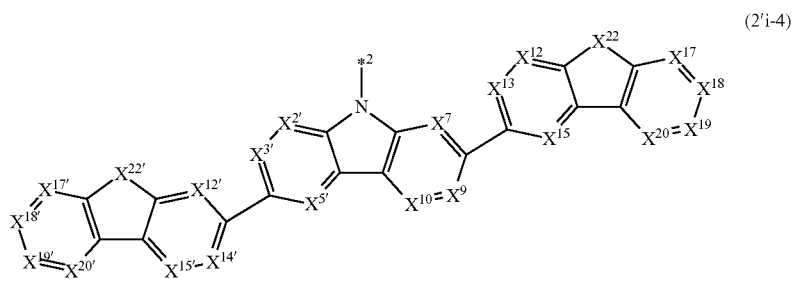
(2'i-4)
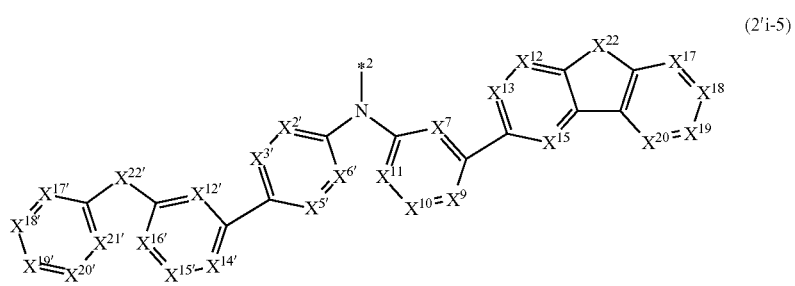
(2'i-5)

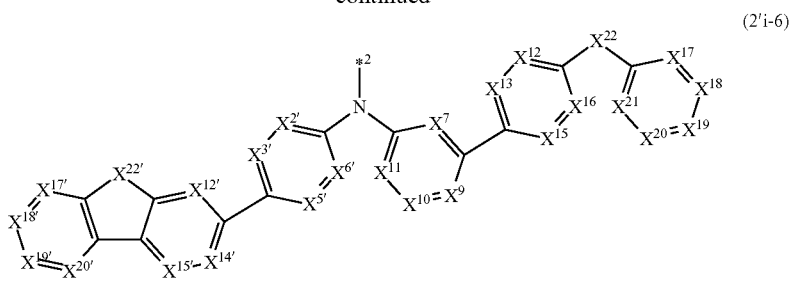

(2'i-6)

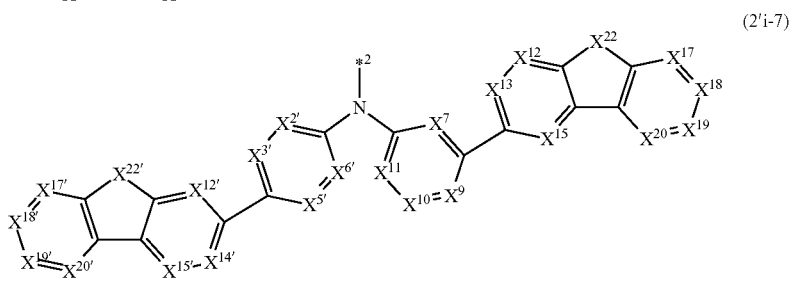

(2'i-7)

wherein *2 and each X are as defined above.

The group represented by formula (3) is preferably represented by any of formula (3a) or (3b):

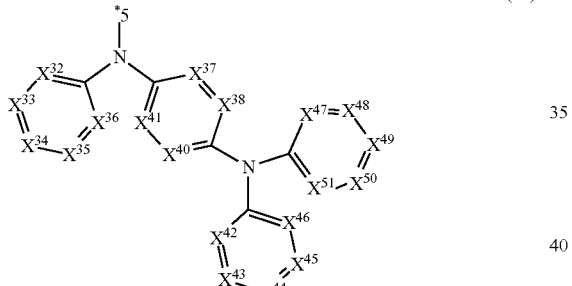

(3a)

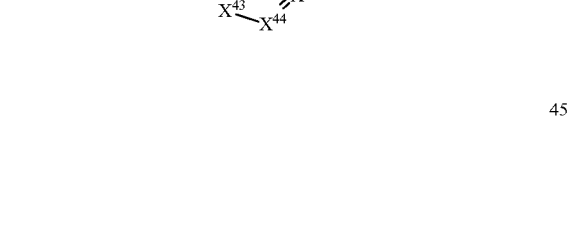

(3b)

wherein *5 and $X^{32}$ to $X^{51}$ are as defined above.

The group represented by formula (3a) is preferably represented by any of formulae (3a-1) to (3a-3):

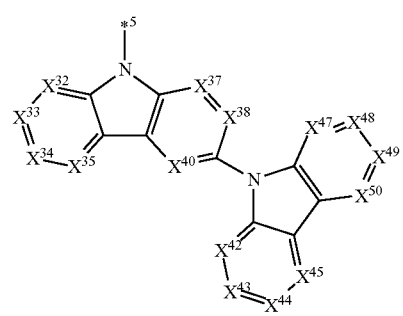

(3a-1)

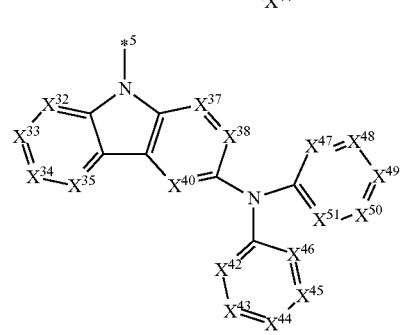

(3a-2)

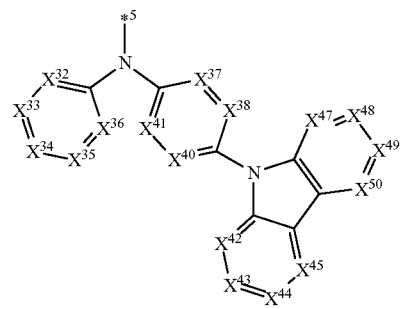

(3a-3)

wherein *5 and each X are as defined above.

The group represented by formula (3b) is preferably represented by any of formulae (3b-1) to (3b-3):

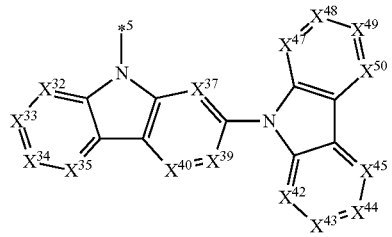
(3b-1)
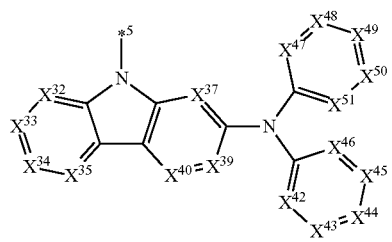
(3b-2)
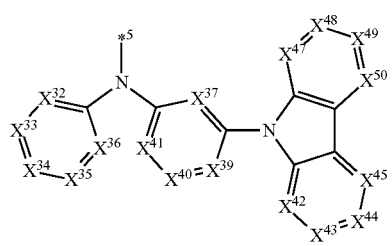
(3b-3)
wherein *5 and each X are as defined above.
The group represented by formula (3') is preferably represented by any of formulae (3'a) to (3'c):
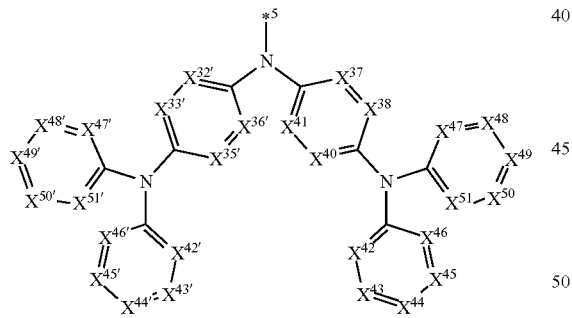
(3'a)
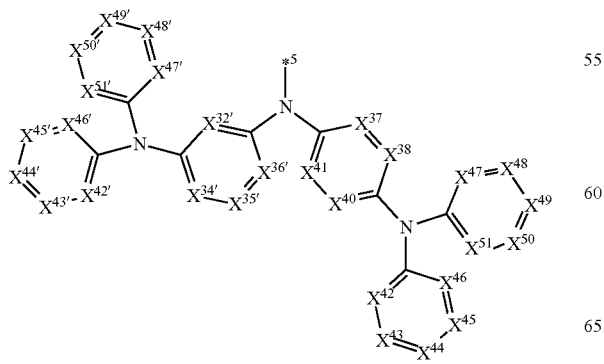
(3'b)
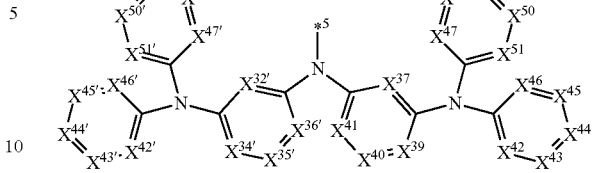
(3'c)
wherein 5*, $X^{37}$ to $X^{51}$, $X^{32'}$ to $X^{36'}$, 及び $X^{42'}$ to $X^{51'}$ are as defined above.
The group represented by formula (3'a) is preferably represented by any of formulae (3'a-1) to (3'a-5):
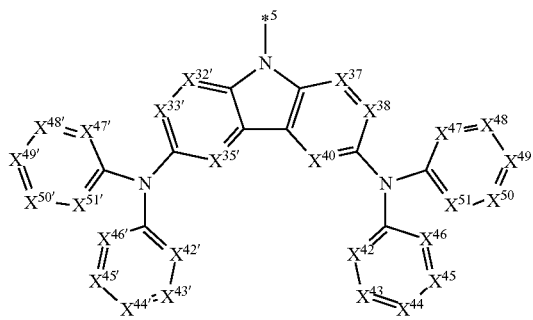
(3'a-1)
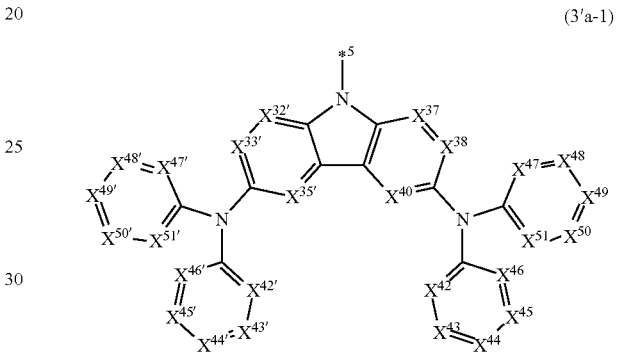
(3'a-2)
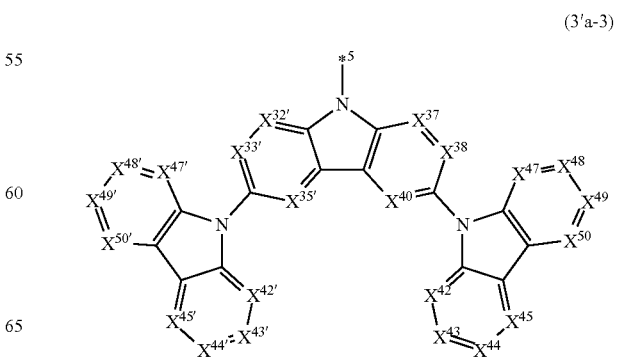
(3'a-3)

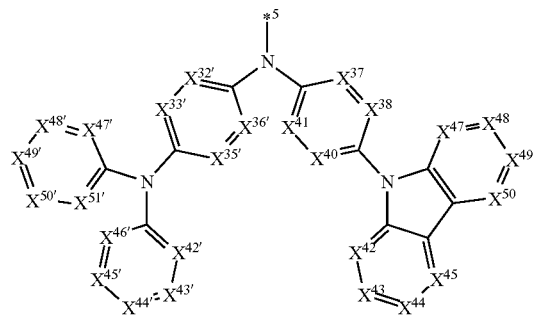
(3′a-4)
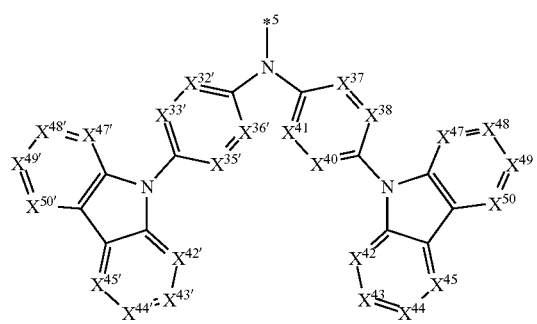
(3′a-5)
wherein *5 and each X are as defined above.
The group represented by formula (3′b) is preferably represented by any of formulae (3′b-1) to (3′b-7):
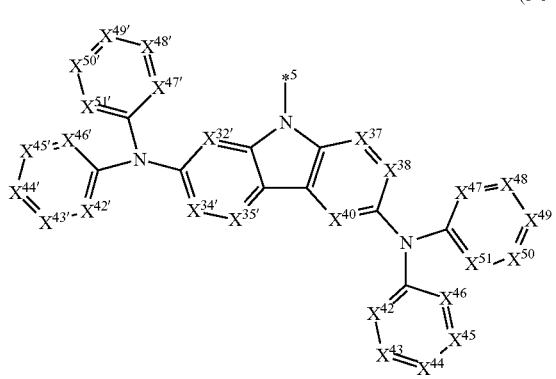
(3′b-1)
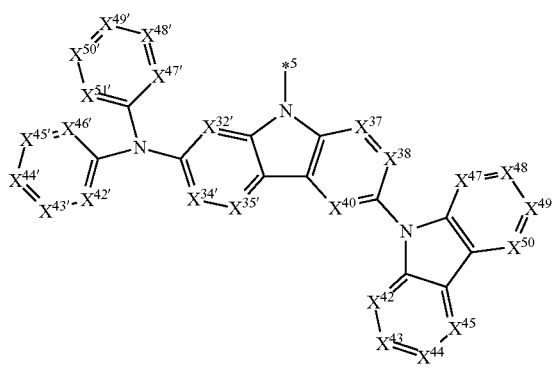
(3′b-2)
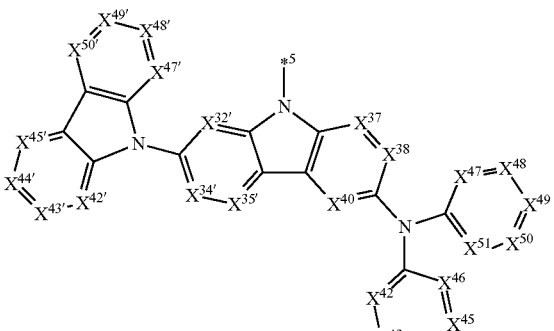
(3′b-3)
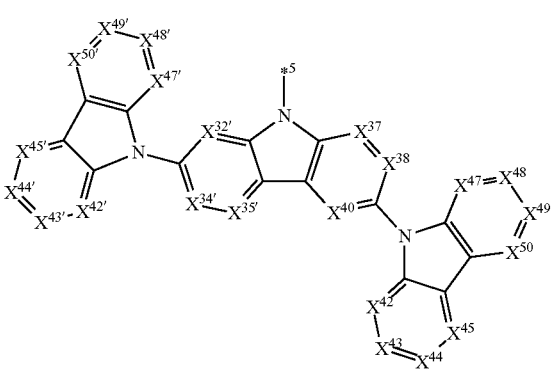
(3′b-4)
(3′b-5)
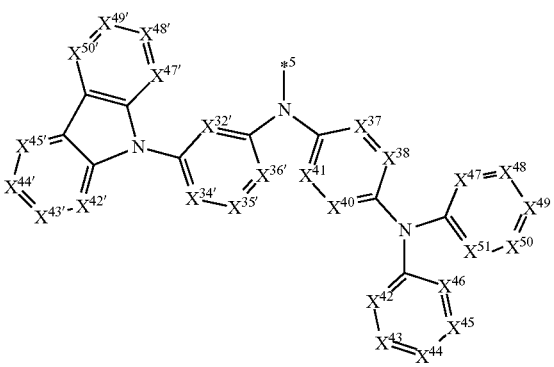
(3′b-6)

(3'b-7)
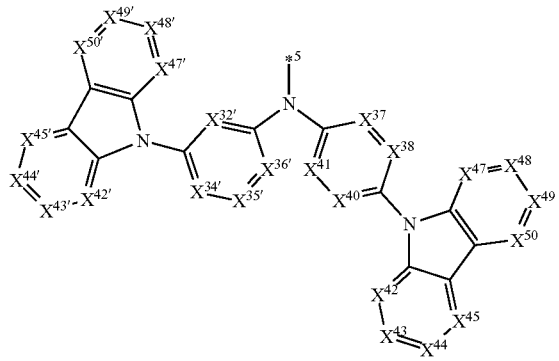
wherein *5 and each X are as defined above.
The group represented by formula (3'c) is preferably represented by any of formulae (3'c-1) to (3'c-5):
(3'c-1)
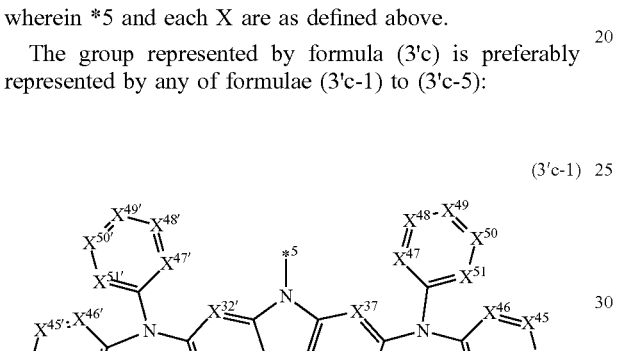
(3'c-2)
(3'c-3)
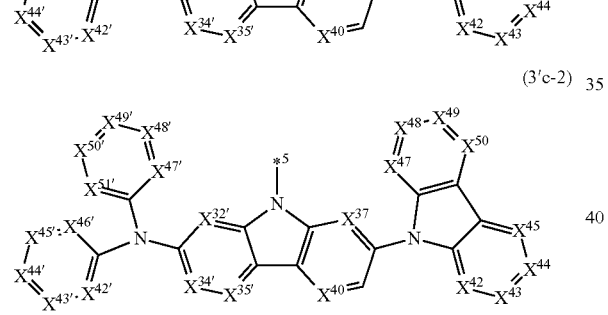
(3'c-4)
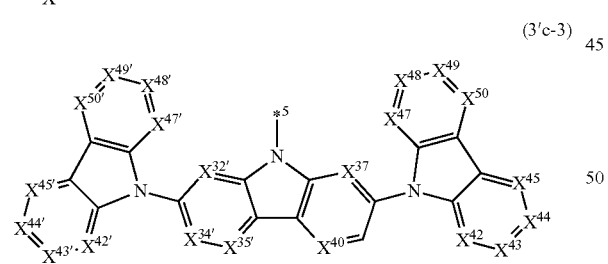
(3'c-5)
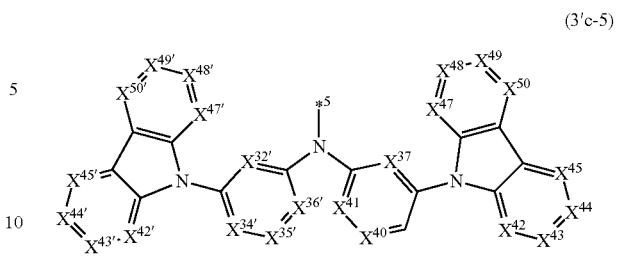
wherein *5 and each X are as defined above.
The group represented by formula (3") is preferably represented by any of formulae (3"a) to (3"f):
(3"a)
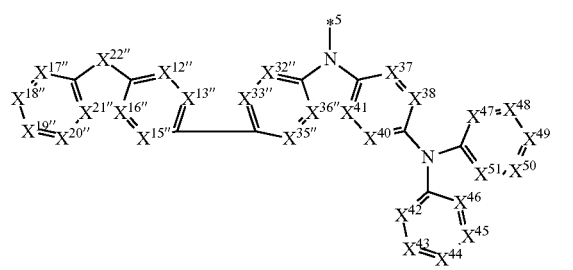
(3"b)
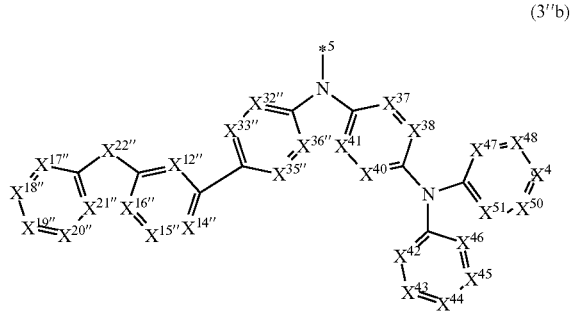
(3"c)
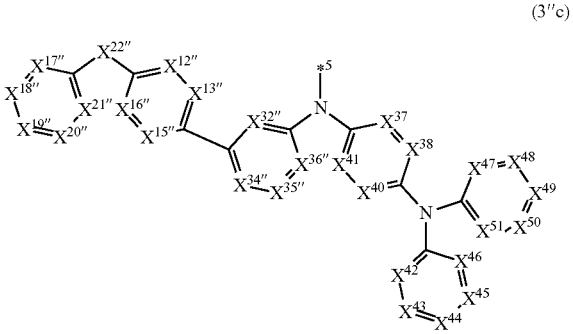
(3"d)
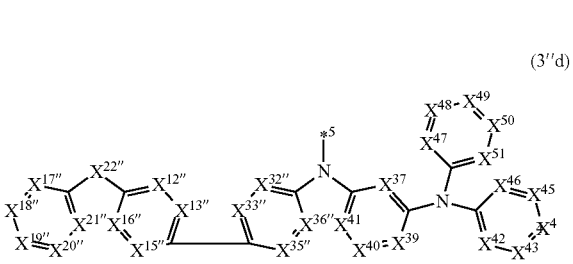

(3″e)
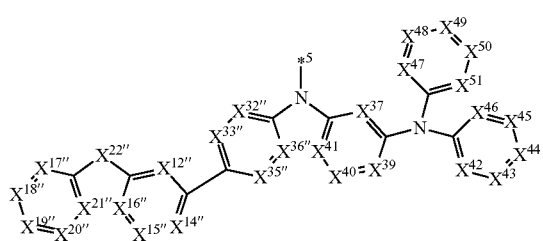
(3″f)
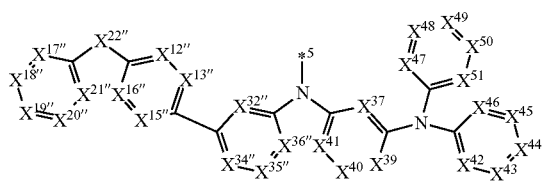
wherein 5*, $X^{37}$ to $X^{51}$, $X^{32''}$ to $X^{36''}$, and $X^{12''}$ to $X^{22''}$ are as defined above.
The group represented by formula (3″a) is preferably represented by any of formulae (3″a-1) to (3″a-7):
(3″a-1)
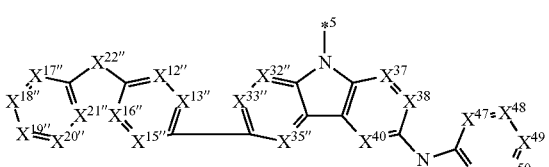
(3″a-2)
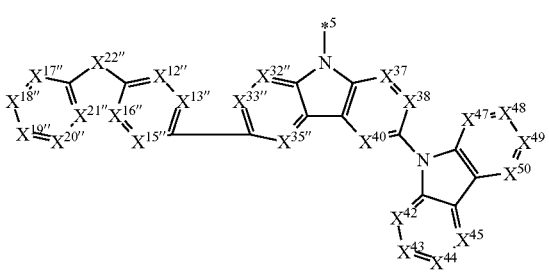
(3″a-3)
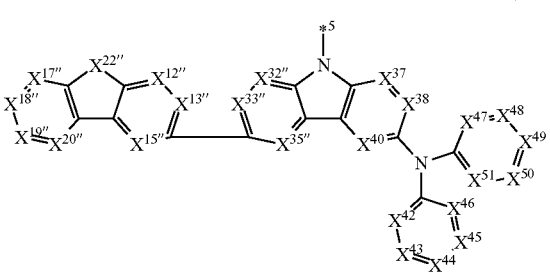
(3″a-4)
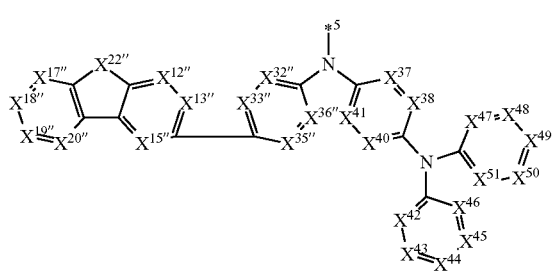
(3″a-5)
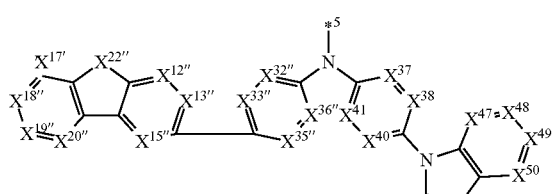
(3″a-6)
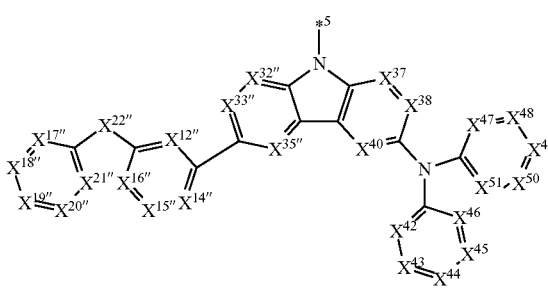
(3″a-7)
wherein *5 and each X are as defined above.
The group represented by formula (3″b) is preferably represented by any of formulae (3″b-1) to (3″b-7):
(3″b-1)

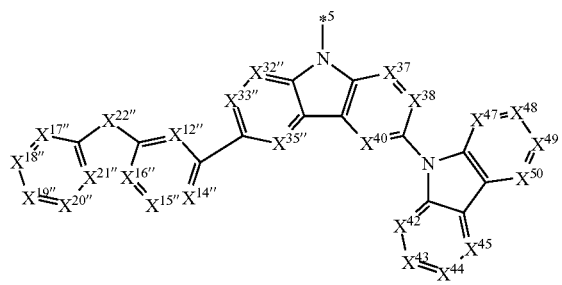
(3″b-2)
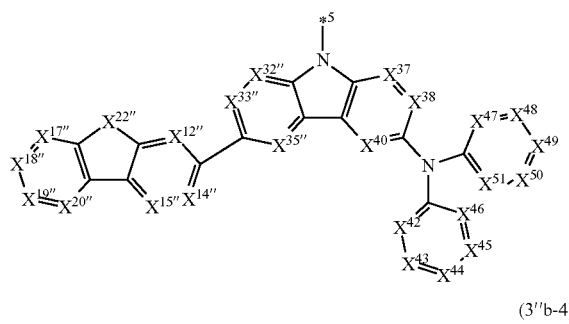
(3″b-3)
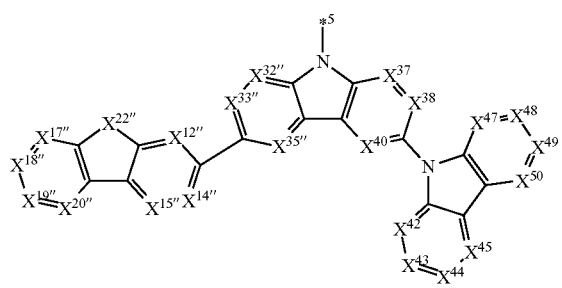
(3″b-4)
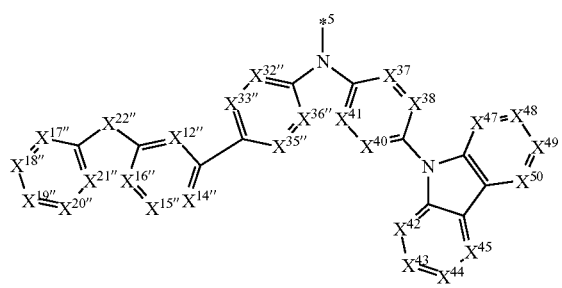
(3″b-5)
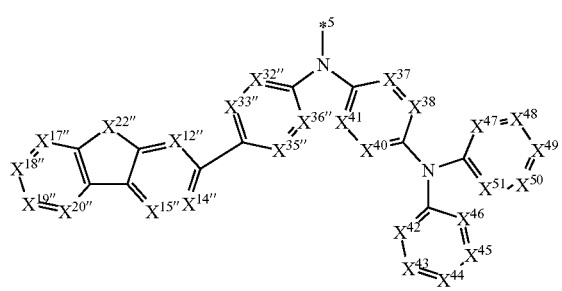
(3″b-6)

(3″b-7)
wherein *5 and each X are as defined above.
The group represented by formula (3″c) is preferably represented by any of formulae (3″c-1) to (3″c-7):
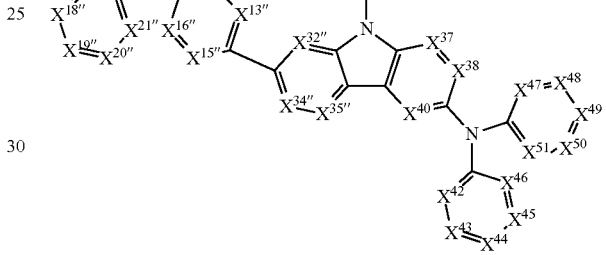
(3″c-1)
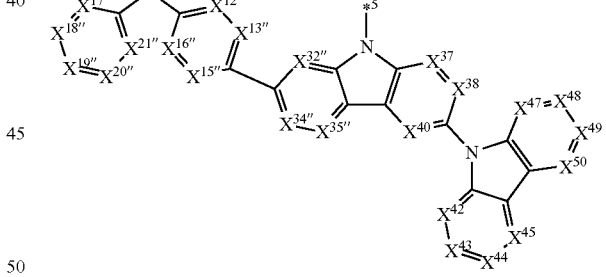
(3″c-2)
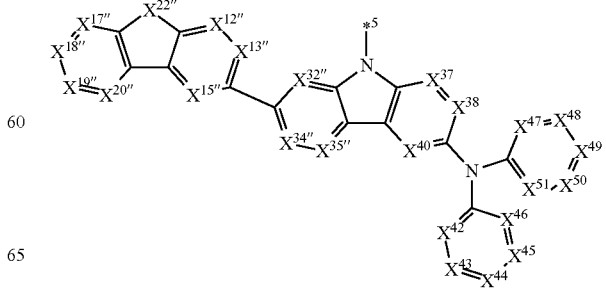
(3″c-3)

(3″c-4)
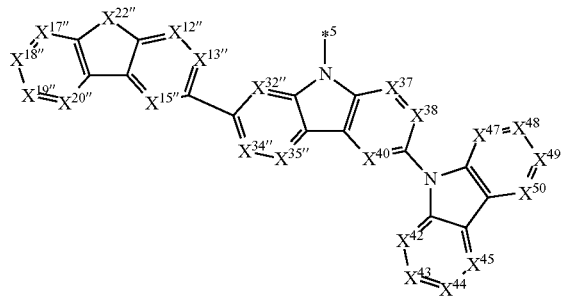
(3″d-1)
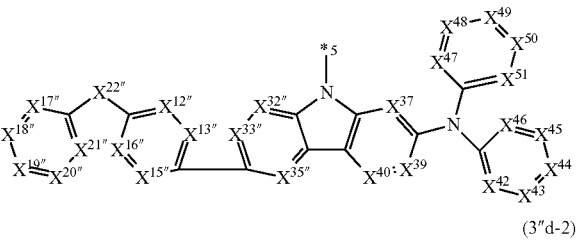
(3″d-2)
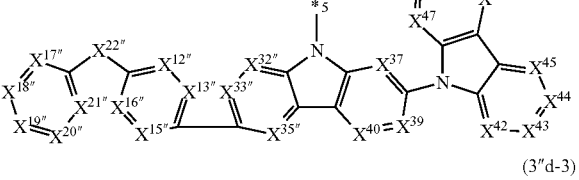
(3″c-5)
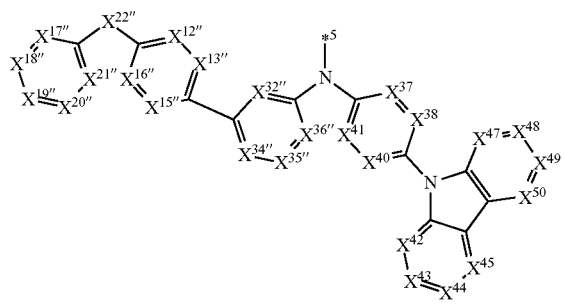
(3″d-3)
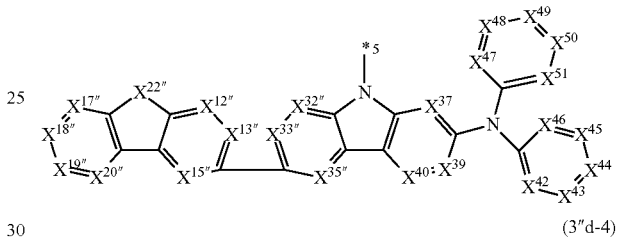
(3″c-6)
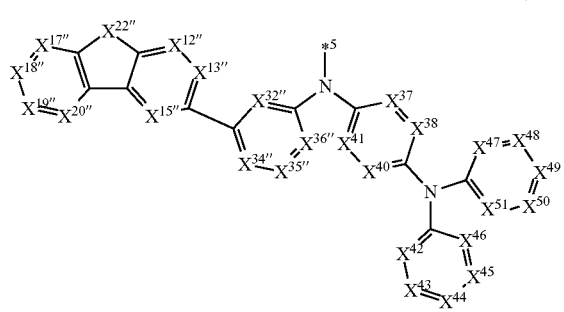
(3″d-4)
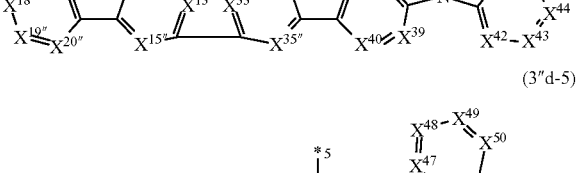
(3″d-5)
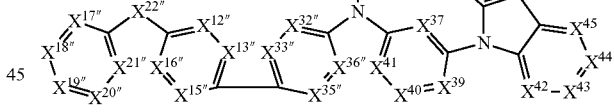
(3″c-7)
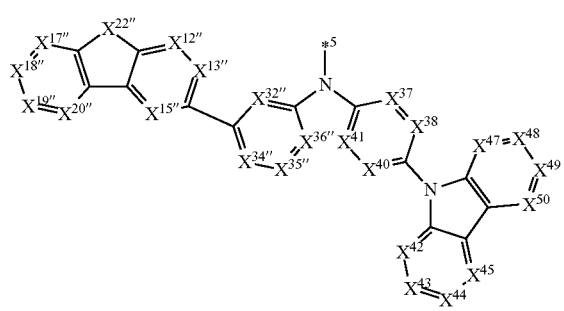
(3″d-6)
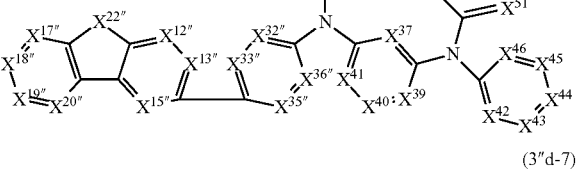
(3″d-7)
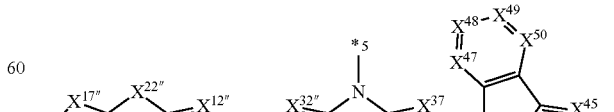
wherein *5 and each X are as defined above.
The group represented by formula (3″d) is preferably represented by any of formulae (3″d-1) to (3″d-7):
wherein *5 and each X are as defined above.

The group represented by formula (3″e) is preferably represented by any of formulae (3″e-1) to (3″e-7):
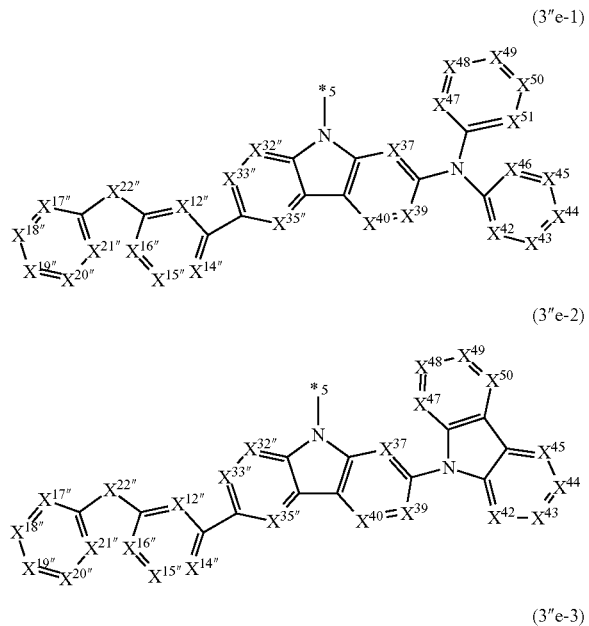
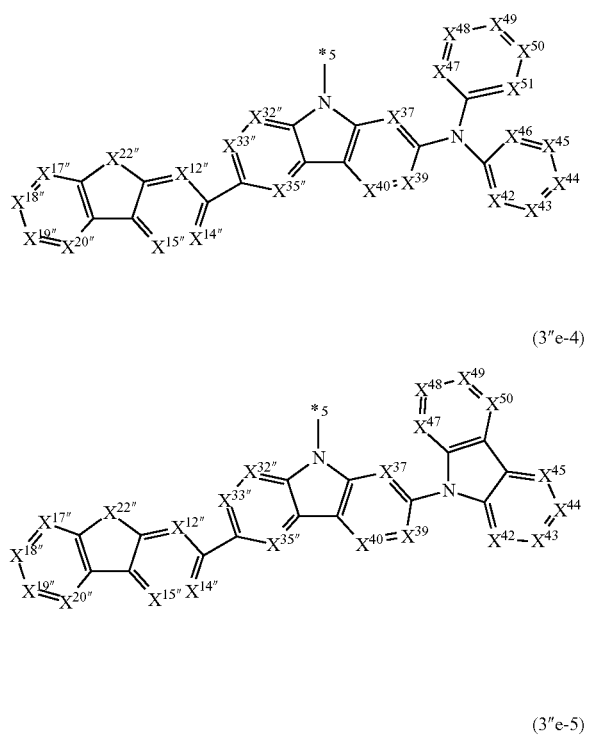
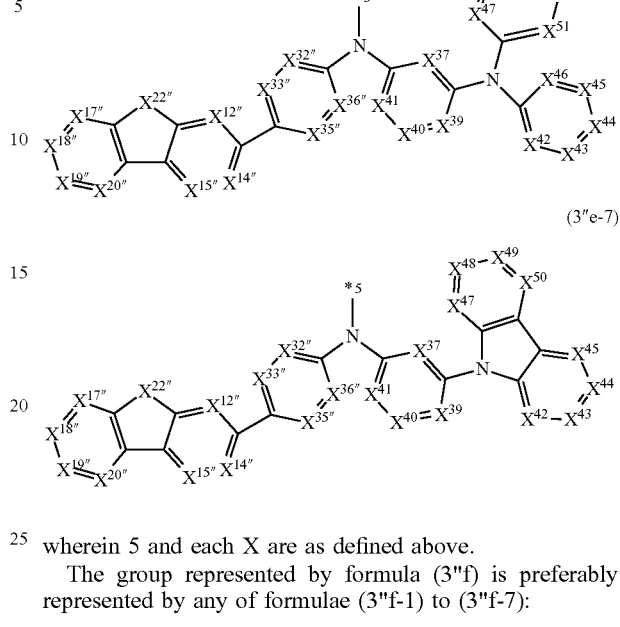
wherein 5 and each X are as defined above.
The group represented by formula (3″f) is preferably represented by any of formulae (3″f-1) to (3″f-7):
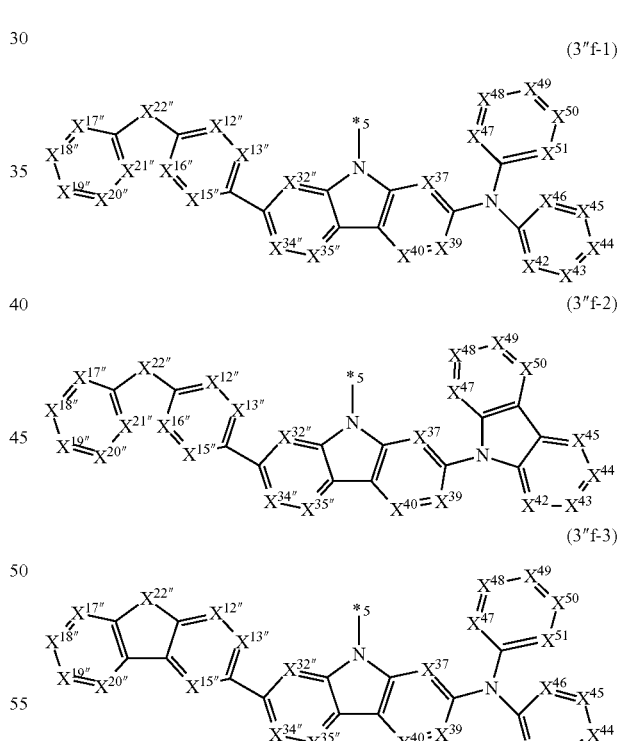

-continued
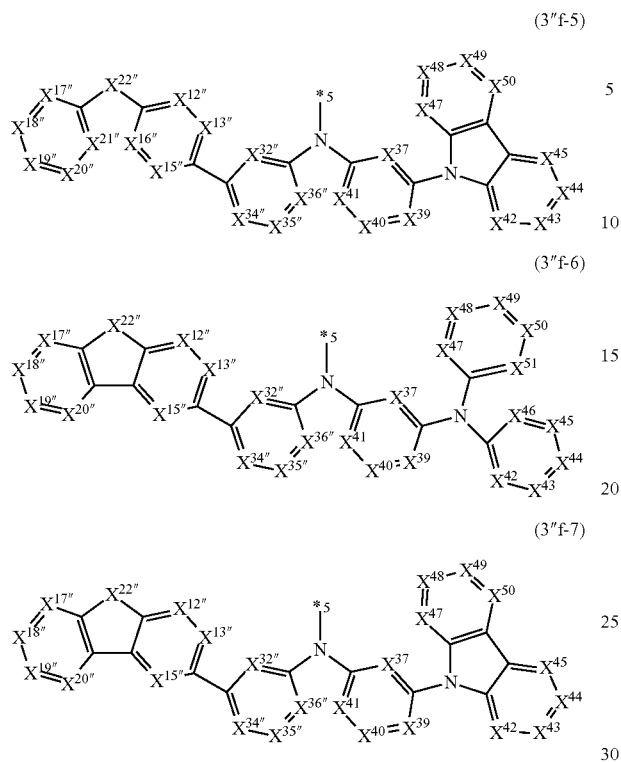
(3″f-5)
(3″f-6)
(3″f-7)
wherein *5 and each X are as defined above.
The group represented by formula (4) is preferably represented by any of formulae (4a) to (4f):
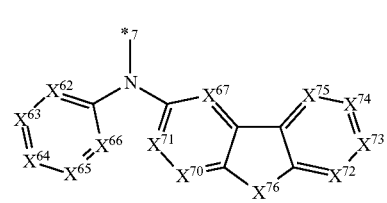
(4a)
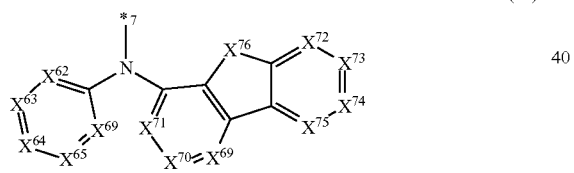
(4b)
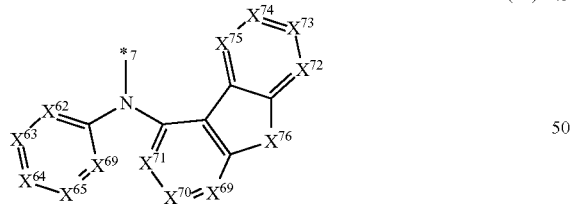
(4c)
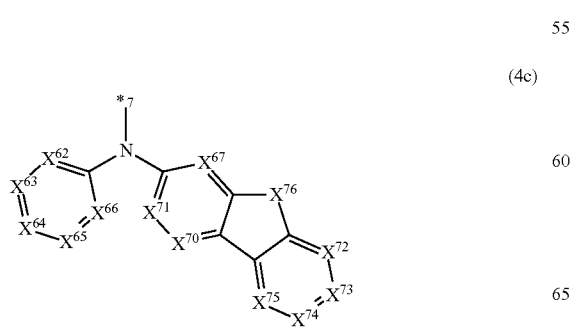
-continued
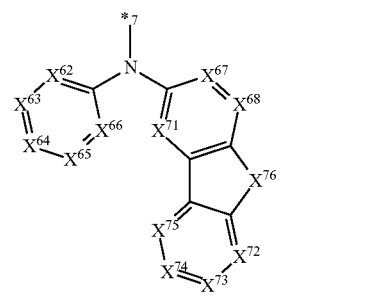
(4d)
(4e)
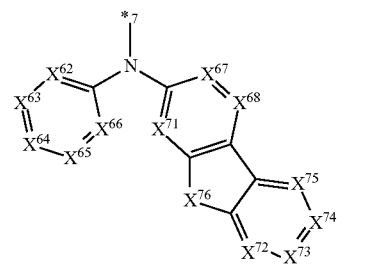
(4f)
wherein *7 and $X^{62}$ to $X^{76}$ are as defined above.
The groups represented by formulae (4a) to (4f) are preferably represented by formulae (4a-1) to (4f-1), respectively:
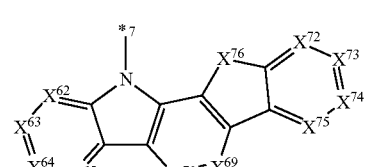
(4a-1)
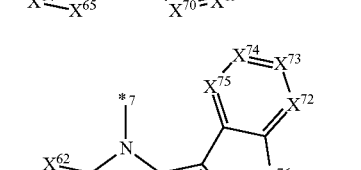
(4b-1)
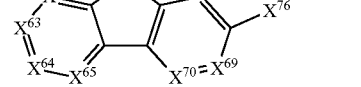
(4c-1)
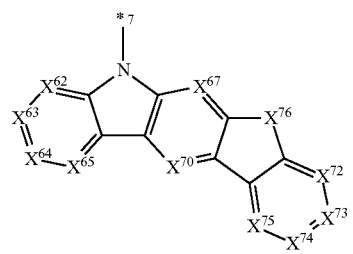

-continued (4d-1)

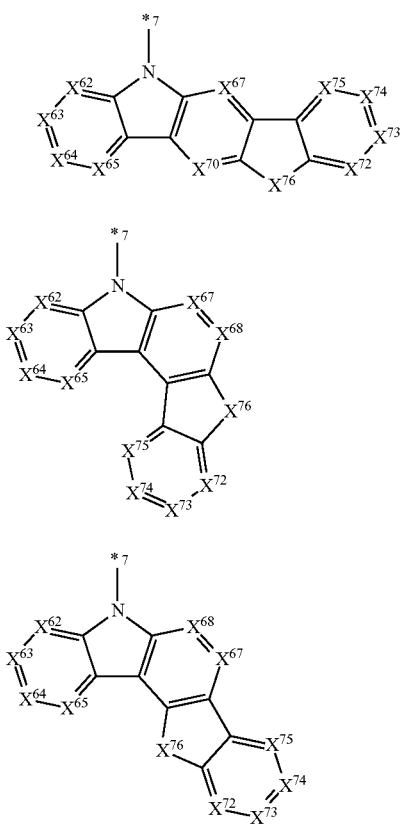

(4e-1)

(4f-1)

wherein *7 and each X are as defined above.

The production method of the compound (1) will be described below.

When introducing a first substituent into one of two active sites of a starting compound and then introducing a second substituent which is different from the first substituent into the other active site, it is generally required to control the reaction so as to prevent the first substituent from being introduced into both the two active sites.

For example, in the Ullmann reaction and the Buchwald reaction, which have been generally used in a coupling reaction between an aryl halide and an amine, it is difficult to control the reaction so as to prevent the first substituent from being introduced into both the two active sites. Thus, it has been difficult to produce a compound in which different substituents are introduced into two active sites easily in a good yield.

As a result of research on the synthetic method solving the above problem, the inventors have found that, for example, in the following dihalides:

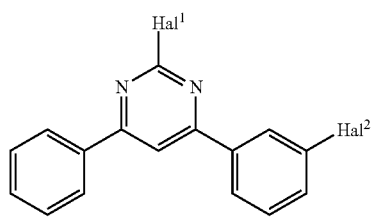

and

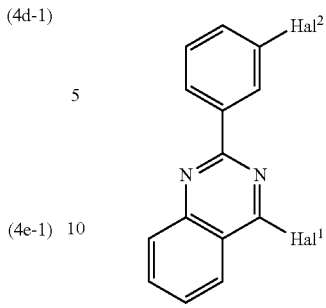

wherein $Hal^1$ and $Hal^2$ are the same or different halogen atoms, the reactivity of $Hal^2$ to an amine compound and a carbazole compound is extremely low as compared with that of $Hal^1$ in a specific reaction condition, and further found that in such a specific reaction condition, the first substituent is selectively introduced only to the carbon atom to which $Hal^1$ is bonded. On the basis of this finding, the inventors have found that a compound to which different substituents are introduced can be synthesized in a good yield by (1) selectively introducing the first substituent only to the carbon atom to which $Hal^1$ is bonded in the specific reaction condition and then (2) introducing the second substituent which is different from the first substituent to the carbon atom to which $Hal^2$ is bonded in a reaction condition which increases the reactivity of $Hal^2$ to an amine compound and a carbazole compound, for example, the reaction condition of the Buchwald reaction.

For example, the compound (1) can be produced by the following method.

Synthetic Method 1

First Reaction

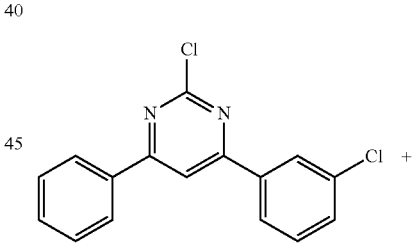

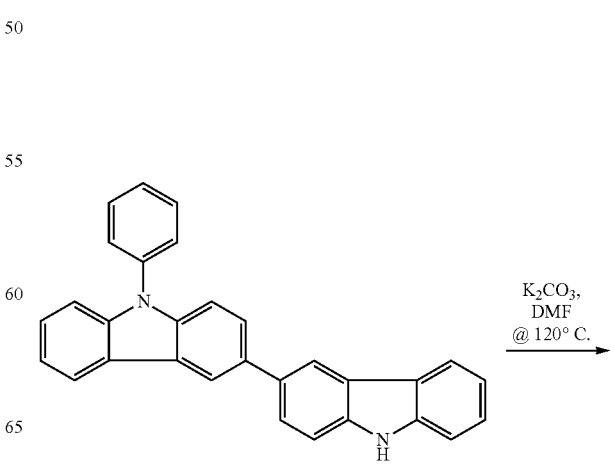

69
-continued
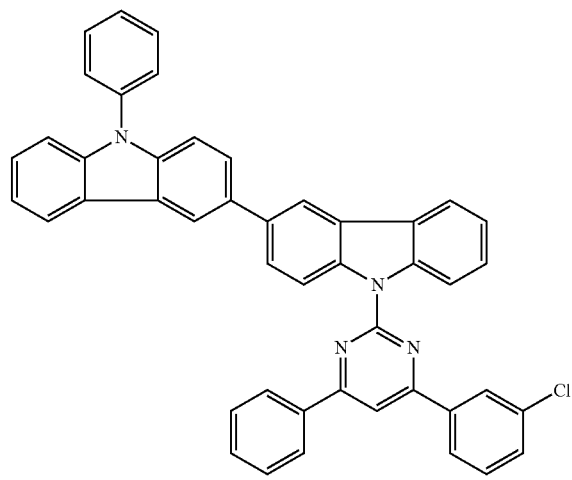
Second Reaction
70
-continued
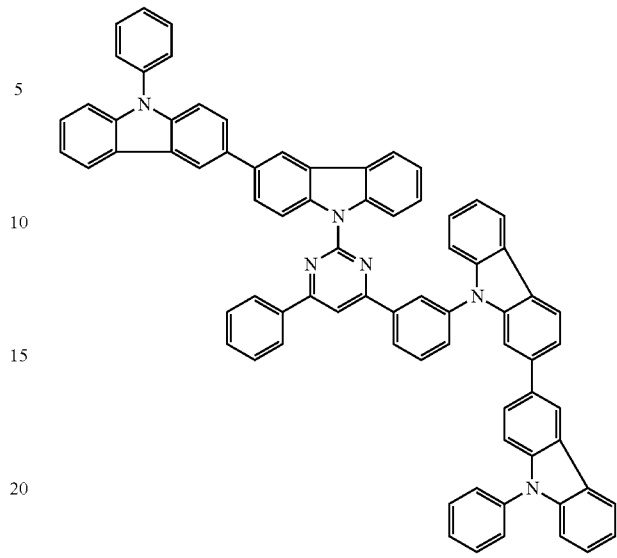
Synthetic Method 2
First Reaction
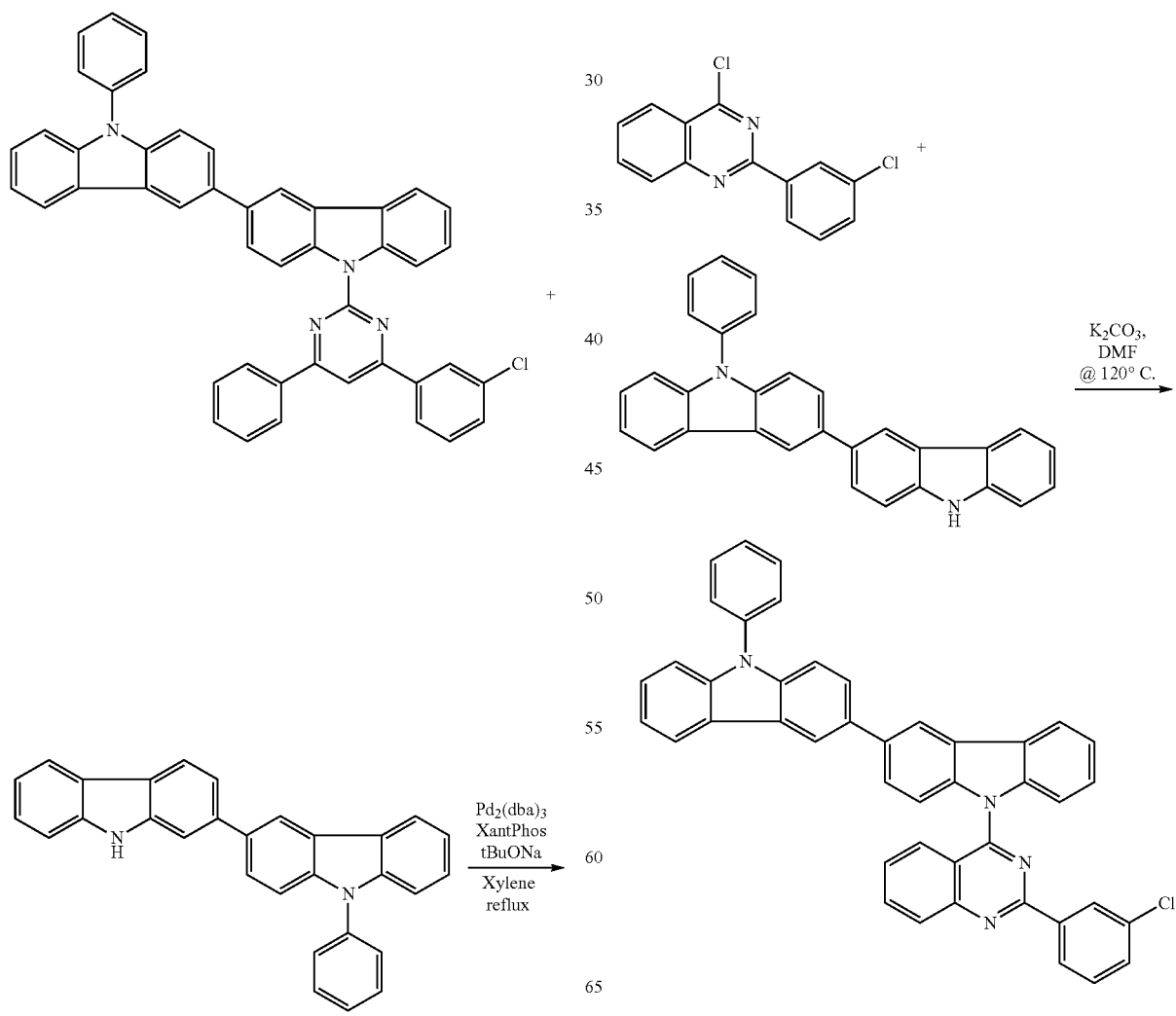

Second Reaction

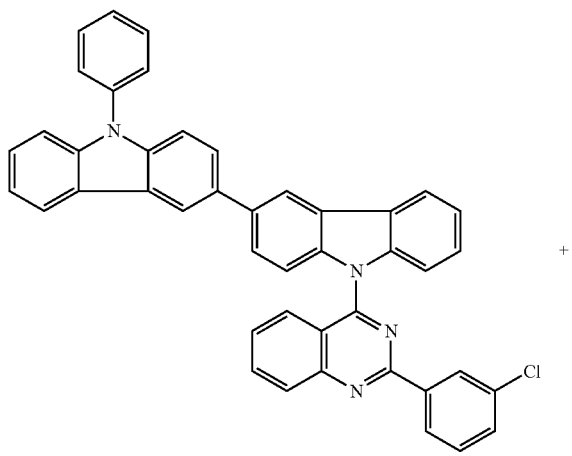

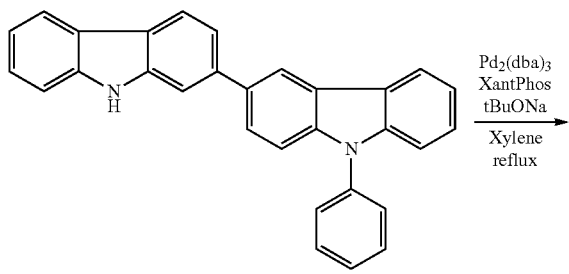

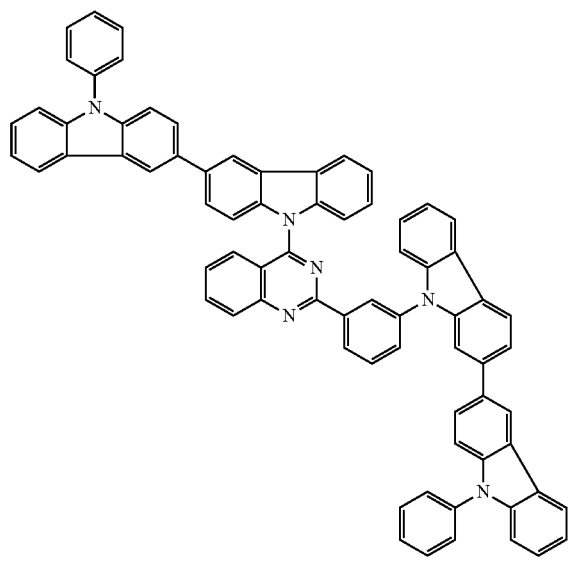

The production method of the compound (1) will be described below in more detail.

First Reaction

In the first reaction, a compound represented by formula (I) (also referred to as "compound (I)"):

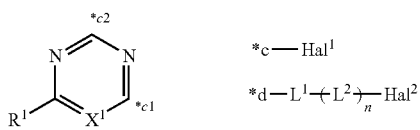

(I)

wherein $R^1$, $X^1$, $L^1$, and n are as defined in formula (1);

one of *c and *d is bonded to a carbon atom *c1 and the other is bonded to a carbon atom *c2;

$Hal^1$ and $Hal^2$ may be the same or different and each represent a halogen atom selected from a fluorine atom, a bromine atom, and iodine atom;

when n is 0, $L^1$ may have one or more halogen atoms which may be the same or different; and when n is an integer of 1 to 3, $L^2$ may have one or more halogen atoms which may be the same or different.

is allowed to react with an amine compound represented by any of formulae (II), (II'), (III), (III'), (III''), and (IV):

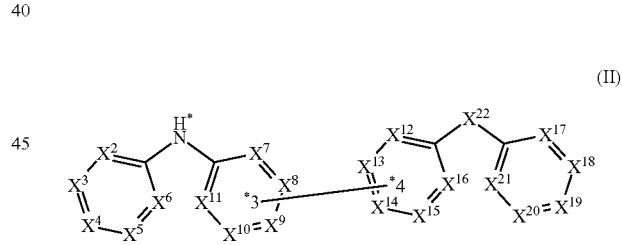

(II)

wherein $X^2$ to $X^{22}$ are as defined in formula (2) and H* represents a hydrogen atom to be reacted with $Hal^1$ of formula (I);

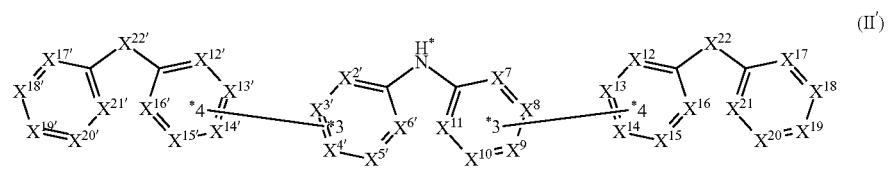

(II')

wherein $X^7$ to $X^{22}$, $X^{2'}$ to $X^{6'}$, and $X^{12'}$ to $X^{22'}$ are as defined in formula (2') and H* represents a hydrogen atom to be reacted with $Hal^1$ of formula (I);

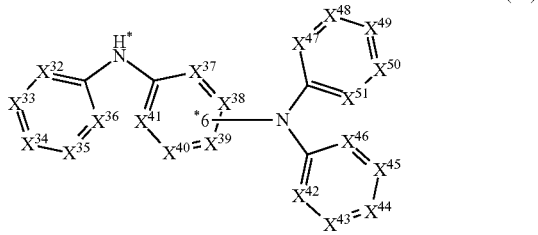
(III)

wherein $X^{32}$ to $X^{51}$ are as defined in formula (3) and H* represents a hydrogen atom to be reacted with $Hal^1$ of formula (I);

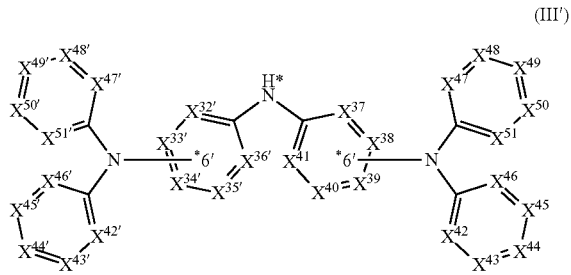
(III')

wherein $X^{37}$ to $X^{51}$, $X^{32'}$ to $X^{36'}$, and $X^{42'}$ to $X^{51'}$ are as defined in formula (3') and H* represents a hydrogen atom to be reacted with $Hal^1$ of formula (I);

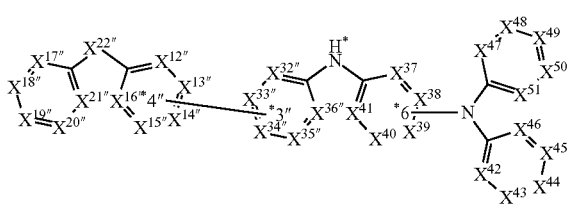
(III")

wherein $X^{37}$ to $X^{51}$, $X^{32'}$ to $X^{36'}$, and $X^{12'}$ to $X^{22'}$ are as defined in formula (3") and H* represents a hydrogen atom to be reacted with $Hal^1$ of formula (I); and

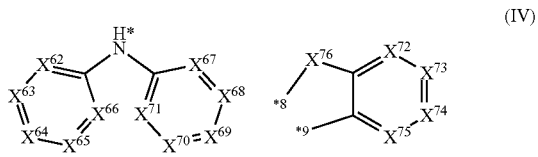
(IV)

wherein $X^{62}$ to $X^{76}$ are as defined in formula (4) and H* represents a hydrogen atom to be reacted with $Hal^1$ of formula (I).

The first reaction is conducted in an organic solvent, preferably in an aprotic polar organic solvent in the presence of a basic catalyst and in the absence of a transition metal catalyst.

The basic catalyst catalyzes the elimination of H* in each of formulae (II), (II'), (III), (III'), (III"), and (IV) and is preferably less nucleophilic to the halogenated aromatic carbon atom. Examples thereof include an alkali metal carbonate, such as $K_2CO_3$ and $Na_2CO_3$; an alkali metal hydrogencarbonate, such as $KHCO_3$ and $NaHCO_3$; an alkaline earth metal carbonate, such as $CaCO_3$ and $CsCO_3$; a metal phosphate, such as $K_3PO_4$; an alkali metal hydride, such as KH, NaH, and LiH; and a metal amide, such as lithium diisopropylamide (LDA), with $K_2CO_3$, $Na_2CO_3$, $CaCO_3$, $CsCO_3$, KH, NaH, LiH, and LDA being preferred.

The organic solvent used in the first reaction is not limited as long as it is inert to the basic catalyst, and an amide solvent, such as dimethylformamide, dimethylacetamide, and N-methylpyrrolidone, and an aprotic polar organic solvent, such as dimethylsulfoxide, are preferred in view of the solubility of the basic catalyst. A mixed solvent of an aprotic polar organic solvent with an aromatic solvent, such as benzene, toluene, and xylene, is also usable.

The amine compound represented by any of formulae (II), (II'), (III), (III'), (III"), and (IV) is used preferably in an amount of 1 to 2 mol to one mole of $Hal^1$ which is directly bonded to the azine ring of formula (I). The basic catalyst is used preferably in an amount of 1 to 10 equiv to one mole of $Hal^1$ which is directly bonded to the azine ring of formula (I). The amount of the organic solvent to be used depends on the solubility of the compound (1) and an amount which regulates the concentration thereof within about 0.01 to 2.0 mol/L is preferred.

The reaction temperature is preferably from room temperature to 200° C. The reaction time depends on the kinds and amounts of the compound (1), the amine compound, and the basic catalyst, and generally 1 to 24 h.

By the first reaction, the following halide represented by formula (V) (also referred to as "compound (V)") is obtained:

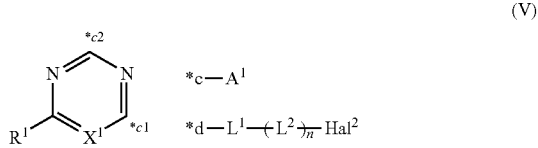
(V)

wherein *c, *d, $A^1$, $R^1$, $X^1$, $L^1$, and n are as defined in formula (1) and $Hal^2$ is as defined in formula (I).

By conducting the first reaction under the reaction conditions mentioned above, the target compound (V) is obtained in a high yield of 50 to 100%.

If the first reaction is conducted in the presence of a transition metal catalyst comprising a metal, such as palladium, copper, platinum, rhodium, ruthenium, nickel, and iron, the reactivity of $Hal^2$ in formula (I) becomes high, and therefore the amine compound (II), (II'), (III), (III'), (III"), or (IV) is introduced not only to the carbon atom to which $Hal^1$ is bonded but also to the carbon atom to which $Hal^2$ is bonded. Therefore, the first reaction is conducted preferably in the absence of a transition metal catalyst.

If the first reaction is conducted in the presence of a transition metal catalyst, such as $Pd_2(dba)_3$ (tris(dibenzylideneacetone)dipalladium(0)), and a strong base, such as tBuONa (sodium t-butoxide), a compound in which the halogen atoms $Hal^1$ and $Hal^2$ are both replaced with the carbazole compound, a compound in which one of the halogen atoms is replaced with the carbazole compound and the other is replaced with tBuO, and a compound in which the halogen atoms are both replaced with tBuO are by-produced. The by-produced compounds make the operations of separation and purification complicated, and therefore the target compound represented by formula (V) cannot be obtained in a yield sufficient for industrial production.

Second Reaction

In the second reaction, the compound (V) is allowed to react with an amine compound which is represented by any of formulae (II), (II'), (III), (III'), (III'), and (IV), but different from the amine compound used in the first reaction to synthesize the compound (1).

The second reaction is conducted under the conditions in which the reactivity of $Hal^2$ is higher than that in the first reaction, for example, under the amination conditions, such as Buchwald reaction and Ullmann reaction.

Thus, the second reaction is conducted in an organic solvent in the presence of a transition metal catalyst comprising a metal selected from palladium, copper, platinum, rhodium, ruthenium, nickel, and iron; a ligand selected from a monophosphine, a diphosphine, a diamine, pyridine and its derivative, and quinoline and its derivative; and an optional base, such as an alkoxide, a carbonate salt, and a phosphate salt.

When employing the Buchwald reaction, $Pd_2(dba)_3$ (tris(dibenzylideneacetone)dipalladium(0)) or $Pd(OAc)_2$ (palladium acetate) is generally used as a palladium catalyst. Various phosphines are mainly used as the ligand. Preferred examples thereof include $P(oTol)_3$ (tri(o-tolyl)phosphine), $PtBu_3$ (tri(t-butyl)phosphine), BINAP (bis(diphenylphosphino)-1,1'-binaphthyl), DPPF (bis(diphenylphosphino)ferrocene), XantPhos (4,5-bis(diphenylphosphino)-9,9-dimethylxanthene), DPEPhos (oxydi-2,1-phenylene)bis(diphenylphosphine), JhonPhos (2-(di-t-butyl phosphino)biphenyl), DavePhos (2-dicyclohexylphosphino-2'-(N,N-dimethylamino)biphenyl), X-Phos (2-dicyclohexylphosphino-2',4',6'-triisopropylbiphenyl), and AmPhos (N,N-dimethyl-4-(di-t-butylphosphino)aniline). A complex in which a phosphine is coordinated to palladium, such as $PdCl_2$ $(P(oTol)_3)_2$ and $PdCl_2$ (dppf), is also preferably used. The base is most preferably a strongly basic alkoxide, such as tBuONa (sodium t-butoxide). If the reactant includes a functional group susceptible to an strong base, a weak base, such as $CsCO_3$ and $K_3PO_4$, may be used.

When employing the Ullmann reaction, a copper catalyst, such as copper metal, copper(I) chloride, copper(I) bromide, copper(I) iodide, copper(I) oxide, and copper(II) oxide is preferably used. A diamine, such as tetramethylethylenediamine and 1,2-bisdimethylaminocyclohexane, pyridine and its derivative, and quinoline and its derivative are preferably used as the ligand.

In both the reactions, an aromatic hydrocarbon solvent, such as benzene, toluene, xylene, and mesitylene, is preferably used as the organic solvent. An ether solvent, such as tetrahydrofuran, 1,2-dimethoxyethane, 1,4-dioxane, and anisole, and a amide solvent, such as dimethylformamide and dimethylacetamide, are also usable alone or as a cosolvent.

The amine compound represented by any of formulae (II), (II'), (III), (III'), (III"), and (IV) is used preferably in an amount of 1 to 1.5 mol per one mole of $Hal^2$ in the compound (V). The transition metal catalyst is used in an amount of 0.01 to 100 mol, preferably 0.5 to 10 mol per one mole of $Hal^2$. The ligand is used preferably in an amount of 1 to 5 equiv to the transition metal catalyst. The base is used preferably in an amount of 1 to 20 equiv per one mole of $Hal^2$. The amount of the organic solvent depends on the solubility of the compound (V) and an amount which regulates the concentration thereof within about 0.01 to 2.0 mol/L is preferred.

The second reaction is conducted at room temperature to 200° C. The reaction time varies according to the kinds and amounts of the compound (V), the amine compound, the transition metal catalyst, the ligand, and the base, and generally 1 to 24 h.

By the second reaction, the halogen atom of the compound (V) and the hydrogen atom H* of the amine compound represented by any of formulae (II), (II'), (III), (III'), (III"), and (IV) are eliminated to give the compound (1). The formed compound (1) is isolated from the reaction mixture by a known separation process, extraction process, purification process, etc. The overall yield of the compound (1) obtained by the first reaction and the second reaction is about 50 to 95% based on the compound (I).

According to the production method described above, the compound (1) in which different kinds of substituents selected from formulae (2), (2'), (3), (3'), (3"), and (4) are introduced into the nitrogen-containing heterocyclic ring is obtained in a high yield. As compared with a compound in which the same substituents are introduced into the nitrogen-containing heterocyclic ring, the compound (1) can meet an increased variety of properties because of the different kinds of substituents introduced.

The properties required for the material for organic EL device vary, for example, according to the difference in the method of forming layers between a vapor deposition method and a coating method; the difference in the materials in a fluorescent emitting layer, a phosphorescent emitting layer, an electron transporting layer, and a hole transporting layer; and the difference in the emission color. The compound (1) can meet such a variety of property requirements. The production method described above provides the compound (1) in a simpler manner in a high yield.

Examples of the compound (1) are shown below, although not limited thereto.

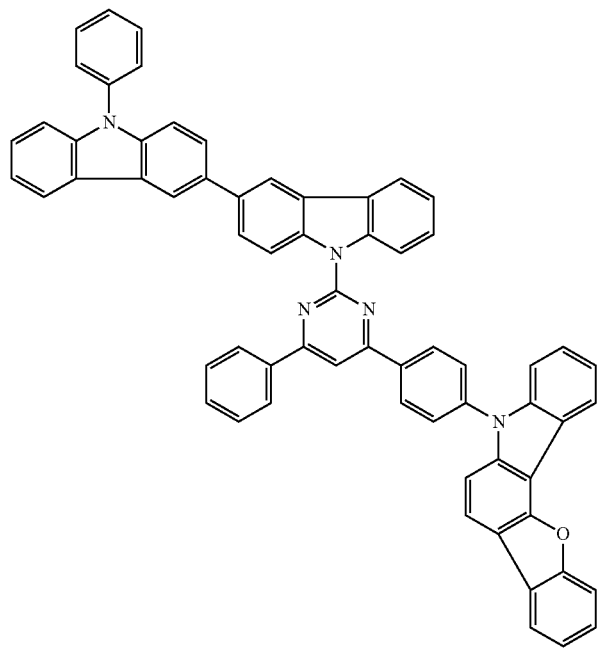
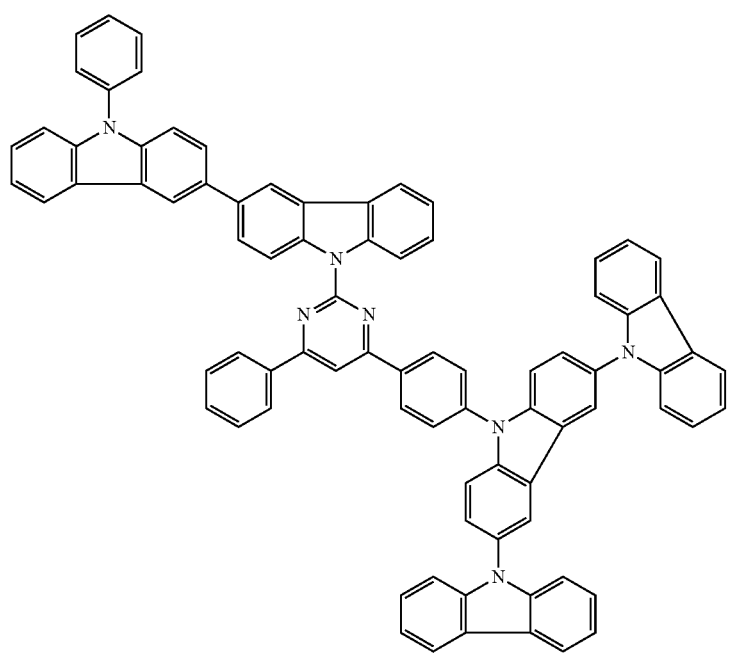

-continued
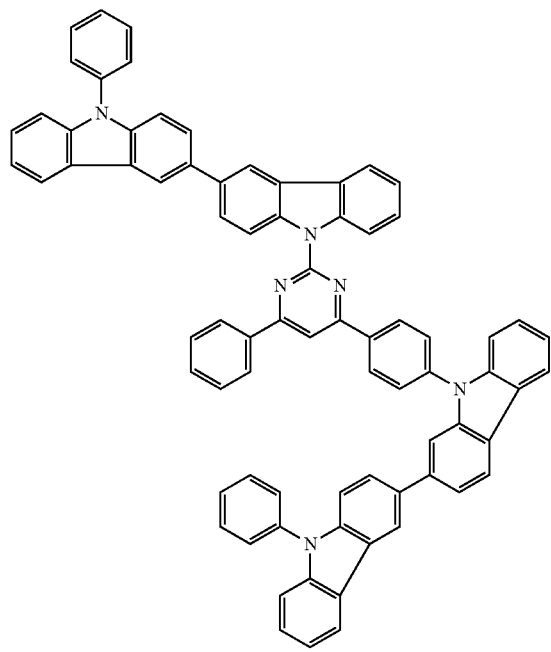
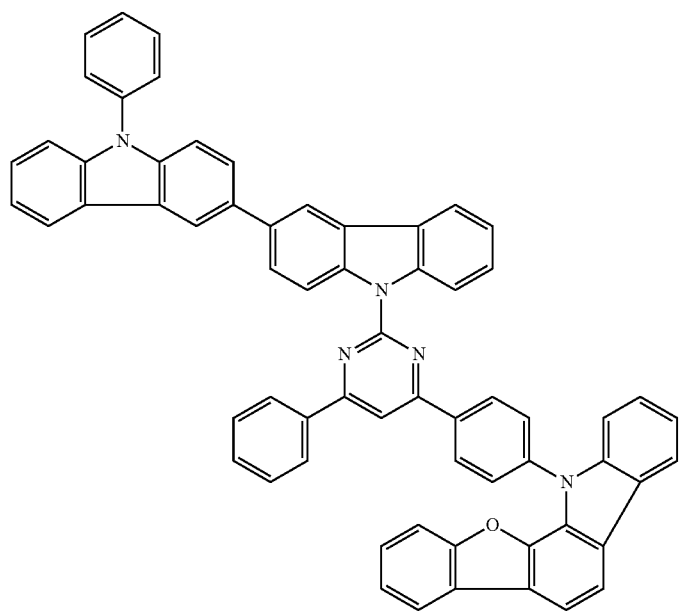

81
82
-continued
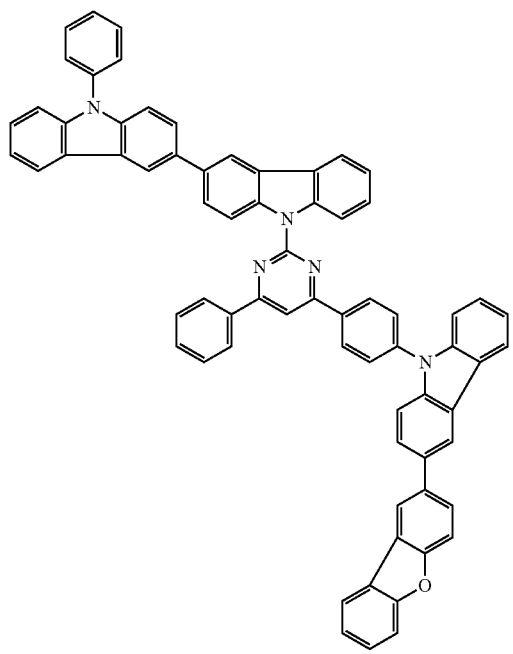
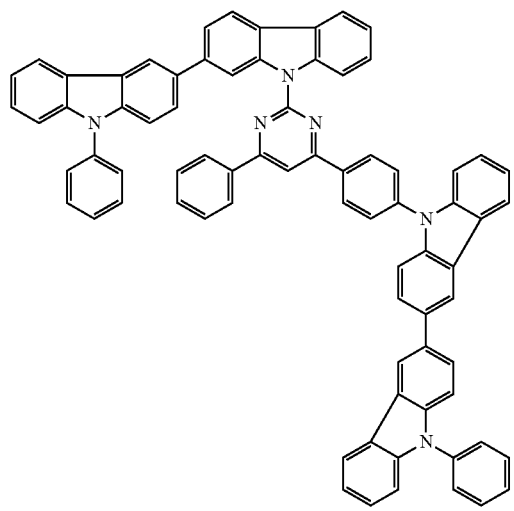
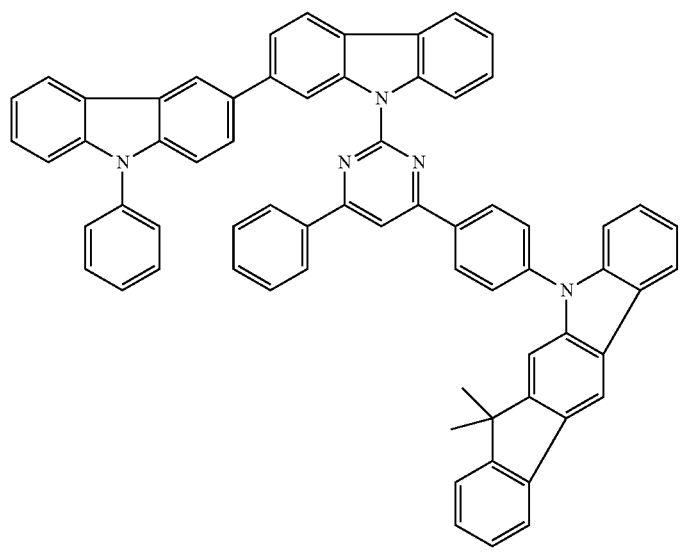

-continued
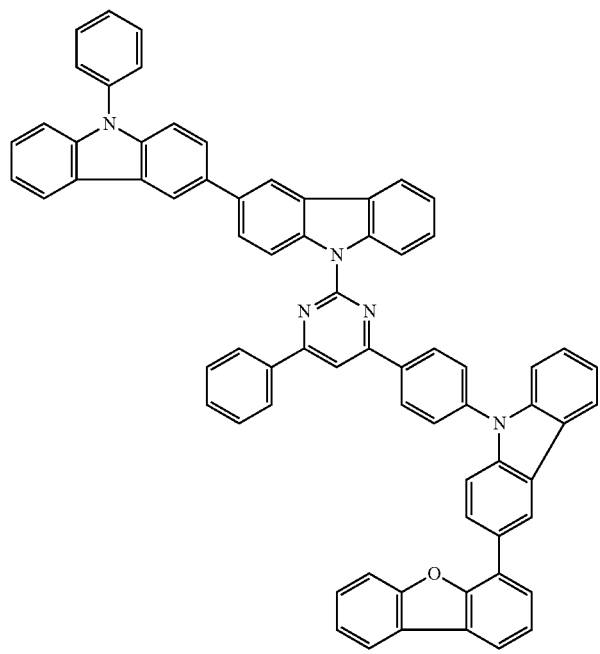
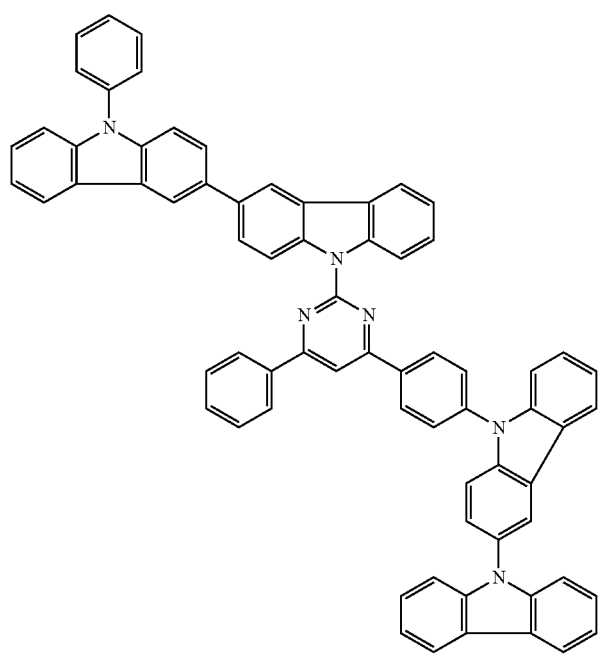

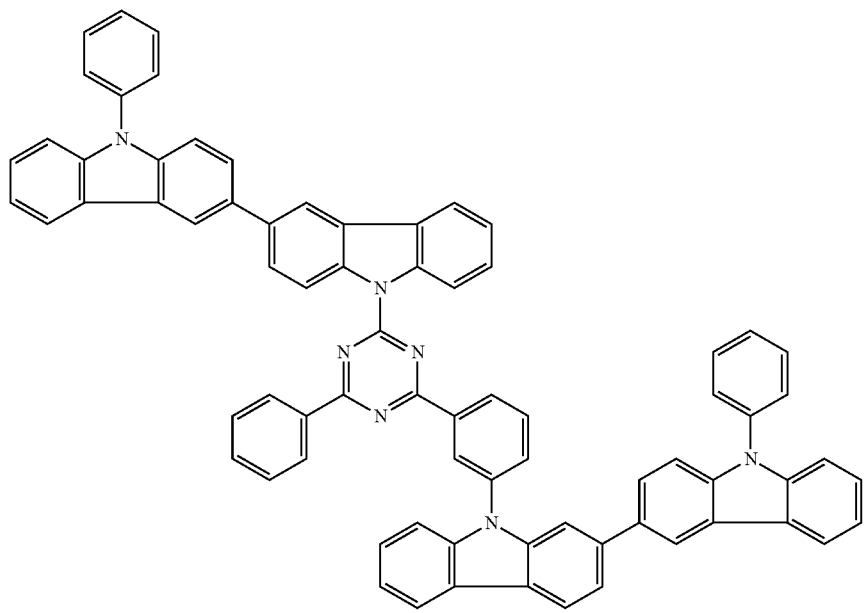
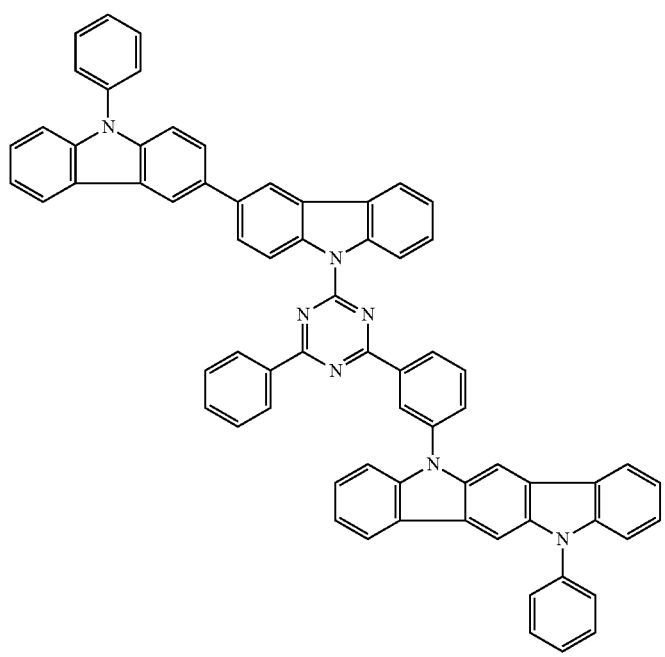

-continued
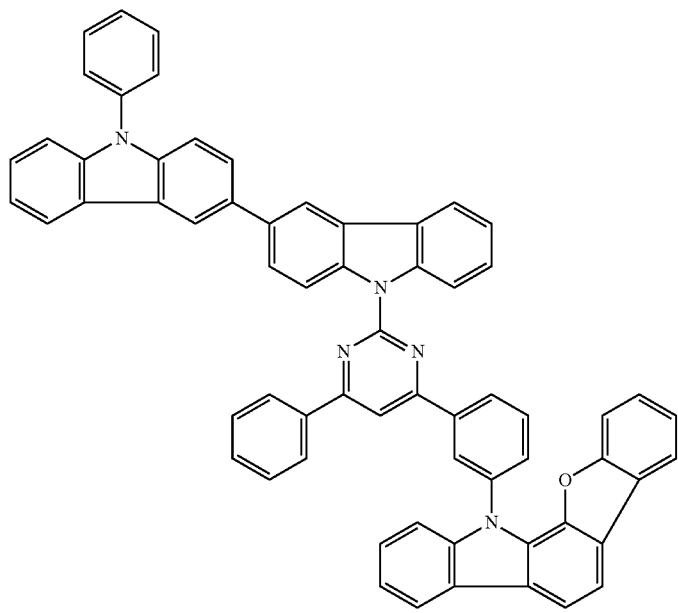
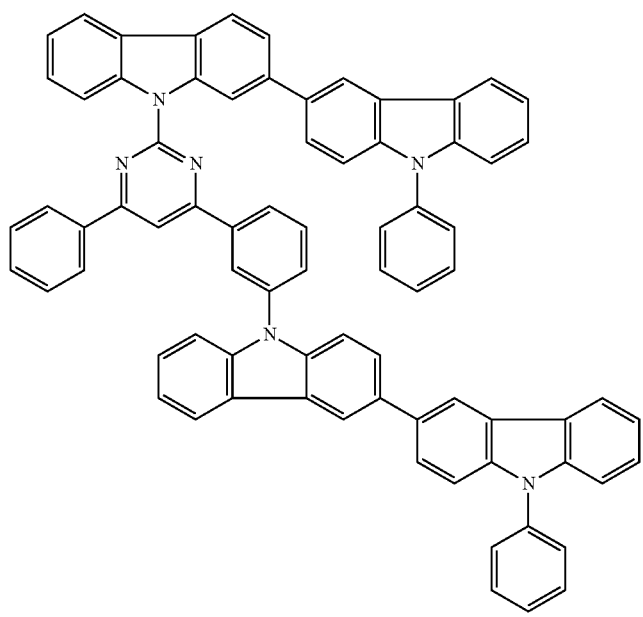

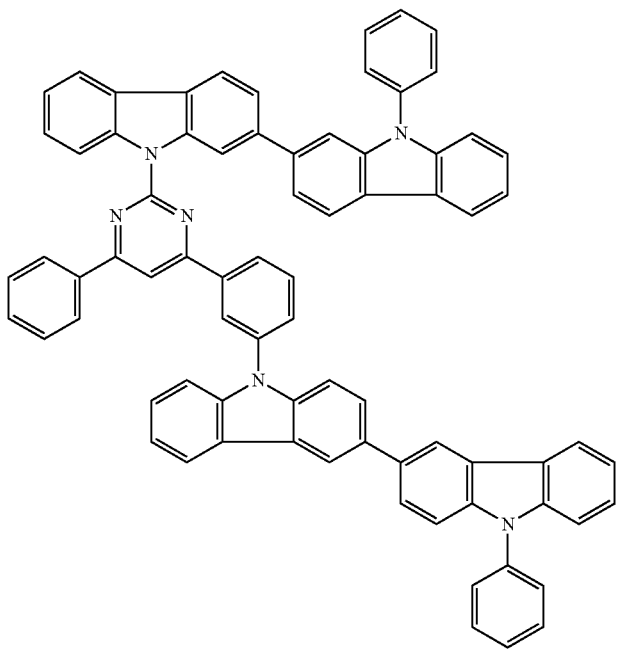
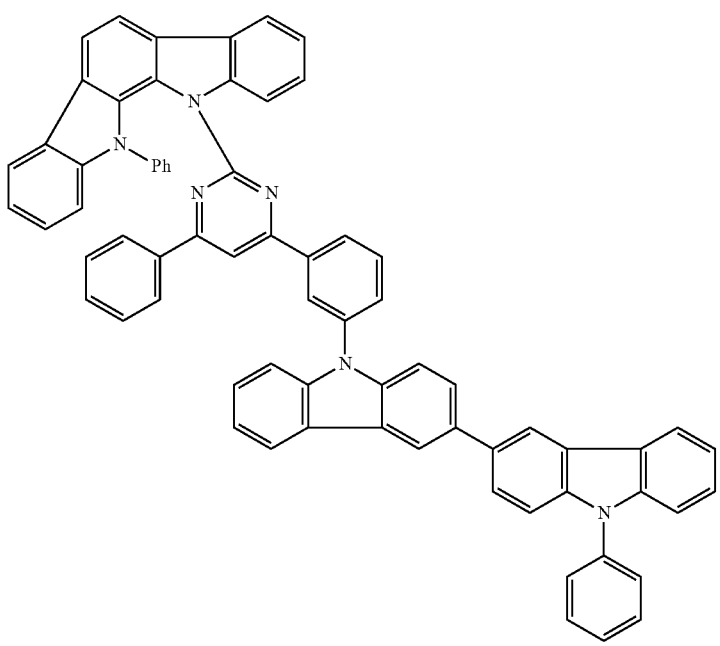

-continued
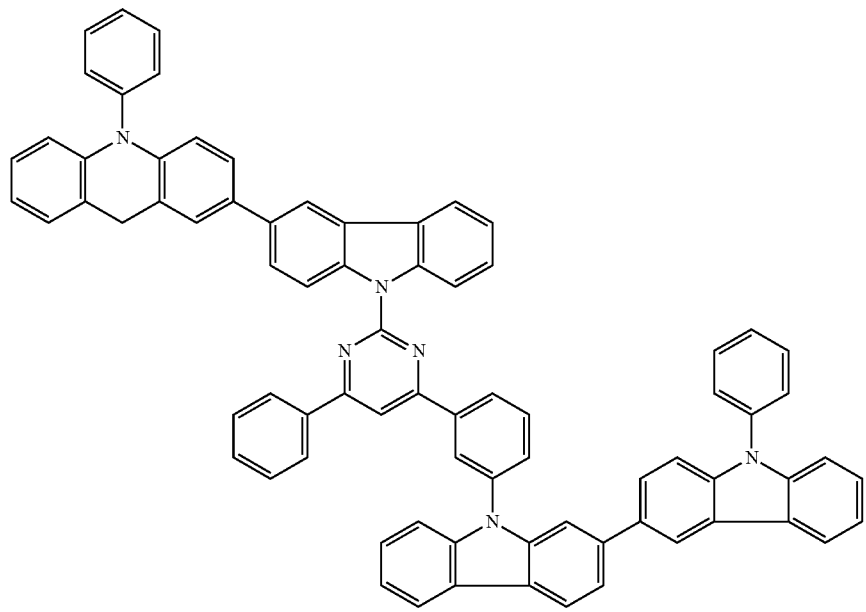
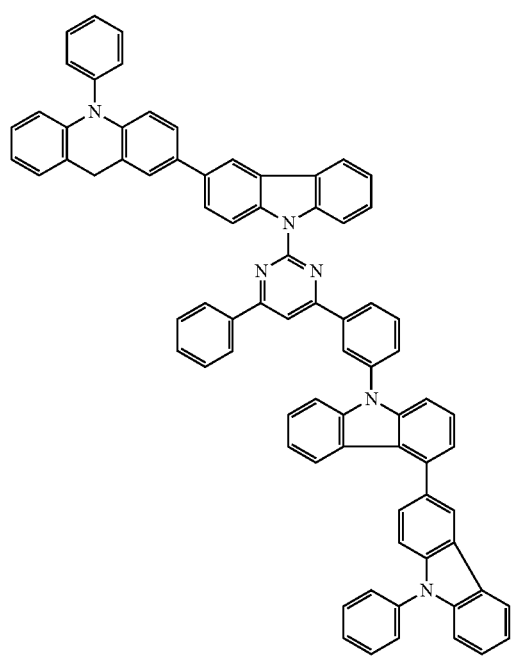

-continued
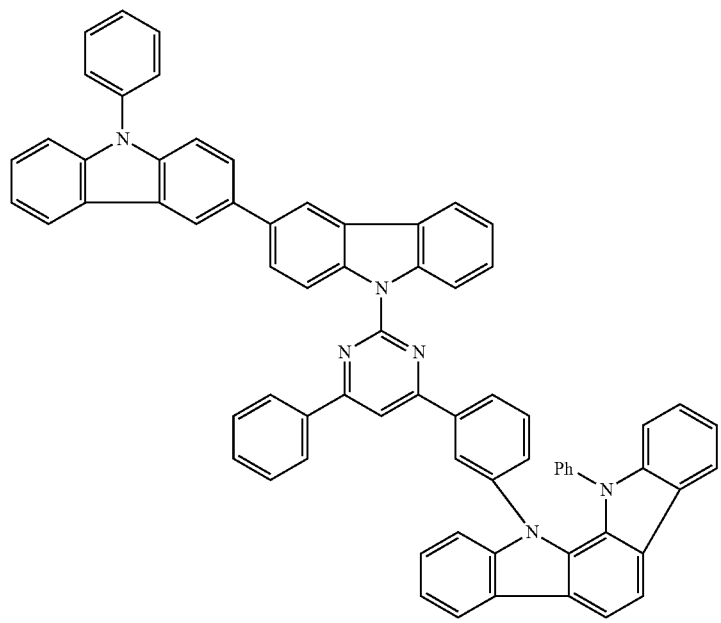
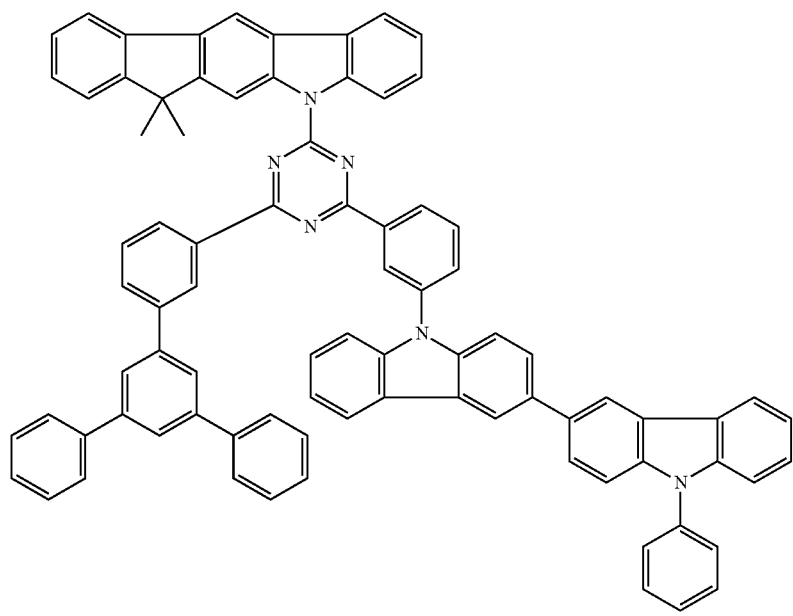

-continued
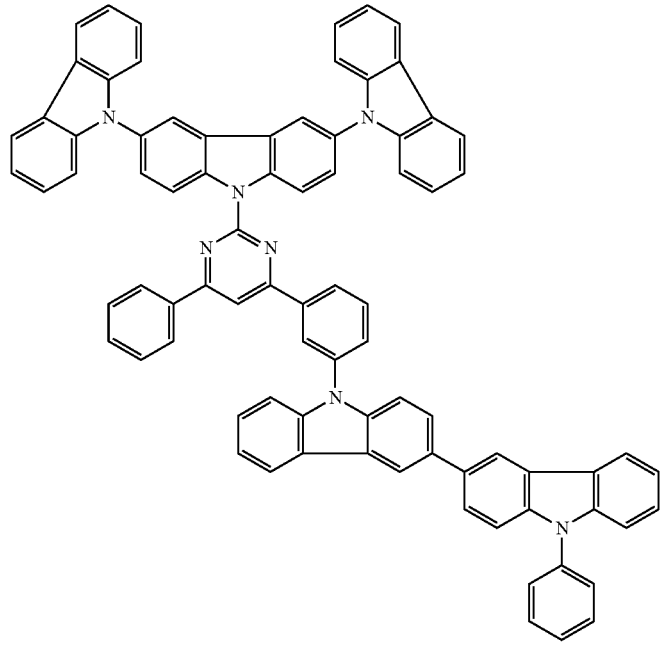
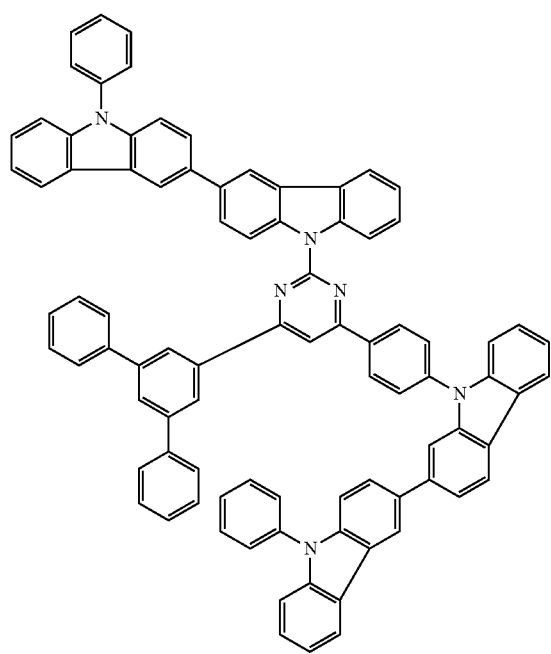

-continued
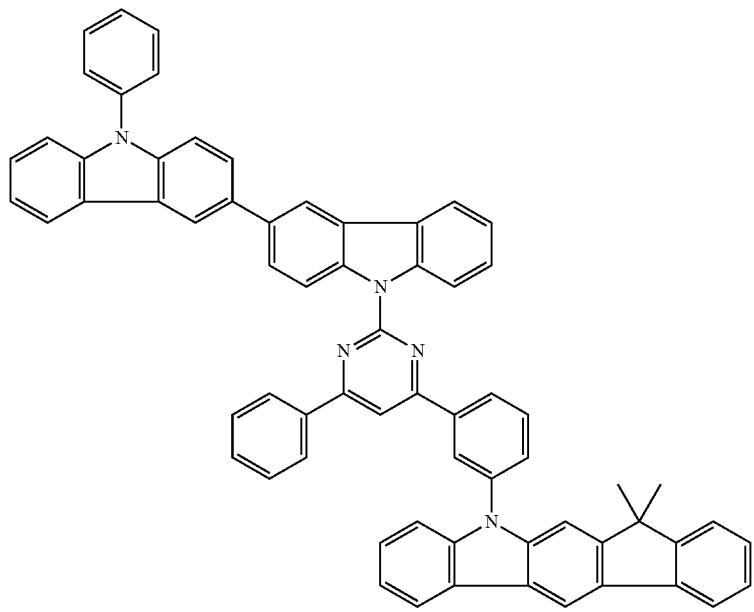
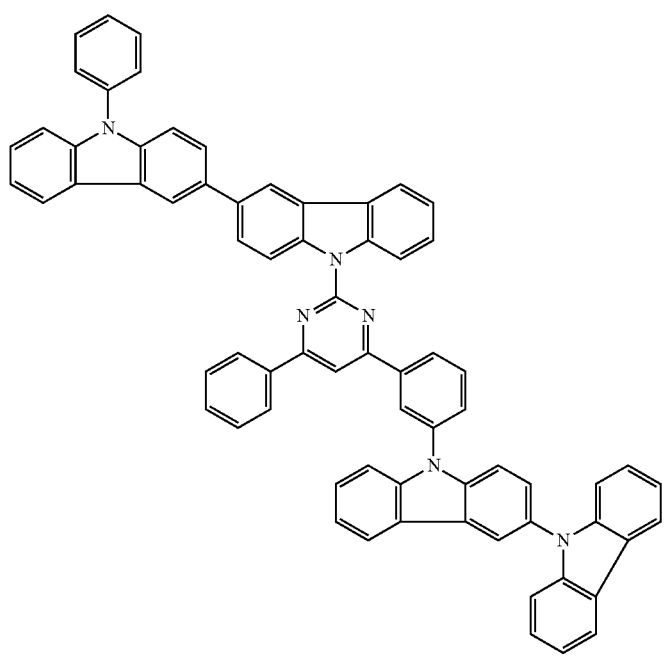

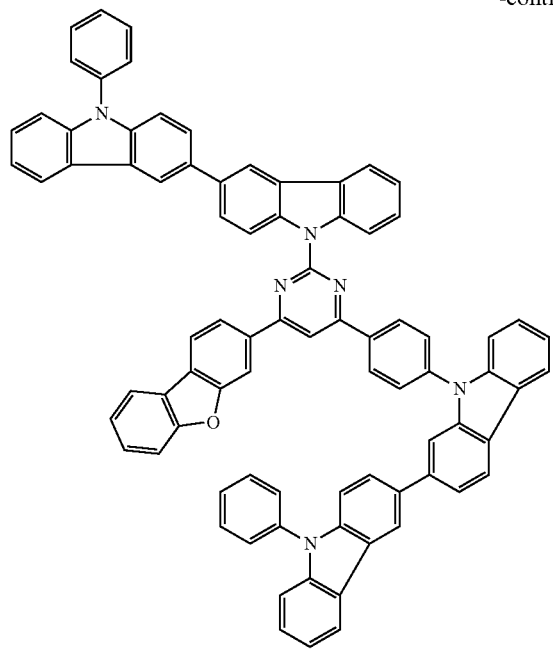
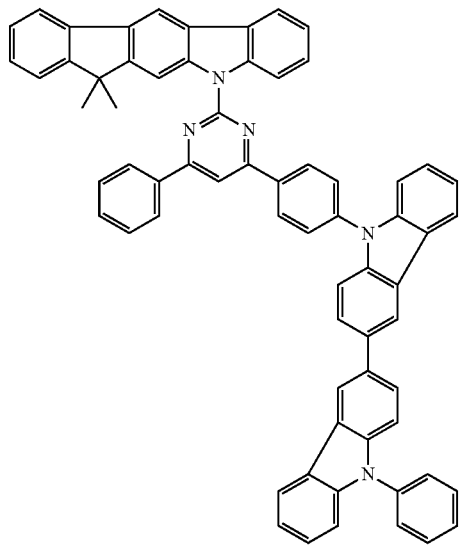
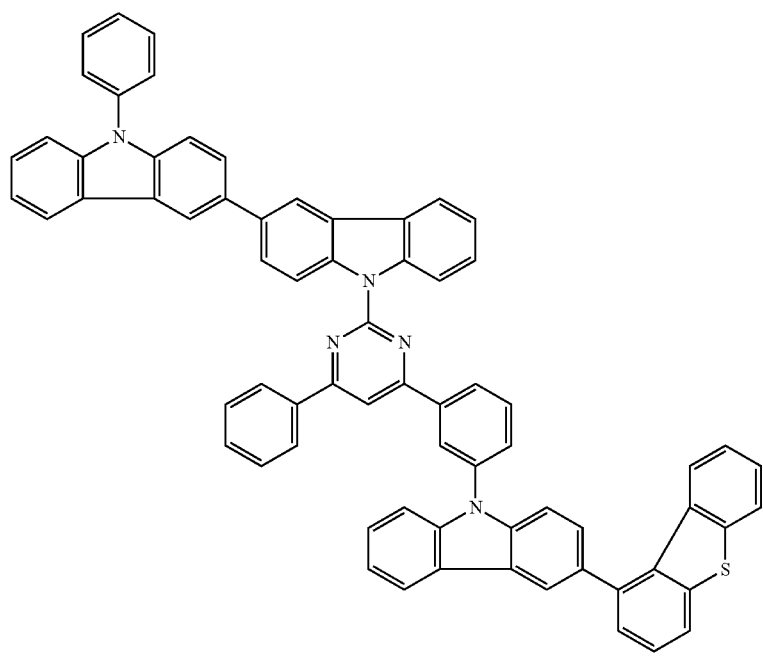

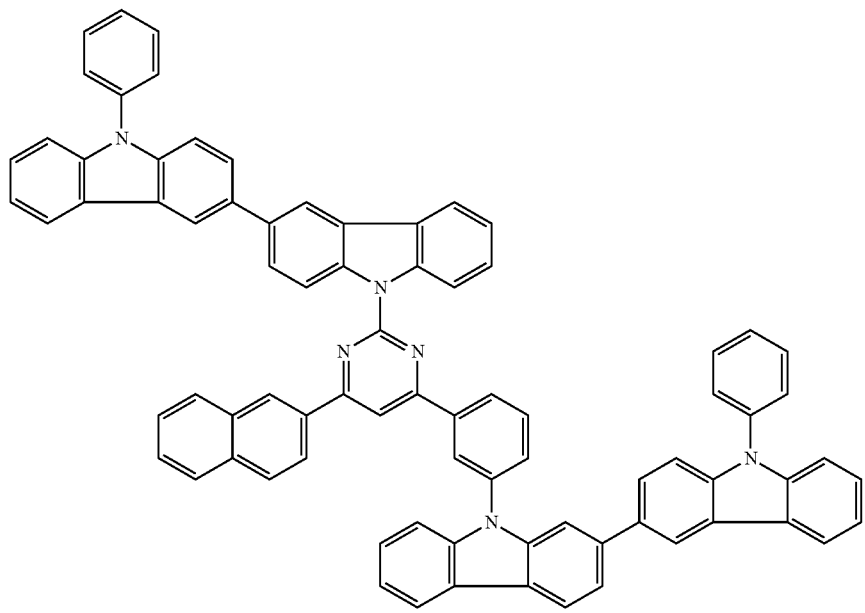
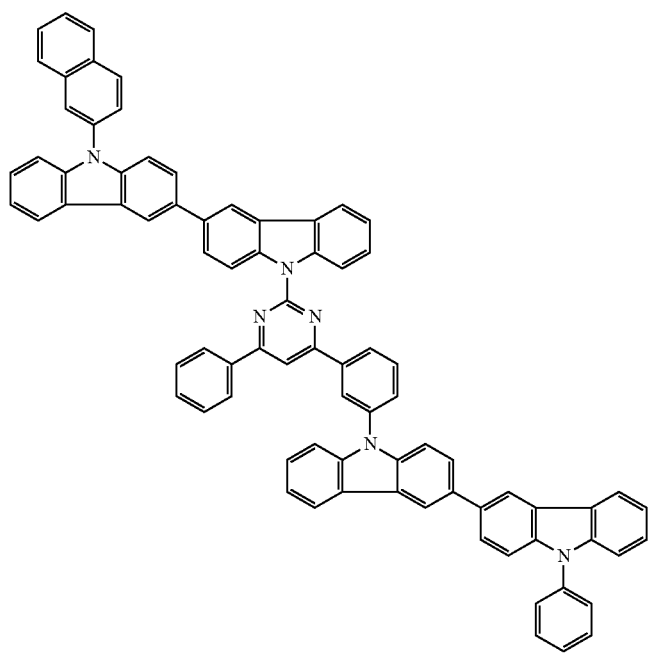

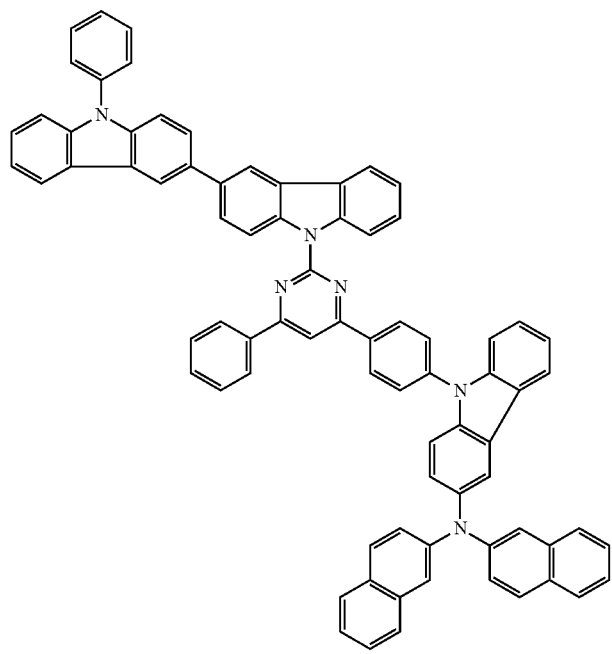
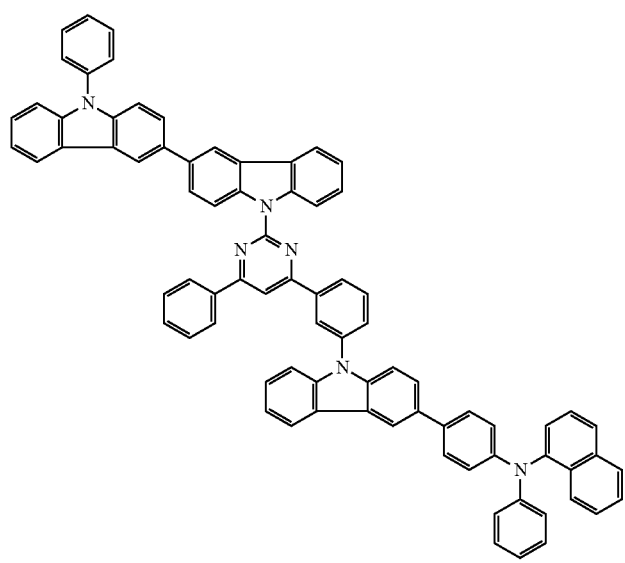
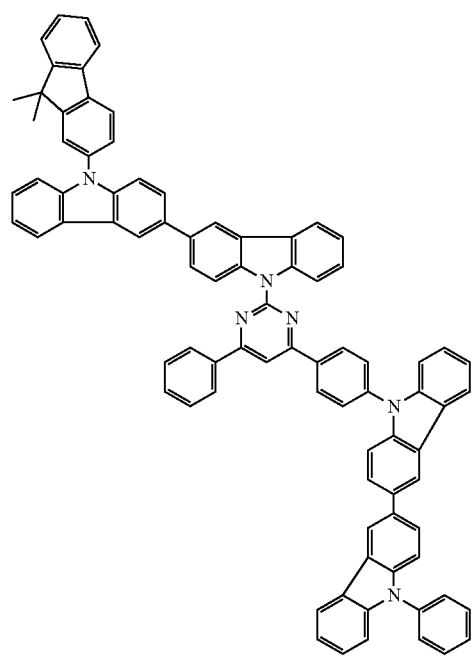

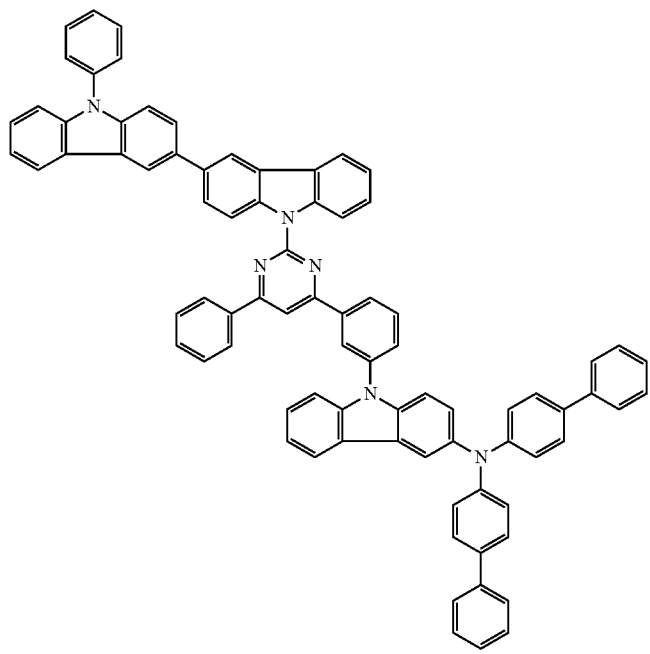
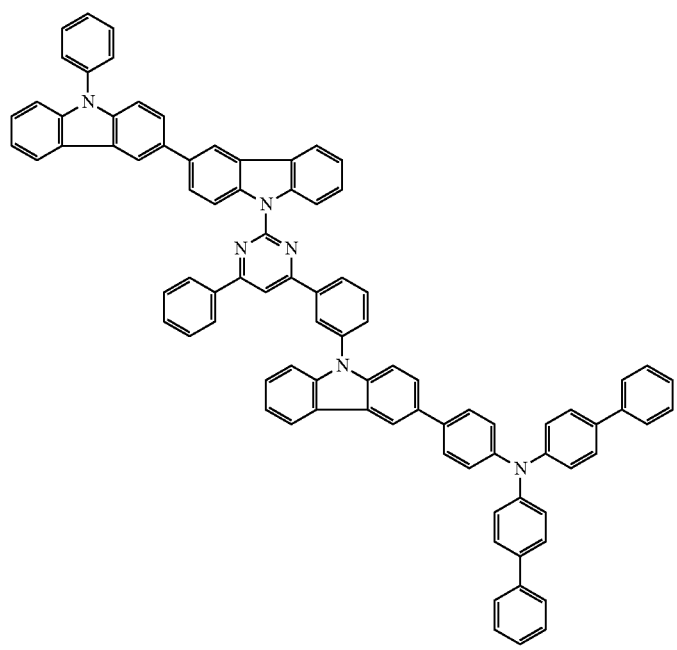

-continued
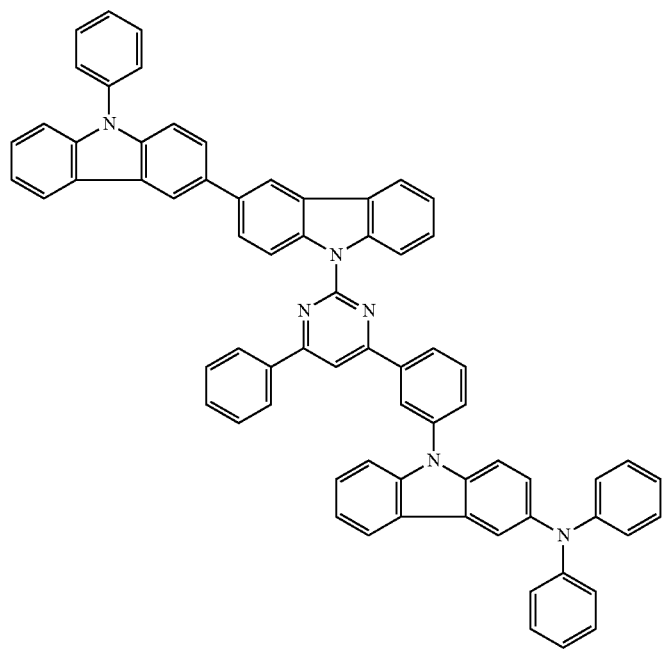
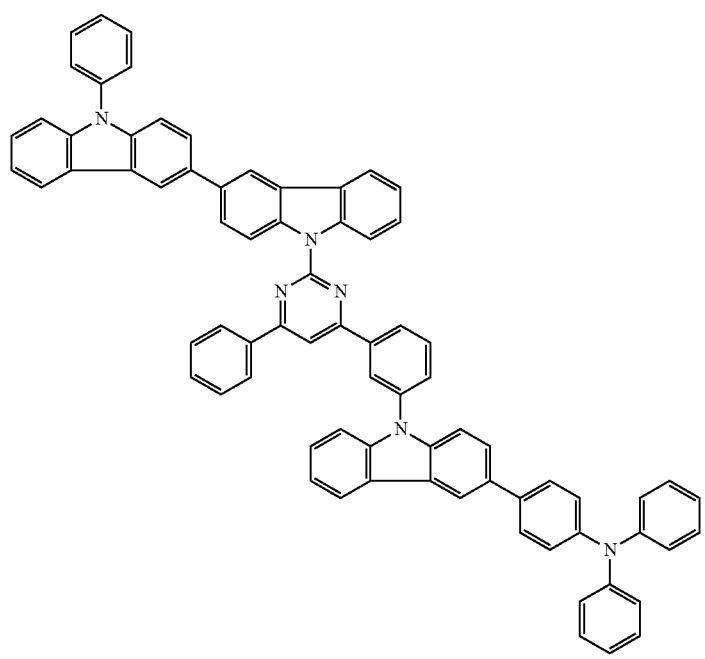

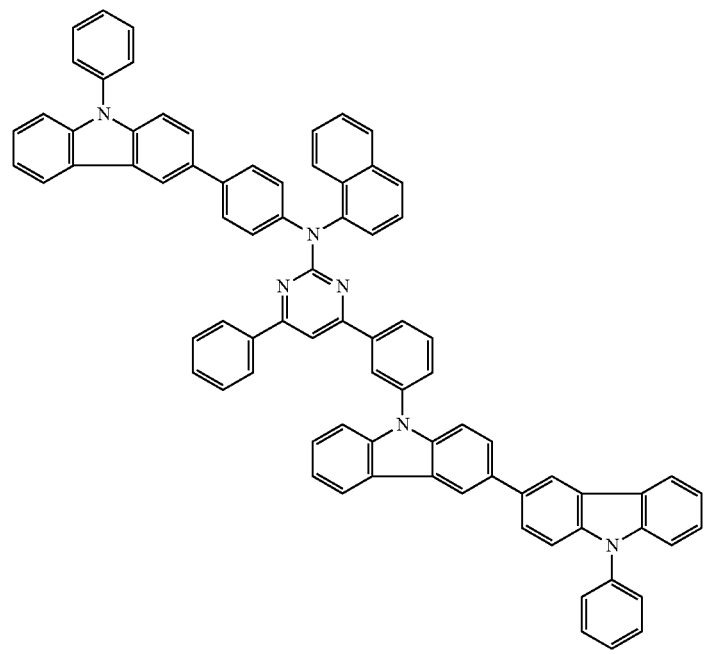
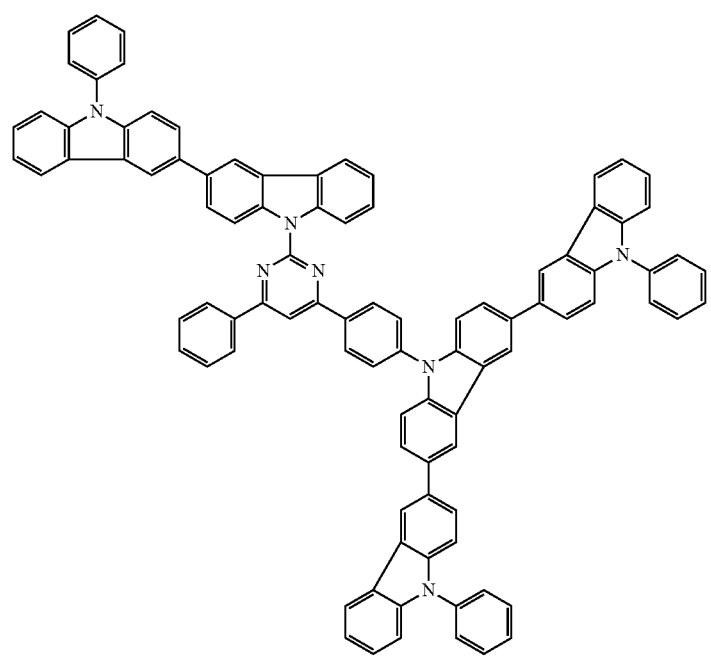

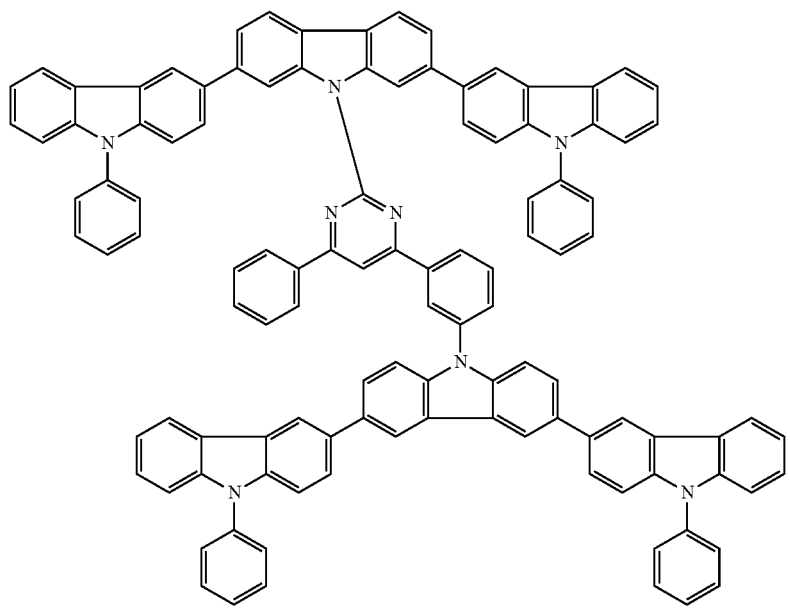
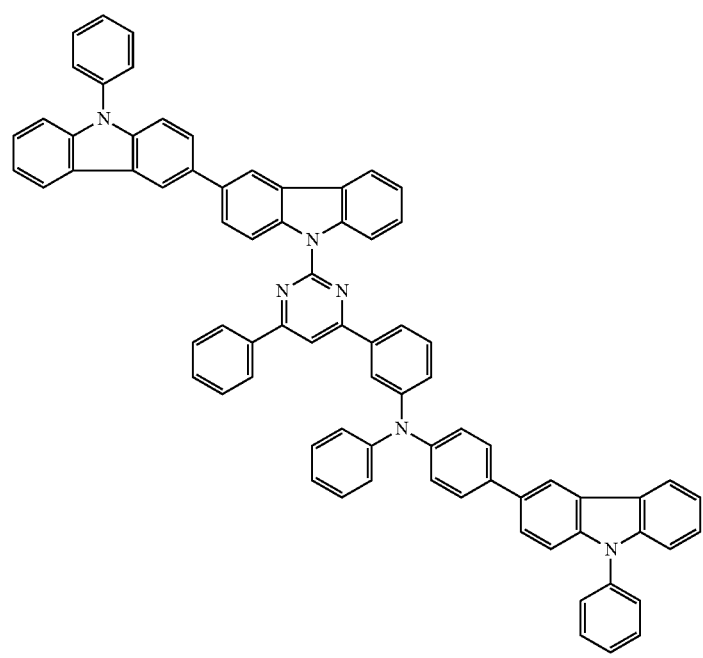

-continued
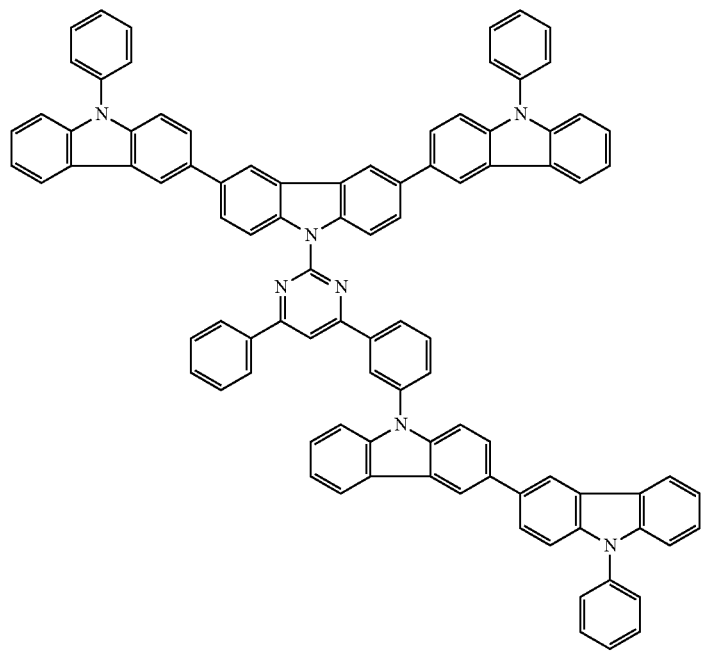
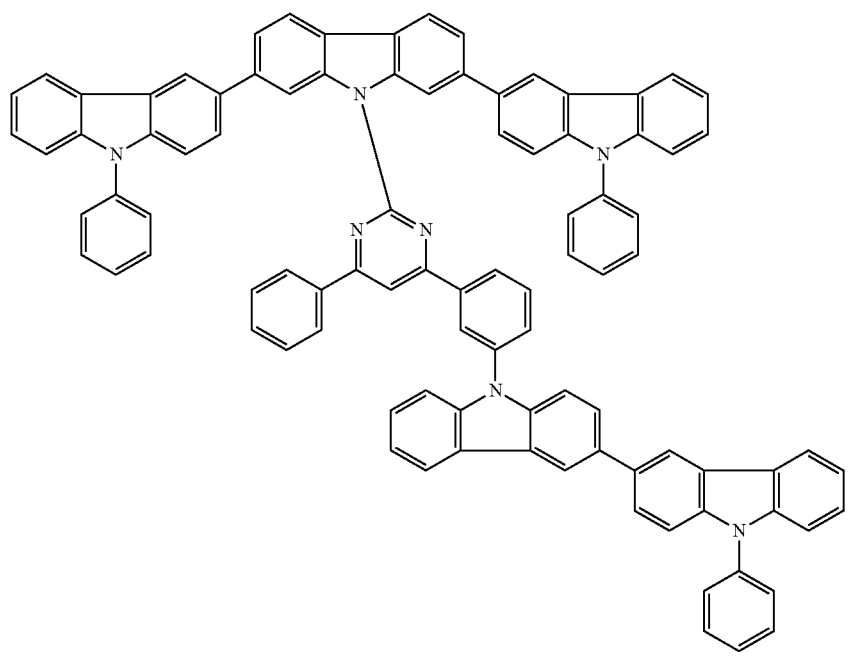

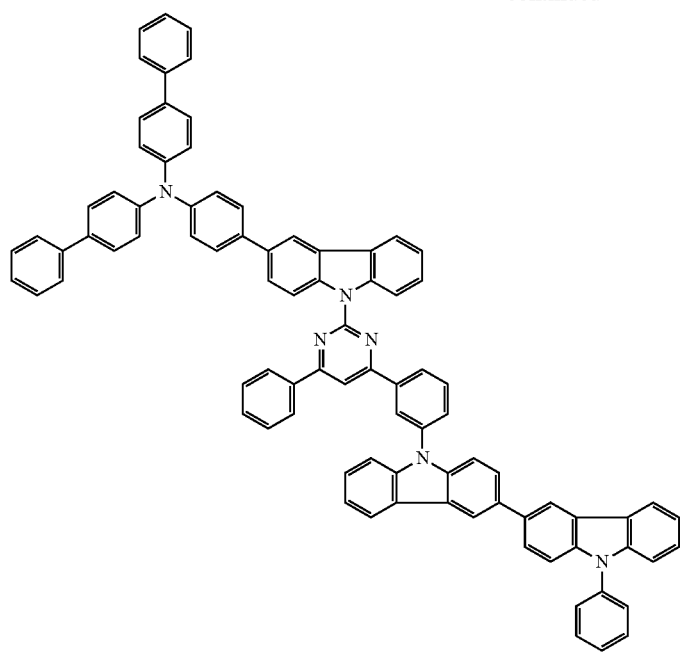
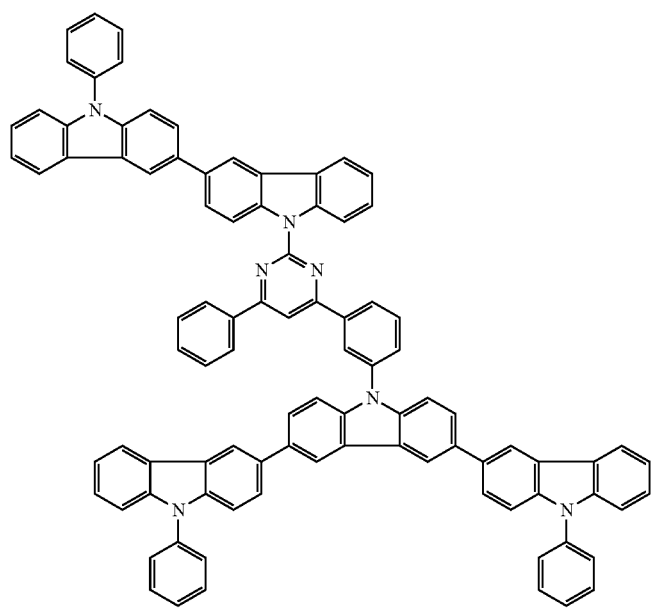

-continued
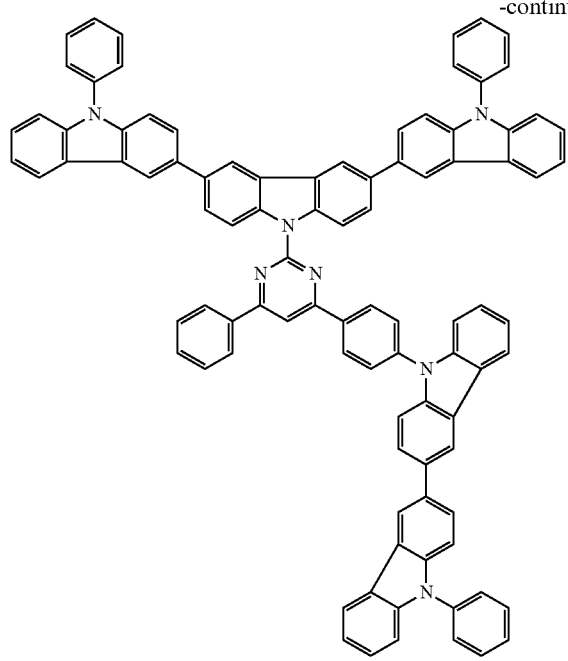
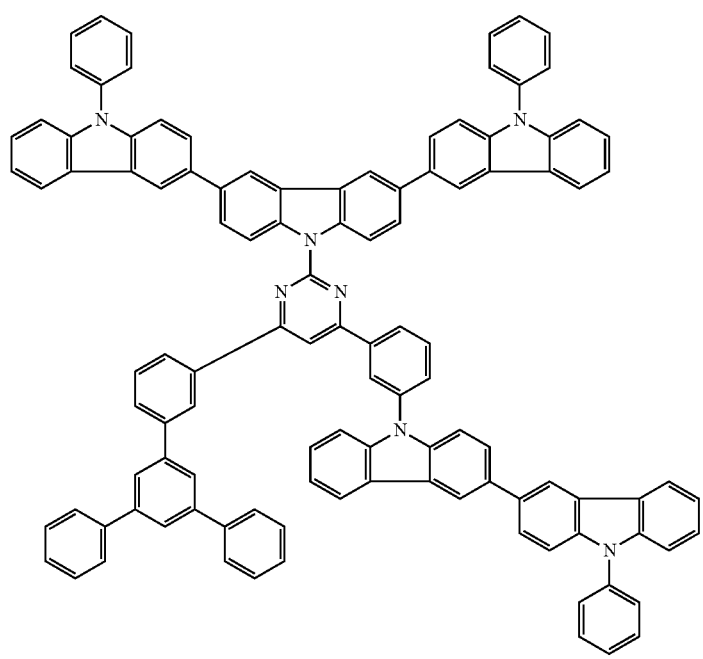

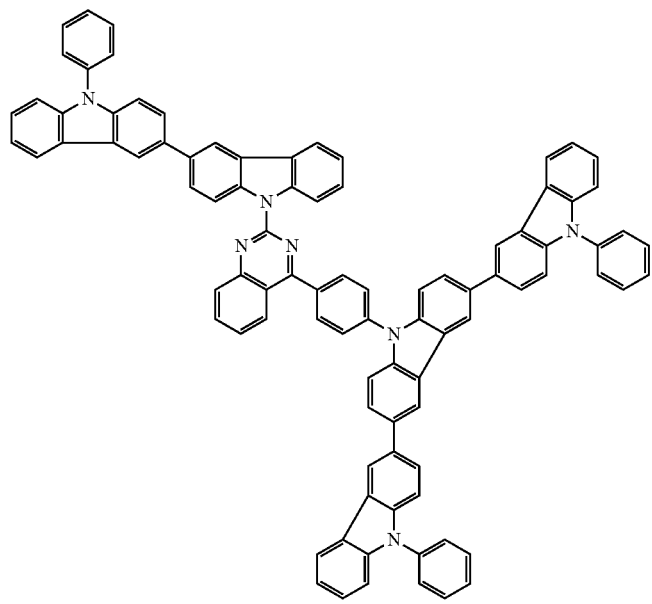
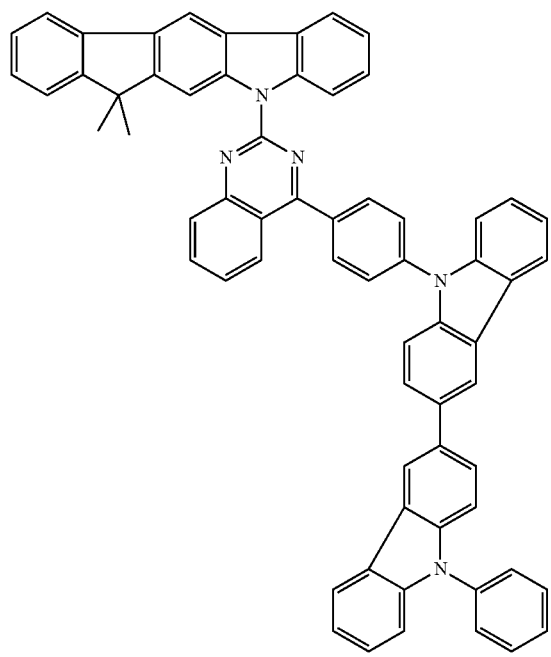

-continued
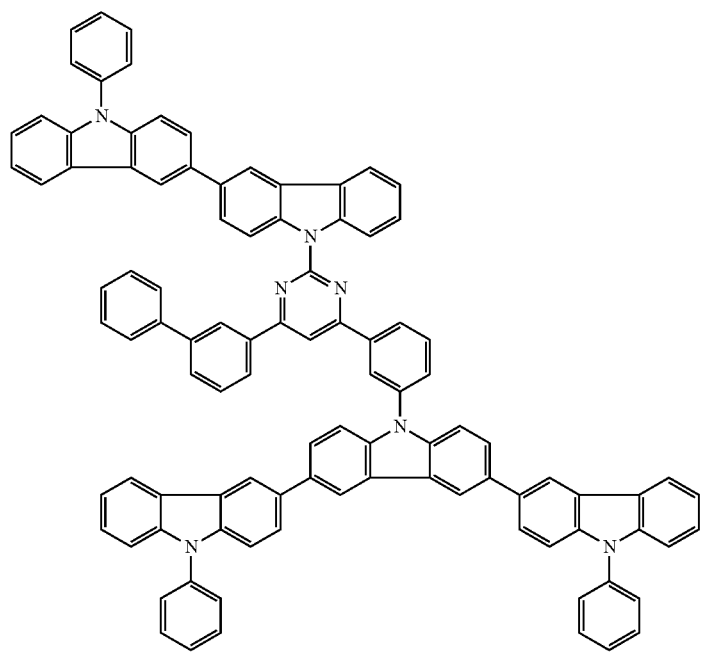
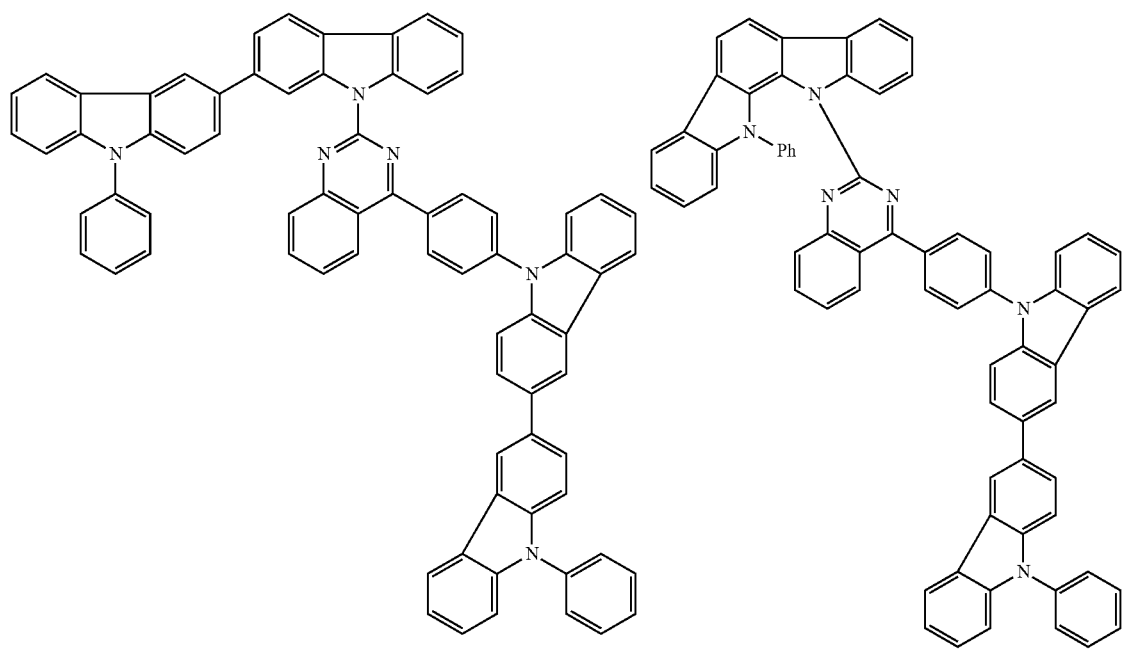

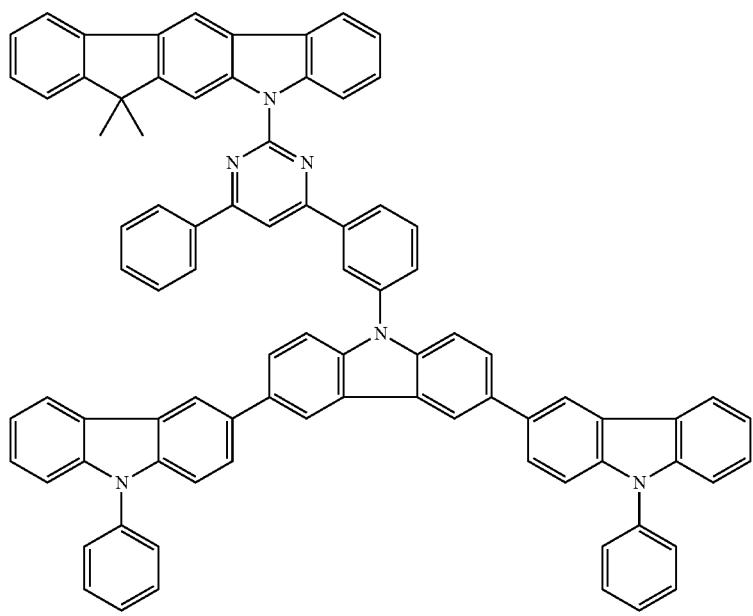
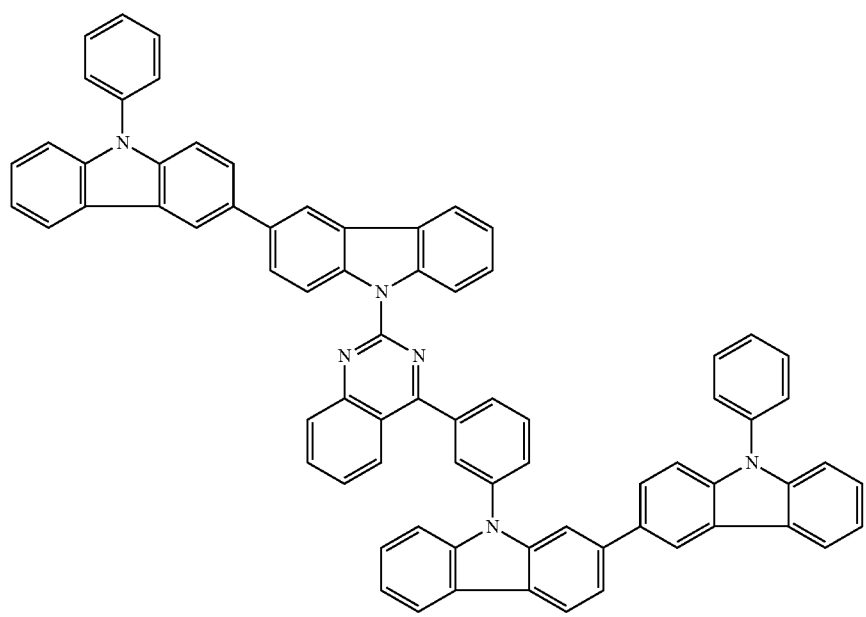

-continued
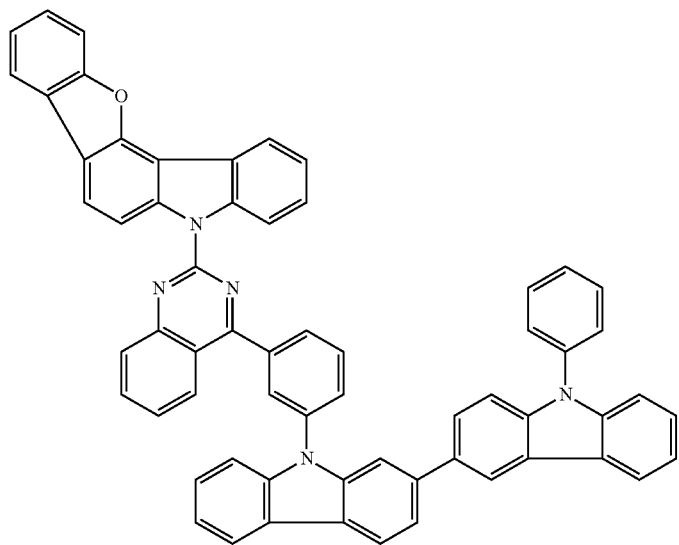
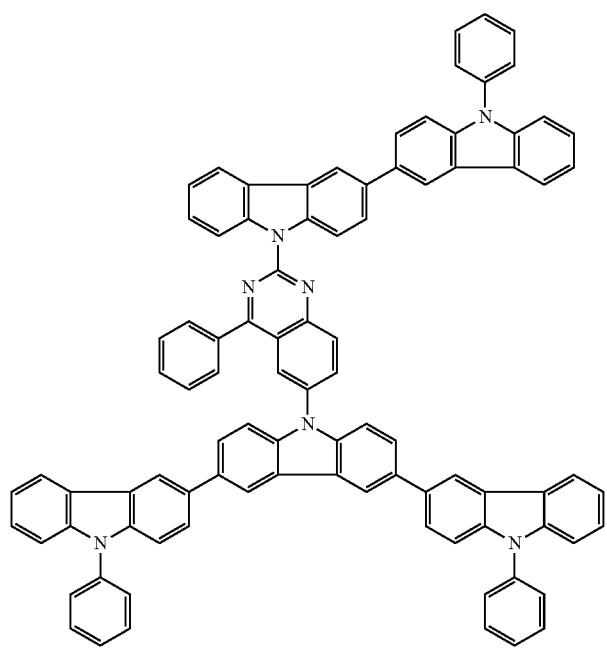

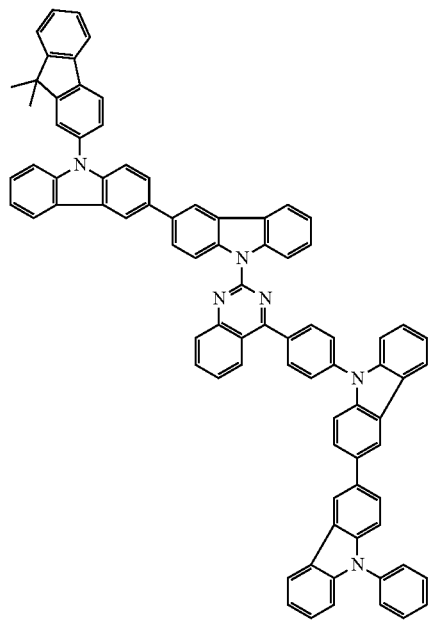
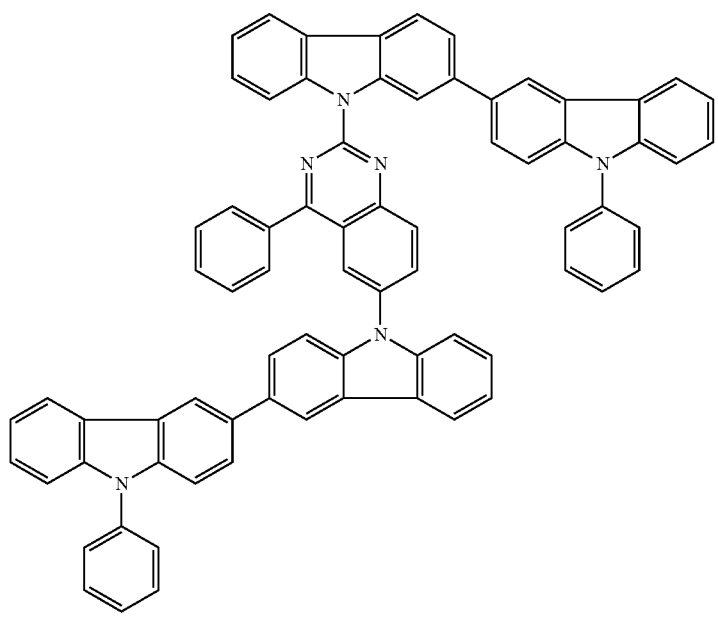

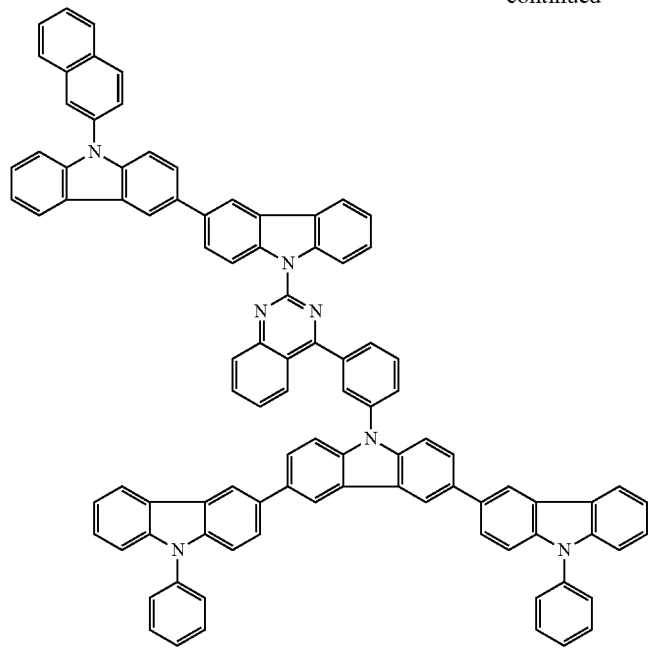
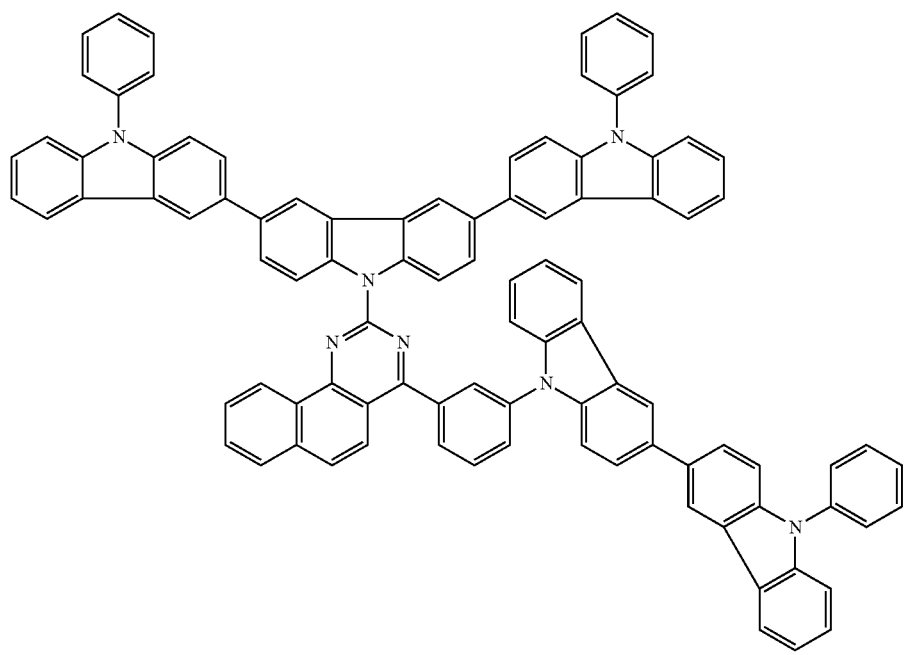 [SMILES: c1ccc(-n2c3ccccc3c3cc(-c4ccc5c(c4)c4ccccc4n5-c4cccc(-c5nc(-n6c7ccc(-c8ccc9c(c8)c8ccccc8n9-c8ccccc8)cc7c7cc(-c8ccc9c(c8)c8ccccc8n9-c8ccccc8)ccc76)c6ccc7ccccc7c6n5)c4)ccc32)cc1]

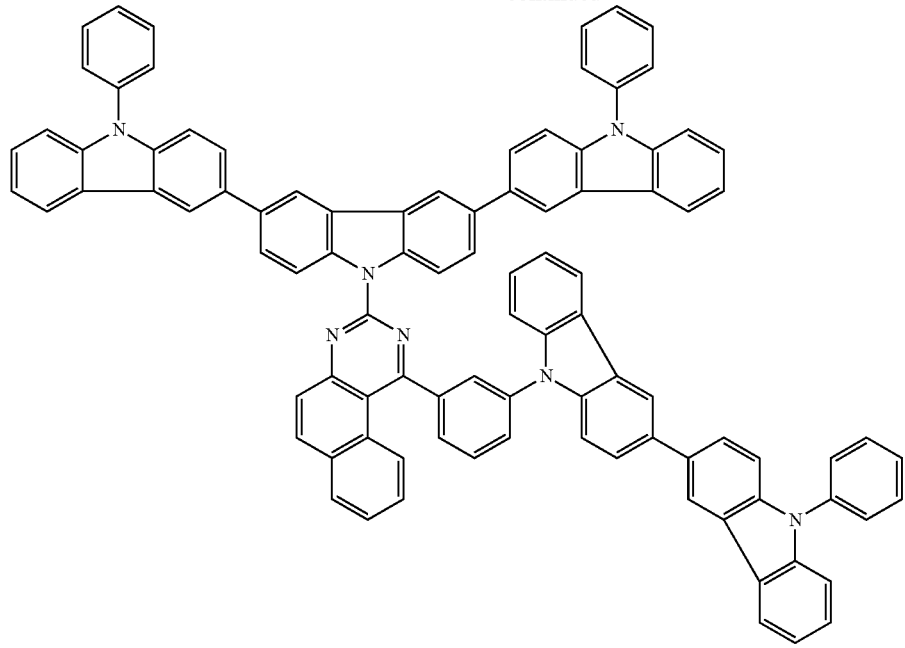
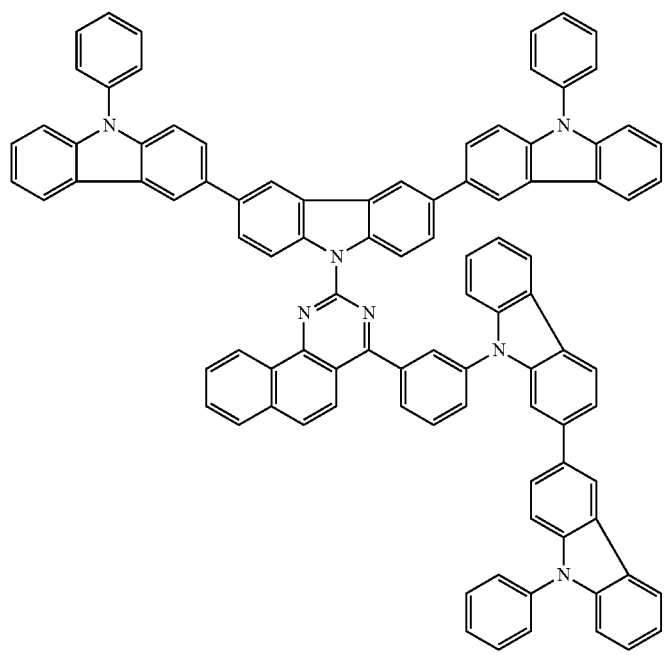

-continued
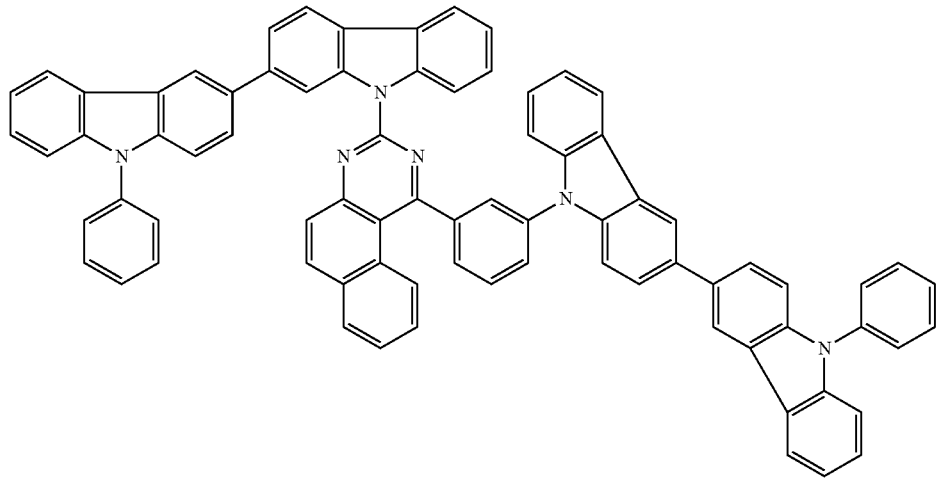
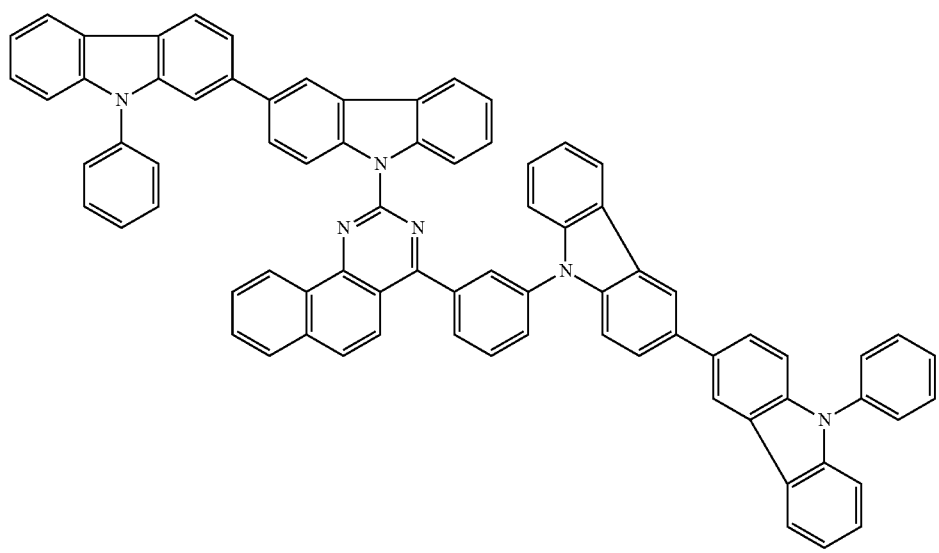
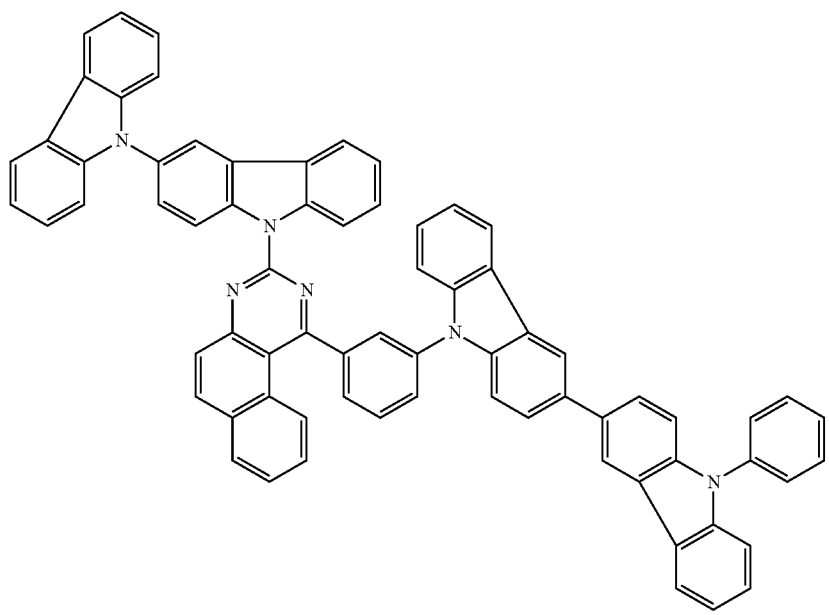

-continued
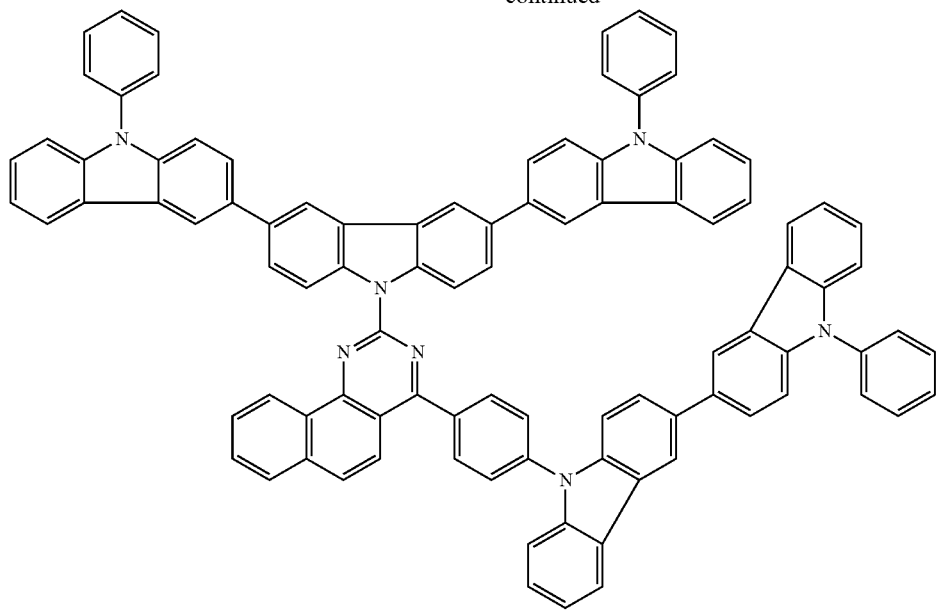
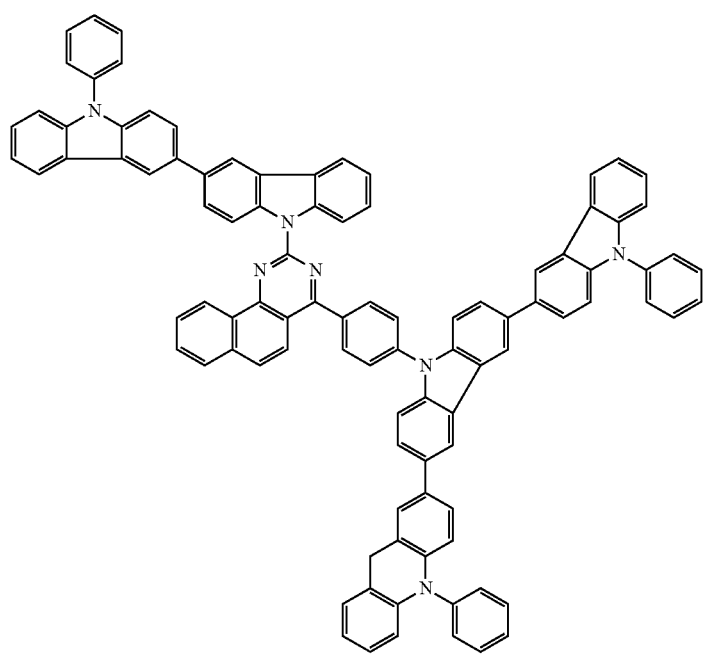

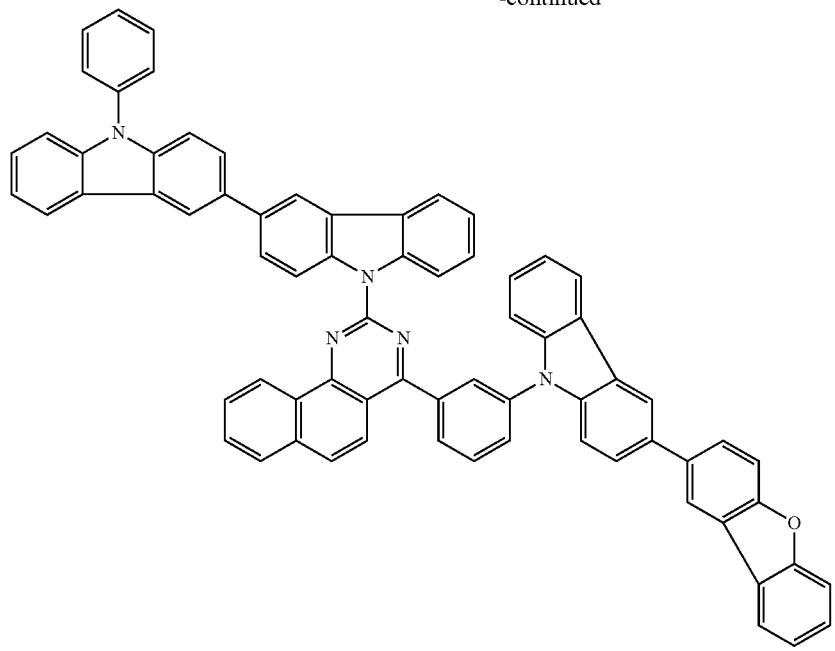
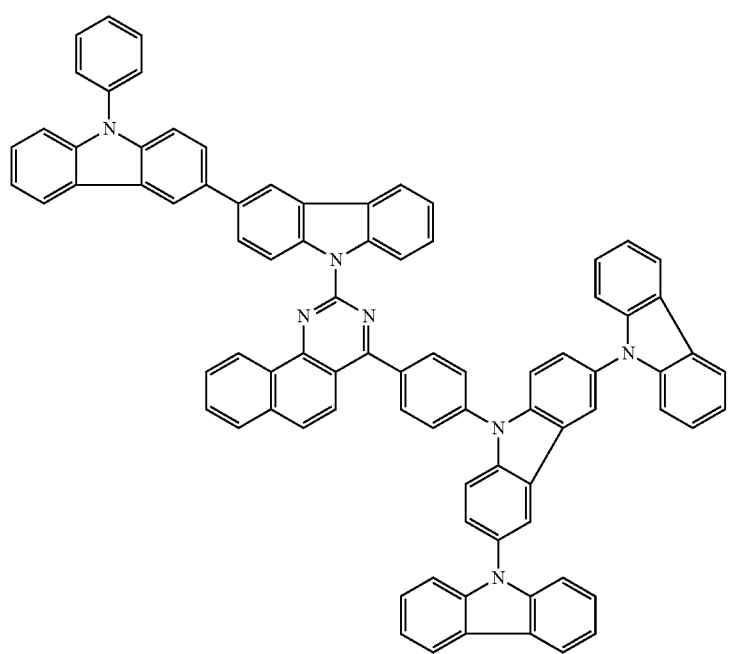

-continued
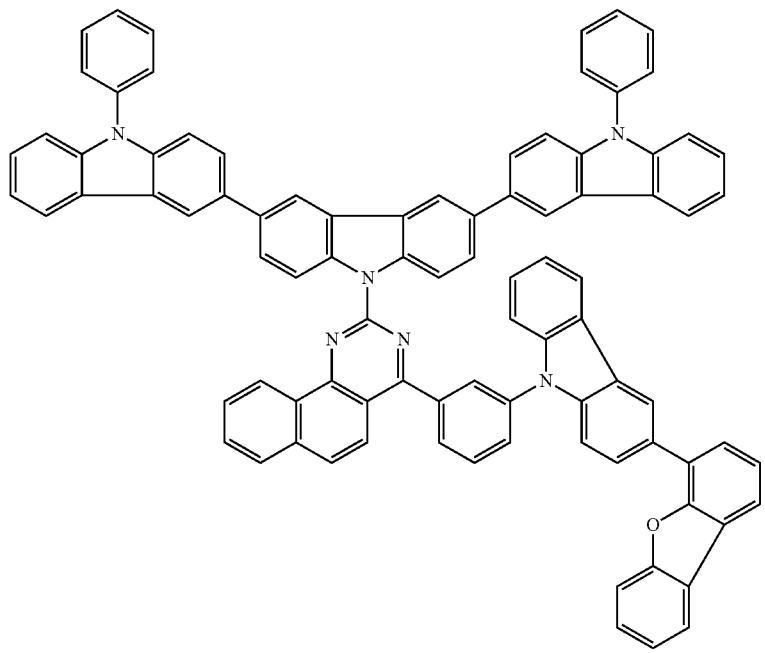
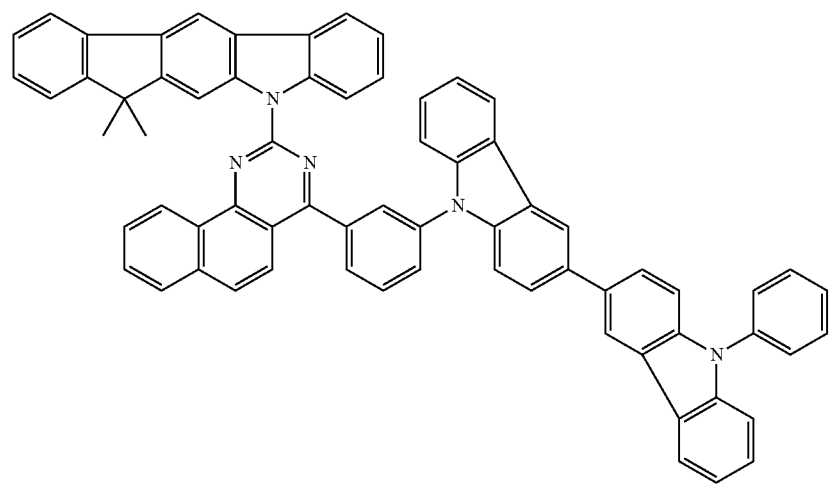

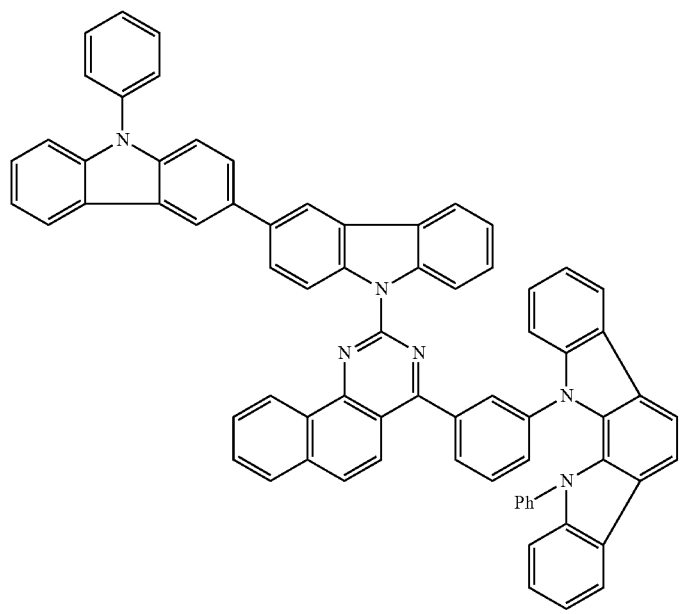
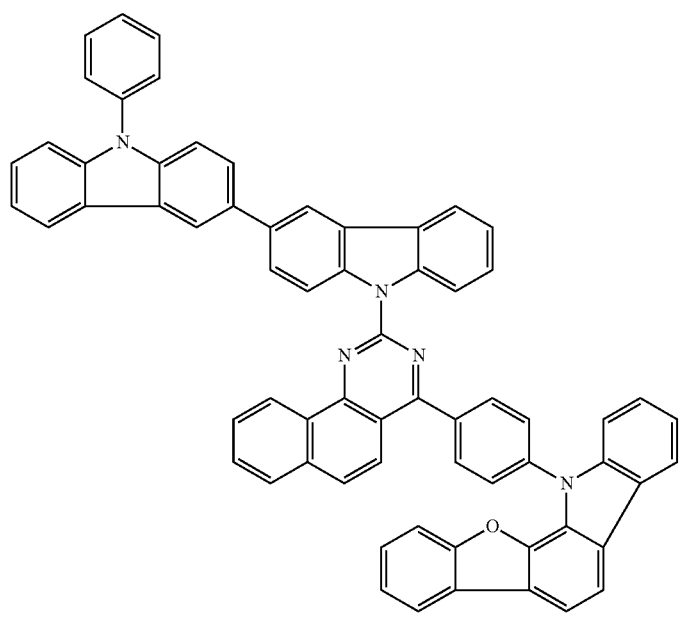

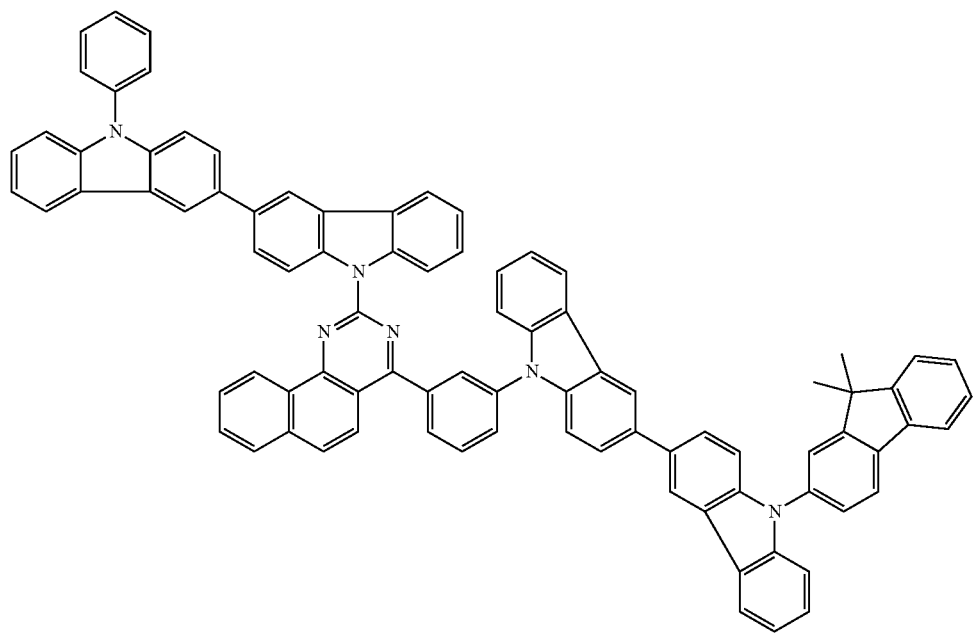
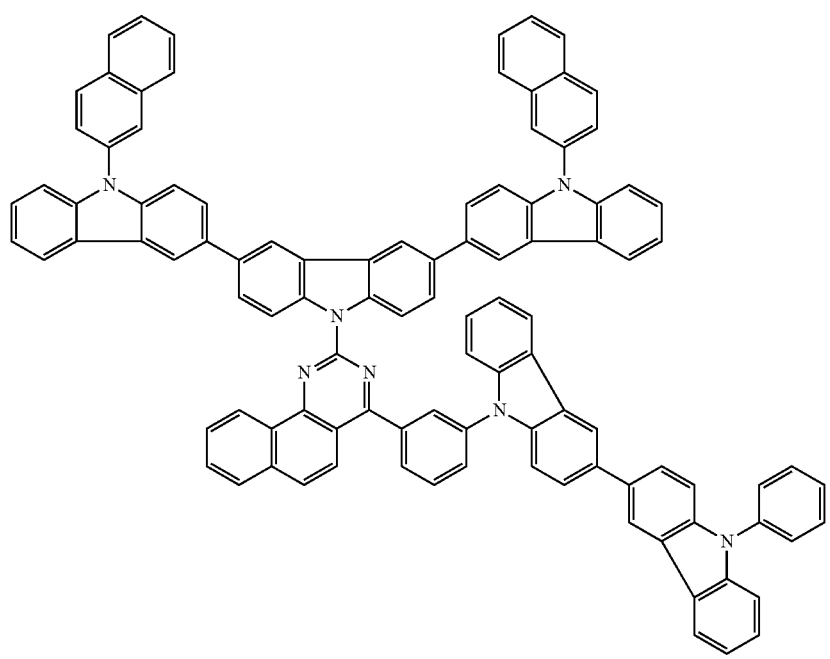

-continued
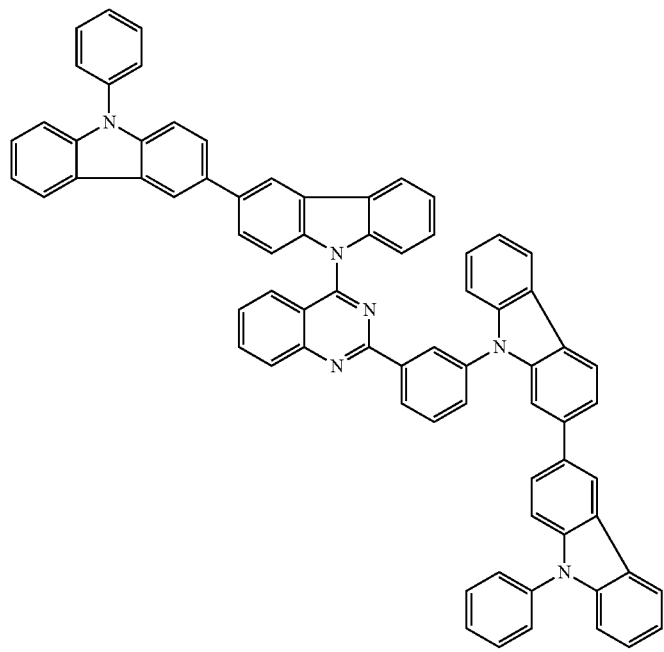
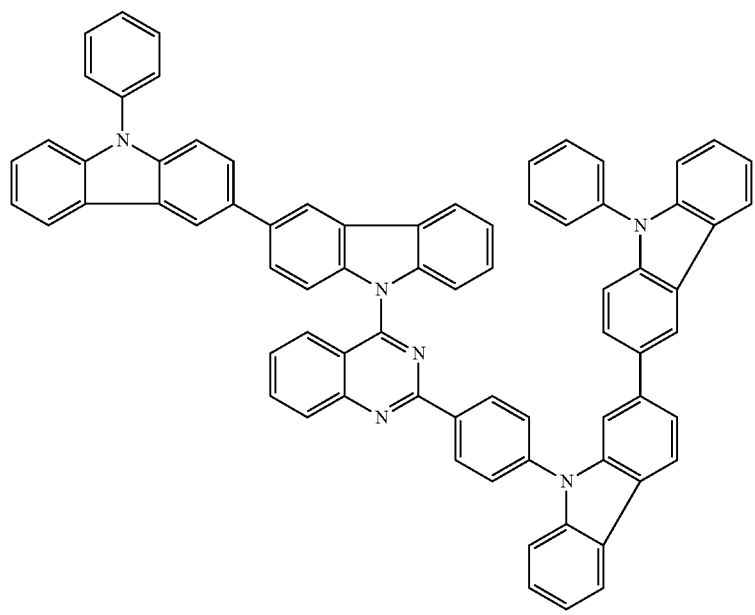

-continued
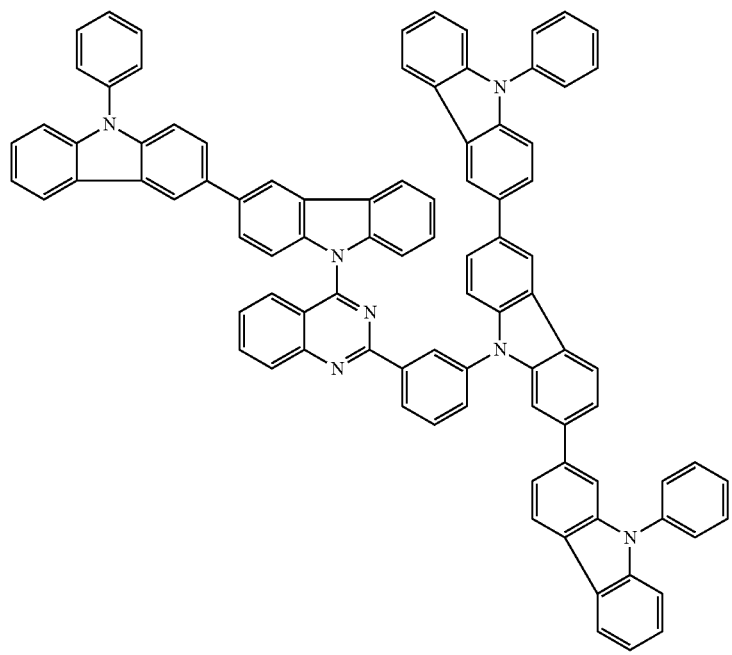
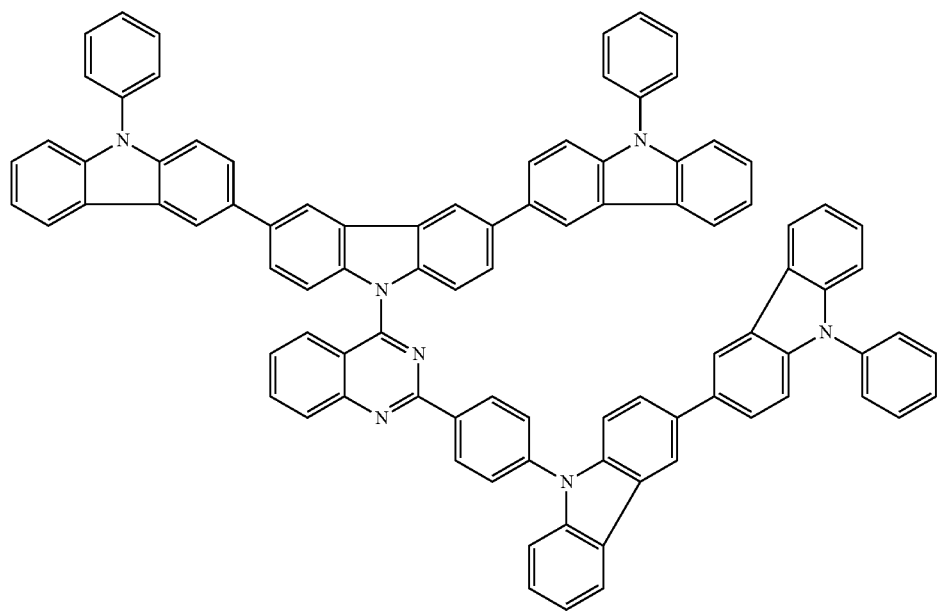

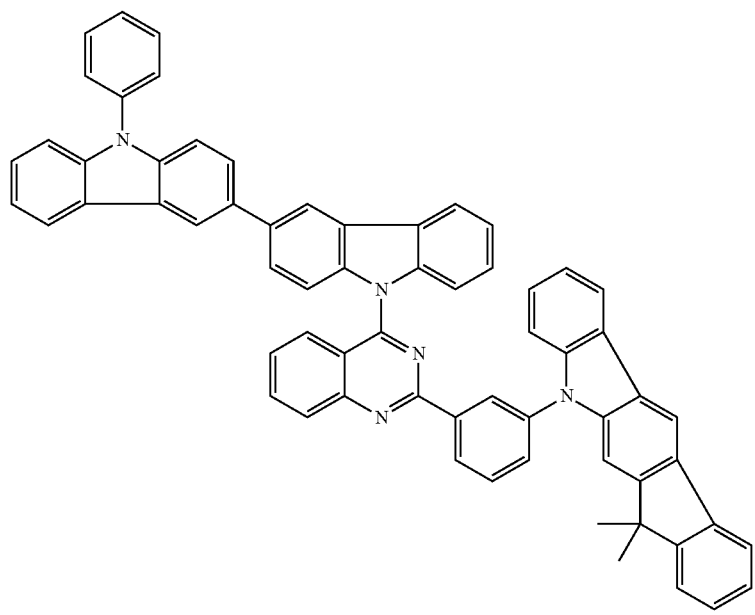
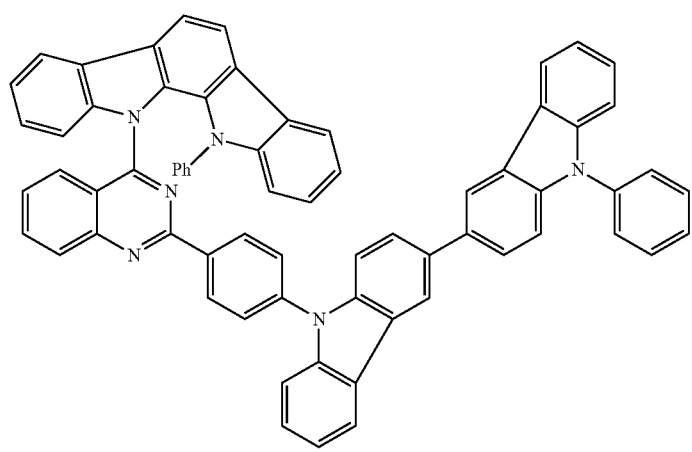
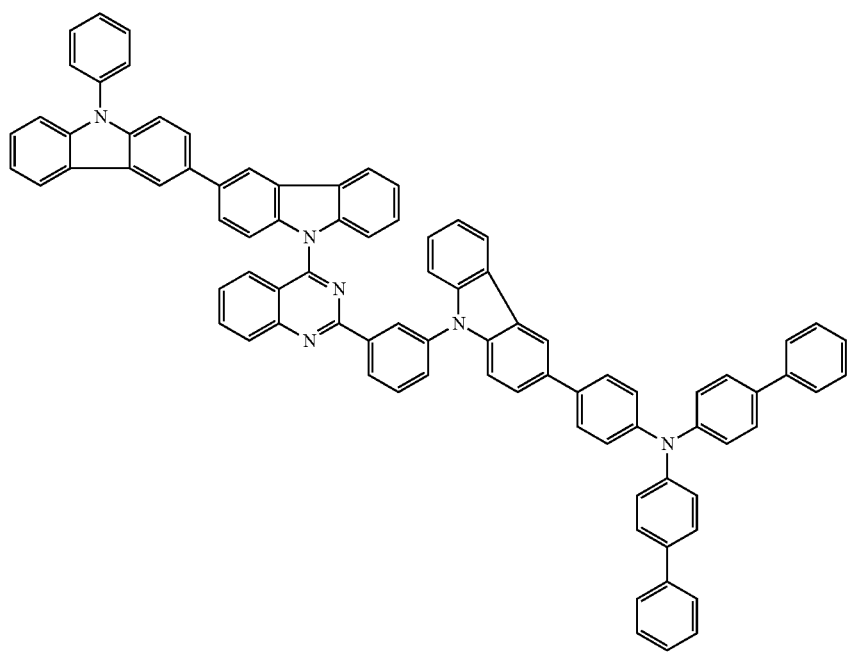

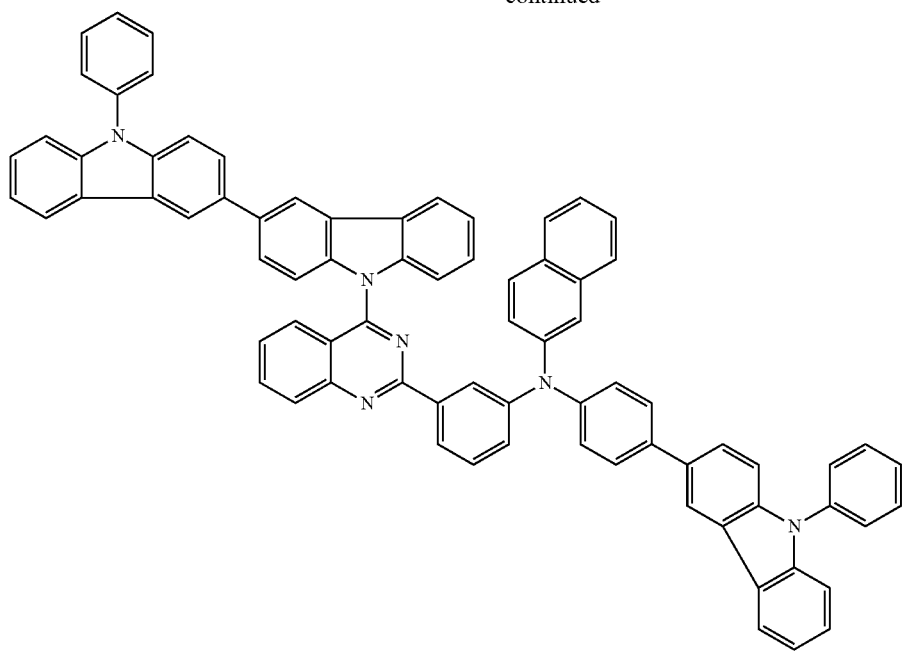
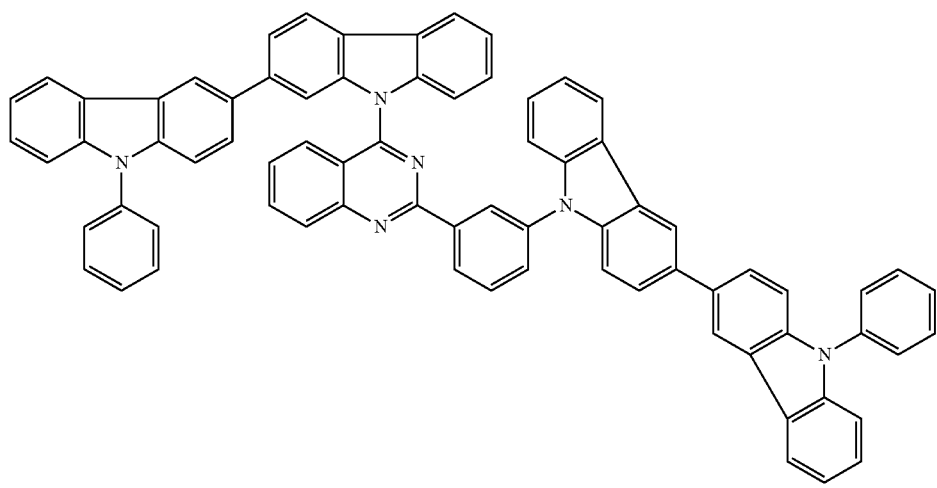
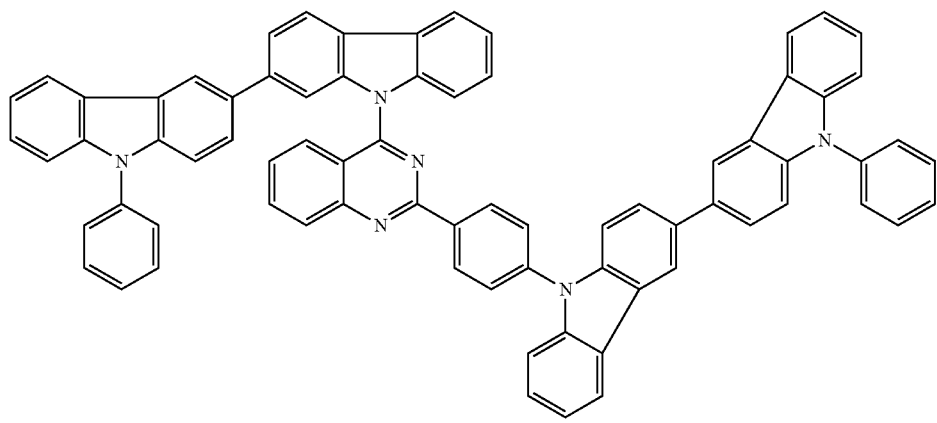

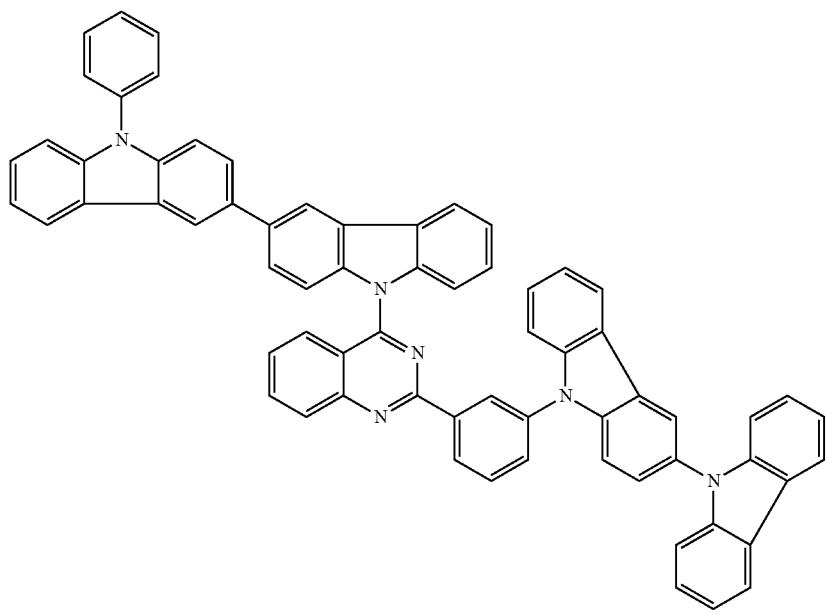
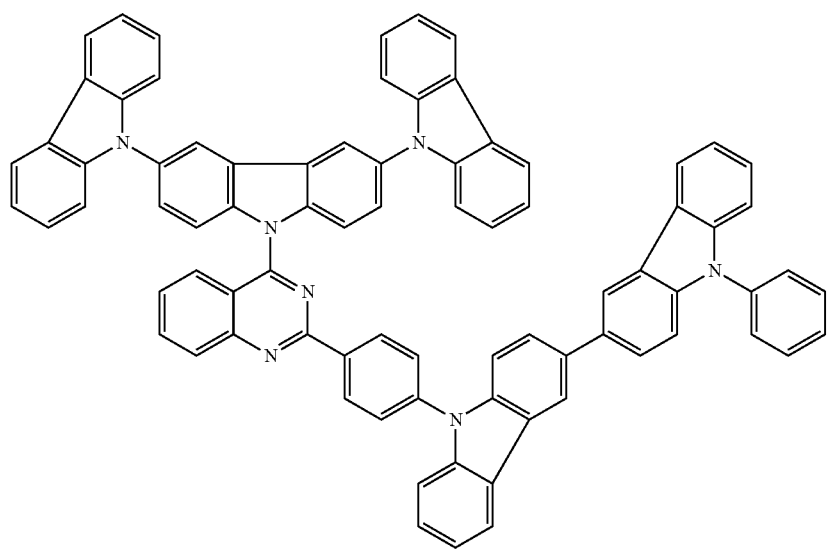

-continued
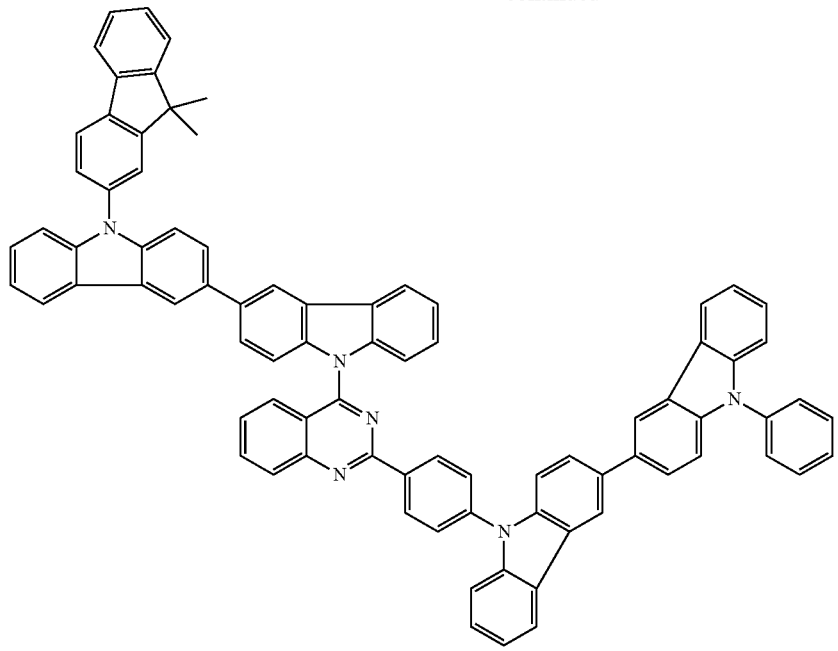
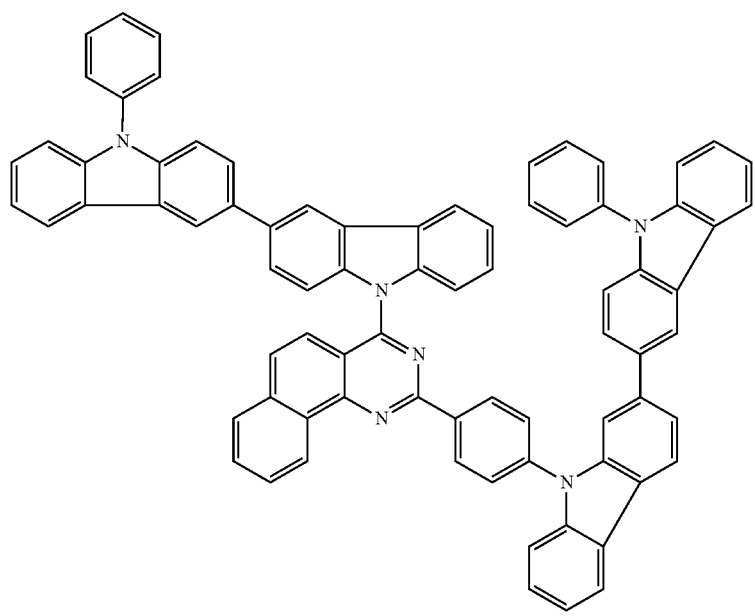

-continued

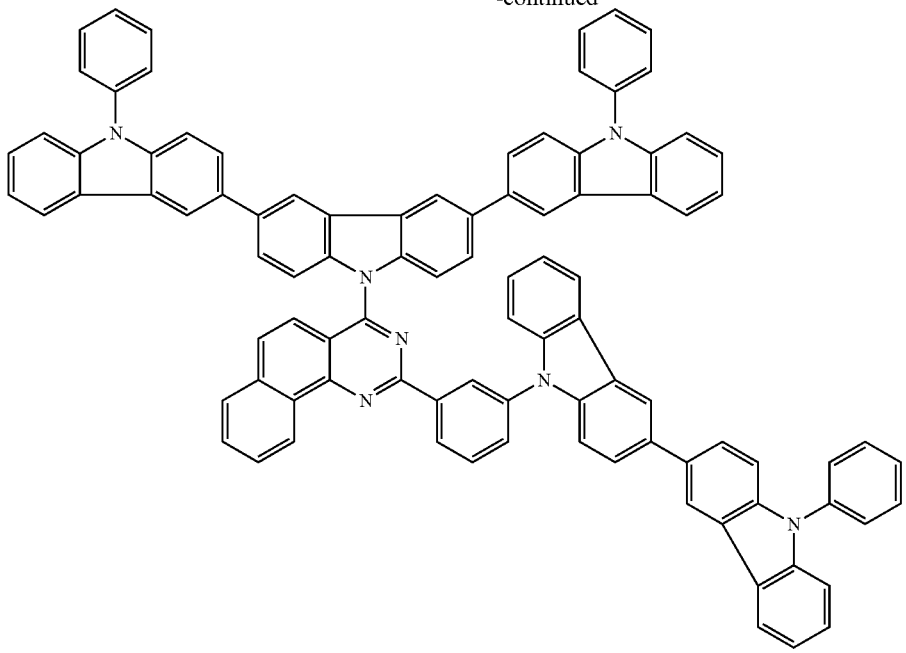

Organic EL Device

The organic EL device in an aspect of the invention will be described below.

The organic EL device comprises at least one organic thin film layer between a cathode and an anode. The organic thin film layer comprises a light emitting layer and at least one layer of the organic thin film layer comprises the compound represented by formula (1) (compound (1)) described above.

Examples of the organic thin film layer comprising the compound (1) include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto. The compound (1) may be used in any of the above layers, for example, used in a light emitting layer of a fluorescent emission unit as a host material or a dopant material, in a light emitting layer of a phosphorescent emitting unit as a host material, or in a hole transporting layer, an electron transporting layer, etc. of an emission unit.

In an embodiment of the invention, the organic EL device may be any of a single color emitting device of fluorescent or phosphorescent type, a white-emitting device of fluorescent-phosphorescent hybrid type, an emitting device of a simple type having a single emission unit, and an emitting device of a tandem type having two or more emission units, with the phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more phosphorescent emitting layers and two or more phosphorescent emitting layers. A space layer may be disposed between light emitting layers to prevent the diffusion of excitons generated in a phosphorescent emitting layer into a phosphorescent emitting layer. Representative layered structures of the emission unit are shown below:

((a) hole transporting layer/light emitting layer (/electron transporting layer);
(b) hole transporting layer/first phosphorescent emitting layer/second phosphorescent emitting layer (/electron transporting layer);
(c) hole transporting layer/phosphorescent emitting layer/space layer/phosphorescent emitting layer (/electron transporting layer);
(d) hole transporting layer/first phosphorescent emitting layer/second phosphorescent emitting layer/space layer/phosphorescent emitting layer (/electron transporting layer);
(e) hole transporting layer/first phosphorescent emitting layer/space layer/second phosphorescent emitting layer/space layer/phosphorescent emitting layer (/electron transporting layer);
(f) hole transporting layer/phosphorescent emitting layer/space layer/first phosphorescent emitting layer/second phosphorescent emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/phosphorescent emitting layer/triplet blocking layer (/electron transporting layer).

The emission color of a phosphorescent emitting layer and that of a phosphorescent emitting layer may be different. For example, the layered structure of the laminated light emitting unit (d) may be hole transporting layer/first phosphorescent emitting layer (red)/second phosphorescent emitting layer (green)/space layer/phosphorescent emitting layer (blue)/electron transporting layer.

An electron blocking layer may be disposed between a light emitting layer and a hole transporting layer or between a light emitting layer and a space layer, if necessary. Also, a hole blocking layer may be disposed between a light emitting layer and a electron transporting layer, if necessary. With such an electron blocking layer or a hole blocking layer, electrons and holes are confined in a light emitting layer to increase the degree of charge recombination in the light emitting layer, thereby improving the lifetime.

A representative device structure of the tandem-type organic EL device is shown below:
(2) Anode/First Emission Unit/Intermediate Layer/Second Emission Unit/Cathode.

The layered structures of the first emission unit and the second emission unit may be independently selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by a known material capable of supplying electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5 which comprises at least one phosphorescent emitting layer comprising a phosphorescent host and a phosphorescent dopant (phosphorescent emitting material). A hole injecting/transporting layer (an anode-side organic thin film layer) 6 may be disposed between the light emitting layer 5 and the anode 3, and an electron injecting/transporting layer (a cathode-side thin film layer) 7 may be disposed between the light emitting layer 5 and the cathode 4. An electron blocking layer (not shown) may be disposed on the anode 3 side of the light emitting layer 5, and a hole blocking layer (not shown) may be disposed on the cathode 4 side of the light emitting layer 5. With these blocking layers, electrons and holes are confined in the light emitting layer 5 to increase the degree of exciton generation in the light emitting layer 5.

In the present invention, a host material is referred to as a fluorescent host material when combinedly used with a fluorescent dopant material (fluorescent emitting material) and as a phosphorescent host material when combinedly used with a phosphorescent dopant material. Therefore, the fluorescent host material and the phosphorescent host material are not distinguished from each other merely by the difference in their molecular structures. Namely, in the present invention, the term "phosphorescent host material" means a material for constituting a phosphorescent emitting layer containing a phosphorescent dopant material and does not necessarily mean a material that cannot be used as a material for a fluorescent emitting layer. The same applies to the fluorescent host material.

Substrate

In an embodiment of the invention, the organic EL device is formed on a light-transmissive substrate. The light-transmissive substrate serves as a support for the organic EL device and is preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

The substrate may be a flexible plate, for example, a plastic plate of polycarbonate and polyvinyl chloride.

Anode

The anode to be formed on the substrate injects holes to a hole transporting layer or a light emitting layer, and a metal, an alloy, an electroconductive compound, and a mixture thereof, each having a work function of 4.5 eV or more, is effective for the anode. Examples of the material for anode include indium tin oxide alloy (ITO), indium tin oxide alloy doped with silicon or silicon oxide, tin oxide (NESA), indium zinc oxide alloy, tungsten oxide, graphene, gold, silver, platinum, cupper, and a metal nitride, such as titanium nitride. The anode is formed by making the material for anode into a thin film by a method, such as a vapor deposition method or a sputtering method. When getting the light emitted from a light emitting layer through the anode, the transmittance of anode to visible light is preferably 10% or more. The sheet resistance of anode is preferably several hundreds $\Omega$/or less. The film thickness of anode depends upon the kind of material and generally 10 nm to 1 µm, preferably 10 to 200 nm.

Cathode

The cathode injects electrons to an electron injecting layer, an electron transporting layer or a light emitting layer, and formed preferably by a material having a small work function (for example 3.8 eV or lower), for example, a metal, an alloy, an electroconductive compound, and a mixture thereof. Examples of the material for cathode include, but not limited to, the groups 1 and 2 elements of the periodic table, i.e., an alkali metal, such as lithium and cesium, an alkaline earth metal, such as magnesium, a rare earth metal, and an alloy of such a metal, for example, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material for cathode into a thin film by a method, such as a vapor deposition method and a sputtering method. The emitted light may be taken through the cathode, if necessary.

Light Emitting Layer

The light emitting layer is an organic layer having a light emitting function and comprises a host material and a dopant material (highly emitting material) when a doping system is employed. The dopant material may be a fluorescent emitting material or a phosphorescent emitting material. The fluorescent emitting material is a compound capable of emitting light from a singlet excited state, and the phosphorescent emitting compound is a compound capable of emitting light from a triplet exciting state. The host material mainly promotes the recombination of electrons and holes and confines the excitons within the light emitting layer. The dopant material lets the excitons generated by the recombination emit light efficiently.

In a phosphorescent device, the major function of the host material is to confine the excitons generated on the dopant within a light emitting layer.

To control the carrier balance in a light emitting layer, the light emitting layer may be made into a double host (host/co-host) layer, for example, by combinedly using an electron transporting host material and a hole transporting host material.

The light emitting layer may be also made into a double dopant layer, in which two or more kinds of dopant materials having a high quantum yield are combinedly used and each dopant material emits light with its own color. For example, a yellow emission can be obtained by a light emitting layer which is formed by co-depositing a host material, a red-emitting dopant material, and a green-emitting dopant material.

In a laminate of two or more light emitting layers, electrons and holes can be accumulated in the interface between the light emitting layers, and therefore, the recombination region is localized in the interface between the light emitting layers. With this structure, the quantum efficiency can be enhanced.

The easiness of hole injection to a light emitting layer and the easiness of electron injection to a light emitting layer may be different from each other. Also, the hole transporting ability and the electron transporting ability each being expressed by mobility of holes and electrons in a light emitting layer may be different from each other.

The phosphorescent dopant material (phosphorescent emitting material) to be used in a light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. For example, a metal complex, such as an iridium complex, an osmium complex, and a platinum complex, is used as a blue-emitting phosphorescent dopant material; an iridium complex is used as a green-emitting phosphorescent dopant material; and a metal complex, such as an iridium complex, a platinum complex, a terbium complex, and a europium complex, is used as a red-emitting phosphorescent dopant material.

The ligand is preferably ortho-metallated. In view of obtaining a high phosphorescent quantum yield and further improving the external quantum efficiency of luminescent device, a metal complex comprising a metal selected from Ir, Os, and Pt is preferred, with a metal complex, such as an iridium complex, an osmium complex and a platinum complex, particularly an ortho-metallated complex being more preferred, an iridium complex and a platinum complex being still more preferred, and an ortho-metallated iridium complex being particularly preferred.

The content of the phosphorescent dopant material in a light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex for the phosphorescent dopant material are shown below.

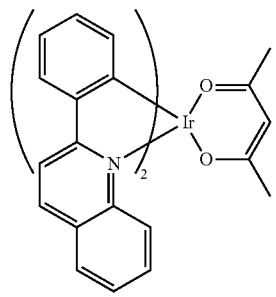

-continued

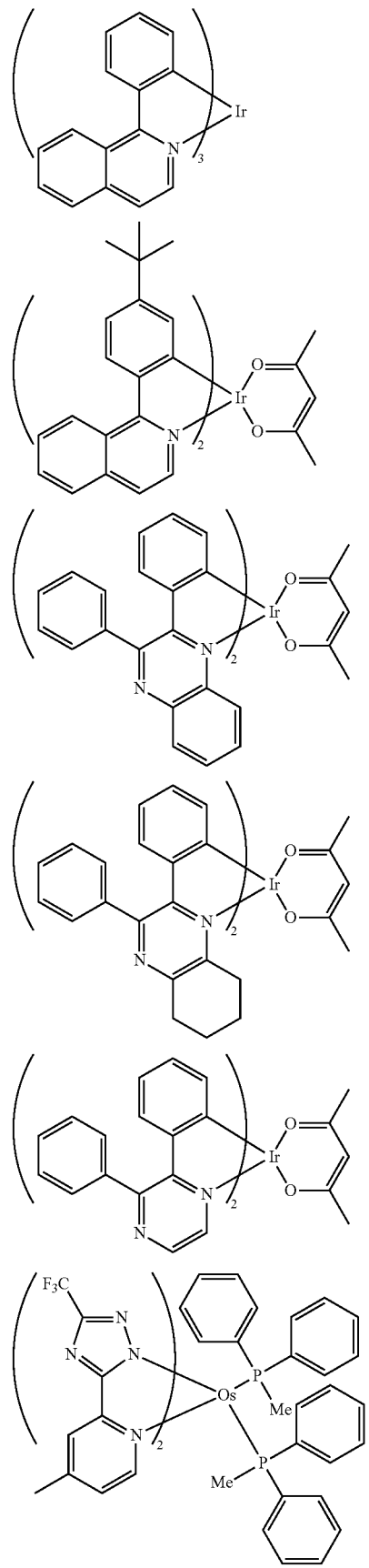

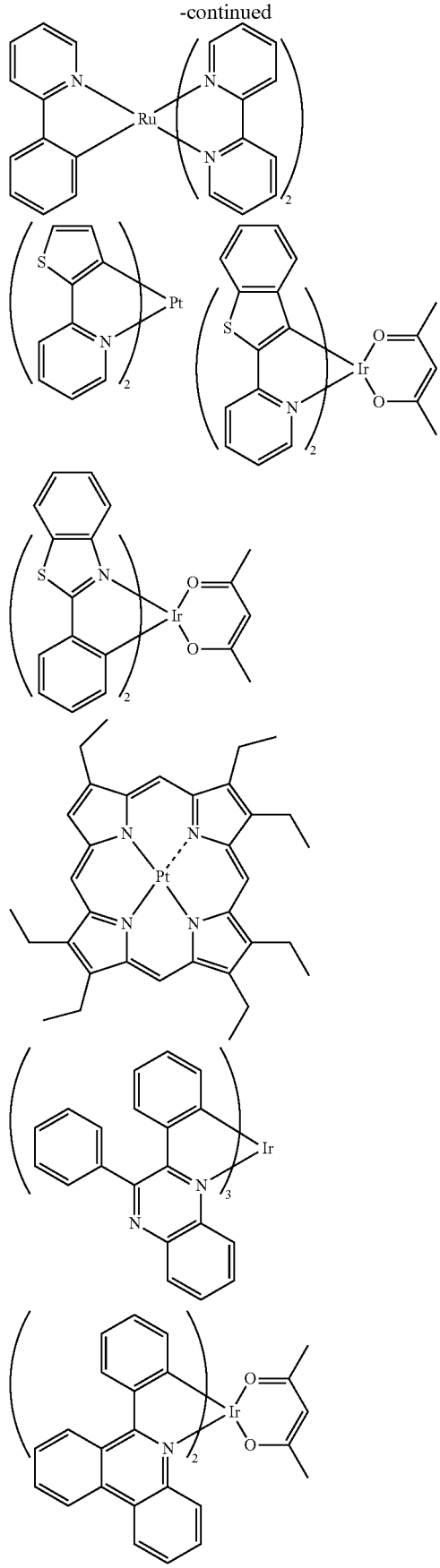
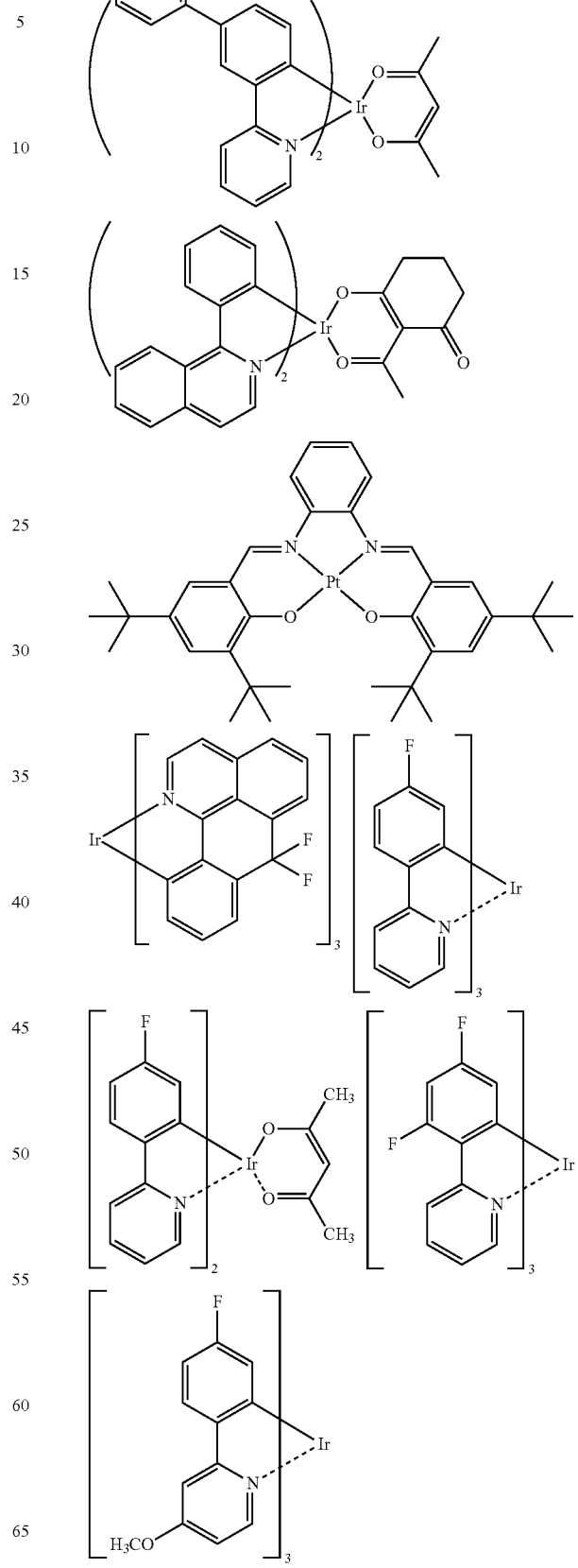

-continued
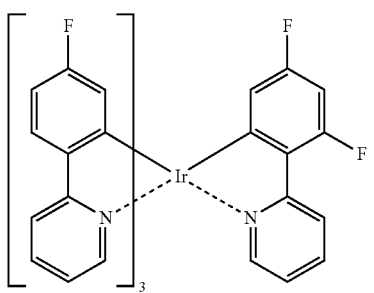
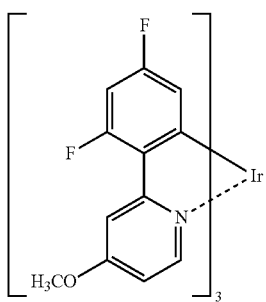
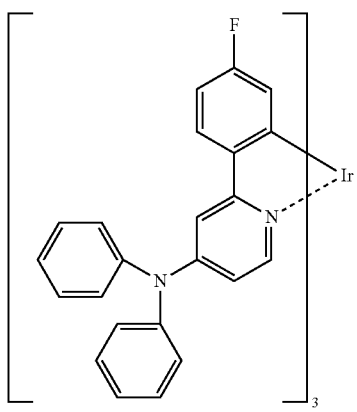
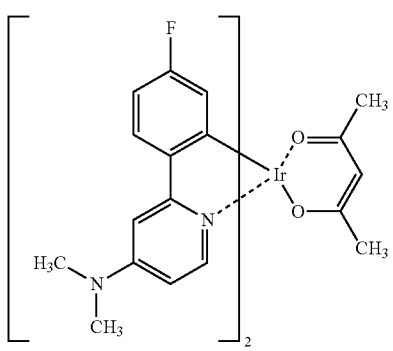
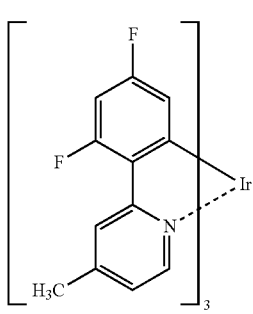
-continued
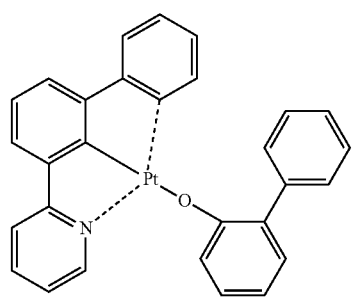
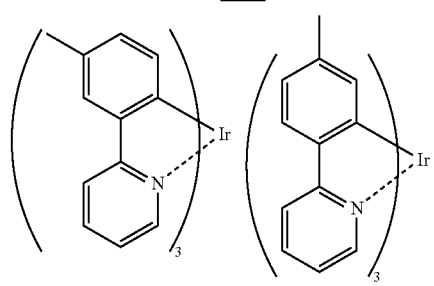
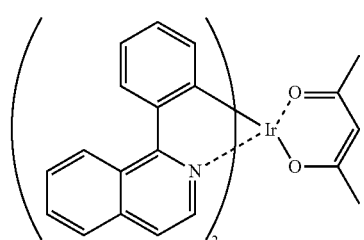
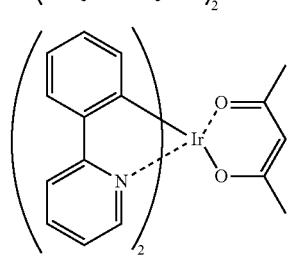
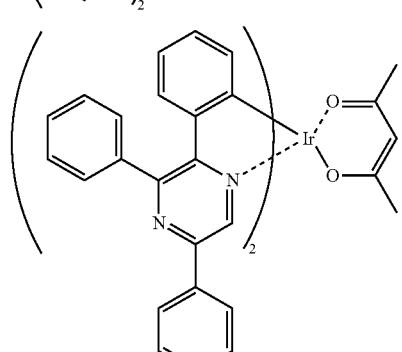
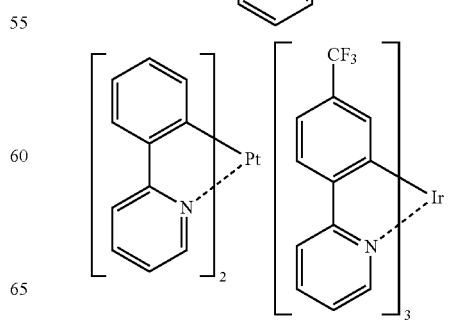

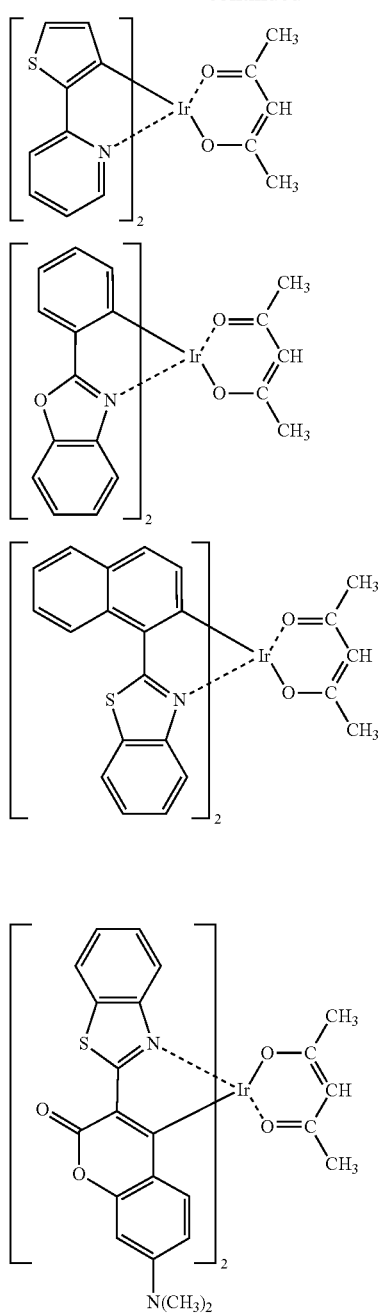
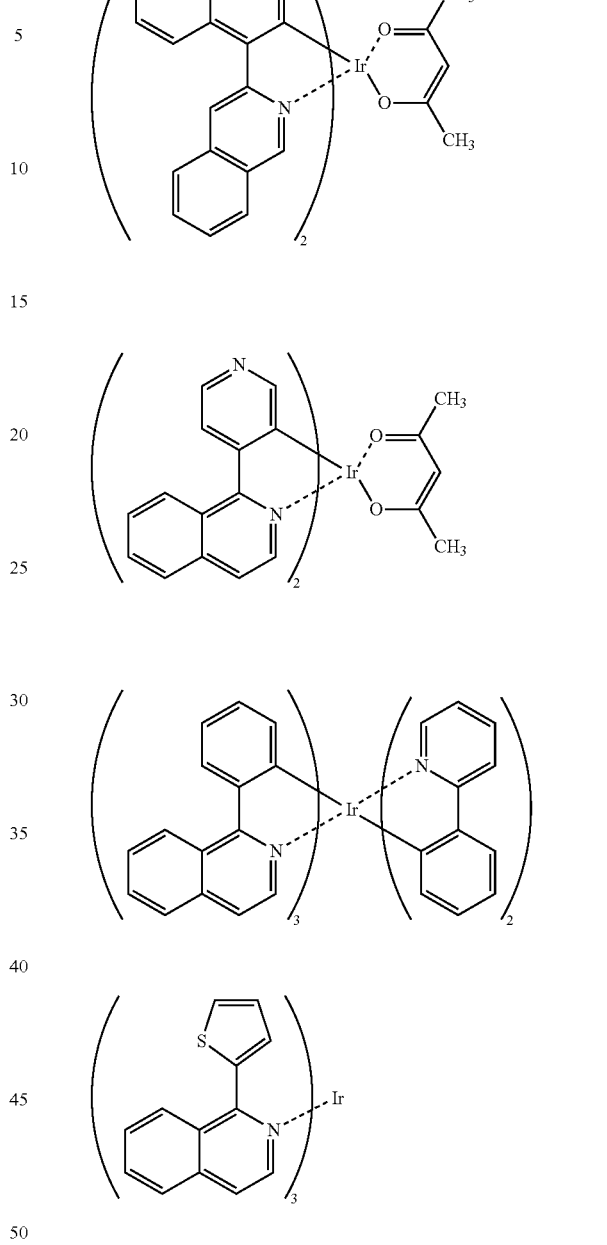
A complex represented by formula (X) or (Y) is preferably used as the phosphorescent dopant material:
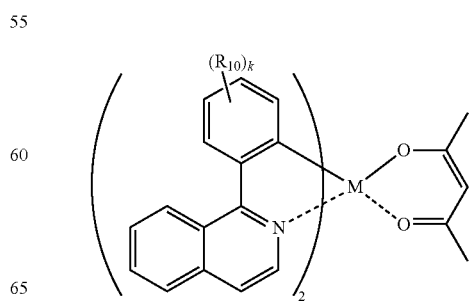
(X)

-continued (Y)

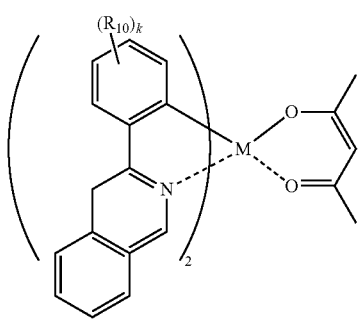

wherein $R_{10}$ represents a hydrogen atom or a substituent, k represents an integer of 1 to 4, and M represents Ir, Os, or Pt.

Examples of the substituent as $R_{10}$ are the same as those mentioned above with respect to $R_0$ to $R_8$, etc. of formula (1).

In an embodiment of the invention, the organic EL device may comprise a light emitting layer comprising a fluorescent material, i.e., a fluorescent emitting layer. The fluorescent emitting layer may be formed from a known fluorescent emitting material.

In an embodiment of the invention, for example, a pyrene derivative, a styrylamine derivative, a chrysene derivative, a fluoranthene derivative, a fluorene derivative, a diamine derivative, and a triarylamine derivative are usable as a blue fluorescent emitting material; an aromatic amine derivative is usable as a green fluorescent emitting material; and a tetracene derivative and a diamine derivative are usable as a red fluorescent emitting material.

In another embodiment of the invention, at least one material selected from an anthracene derivative, a fluoranthene derivative, a styrylamine derivative, and an arylamine derivative is preferably used as the fluorescent emitting material, with the anthracene derivative and the arylamine derivative being more preferred. In particular, the anthracene derivative is preferably used as a host material and the arylamine derivative is preferably used as a dopant. The materials described in WO 2010/134350 and WO 2010/134352 are preferably used. The compound (1) and the material for organic EL devices may be used in a fluorescent emitting layer as a fluorescent emitting material or a host material.

The highly light-emitting material (dopant material) may be dispersed in another material (host material). The host material may be selected from various kinds of materials and is preferably a material having a lowest unoccupied molecular orbital level (LUMO level) higher than that of the dopant material and a highest occupied molecular orbital level (HOMO level) lower than that of the dopant material.

In an embodiment of the invention, the material may include (1) a metal complex, such as an aluminum complex, a beryllium complex, and a zinc complex; (2) a heterocyclic compound, such as an oxadiazole derivative, a benzimidazole derivative, and a phenanthroline derivative; (3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused polycyclic aromatic amine derivative.

The phosphorescent host is a compound which confines the triplet energy of the phosphorescent dopant efficiently within a light emitting layer to cause the phosphorescent dopant to emit light efficiently. Although the compound (1) and the material for organic EL device comprising the compound (1) are useful as a phosphorescent host, a compound other than the compound (1) may be used as the phosphorescent host according to the use of the device. The use of the compound (1) and the material for organic EL devices is not limited to the phosphorescent host.

The compound (1) and a compound other than it may be combinedly used in the same light emitting layer as the phosphorescent host materials. Alternatively, the compound (1) may be used in one of light emitting layers as a phosphorescent host material and a compound other than it may be used in another of the light emitting layers as a phosphorescent host material. The compound (1) may be used in an organic layer other than the light emitting layer. In this case, a compound other than the compound (1) may be used as a phosphorescent host of the light emitting layer.

Examples of the compound other than the compound (1) which is suitable as a phosphorescent host include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Examples thereof are shown below:

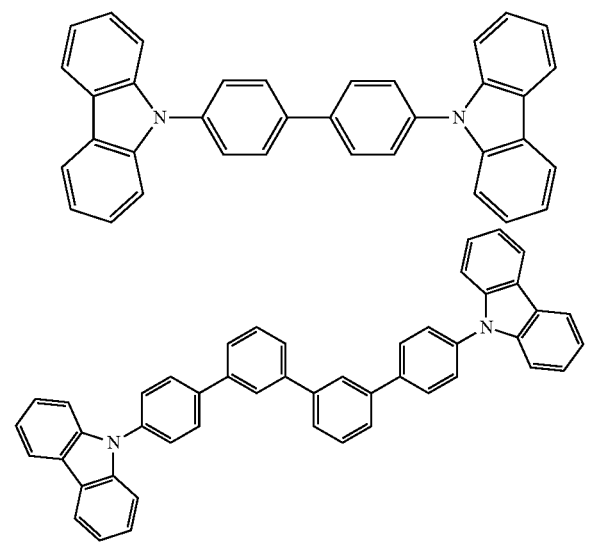

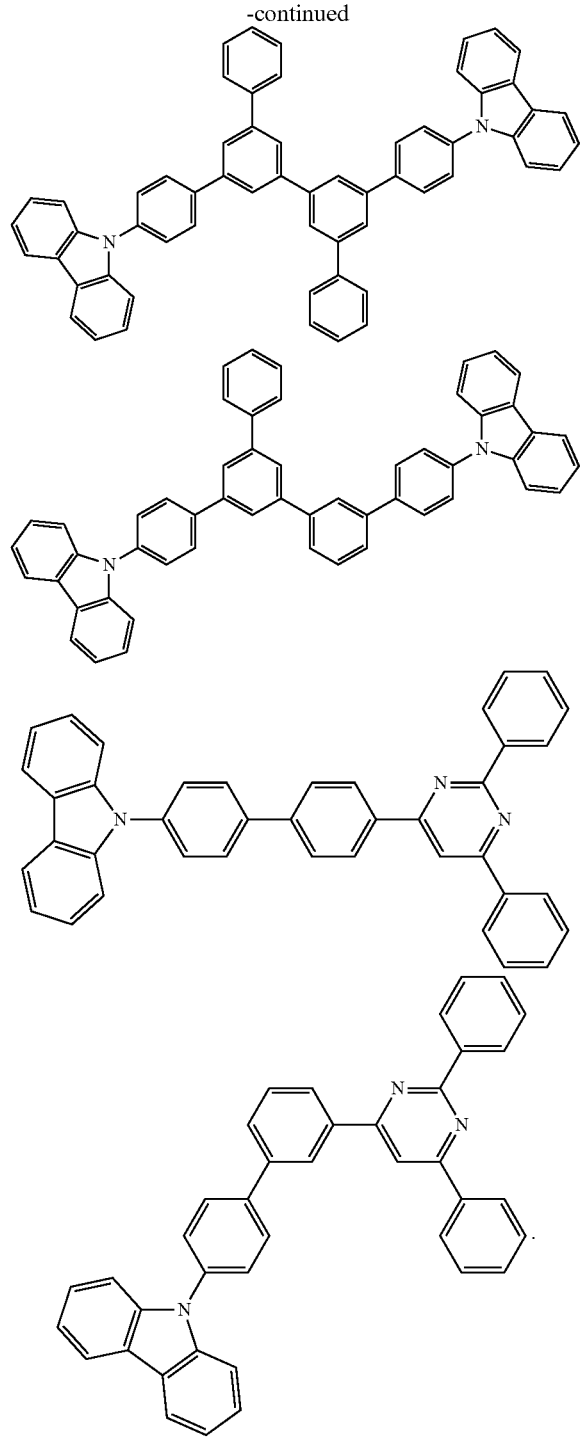

Electron-Donating Dopant

The organic EL device in an aspect of the invention preferably comprises an electron-donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include an alkali oxide, such as $Li_2O$, $Cs_2O$, and $K_2O$, and an alkali halide, such as LiF, NaF, CsF, and KF, with LiF, $Li_2O$, and NaF being preferred. Examples of the alkaline earth metal compound include BaO, SrO, CaO, and a mixture thereof, such as $Ba_xSr_{1-x}O$ (0<x<1) and $Ba_xCa_{1-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, the alkaline earth metal complex, and the rare earth metal are not particularly limited as long as containing at least one metal ion selected from an alkali metal ion, an alkaline earth metal ion, and a rare earth metal ion, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivatives thereof.

The electron-donating dopant is added to the interfacial region preferably into a form of layer or island preferably by co-depositing the electron-donating dopant together with an organic compound for forming the interfacial region (a light emitting material and an electron injecting material) by a resistance heating deposition method, thereby dispersing the electron-donating dopant into the organic compound. The disperse concentration expressed by the molar ratio of organic compound:electron-donating dopant is 100:1 to 1:100 and preferably 5:1 to 1:5.

When the electron-donating dopant is formed into a form of layer, an organic compound (a light emitting material or an electron injecting material) is made into a layer to form an interfacial organic layer, and then, the electron-donating dopant alone is deposited by a resistance heating deposition method into a layer having a thickness of preferably 0.1 to 15 nm. When the electron-donating dopant is formed into a form of island, an organic compound (a light emitting material or an electron injecting material) is made into a form of island to form an interfacial organic layer, and then, the electron-donating dopant alone is deposited by a resistance heating deposition method into a form of island having a thickness of preferably 0.05 to 1 nm.

The molar ratio of the organic compound and the electron-donating dopant in the organic EL device in an aspect of the invention is preferably 5:1 to 1:5 and more preferably 2:1 to 1:2.

Electron Injecting Layer

The electron injecting layer is a layer comprising a compound having a high electron injecting ability, for example, an alkali metal, an alkaline earth metal and a compound thereof, such as lithium (Li), lithium fluoride (LiF), cesium fluoride (CsF), calcium fluoride (CaF2), and lithium oxide (LiOx).

Electron Transporting Layer

The electron transporting layer is an organic layer disposed between a light emitting layer and a cathode and transports electrons from the cathode to the light emitting layer. If two or more electron transporting layers are provided, the organic layer closer to the cathode may be defined as an electron injecting. The electron injecting layer injects electrons from the cathode to the organic layer unit efficiently. The compound (1) and the material for organic EL devices may be used in the electron transporting layer as an electron transporting material.

Another electron transporting material usable in the electron transporting layer may include (1) a metal complex, such as an aluminum complex, a beryllium complex, and a zinc complex; (2) an aromatic heterocyclic compound, such as an imidazole derivative, a benzimidazole derivative, an azine derivative, a carbazole derivative, and a phenanthroline derivative; and (3) a polymer.

In addition, an aromatic heterocyclic compound having one or more heteroatoms in its molecule is preferably used as an electron transporting material for use in the electron transporting layer, and a nitrogen-containing ring derivative is particularly preferred. The nitrogen-containing ring derivative is preferably an aromatic ring compound having a nitrogen-containing 6- or 5-membered ring, or a fused aromatic ring compound having a nitrogen-containing 6- or 5-membered ring.

The nitrogen-containing ring derivative is preferably a metal chelate complex having a nitrogen-containing ring represented by formula (A):

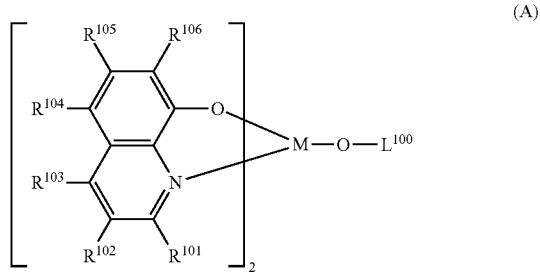

(A)

wherein $R^{101}$ to $R^{105}$ each independently represent a hydrogen atom, a halogen atom, a hydroxyl group, an amino group, a hydrocarbon group having 1 to 40, preferably 1 to 20, more preferably 1 to 10, and still more preferably 1 to 5 carbon atoms, an alkoxy group having 1 to 40, preferably 1 to 20, more preferably 1 to 10, and still more preferably 1 to 5 carbon atoms, an aryloxy group having 6 to 50, preferably 6 to 20, and more preferably 6 to 12 ring carbon atoms, an alkoxycarbonyl group having 2 to 40, preferably 2 to 20, more preferably 2 to 10, and still more preferably 2 to 5 carbon atoms, or an aromatic heterocyclic group having 5 to 50, preferably 5 to 30, and more preferably 5 to 20 ring atoms, each optionally having a substituent.

The halogen atom may include fluorine, chlorine, bromine, and iodine.

The substituted amino group may include an alkylamino group, an arylamino group, and an aralkylamino group.

The alkylamino group and the aralkylamino group are represented by —NQ$^1$Q$^2$. Q$^1$ and Q$^2$ each independently represent an alkyl group having 1 to 20 carbon atoms or an aralkyl group having 1 to 20 carbon atoms. One of Q$^1$ and Q$^2$ may be a hydrogen atom.

The arylamino group is represented by —NAr$^{1'}$Ar$^{2'}$, wherein Ar$^{1'}$ and Ar$^{2'}$ each independently represent a non-fused aromatic hydrocarbon group or a fused aromatic hydrocarbon group, each having 6 to 50 carbon atoms. One of Ar$^{1'}$ and Ar$^{2'}$ may be a hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by —COOY', wherein Y' is an alkyl group having 1 to 20 carbon atoms.

M is aluminum (Al), gallium (Ga), or indium (In), with In being preferred.

$L^{100}$ is a group represented by formula (A') or (A"):

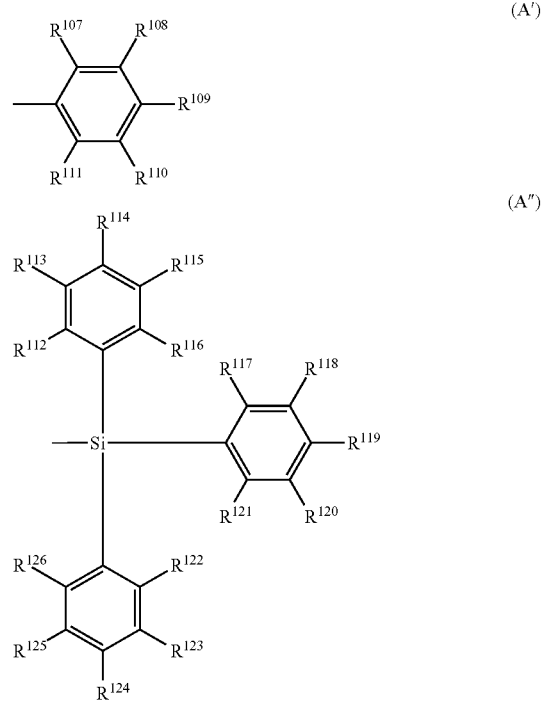

$R^{107}$ to $R^{111}$ of formula (A') each independently represent a hydrogen atom or a substituted or unsubstituted hydrocarbon group having 1 to 40, preferably 1 to 20, more preferably 1 to 10, and still more preferably 1 to 5 carbon atoms, wherein two or more selected from $R^{107}$ to $R^{111}$ may be bonded to each other form a ring structure. $R^{112}$ to $R^{126}$ of formula (A") each independently represent a hydrogen atom or a substituted or unsubstituted hydrocarbon group having 1 to 40, preferably 1 to 20, more preferably 1 to 10, and still more preferably 1 to 5 carbon atoms, wherein two or more selected from $R^{112}$ to $R^{126}$ may be bonded to each other form a ring structure.

Examples of the hydrocarbon group having 1 to 40 carbon atoms for $R^{107}$ to $R^{126}$ of formulae (A') and (A") are the same as those described above with respect to $R^{101}$ to $R^{106}$ of formula (A). Examples of the divalent group formed by two or more selected from $R^{107}$ to $R^{111}$, or two or more selected from $R^{112}$ to $R^{126}$ which completes a ring structure include a tetramethylene group, a pentamethylene group, a hexamethylene group, a diphenylmethane-2,2'-diyl group, a diphenylethane-3,3'-diyl group, and a diphenylpropane-4,4'-diyl group.

The electron transporting compound for use in the electron transporting layer is preferably a metal complex including 8-hydroxyquinoline or its derivative, an oxadiazole derivative, or a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

bon group include a phenylene group, a naphthylene group, a biphenylene group, an anthranylene group, a perylenylene group, and a pyrenylene group. The optional substituent may be an alkyl group having 1 to 10 carbon atoms, an alkoxyl group having 1 to 10 carbon atoms or a cyano group.

An electron transporting compound which has a good thin film-forming property is preferably used. Examples thereof are shown below:

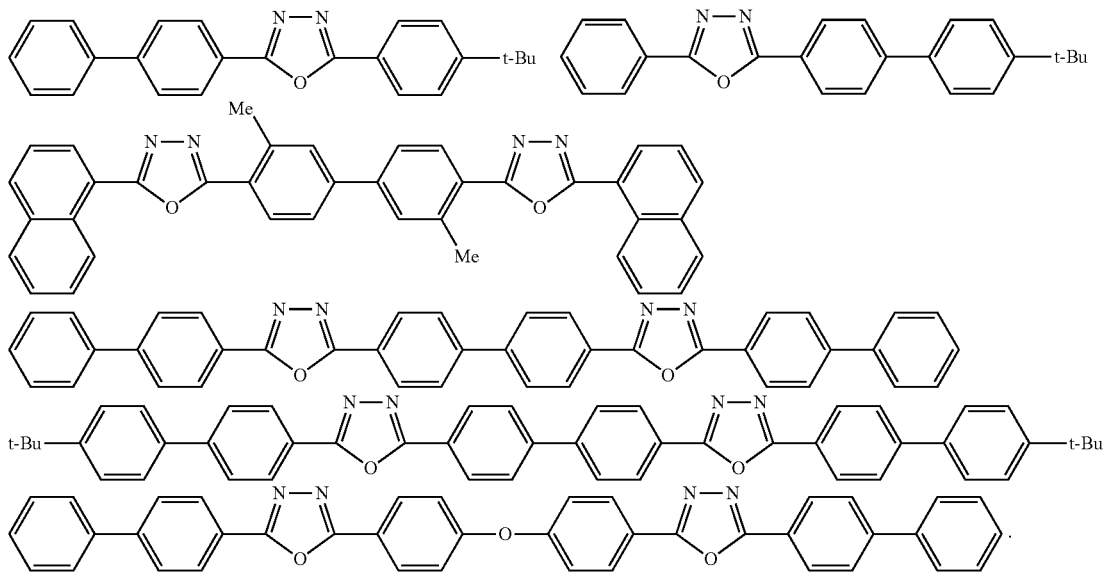

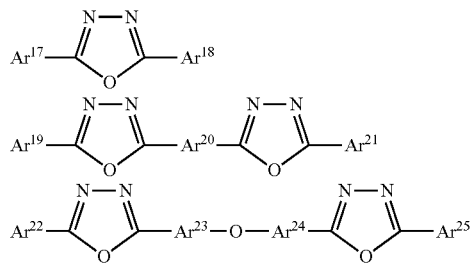

wherein $Ar^{17}$, $Ar^{18}$, $Ar^{19}$, $Ar^{21}$, $Ar^{22}$, and $Ar^{25}$ are each a substituted or unsubstituted aromatic hydrocarbon group or a substituted or unsubstituted fused aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different, respectively. Examples of the aromatic hydrocarbon group and the fused aromatic hydrocarbon group include a phenyl group, a naphthyl group, a biphenyl group, an anthranyl group, a perylenyl group, and a pyrenyl group. The optional substituent may be an alkyl group having 1 to 10 carbon atoms, an alkoxyl group having 1 to 10 carbon atoms or a cyano group.

$Ar^{20}$, $Ar^{23}$, and $Ar^{24}$ are each a substituted or unsubstituted divalent aromatic hydrocarbon group or a substituted or unsubstituted divalent fused aromatic hydrocarbon group each having 6 to 50 carbon atoms, and $Ar^{23}$ and $Ar^{24}$ may be the same or different. Examples of the divalent aromatic hydrocarbon group or the divalent fused aromatic hydrocar- Examples of the nitrogen-containing heterocyclic derivative for use as the electron transporting compound include a nitrogen-containing heterocyclic derivative having the following formulae but exclusive of a metal complex, for example, a compound having a 5- or 6-membered ring which includes a skeleton represented by formula (B) or having a structure represented by formula (C):

 (B)

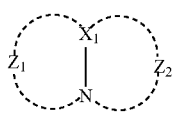 (C)

wherein $X_1$ is a carbon atom or a nitrogen atom and $Z_1$ and $Z_2$ each independently represent a group of atoms for completing the nitrogen-containing heterocyclic ring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of formulae (B) and (C) or a combination of formulae (B) and (D):

(D)

The nitrogen-containing group of the nitrogen-containing aromatic polycyclic compound is selected, for example, from the nitrogen-containing heterocyclic groups shown below:

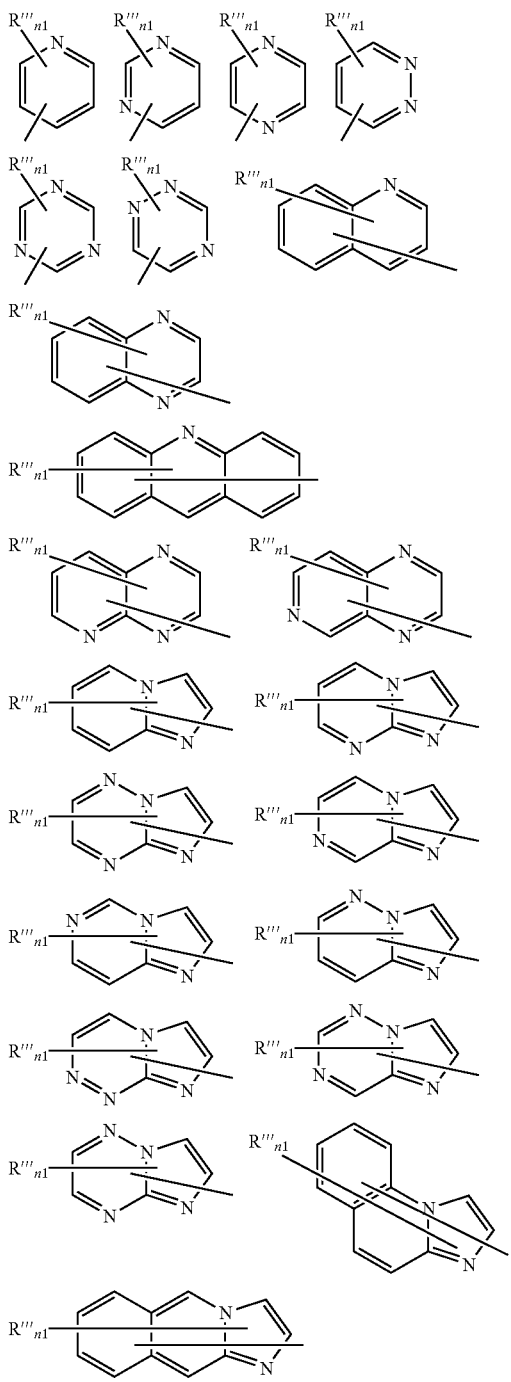

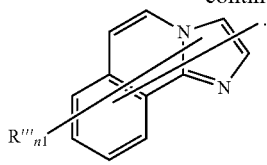

wherein R''' is an aromatic hydrocarbon group having 6 to 40, preferably 6 to 30, more preferably 6 to 20, and still more preferably 6 to 12 ring carbon atoms, a fused aromatic hydrocarbon group having 6 to 40, preferably 6 to 30, more preferably 6 to 20, and still more preferably 6 to 12 ring carbon atoms, an aromatic heterocyclic group having 5 to 40, preferably 5 to 30, more preferably 5 to 20, and still more preferably 5 to 12 ring atoms, a fused aromatic heterocyclic group having 5 to 40, preferably 5 to 30, more preferably 5 to 20, and still more preferably 5 to 12 ring atoms, an alkyl group having 1 to 20, preferably 1 to 10, and more preferably 1 to 5 carbon atoms, or an alkoxy group having 1 to 20, preferably 1 to 10, and more preferably 1 to 5 carbon atoms; and $n_1$ is an integer of 0 to 5 and when $n_1$ is an integer of 2 or more, groups R''' may be the same or different.

A nitrogen-containing heterocyclic derivative represented by formula (D1) is also preferred:

$$HAr\text{-}L^{101}\text{-}Ar^{101}\text{---}Ar^{102} \quad (D1)$$

wherein:

HAr is a substituted or unsubstituted nitrogen-containing heterocyclic group having 5 to 40, preferably 5 to 30, more preferably 5 to 20, and still more preferably 5 to 12 ring atoms;

$L^{101}$ is a single bond, a substituted or unsubstituted aromatic hydrocarbon group or fused aromatic hydrocarbon group each having 6 to 40, preferably 6 to 30, more preferably 6 to 20, and still more preferably 6 to 12 ring carbon atoms, a substituted or unsubstituted aromatic heterocyclic group having 5 to 40, preferably 5 to 30, more preferably 5 to 20, and still more preferably 5 to 12 ring atoms, or a substituted or unsubstituted fused aromatic heterocyclic group having 6 to 40, preferably 6 to 30, more preferably 6 to 20, and still more preferably 6 to 12 ring carbon atoms; and $Ar^{101}$ is a substituted or unsubstituted divalent aromatic hydrocarbon group having 6 to 40, preferably 6 to 30, more preferably 6 to 20, and still more preferably 6 to 12 ring carbon atoms; and $Ar^{102}$ is a substituted or unsubstituted aromatic hydrocarbon group having 6 to 40, preferably 6 to 30, more preferably 6 to 20, and still more preferably 6 to 14 ring carbon atoms, a substituted or unsubstituted fused aromatic hydrocarbon group having 6 to 40, preferably 6 to 30, more preferably 6 to 20, and still more preferably 6 to 12 ring carbon atoms, a substituted or unsubstituted aromatic heterocyclic group having 5 to 40, preferably 5 to 30, more preferably 5 to 20, and still more preferably 5 to 12 ring atoms, or a substituted or unsubstituted fused aromatic heterocyclic group having 5 to 40, preferably 5 to 30, more preferably 5 to 20, and still more preferably 5 to 12 ring atoms.

HAr is selected, for example, from the following groups:
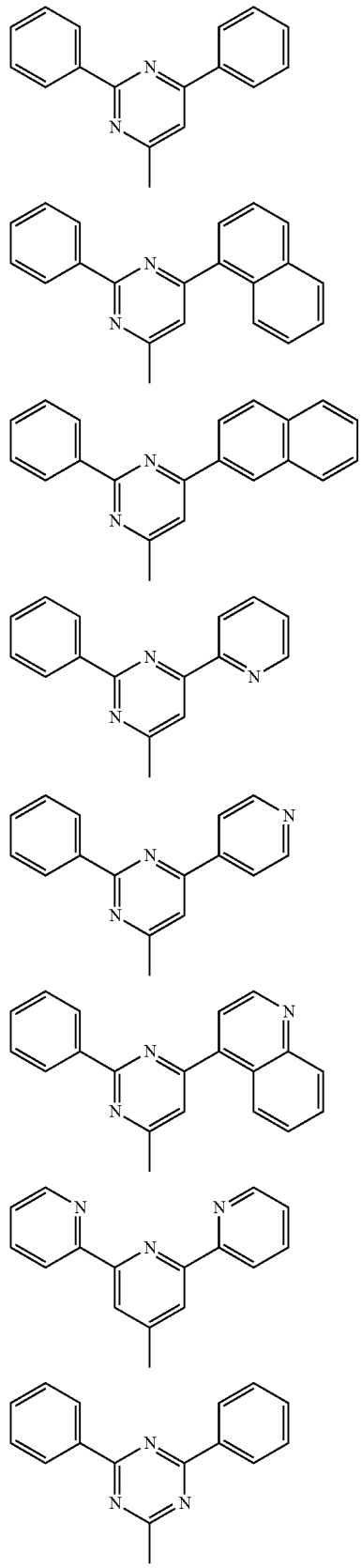
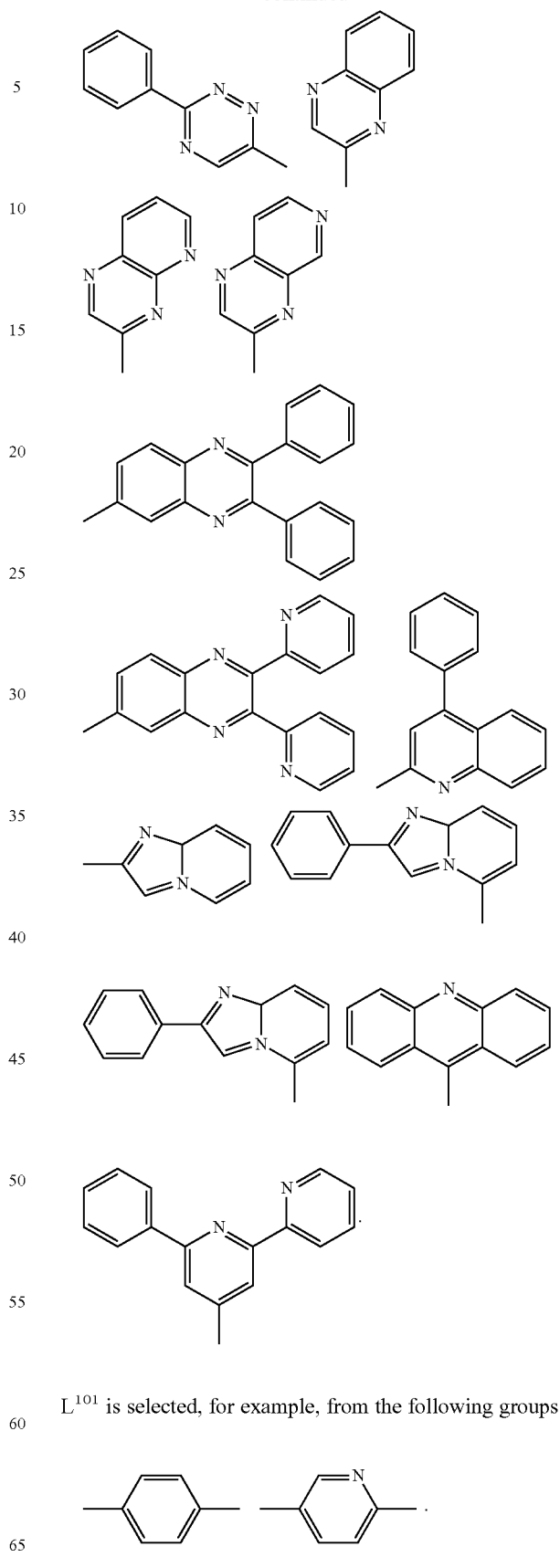
L$^{101}$ is selected, for example, from the following groups:
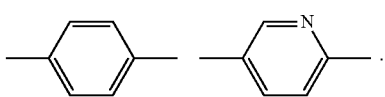

Ar$^{101}$ is selected, for example, from the group represented by formula (D2) or (D3):

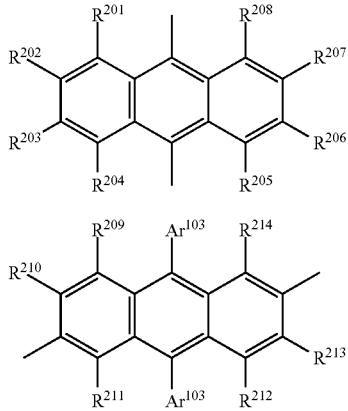

(D2)

(D3)

wherein:
R$^{201}$ to R$^{214}$ are each independently a hydrogen atom, a halogen atom, a substituted or unsubstituted alkyl group having 1 to 20, preferably 1 to 10, and more preferably 1 to 5 carbon atoms, a substituted or unsubstituted alkoxy group having 1 to 20, preferably 1 to 10, and more preferably 1 to 5 carbon atoms, a substituted or unsubstituted aryloxy group having 6 to 40, preferably 6 to 30, more preferably 6 to 20, and still more preferably 6 to 12 ring carbon atoms, a substituted or unsubstituted aromatic hydrocarbon group having 6 to 40, preferably 6 to 30, more preferably 6 to 20, and still more preferably 6 to 12 ring carbon atoms, a substituted or unsubstituted fused aromatic hydrocarbon group having 6 to 40, preferably 6 to 30, more preferably 6 to 20, and still more preferably 6 to 12 ring carbon atoms, a substituted or unsubstituted aromatic heterocyclic group having 5 to 40, preferably 5 to 30, more preferably 5 to 20, and still more preferably 5 to 12 ring atoms, or a substituted or unsubstituted fused aromatic heterocyclic group having 5 to 40, preferably 5 to 30, more preferably 5 to 20, and still more preferably 5 to 12 ring atoms; and Ar$^{103}$ is a substituted or unsubstituted aromatic hydrocarbon group having 6 to 40, preferably 6 to 30, more preferably 6 to 20, and still more preferably 6 to 12 ring carbon atoms, a substituted or unsubstituted fused aromatic hydrocarbon group having 6 to 40, preferably 6 to 30, more preferably 6 to 20, and still more preferably 6 to 12 ring carbon atoms, a substituted or unsubstituted aromatic heterocyclic group having 5 to 40, preferably 5 to 30, more preferably 5 to 20, and still more preferably 5 to 12 ring atoms, or a substituted or unsubstituted fused aromatic heterocyclic group having 5 to 40, preferably 5 to 30, more preferably 5 to 20, and still more preferably 5 to 12 ring atoms.

Ar$^{102}$ is selected, for example, from the following groups:

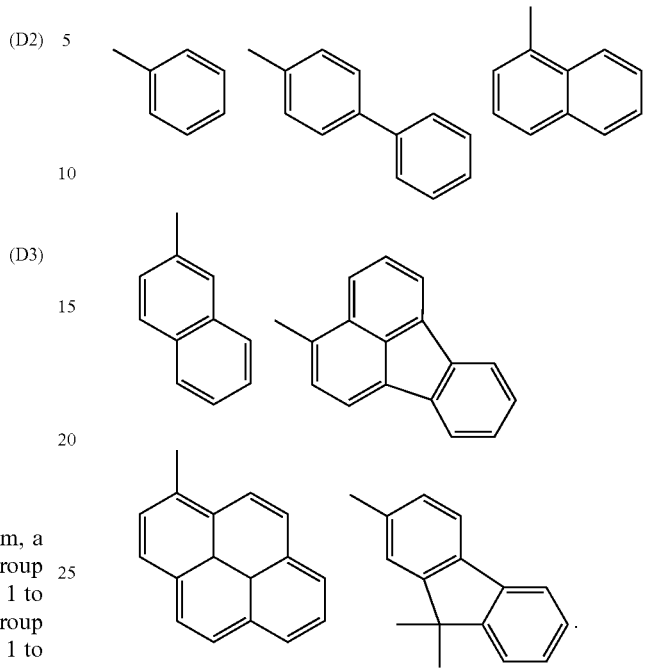

In addition, the following compound is preferably used as the nitrogen-containing aromatic polycyclic compound for use as the electron transporting compound:

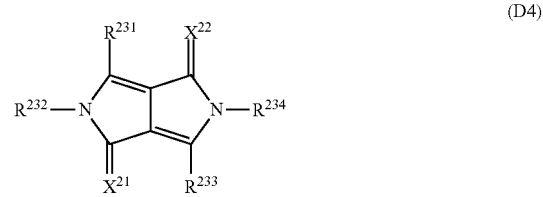

(D4)

wherein R$^{231}$ to R$^{234}$ each independently represent a hydrogen atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and X$^{21}$ and X$^{22}$ each independently represent an oxygen atom, a sulfur atom, or a dicyanomethylene group.

Further, the following compound is also suitable as the electron transporting compound:

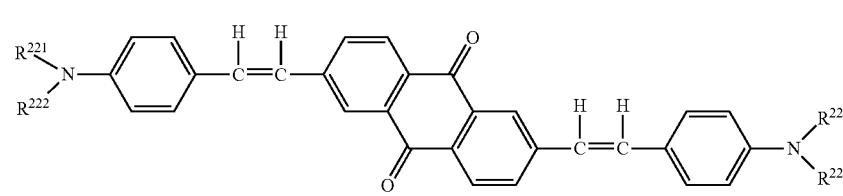

(D5)

wherein $R^{221}$, $R^{222}$, $R^{223}$, and $R^{224}$ may be the same or different and each represent an aromatic hydrocarbon group or a fused aromatic hydrocarbon group each represented by formula (D6):

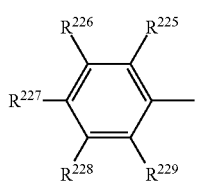

(D6)

wherein $R^{225}$, $R^{226}$, $R^{227}$, $R^{228}$, and $R^{229}$ may be the same or different and each represent a hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms; and at least one selected from $R^{225}$, $R^{22}$, $R^{227}$, $R^{228}$, and $R^{229}$ represents a group other than a hydrogen atom.

Further, a polymer including the nitrogen-containing heterocyclic group or the nitrogen-containing heterocyclic derivative is also usable as the electron transporting compound.

The electron transporting layer of the organic EL device in an aspect of the invention preferably comprises at least one compound selected from the nitrogen-containing heterocyclic derivatives represented by formulae (E) to (G):

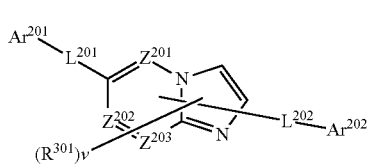

(E)

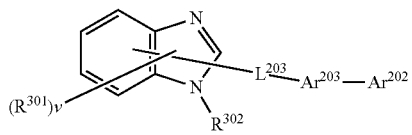

(F)

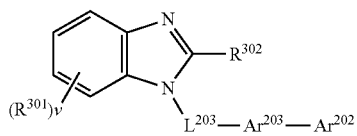

(G)

wherein $Z^{201}$, $Z^{202}$ and $Z^{203}$ each independently represent a nitrogen atom or a carbon atom;

$R^{301}$ and $R^{302}$ each independently represent a substituted or unsubstituted aryl group having 6 to 50, preferably 6 to 30, more preferably 6 to 20, and still more preferably 6 to 12 ring carbon atoms, a substituted or unsubstituted heteroaryl group having 5 to 50, preferably 5 to 30, more preferably 5 to 20, and still more preferably 5 to 12 ring atoms, a substituted or unsubstituted alkyl group having 1 to 20 carbon atoms, a substituted or unsubstituted haloalkyl group having 1 to 20 carbon atoms, or a substituted or unsubstituted alkoxy group having 1 to 20 carbon atoms;

v is an integer of 0 to 5, when v is an integer of 2 or more, groups $R^{301}$ may be the same or different, and adjacent two groups $R^{301}$ may bond to each other to form a substituted or unsubstituted hydrocarbon ring;

$Ar^{201}$ represents a substituted or unsubstituted aryl group having 6 to 50, preferably 6 to 30, more preferably 6 to 20, and still more preferably 6 to 12 ring carbon atoms or a substituted or unsubstituted heteroaryl group having 5 to 50, preferably 5 to 30, more preferably 5 to 20, and still more preferably 5 to 12 ring atoms;

$Ar^{202}$ represents a hydrogen atom, a substituted or unsubstituted alkyl group having 1 to 20, preferably 1 to 10, and more preferably 1 to 5 carbon atoms, a substituted or unsubstituted haloalkyl group having 1 to 20, preferably 1 to 10, and more preferably 1 to 5 carbon atoms, a substituted or unsubstituted alkoxy group having 1 to 20 carbon atoms, a substituted or unsubstituted aryl group having 6 to 50, preferably 6 to 30, more preferably 6 to 20, and still more preferably 6 to 12 ring carbon atoms, or a substituted or unsubstituted heteroaryl group having 5 to 50, preferably 5 to 30, more preferably 5 to 20, and still more preferably 5 to 12 ring atoms;

provided that one of $Ar^{201}$ and $Ar^{202}$ is a substituted or unsubstituted fused aromatic hydrocarbon ring group having 10 to 50, preferably 10 to 30, and more preferably 10 to 20 ring carbon atoms or a substituted or unsubstituted fused aromatic heterocyclic group having 9 to 50, preferably 9 to 30, and more preferably 9 to 20 ring atoms;

$Ar^{203}$ represents a substituted or unsubstituted arylene group having 6 to 50, preferably 6 to 30, more preferably 6 to 20, and still more preferably 6 to 12 ring carbon atoms or a substituted or unsubstituted heteroarylene group having 5 to 50, preferably 5 to 30, more preferably 5 to 20, and still more preferably 5 to 12 ring atoms; and $L^{201}$, $L^{202}$, and $L^{203}$ each independently represent a single bond, a substituted or unsubstituted arylene group having 6 to 50, preferably 6 to 30, more preferably 6 to 20, and still more preferably 6 to 12 ring carbon atoms or a substituted or unsubstituted divalent fused aromatic heterocyclic group having 9 to 50, pre 9 to 30, and more preferably 9 to 20 ring atoms.

Examples of the aryl group having 6 to 50 ring carbon atoms include a phenyl group, a naphthyl group, an anthryl group, a phenanthryl group, a naphthacenyl group, a chrysenyl group, pyrenyl group, a biphenyl group, a terphenyl group, a tolyl group, a fluoranthenyl group, and a fluorenyl group.

Examples of the heteroaryl group having 5 to 50 ring atoms include a pyrrolyl group, a furyl group, a thiophenyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acridinyl group, an imidazo[1,2-a]pyridinyl group, and an imidazo[1,2-a]pyrimidinyl.

Examples of the alkyl group having 1 to 20 carbon atoms include a methyl group, an ethyl group, a propyl group, a butyl group, a pentyl group, and a hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxy group having 1 to 20 carbon atoms include the alkyl group mentioned above.

Examples of the arylene groups include the groups obtained by removing one hydrogen atom from the aryl group mentioned above.

Examples of the divalent fuse aromatic heterocyclic group having 9 to 50 ring atoms include the groups obtained by removing one hydrogen atom from the fused aromatic heterocyclic group mentioned above with respect to the heteroaryl group.

The thickness of the electron transporting layer is preferably 1 to 100 nm, but not particularly limited thereto.

The electron injecting layer optionally formed adjacent to the electron transporting layer preferably comprises an inorganic compound, such as an insulating material and a semiconductor, in addition to the nitrogen-containing ring derivative. The electron injecting layer comprising the insulating material or the semiconductor effectively prevents the leak of electric current to enhance the electron injecting properties.

The insulating material is preferably at least one metal compound selected from the group consisting of an alkali metal chalcogenide, an alkaline earth metal chalcogenide, an alkali metal halide and an alkaline earth metal halide. The electron injecting properties of the electron injecting layer are further enhanced when the alkali metal chalcogenide, etc. is used in the electron injecting layer. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of preferred alkaline earth metal halide include fluorides, such as $CaF_2$, $BaF_2$, $SrF_2$, $MgF_2$ and $BeF_2$, and halides other than fluorides.

Examples of the semiconductor include an oxide, a nitride and an oxynitride of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. The electron injecting layer formed from such an insulating thin film decreases the pixel defects, such as dark spots, because the insulating thin film is highly uniform. Examples of such an inorganic compound include the alkali metal chalcogenide, the alkaline earth metal chalcogenide, the alkali metal halide and the alkaline earth metal halide.

The thickness of a layer comprising the insulating material or the semiconductor is preferably about 0.1 to 15 nm. In an embodiment of the invention, the electron injecting layer may comprise the electron-donating dopant mentioned above.

Hole Injecting Layer

The hole injecting layer comprises a highly hole injecting material, for example, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, and a polymeric compound, such as an oligomer, a dendrimer, and a polymer.

Hole Transporting Layer

The hole transporting layer is an organic layer formed between a light emitting layer and an anode and has a function of transporting holes from the anode to the light emitting layer. If two or more hole transporting layers are provided, the organic layer closer to the anode may be defined as the hole injecting layer in some cases. The hole injecting layer has a function of efficiently injecting holes from the anode to the organic layer unit. In an embodiment of the invention, the compound (1) and the material for organic EL devices may be used in the hole transporting layer as a hole transporting material.

An aromatic amine compound, a carbazole derivative, an anthracene derivative, and a polymeric compound, such as poly(N-vinylcarbazole) (PVK) and poly(4-vinyltriphenylamine) (PVTPA) are also usable as a material for the hole transporting layer. Other materials are also usable if their hole transporting ability is higher than their electron transporting ability. The layer comprising a highly hole-transporting material may be a single layer or a laminate of two or more layers each comprising the material mentioned above.

Another preferred material for use in the hole transporting layer may include an aromatic amine compound, for example, an aromatic amine derivative represented by formula (H):

(H)

wherein:

$Ar^{211}$ to $Ar^{214}$ each represent a substituted or unsubstituted aromatic hydrocarbon group having 6 to 50, preferably 6 to 30, more preferably 6 to 20, and still more preferably 6 to 12 ring carbon atoms, a substituted or unsubstituted fused aromatic hydrocarbon group having 6 to 50, preferably 6 to 30, more preferably 6 to 20, and still more preferably 6 to 12 ring carbon atoms, a substituted or unsubstituted aromatic heterocyclic group having 5 to 50, preferably 5 to 30, more preferably 5 to 20, and still more preferably 5 to 12 ring atoms, a substituted or unsubstituted fused aromatic heterocyclic group having 5 to 50, preferably 5 to 30, more preferably 5 to 20, and still more preferably 5 to 12 ring atoms, or a group wherein the aromatic hydrocarbon group or fused aromatic hydrocarbon group is bonded to the aromatic heterocyclic group or fused aromatic heterocyclic group;

$Ar^{211}$ and $Ar^{212}$ or $Ar^{213}$ and $Ar^{214}$ may be bonded to each other to form a saturated or unsaturated ring structure; and $L^{211}$ represents a substituted or unsubstituted aromatic hydrocarbon group having 6 to 50, preferably 6 to 30, more preferably 6 to 20, and still more preferably 6 to 12 ring carbon atoms, a substituted or unsubstituted fused aromatic hydrocarbon group having 6 to 50, preferably 6 to 30, more preferably 6 to 20, and still more preferably 6 to 12 ring carbon atoms, a substituted or unsubstituted aromatic heterocyclic group having 5 to 50, preferably 5 to 30, more preferably 5 to 20, and still more preferably 5 to 12 ring atoms, or a substituted or unsubstituted fused aromatic heterocyclic group having 5 to 50, preferably 5 to 30, more preferably 5 to 20, and still more preferably 5 to 12 ring atoms.

Examples of the compound represented by formula (H) are shown below:
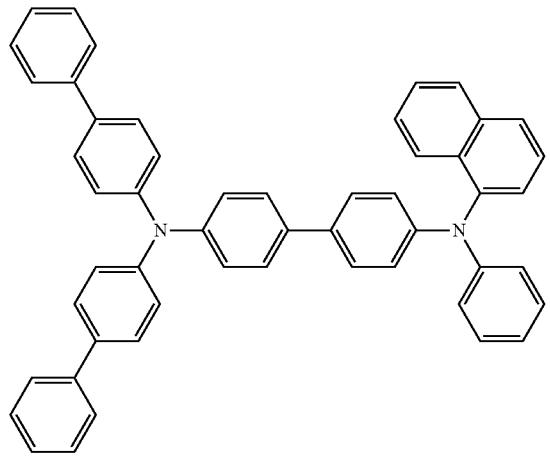
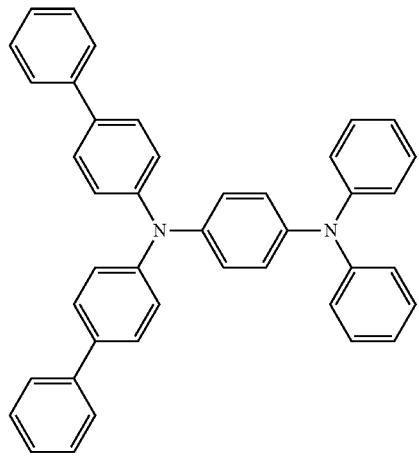
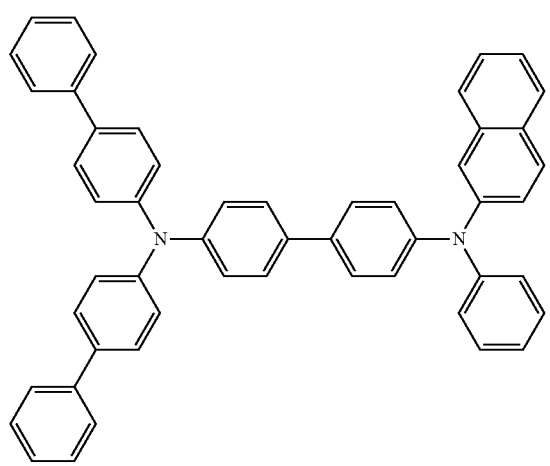
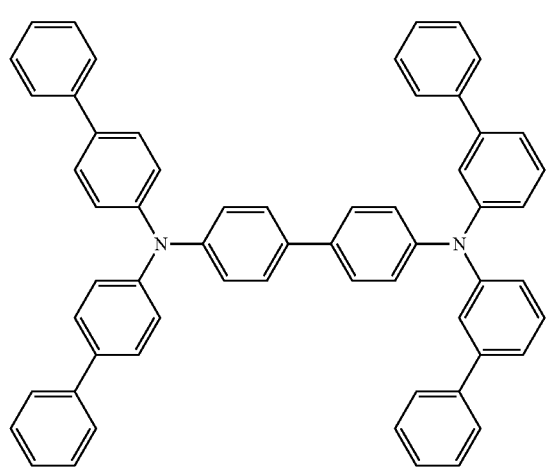
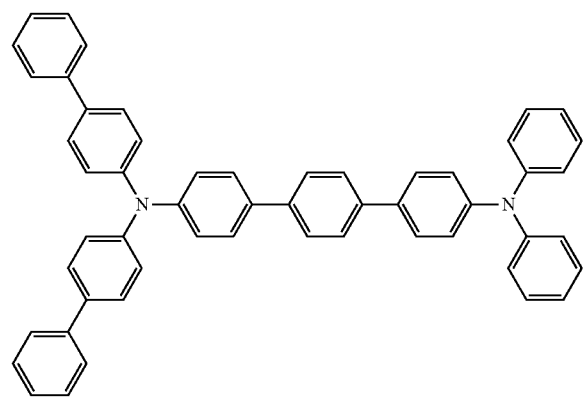
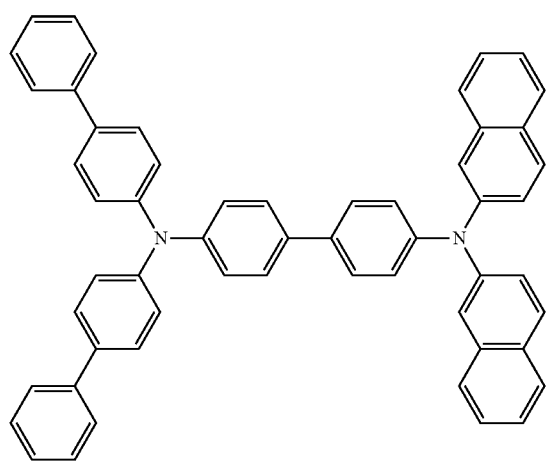

189
-continued
190
-continued
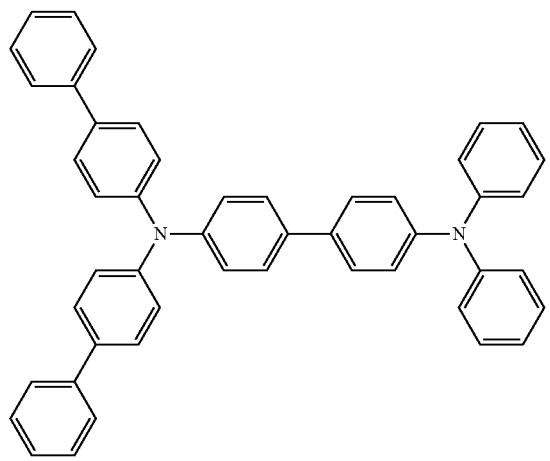
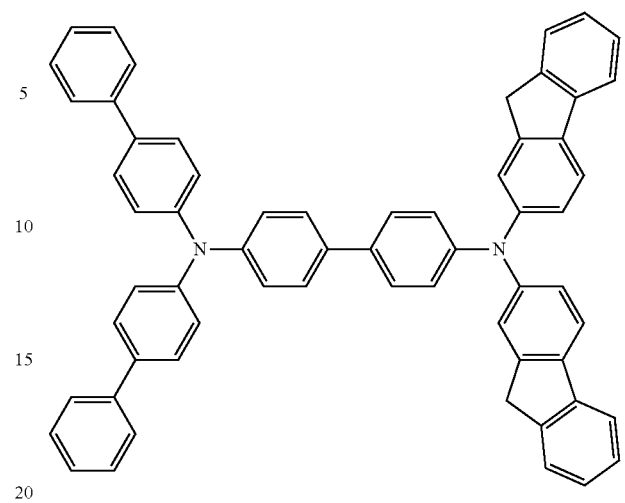
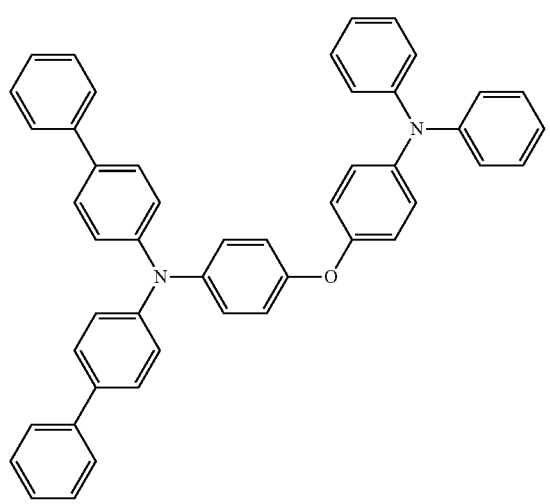
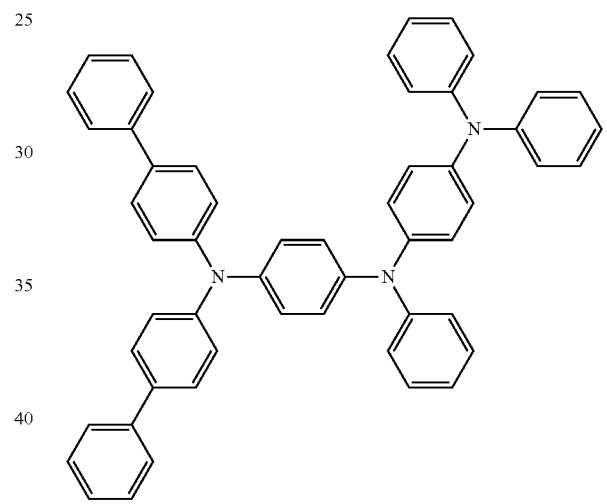
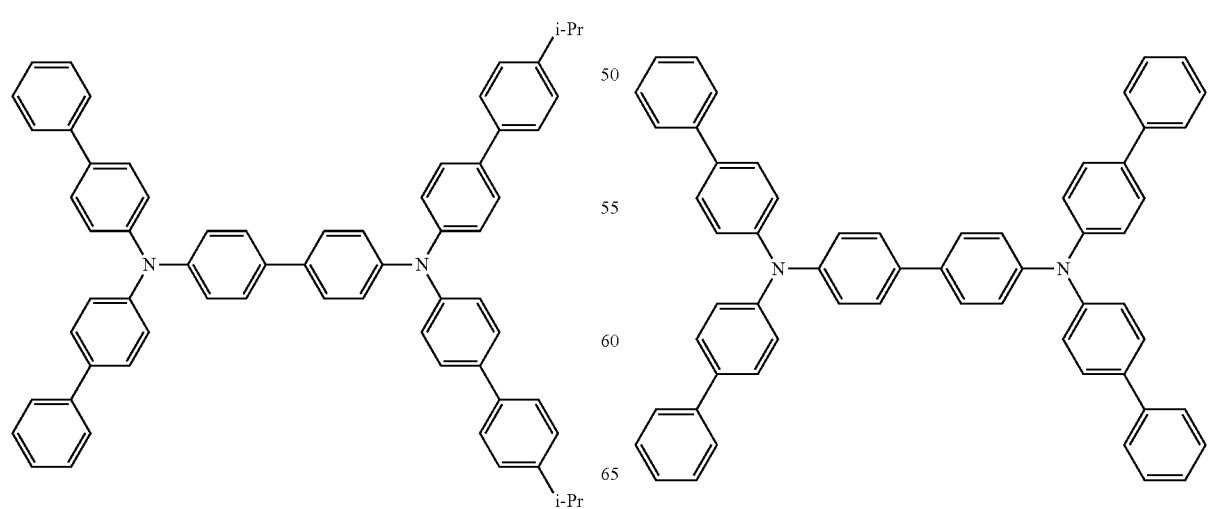

191
-continued
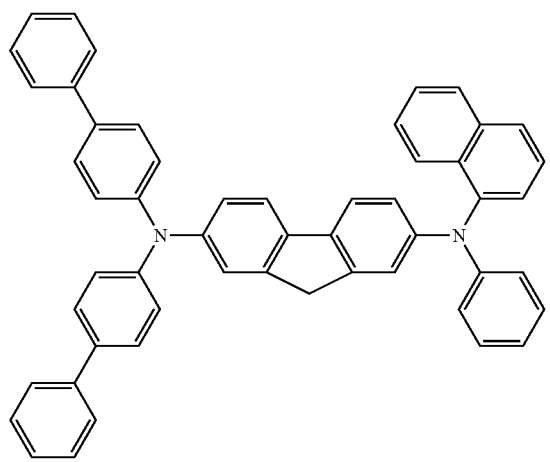
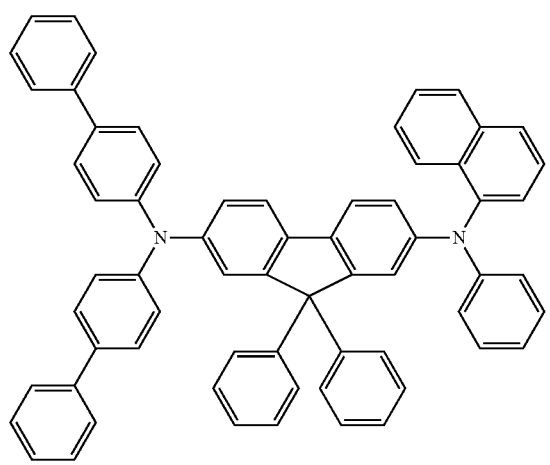
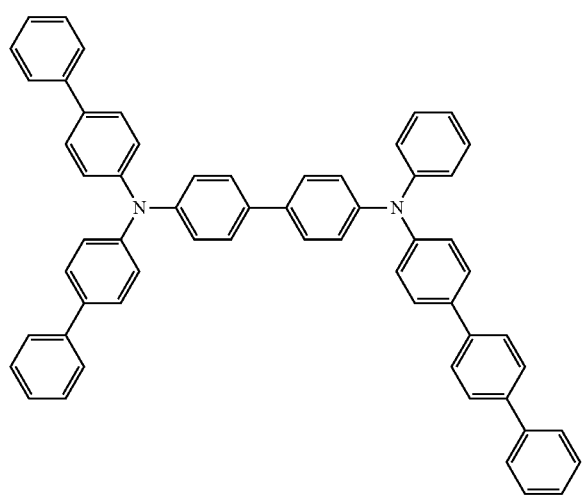
192
-continued
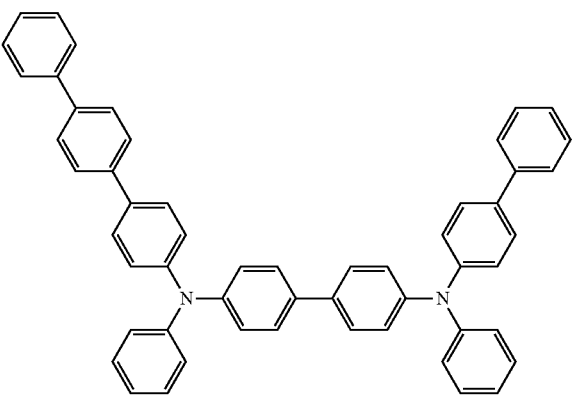
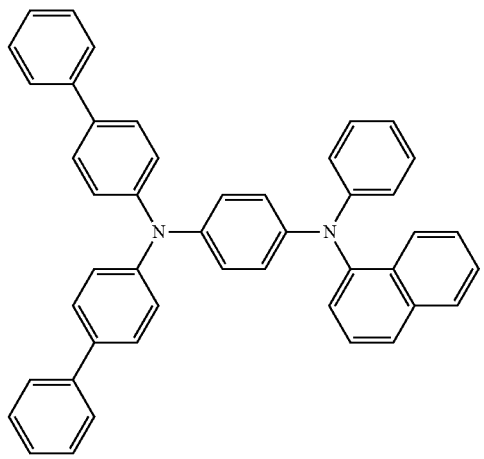
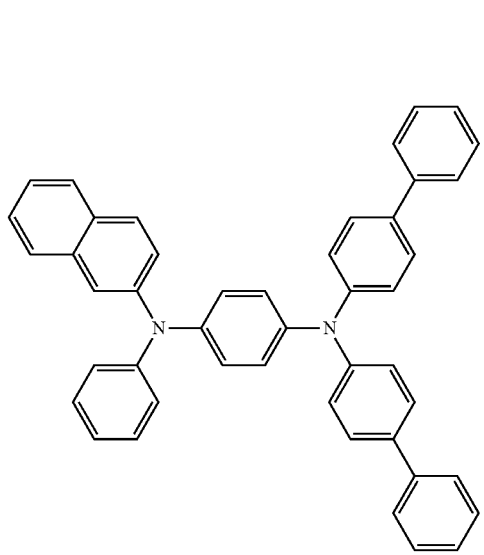

193
-continued
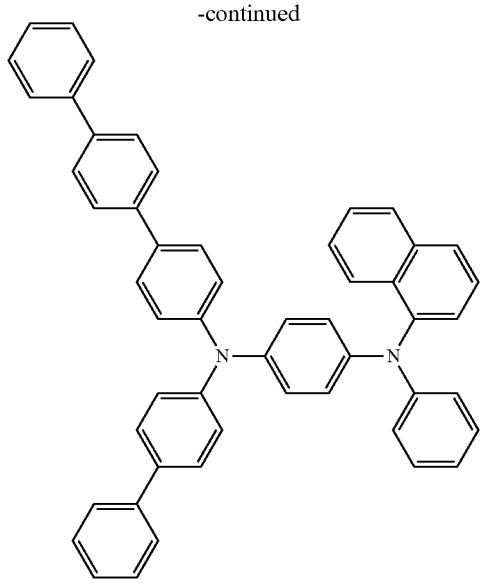
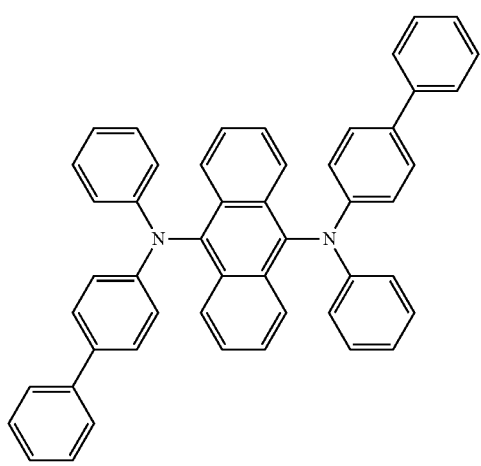
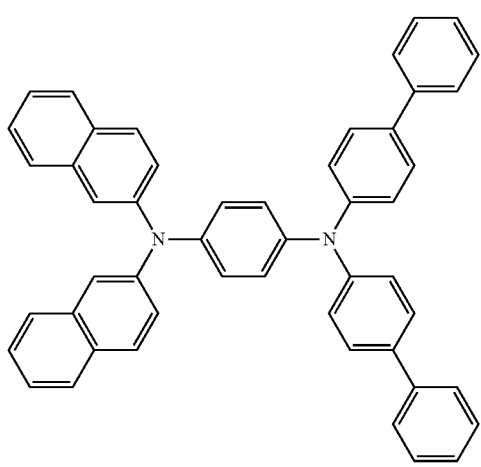
194
-continued
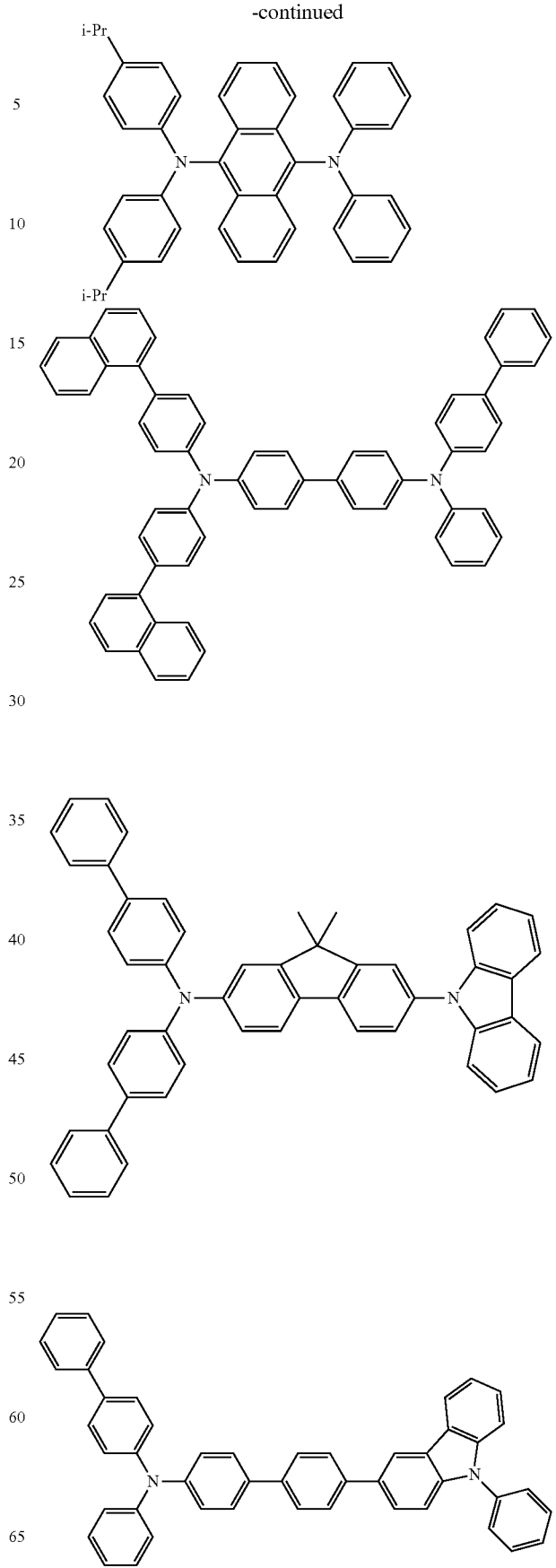

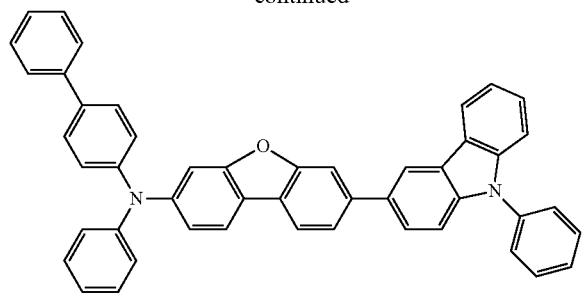
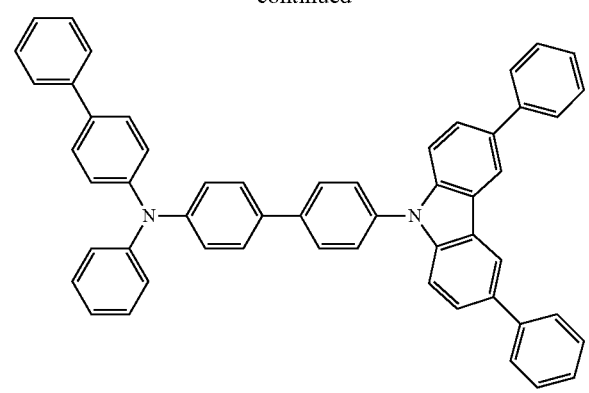
In addition, an aromatic amine represented by formula (J) is preferably used in the hole transporting layer:
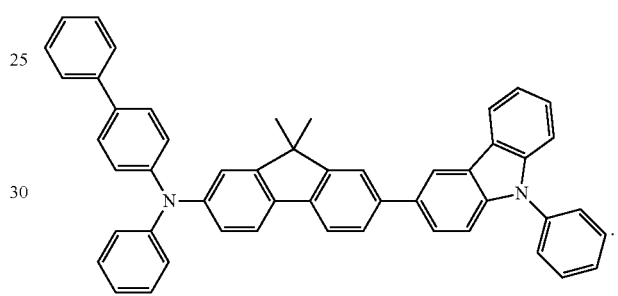
wherein $Ar^{221}$ to $Ar^{223}$ are the same as defined above with respect to $Ar^{211}$ to $Ar^{214}$ of formula (H). Examples of the compound represented by formula (J) are shown below, although not limited thereto.
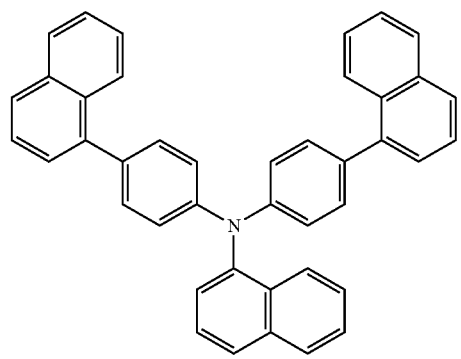

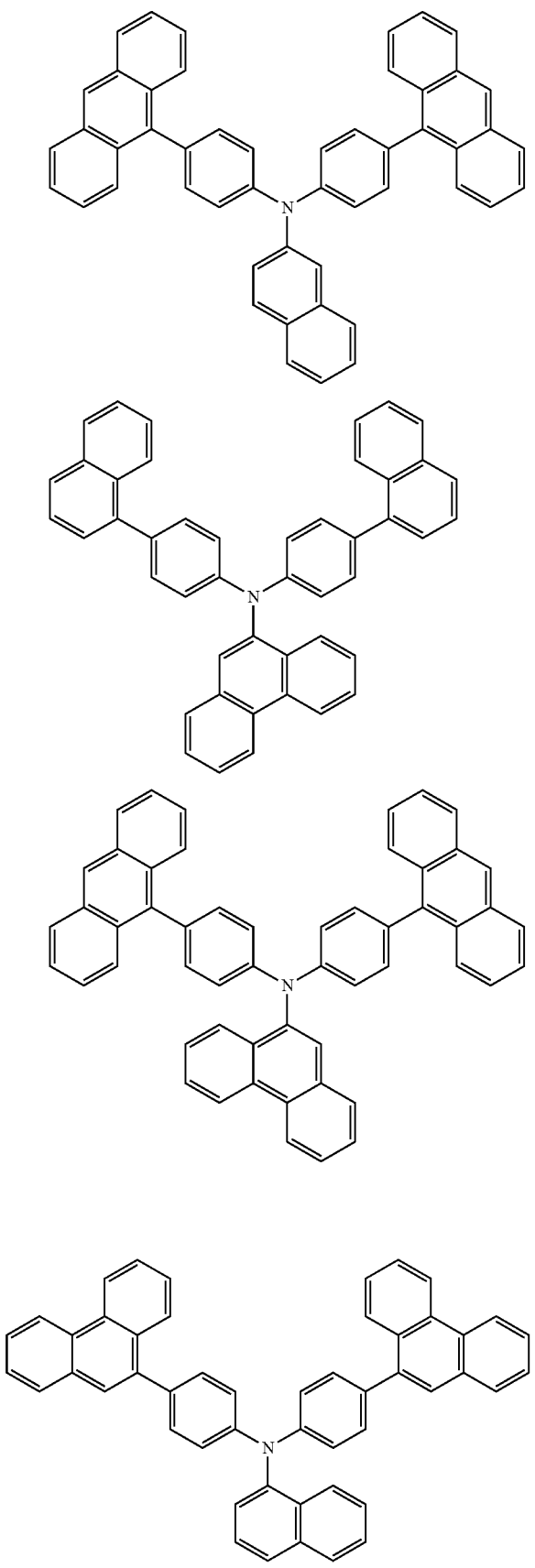
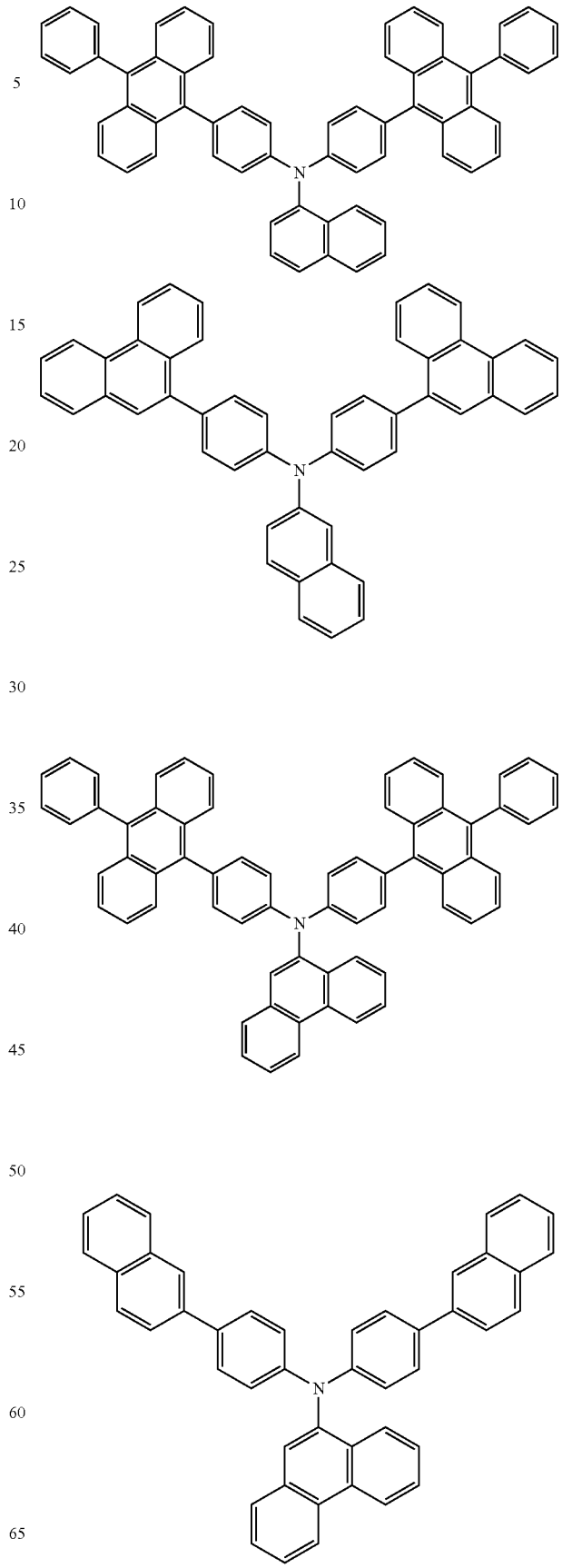

199
-continued
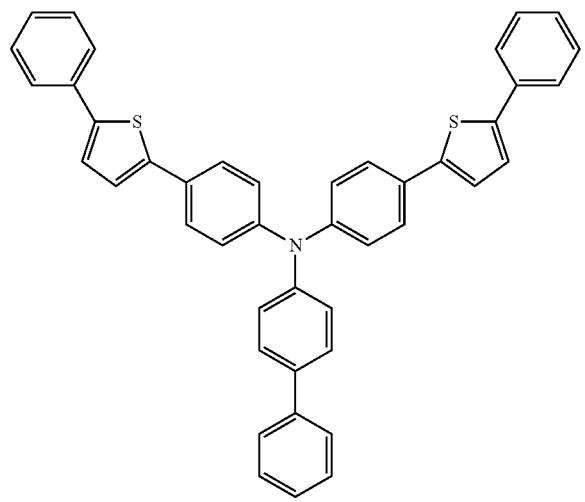
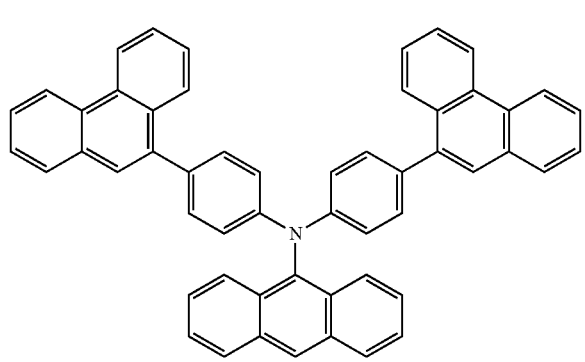
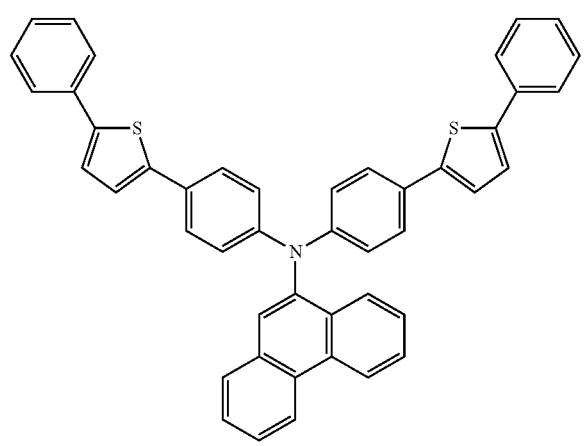
200
-continued
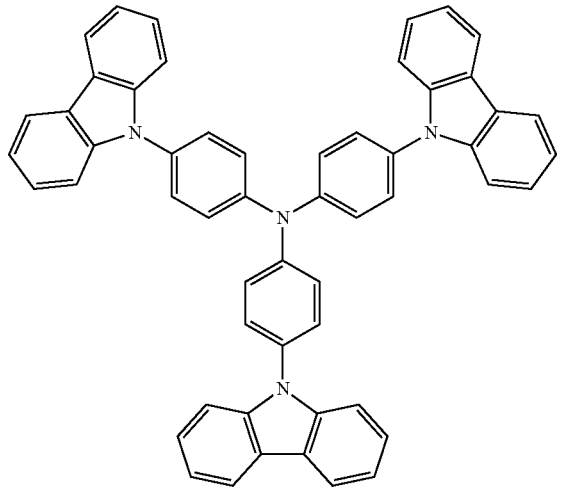
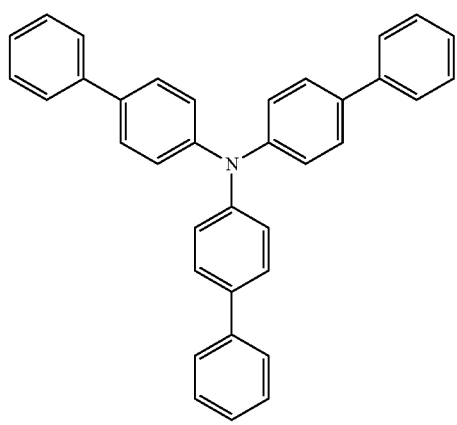
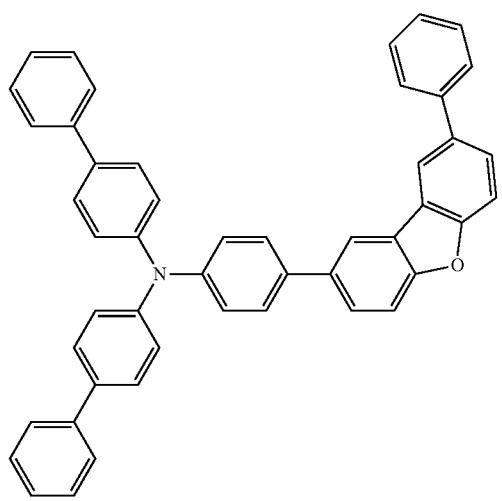

201
-continued
202
-continued
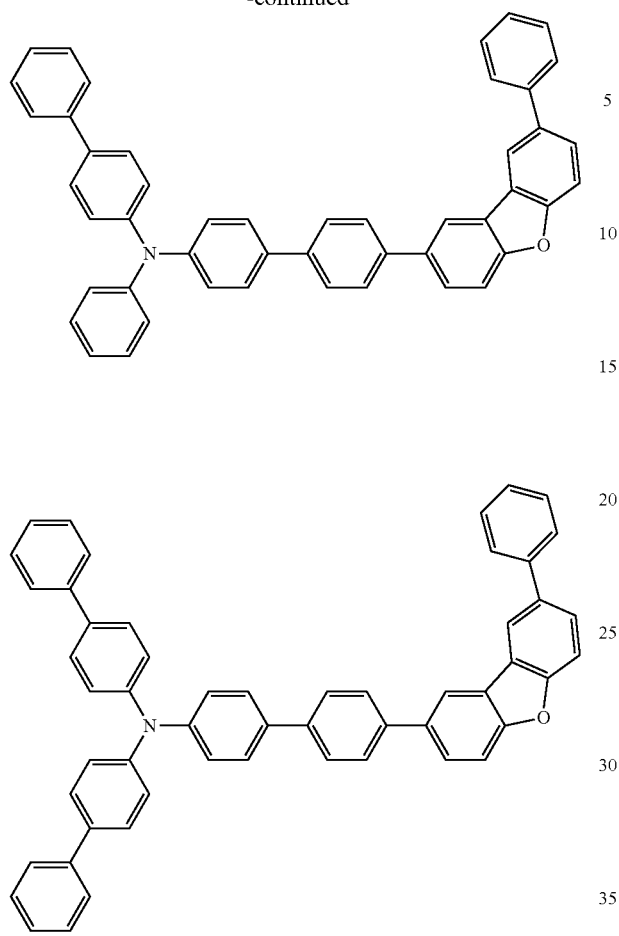
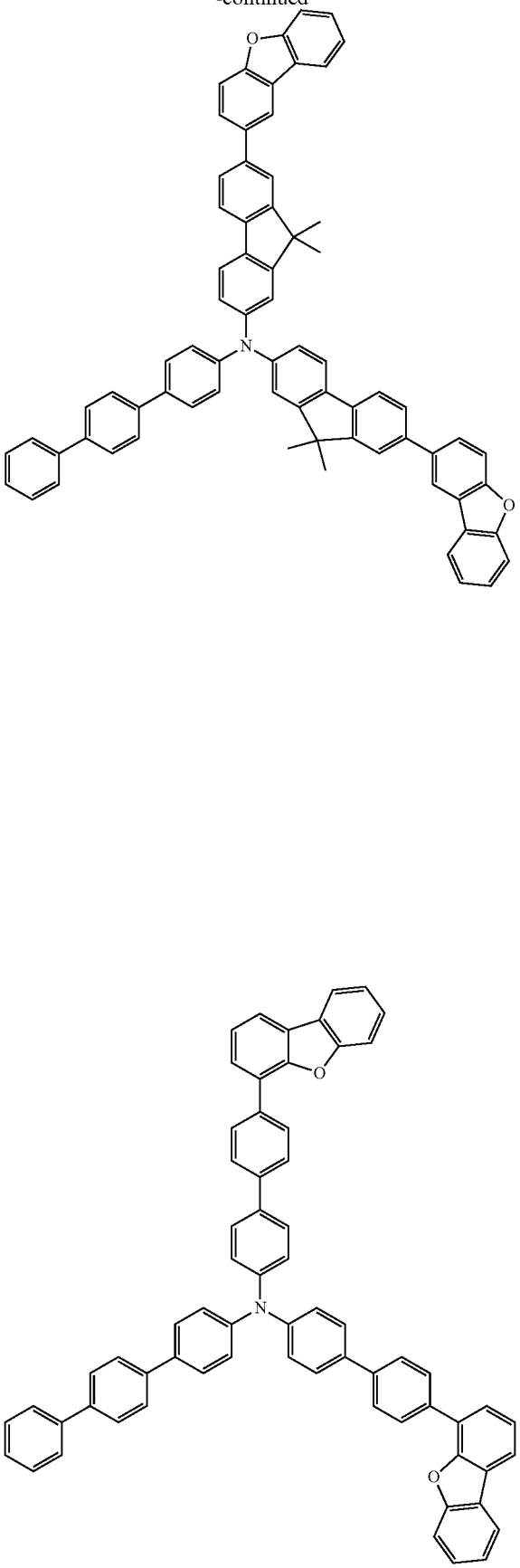

203
-continued
204
-continued
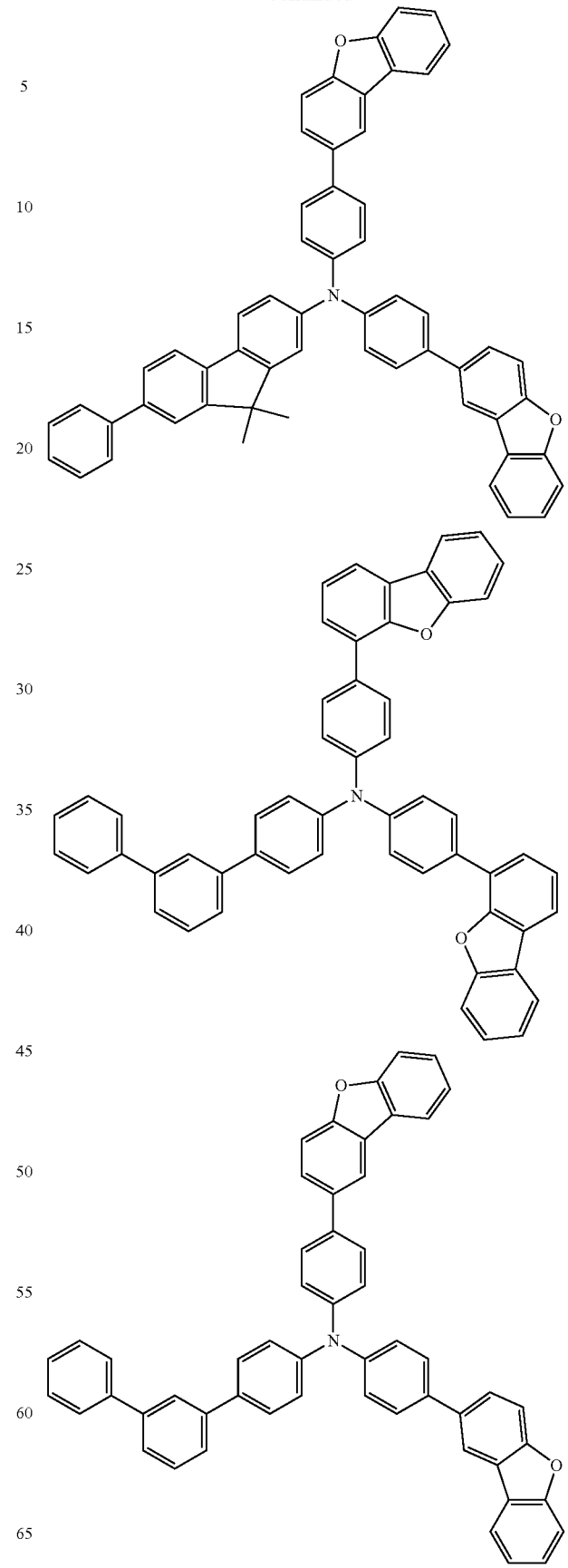

205
-continued
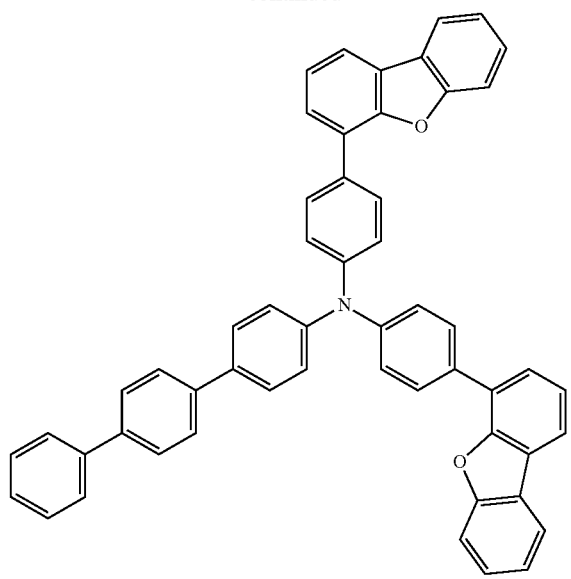
206
-continued
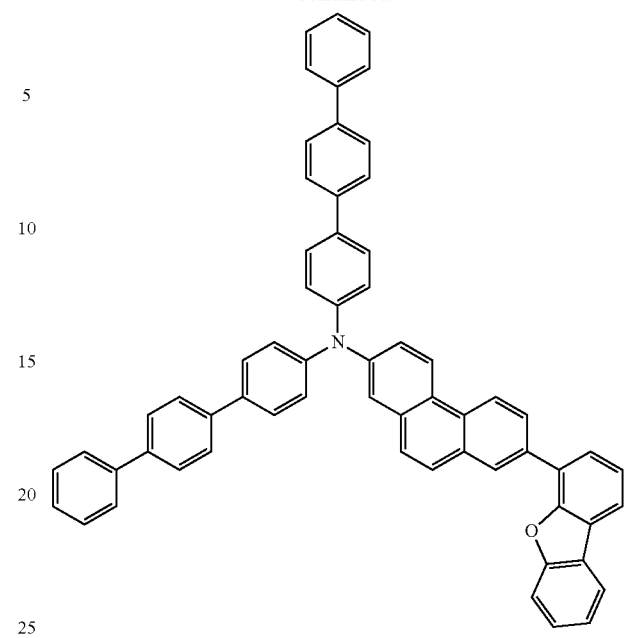
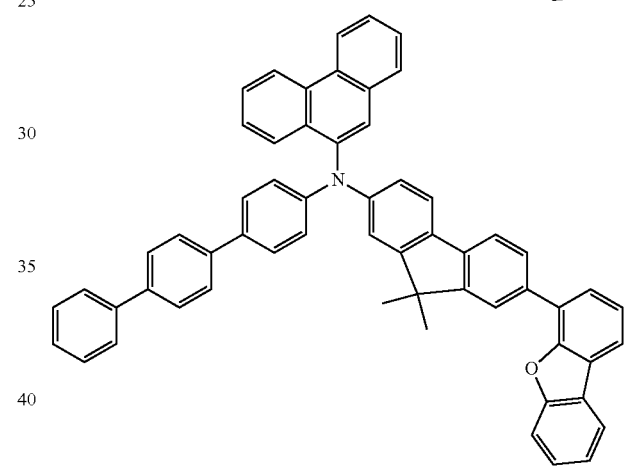
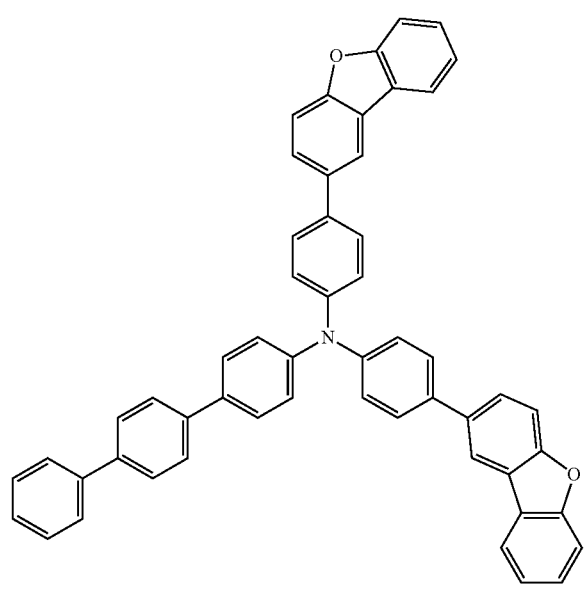
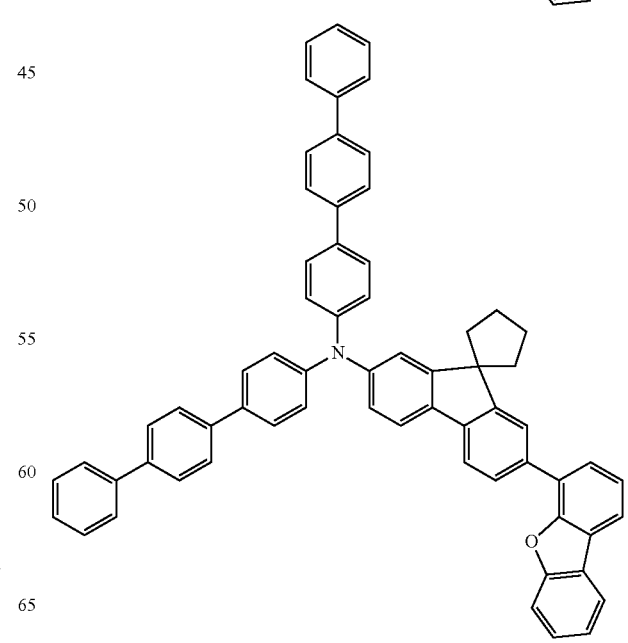

207
-continued
208
-continued
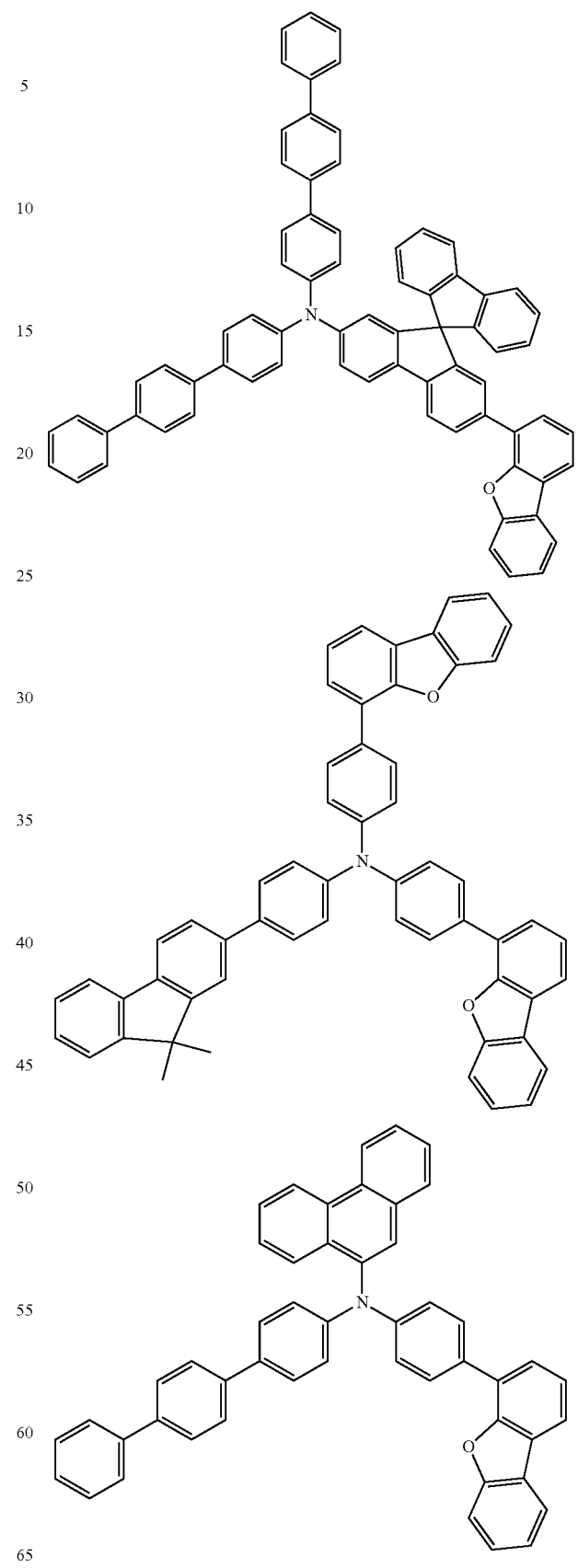

209
-continued
210
-continued
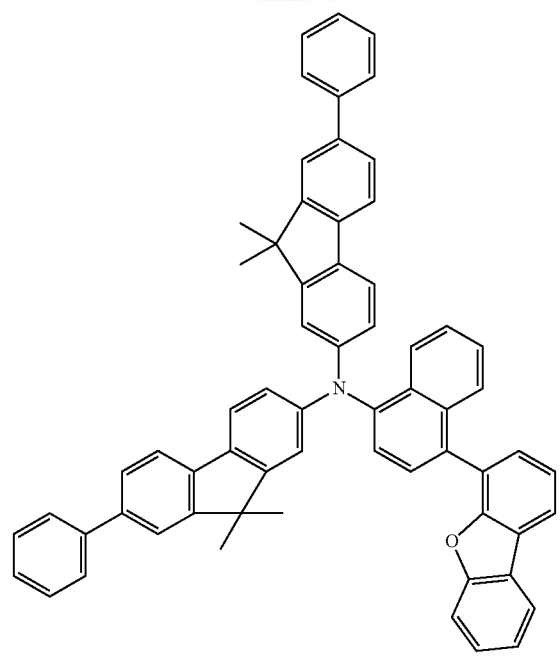
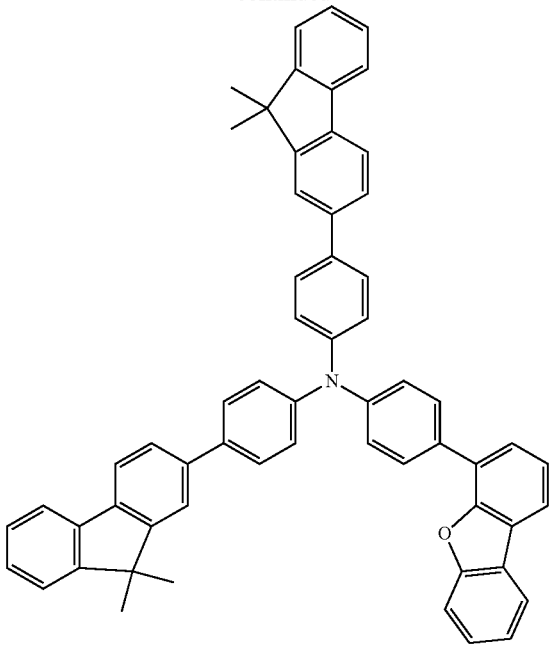
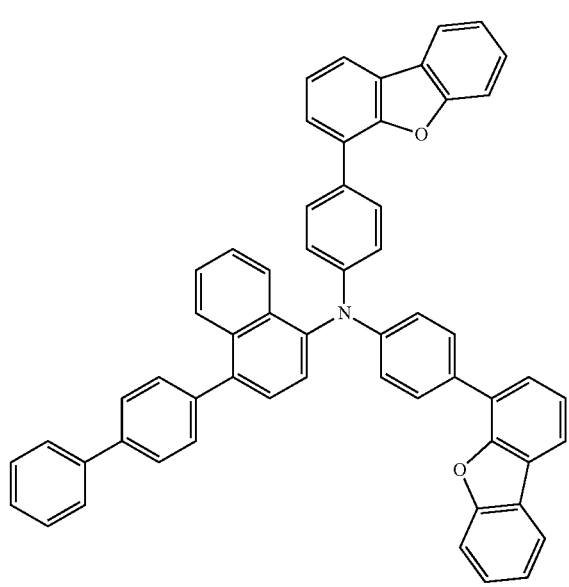

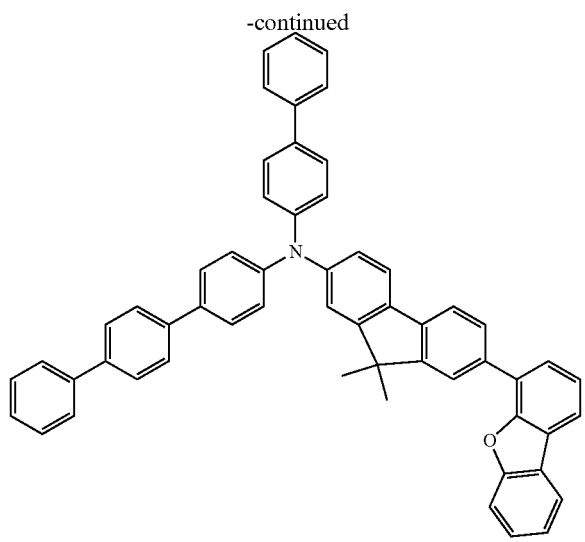

In addition, an aromatic tertiary amine compound and a styrylamine compound may be used in the hole transporting layer, which is selected from N,N,N',N'-tetraphenyl-4,4'-diaminophenyl; N,N'-diphenyl-N,N'-bis(3-methylphenyl)-[1,1'-biphenyl]-4,4'-diamine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diamino diphenyl ether; 4,4'-bis(diphenylamino)quadriphenyl; N,N,N-tri(p-tolyl)amine; 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostyrylbenezene; N-phenylcarbazole; a compound having two fused aromatic rings in its molecule, such as 4,4'-bis[N-(1-naphthyl)-N-phenylamino]biphenyl (NPD); and a starburst compound having three triphenylamine units, such as 4,4',4"-tris[N-(3-methylphenyl)-N-phenylamino]triphenylamine (MTDATA).

In an embodiment of the invention, the hole transporting layer may be formed by using a composition for hole transporting layer with comprises a hole transporting material and a solvent.

The hole transporting material may be either of a macromolecule, such as a polymer, and a low molecular compound, such as a monomer. In view of the charge injection barrier, a compound having an ionization potential of 4.5 to 6.0 eV is preferred. Examples of such a hole transporting material include an aromatic amine derivative, a phthalocyanine derivative, a porphyrin derivative, an oligothiophene derivative, a polythiophene derivative, a benzylphenyl derivative, a compound wherein tertiary amines are linked via a fluorene group, a hydrazone derivative, a silazane derivative, a silanamine derivative, a phosphamine derivative, a quinacridone derivative, a polyaniline derivative, a polypyrrole derivative, a polyphenylene vinylene derivative, a polythienylene vinylene derivative, a polyquinoline derivative, a polyquinoxaline derivative, and carbon.

The derivative used herein includes, when using an aromatic amine derivative as an example, an aromatic amine itself and a compound wherein the main skeleton comprises an aromatic amine and may be a polymer or a monomer.

Of the above, in view of the amorphous nature and the visual light transmittance, preferred is an aromatic amine compound, with an aromatic tertiary amine compound being particularly preferred. The aromatic tertiary amine compound used herein is a compound having an aromatic tertiary amine structure and includes a compound having a substituent derived from an aromatic tertiary amine.

The aromatic tertiary amine compound is more preferably a macromolecular compound (a polymeric compound having repeating units) having a weight average molecular weight of 1,000 to 1,000,000 in view of obtaining a uniform emission due to smooth surface, although not particularly limited thereto. Preferred example thereof is a macromolecular compound having the following repeating unit represented by formula (I):

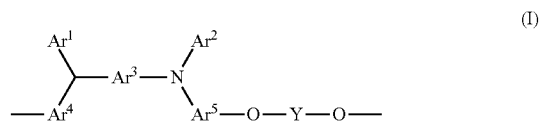

wherein
$Ar^1$ and $Ar^2$ each independently represent a substituted or unsubstituted aromatic hydrocarbon group or a substituted or unsubstituted aromatic heterocyclic group; $Ar^3$ to $Ar^6$ each independently represent a substituted or unsubstituted aromatic hydrocarbon group or a substituted or unsubstituted aromatic heterocyclic group; two groups bonded to the same nitrogen atom selected from $Ar^1$ to $Ar^6$ may be bonded to each other to form a ring; and Y represents a linking group selected from the following groups:

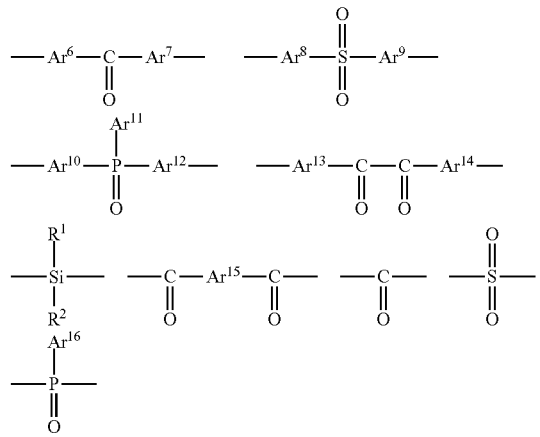

wherein $Ar^6$ to $Ar^{16}$ each independently represent a substituted or unsubstituted aromatic hydrocarbon group or a substituted or unsubstituted aromatic heterocyclic group; and $R^1$ and $R^2$ each independently represent a hydrogen atom or a substituent.

In view of the solubility, heat resistance, and hole injecting/transporting ability of the macromolecular compound, the aromatic hydrocarbon group and the aromatic heterocyclic group for $Ar^1$ to $Ar^{16}$ is preferably a group having a ring selected from a benzene ring, a naphthalene ring, a phenanthrene ring, a thiophene ring, and a pyridine ring and more preferably a group having a ring selected from a benzene ring and a naphthalene ring.

The optional substituent of the aromatic hydrocarbon group and the aromatic heterocyclic group for $Ar^1$ to $Ar^{16}$ has a molecular weight of generally 400 or less and preferably about 250 or less. The substituent is preferably an alkyl group, an alkenyl group, an alkoxy group, an aromatic hydrocarbon group, or an aromatic heterocyclic group.

The substituent represented by $R^1$ and $R^2$ may include an alkyl group, an alkenyl group, an alkoxy group, a silyl group, a siloxy group, an aromatic hydrocarbon group, and an aromatic heterocyclic group.

A polythiophene derivative, such as an electroconductive polymer (PEDOT/PSS) obtained by polymerizing 3,4-ethylenedioxythiophene in a high molecular weight polystyrenesulfonic acid, is also preferred as the hole transporting material. The terminal ends of this polymer may be capped with a methacrylate.

The concentration of the hole transporting material in the composition for hole transporting layer is arbitrary and, in view of uniform thickness of film, generally 0.01% by mass or more, preferably 0.1% by mass or more, more preferably 0.5% by mass or more, and generally 70% by mass or less, preferably 60% by mass or less, and more preferably 50% by mass or less. Within the above ranges, uneven thickness of film and defect in the hole transporting layer can be avoided.

The composition for hole transporting layer may contain an electron-accepting compound.

The electron-accepting compound is preferably a compound having an oxidation ability to receive one electron from the hole transporting material and more preferably a compound having an electron affinity of 4 eV or more, preferably 5 eV or more.

Examples of such an electron-accepting compound include at least one compound selected from the group consisting of a triarylboron compound, a metal halide, a Lewis acid, an organic acid, an onium salt, a salt between an arylamine and a metal halide, and a salt between an arylamine and a Lewis acid. More specific examples include an onium salt having an organic group, such as 4-isopropyl-4'-methyldiphenyliodonium tetrakis(pentafluorophenyl)borate and triphenylsulfonium tetrafluoroborate; iron(III) chloride; a high valence inorganic compound, such as ammonium peroxodisulfate; a cyano compound, such as tetracyanoethylene; an aromatic boron compound, such as tris(pentafluorophenyl)borane; a fullerene derivative; iodine; and a sulfonate ion, such as polystyrenesulfonate ion, alkylbenzenesulfonate ion, and camphorsulfonate ion.

These electron-accepting compounds improve the electroconductivity of the hole transporting layer by oxidizing the hole transporting material.

The content of the electron-accepting compound to the hole transporting material in the composition for hole transporting layer is generally 0.1 mol % or more, preferably 1 mol % or more, and generally 100 mol % or less, preferably 40 mol % or less.

In addition to the hole transporting material and the electron-accepting compound, the composition for hole transporting layer may contain other component, such as a light emitting material, an electron transporting material, a binder resin, and a coating improver, which may be used alone or in combination of two or more in an arbitrary ratio.

In an embodiment of the invention, a hole transporting material suitable for use in a coating method is preferably used. Examples of such a hole transporting material include polyvinylcarbazole and its derivative, polysilane and its derivative, polysiloxane derivative having an aromatic amine residue in its side chain or main chain, pyrazoline derivative, an arylamine derivative, stilbene derivative, triphenyldiamine derivative, polyaniline and its derivative, polythiophene and its derivative, polypyrrole and its derivative, polyarylamine and its derivative, poly(p-phenylenevinylene) and its derivative, polyfluorene derivative, a macromolecular compound having an aromatic amine residue, and poly(2,5-thienylenevinylene) and its derivative.

The hole transporting material is preferably a macromolecular compound, for example, a polymer. By using a macromolecular compound, the film-forming properties are improved and a uniform emission of organic EL device is obtained. The number average molecular weight of such a hole transporting material is 10,000 or more, preferably $3.0 \times 10^4$ to $5.0 \times 10^5$, and more preferably $6.0 \times 10^4$ to $1.2 \times 10^5$ when calibrated with a standard polystyrene. The weight average molecular weight of the hole transporting material is $1.0 \times 10^4$ or more, preferably $5.0 \times 10^4$ to $1.0 \times 10^6$, and more preferably $1.0 \times 10^5$ to $6.0 \times 10^6$.

Such a hole transporting material is preferably a macromolecular compound, such as polyvinylcarbazole and its derivative, polysilane and its derivative, polysiloxane derivative having an aromatic amine residue in its side chain or main chain, polyaniline and its derivative, polythiophene and its derivative, polyfluorene derivative, a macromolecular compound having an aromatic amine residue, poly(p-phenylenevinylene) and its derivative, and poly(2,5-thienylenevinylene) and its derivative, with polyvinylcarbazole and its derivative, polysilane and its derivative, polysiloxane derivative having an aromatic amine residue in its side chain or main chain, polyfluorene derivative, and a macromolecular compound having an aromatic amine residue being more preferred. A low molecular hole transporting material is used preferably by dispersing into a macromolecular binder.

Polyvinylcarbazole and its derivative is obtained, for example, by a cation polymerization or a radical polymerization of a vinyl monomer.

Since the siloxane structure is little hole transporting, a residue of the low molecular hole transporting material mentioned above is introduced into the side chain or main chain of polysiloxane and its derivative. A compound having a residue of a hole transporting aromatic amine in its side chain or main chain is particularly preferred.

A polymer comprising a fluorenediyl unit represented by formula (J) is also preferred as the hole transporting material. When this polymer is used in the hole transporting layer of organic EL device in contact with an organic compound having a fused ring or more than one aromatic ring, the efficiency of hole injection is enhanced and the current density at driving is large.

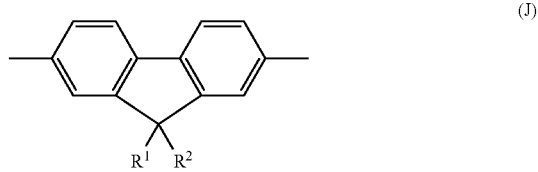

(J)

In formula (J), $R^1$ and $R^2$ may be the same or different and each independently represent a hydrogen atom, an alkyl group, an alkoxy group, an aryl group, or a monovalent heterocyclic group. The alkyl group has 1 to 10 carbon atoms. The alkoxy group has 1 to 10 carbon atoms. Examples of the aryl group include a phenyl group and a naphthyl group. Example of the monovalent heterocyclic group include a pyridyl group. The aryl group and the monovalent heterocyclic group may have a substituent. In view of improving the solubility of the macromolecular compound, the substituent is preferably an alkyl group having 1 to 10 carbon atoms and an alkoxy group having 1 to 10 carbon atoms.

In formula (J), then aryl group and the monovalent heterocyclic group may have a crosslinkable group, such as a vinyl group, an ethynyl group, a butenyl group, an acryl-containing group, an acrylate-containing group, an acrylamide-containing group, a methacryl-containing group, a methacrylate-containing group, a methacrylamide-containing group, a vinyl ether-containing group, a vinylamino group, a silanol-containing group, and a group containing a small-membered ring, for example, cyclopropane, cyclobutane, epoxide, oxetane, diketene, and episulfide.

Preferred examples of the fluorenediyl unit are shown below:

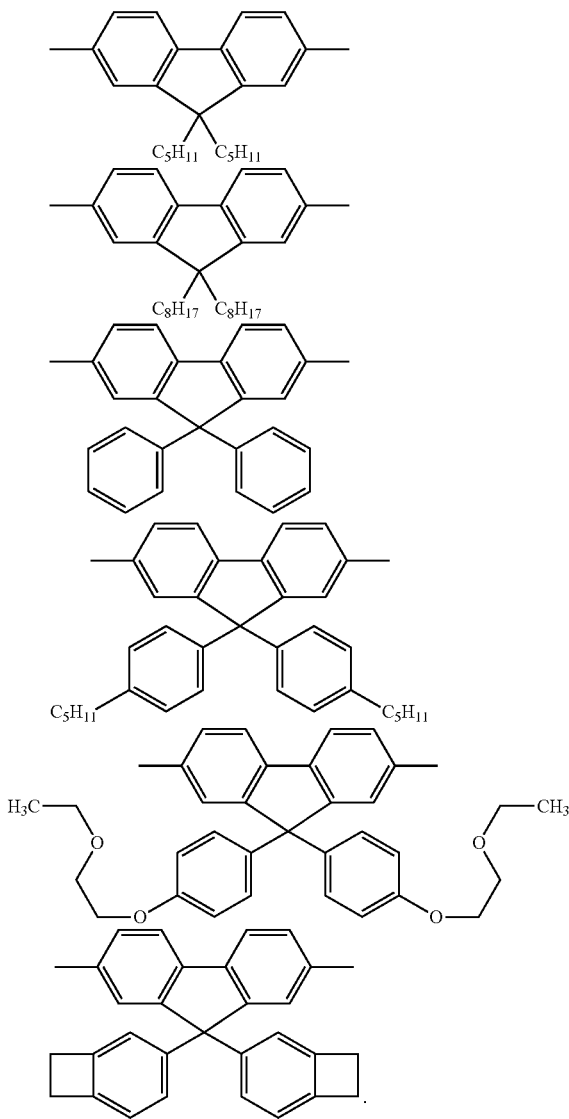

A polymer, for example, a polyarylamine having a repeating unit comprising the above fluorenediyl unit and an aromatic tertiary amine compound unit is particularly preferred as the hole transporting material.

Example of the aromatic tertiary amine compound unit includes a repeating unit represented by formula (K):

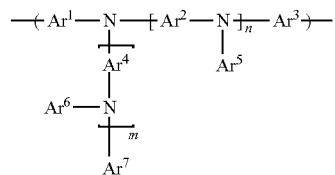

wherein $Ar^1$, $Ar^2$, $Ar^3$, and $Ar^1$ each independently represent an arylene group or a divalent heterocyclic group, $Ar^6$, $Ar^5$ and $Ar^7$ each independently represent an aryl group or a monovalent heterocyclic group, $Ar^6$ and $Ar^7$ may form a ring together with the nitrogen atom to which $Ar^6$ and $Ar^7$ are bonded, and m and n each independently represent 0 or 1.

Example of the arylene group includes a phenylene group, and example of the divalent heterocyclic group includes a pyridinediyl group. These groups may have a substituent Examples of the aryl group include a phenyl group and a naphthyl group. Example of the monovalent heterocyclic group includes a pyridyl group. These groups may have a substituent.

Examples of the monovalent heterocyclic group include a thienyl group, a furyl group, and a pyridyl group.

In view of the solubility of the macromolecular compound, the optional substituent for the arylene group, the aryl group, the divalent heterocyclic group, and the monovalent heterocyclic group is preferably an alkyl group, an alkoxy group, and an aryl group, with an alkyl group being more preferred. The alkyl group has 1 to 10 carbon atoms and the alkoxy group has 1 to 10 carbon atoms. Examples of the aryl group include a phenyl group and a naphthyl group.

The substituent may include a crosslinkable group, such as a vinyl group, an ethynyl group, a butenyl group, an acryl-containing group, an acrylate-containing group, an acrylamide-containing group, a methacryl-containing group, a methacrylate-containing group, a methacrylamide-containing group, a vinyl ether-containing group, a vinylamino group, a silanol-containing group, and a group containing a small-membered ring, for example, cyclopropane, cyclobutane, epoxide, oxetane, diketene, and episulfide.

In formula (K), $Ar^1$, $Ar^2$, $Ar^3$, and $Ar^4$ are each preferably an arylene group and more preferably a phenylene group. $Ar^5$, $Ar^6$ and $Ar^7$ are each preferably an aryl group and more preferably a phenyl group.

The carbon atom in $Ar^2$ and the carbon atom in $Ar^a$ may be bonded to each other directly or via a divalent group, such as —O— and —S—.

In view of easily synthesizing the monomer, m and n are each preferably 0.

Examples of the repeating unit represented by formula (K) include the following repeating units:

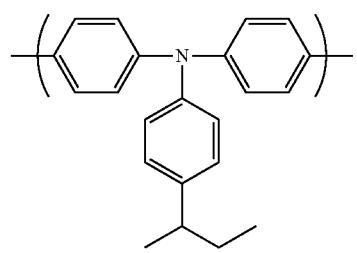

-continued

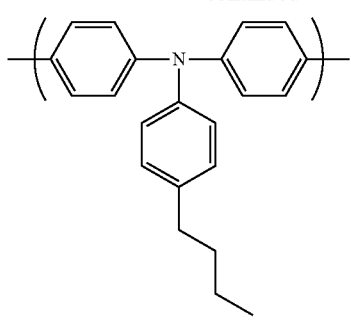
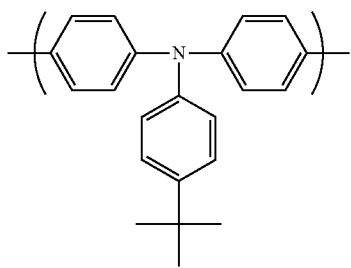
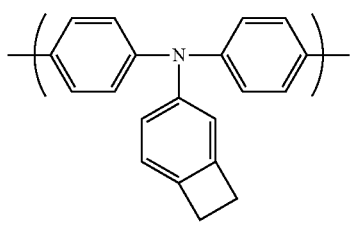
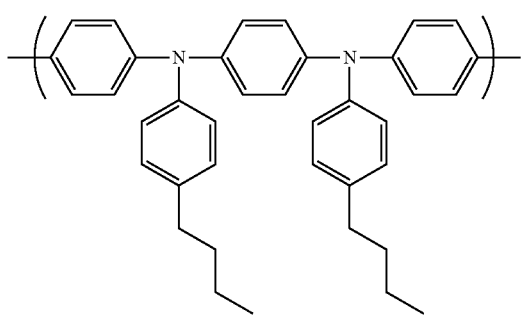
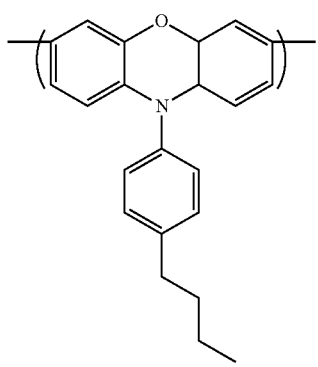

-continued

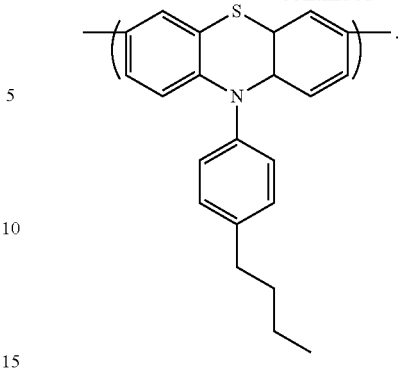

When the hole transporting material has no crosslinkable group, a crosslinking agent having a crosslinkable group is preferably used. Example of the crosslinking agent includes a compound having a polymerizable group selected from the group consisting of a vinyl group, an acetyl group, a butenyl group, an acryl group, an acrylamido group, an methacryl group, an methacrylamido group, a vinyl ether group, a vinylamino group, a silanol group, a cyclopropyl group, a cyclobutyl group, an epoxy group, an oxetane group, a diketone group, an episulfide group, a lactone group, and a lactam group. Preferred as the crosslinking agent is a polyfunctional acrylate, such as dipentaerythritol hexaacrylate (DPHA) and trispentaerythritol octaacrylate (TPEA).

By using the material having a crosslinkable group or the crosslinking agent, the underlayer (hole transporting layer) is prevented from being dissolved in the solvent for forming the upper layer even when another functional layer (upper layer) is formed on the underlayer by a coating method.

In an embodiment of the invention, a hole transporting material having a hole transporting portion and a crosslinkable group is also preferably used. The hole transporting portion may include a triarylamine structure; an aromatic ring structure having three or more rings, such as a fluorene ring, an anthracene ring, a pyrene ring, a carbazole ring, a dibenzofuran ring, a dibenzothiophene ring, a phenoxazine ring, and a phenanthroline ring; an aromatic heterocyclic structure, such as a thiophene ring and a silole ring; and a metal complex structure.

Of the above, in view of improving the electrochemical stability and the hole transporting ability, the triarylamine structure is preferred as the hole transporting portion.

In addition, the hole transporting portion is preferably a polymer because it easily becomes insoluble in an organic solvent by crosslinking, and a polymer having a repeating unit represented by formula (L) is particularly preferred in view of improving the electrochemical stability and the hole transporting ability:

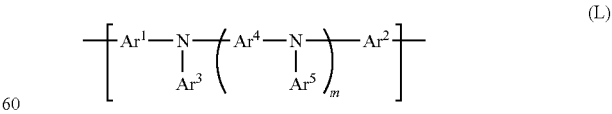

wherein m represents an integer of 0 to 3; $Ar^1$ and $Ar^2$ each independently represent a single bond, a substituted or unsubstituted aromatic hydrocarbon group, or a substituted or unsubstituted aromatic heterocyclic group; and $Ar^3$ to $Ar^5$ each independently represent a substituted or unsubstituted aromatic hydrocarbon group or a substituted or unsubstituted aromatic heterocyclic group; provided that $Ar^1$ and $Ar^2$ do not represent a single bond simultaneously.

The aromatic hydrocarbon group may include, for example, a six-membered monocyclic group or a monovalent fused ring group having 2 to 5 six-membered rings, such as a benzene ring, a naphthalene ring, an anthracene ring, a phenanthrene ring, a perylene ring, a tetracene ring, a pyrene ring, a benzopyrene ring, a chrysene ring, a triphenylene ring, an acenaphthene ring, a fluoranthene ring, and a fluorene ring.

The aromatic heterocyclic group may include, for example, a five- or six-membered monocyclic group or a monovalent fused ring group having 2 to 4 five- or six-membered rings, such as a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, a benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a phenanthridine ring, a benzimidazole ring, a perimidine ring, a quinazoline ring, a quinazoline ring, and an azulene ring.

In view of the solubility to a solvent and the heat resistance, $Ar^1$ to $Ar^3$ each independently and preferably represent a monovalent group of a ring selected from the group consisting of a benzene ring, a naphthalene ring, an anthracene ring, a phenanthrene ring, a triphenylene ring, a pyrene ring, a thiophene ring, a pyridine ring, and a fluorene ring.

A group wherein one or more kinds of rings selected from the above group are linked via a single bond is also preferred as $Ar^1$ to $Ar^5$, with a biphenyl group, a biphenylene group, a terphenyl group, and a terphenylene group being more preferred.

The optional group of the aromatic hydrocarbon group and the aromatic heterocyclic group may include a linear, branched or cyclic alkyl group having 1 to 24, preferably 1 to 12 carbon atoms, such as a methyl group, an ethyl group, a n-propyl group, an isopropyl group, a n-butyl group, an isobutyl group, a sec-butyl group, a tert-butyl group, a n-hexyl group, a cyclohexyl group, and a dodecyl group; an alkenyl group having 2 to 24, preferably 2 to 12 carbon atoms, such as a vinyl group; an alkynyl group having 2 to 24, preferably 2 to 12 carbon atoms, such as an ethynyl group; an alkoxy group having 1 to 24, preferably 1 to 12 carbon atoms, such as a methoxy group and an ethoxy group; an aryloxy group having 4 or more, preferably 5 or more and 36 or less, preferably 24 or less carbon atoms, such as a phenoxy group, a naphthoxy group, and a pyridyloxy group; an alkoxycarbonyl group having 2 to 24, preferably 2 to 12 carbon atoms, such as a methoxycarbonyl group and an ethoxycarbonyl group; a dialkylamino group having 2 to 24, preferably 2 to 12 carbon atoms, such as a dimethylamino group and a diethylamino group; a diarylamino group having 10 or more, preferably 12 or more and 36 or less, preferably 24 or less carbon atoms, such as a diphenylamino group, a ditolylamino group, and a N-carbazolyl group; an arylalkylamino group having 7 to 36, preferably 7 to 24 carbon atoms, such as a phenylmethylamino group; an acyl group having 2 to 24, preferably 2 to 12 carbon atoms, such as an acetyl group and a benzoyl group; a halogen atom, such as a fluorine atom and a chlorine atom; a haloalkyl group having 1 to 12, preferably 1 to 6 carbon atoms, such as a trifluoromethyl group; an alkylthio group having 1 to 24, preferably 1 to 12 carbon atoms, such as a methylthio group and an ethylthio group; an arylthio group having 4 or more, preferably 5 or more and 36 or less, preferably 24 or less carbon atoms, such as a phenylthio group, a naphthylthio group, and a pyridylthio group; a silyl group having 2 or more, preferably 3 or more and 36 or less, preferably 24 or less carbon atoms, such as a trimethylsilyl group and a triphenylsilyl group; a siloxy group having 2 or more, preferably 3 or more and 36 or less, preferably 24 or less carbon atoms, such as a trimethylsiloxy group and a triphenylsiloxy group; a cyano group; an aromatic hydrocarbon group having 6 to 36, preferably 6 to 24 carbon atoms, such as a phenyl group and a naphthyl group; and an aromatic heterocyclic group having 3 or more, preferably 4 or more and 36 or less, preferably 24 or less carbon atoms, such as a thienyl group and a pyridyl group.

Of the above optional substituents, an alkyl group having 1 to 12 carbon atoms and an alkoxy group having 1 to 12 carbon atoms are preferred in view of the solubility.

Each of the above optional substituents may further have a substituent which is selected from the optional substituents mentioned above.

The number of carbon atoms of Art to $Ar^5$ inclusive of the carbon atoms in the substituent is 3 or more, preferably 5 or more, and more preferably 6 or more, and 72 or less, preferably 48 or less, and more preferably 25 or less.

In formula (L), m is an integer of 0 to 3 and preferably m is 0 because the film-forming properties are improved. In view of improving the hole transporting ability, m is preferably 1 to 3.

When m is 2 or more, two or more groups $Ar^4$ and two or more groups $Ar^6$ may be the same or different, respectively. Groups $Ar^4$ and groups $Ar^5$ may be bonded to each other directly or via a linking group, respectively to form a ring structure.

When the hole transporting material includes a crosslinkable group, the solubility to a solvent is largely changed before and after the reaction (insolubilization) caused by exposing to heat and/or an active energy ray.

The crosslinkable group used herein is a group which reacts with the same of different group in another molecule in the vicinity thereof by exposing to heat and/or an active energy ray, thereby forming a new chemical bond.

For example, the following crosslinkable groups are easily insolubilized:

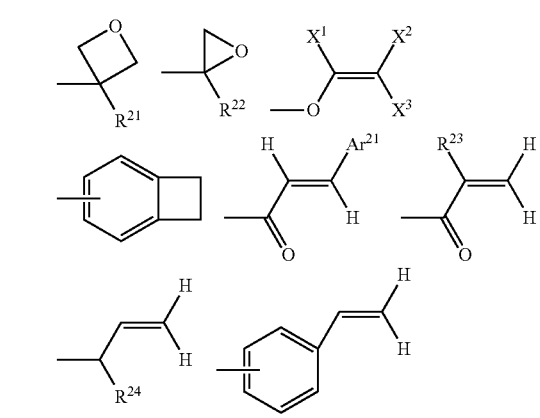

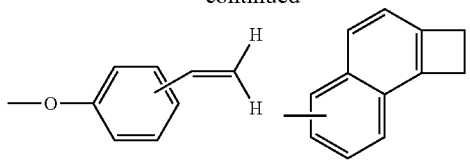

wherein $R^{21}$ to $R^{23}$ each independently represent a hydrogen atom or a substituted or unsubstituted alkyl group;

$Ar^{21}$ represents a substituted or unsubstituted aromatic group;

$X^1$, $X^2$ and $X^3$ each independently represents a hydrogen atom or a halogen atom; and $R^{24}$ represents a hydrogen atom or a vinyl group.

The benzocyclobutene ring may have a substituent and the substituents may be bonded to each other to form a ring.

The alkyl group for $R^{21}$ to $R^{23}$ may include an alkyl group having 1 to 24, preferably 1 to 12 carbon atoms, such as a methyl group and an ethyl group.

Example of the aromatic group for $Ar^{21}$ is the same as those described above with respect to $Ar^1$ to $Ar^5$.

The optional substituent for $R^{21}$ to $R^{23}$ and $Ar^{21}$ is not particularly limited and, for example, selected from those mentioned above.

A group which is insolubilized by a cation polymerization, for example, a cyclic ether group, such as an epoxy group and an oxetane group, and a vinyl ether group, is preferred as the crosslinkable group because such a group is highly reactive and easily insolubilized. The oxetane group is particularly preferred because the rate of cation polymerization is easily controlled and the vinyl ether group is particularly preferred because a hydroxyl group which may damage a device during the cation polymerization is difficult to be formed.

A group capable of a cycloaddition, for example, an arylvinylcarbonyl group, such as a cinnamoyl, and a group having a benzocyclobutene ring, is also preferred in view of further enhancing the electrochemical stability.

A group having a benzocyclobutene ring is particularly preferred because the structure after insolubilization is very stable.

For example, a group represented by formula (M) is preferred:

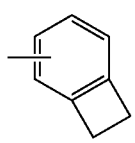

(M)

wherein the benzocyclobutene ring may have a substituent and the substituents may be bonded to each other to form a ring.

The crosslinkable group may be bonded to a mono- or di-valent aromatic group in the molecule directly or via a divalent group. The divalent group preferably comprises 1 to 30 groups selected from —O—, —C(=O)—, and —CH$_2$— wherein the hydrogen atom may be substituted, which are linked together in an arbitrary order. Examples of the crosslinkable group to be bonded via a divalent group are shown below, although not limited thereto.

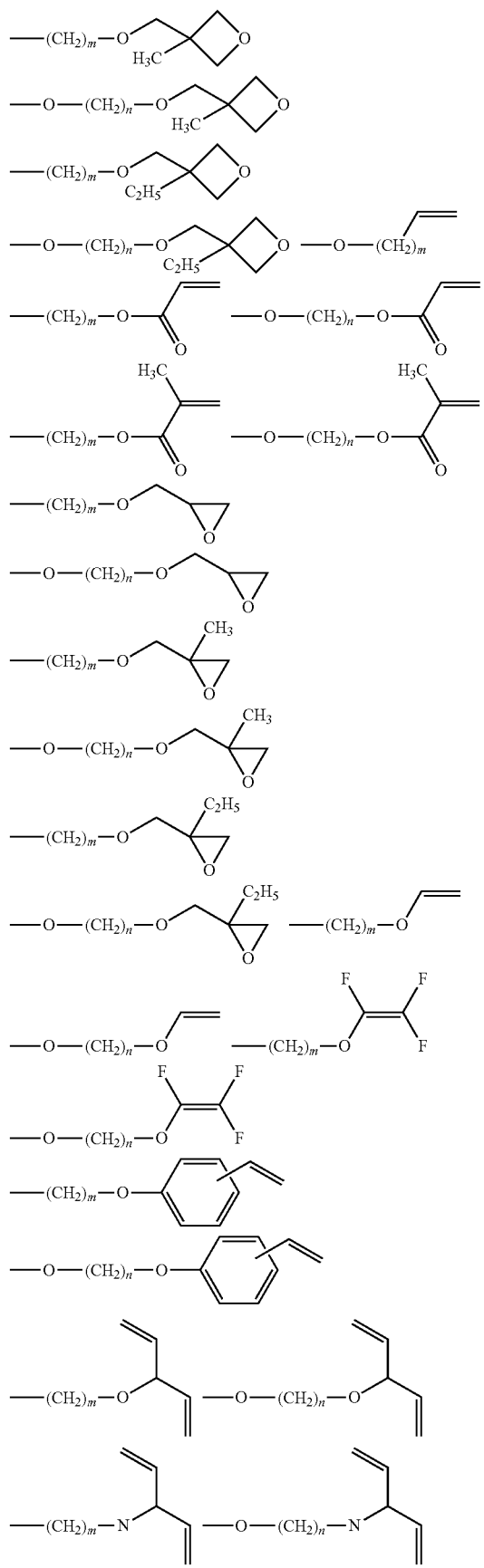

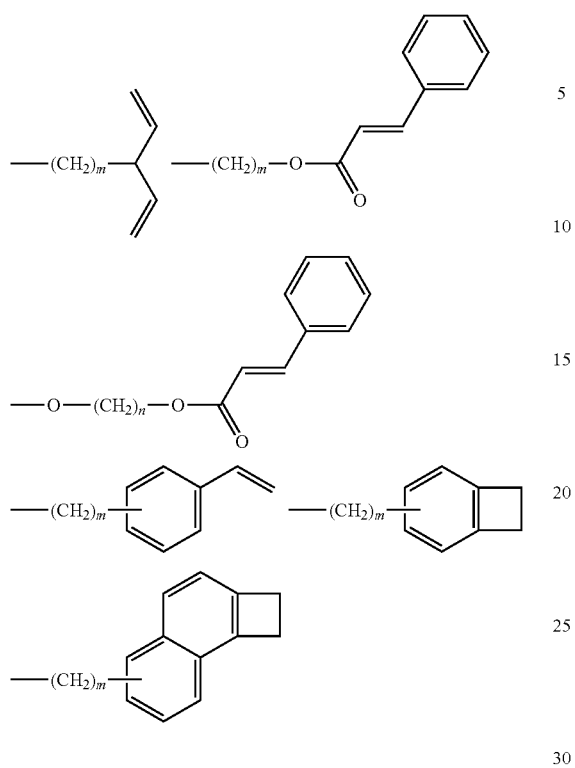
In the above formulae, m is an integer of 0 to 12 and n is an integer of 1 to 12.
Other examples of the group having a crosslinkable group are shown below.
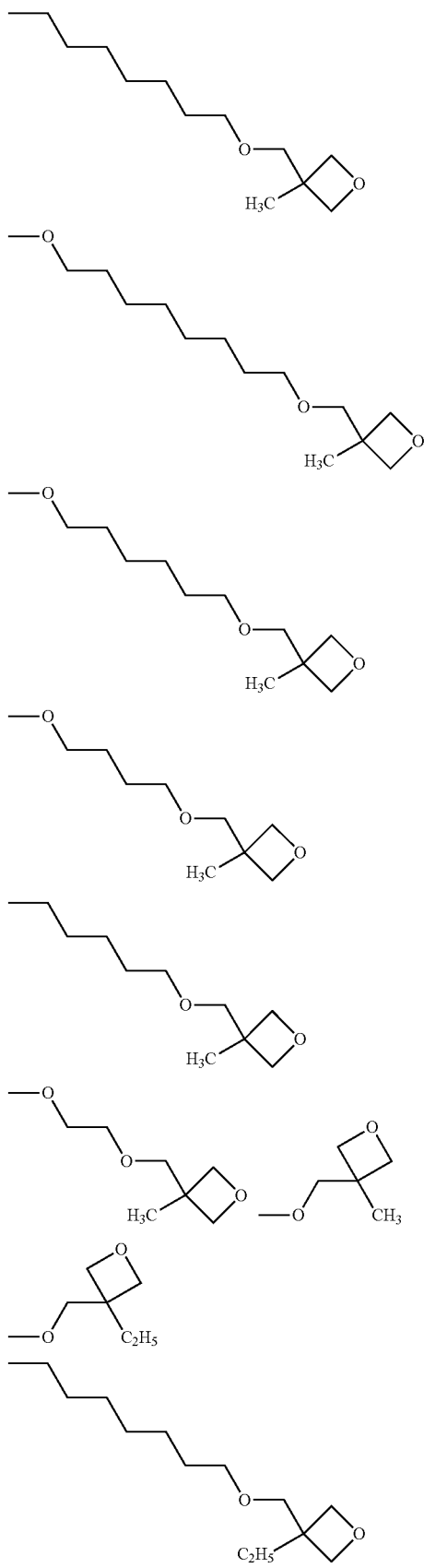

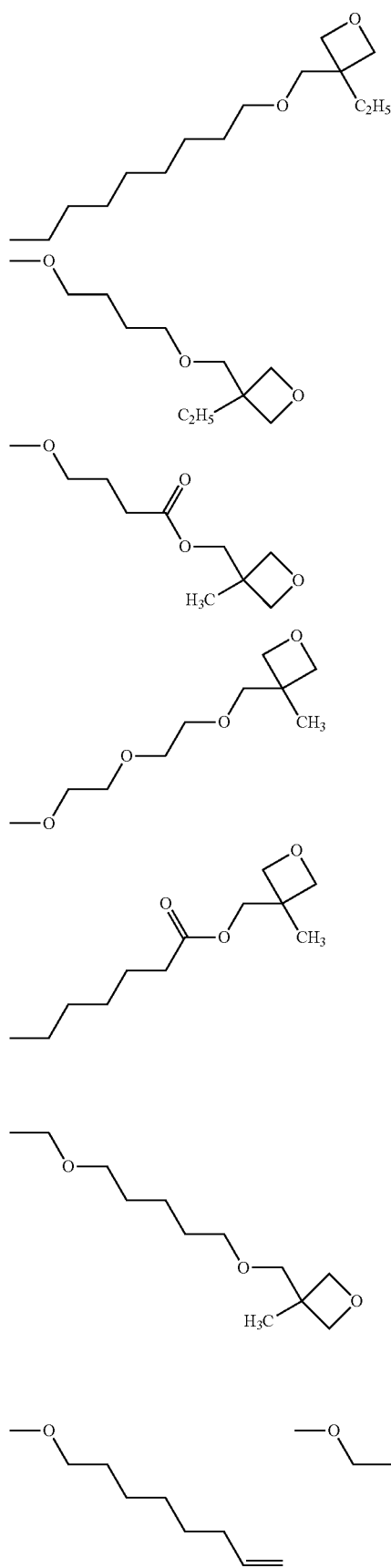
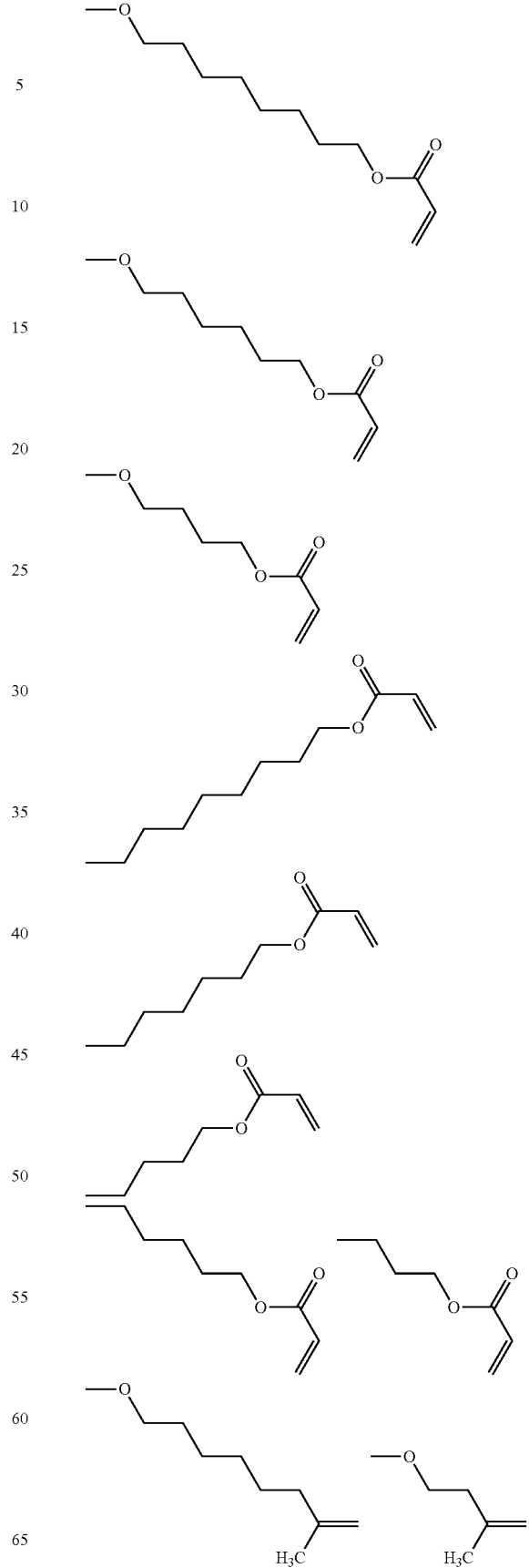

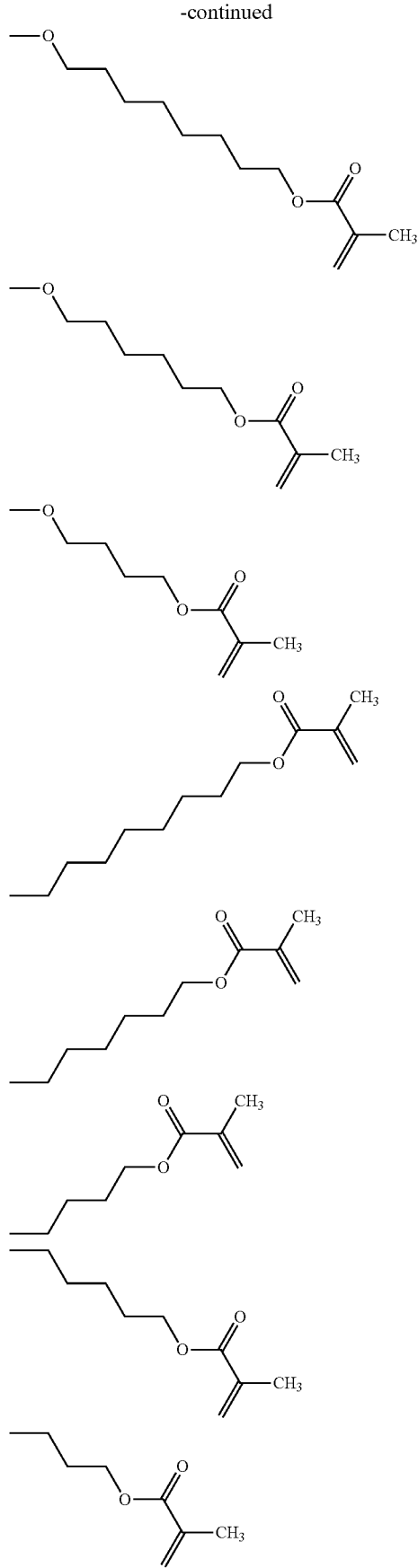
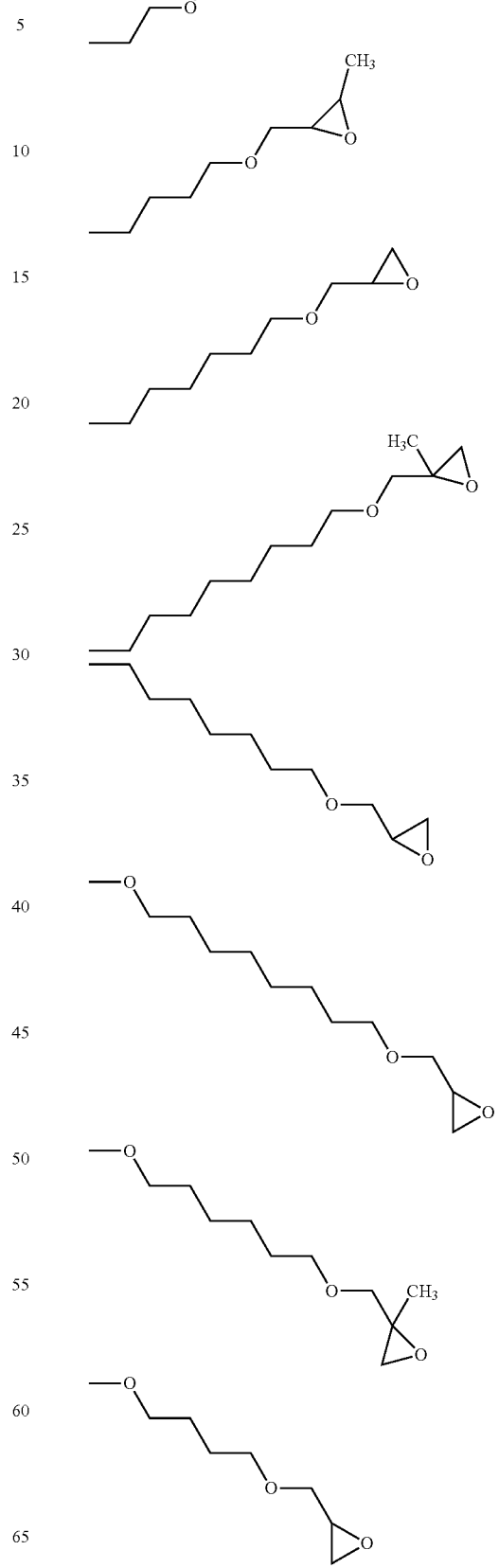

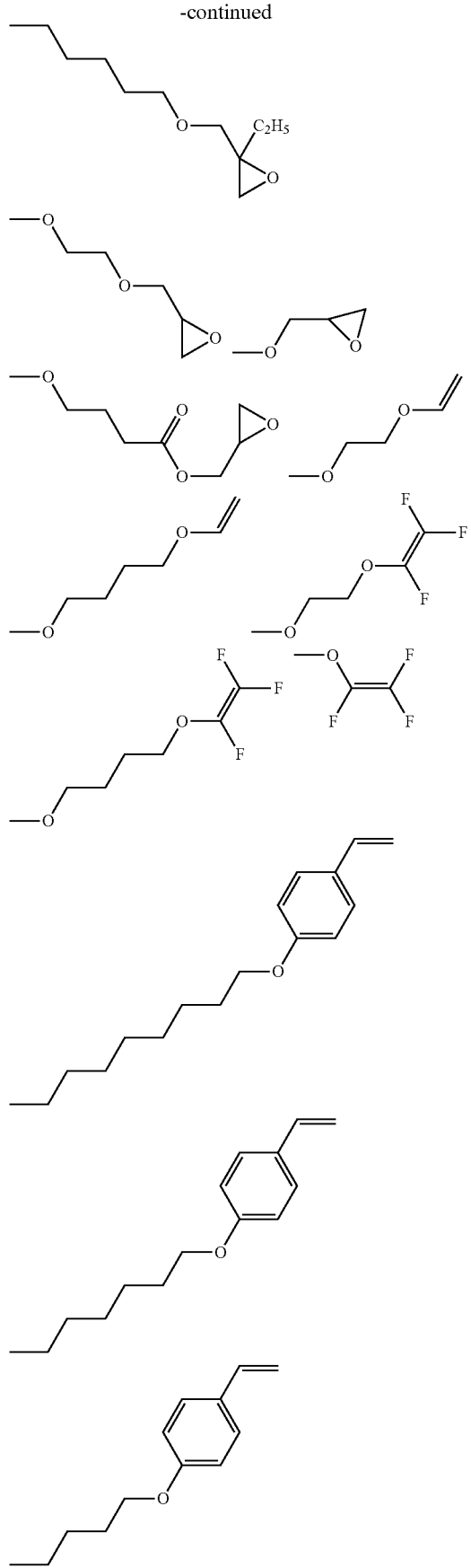
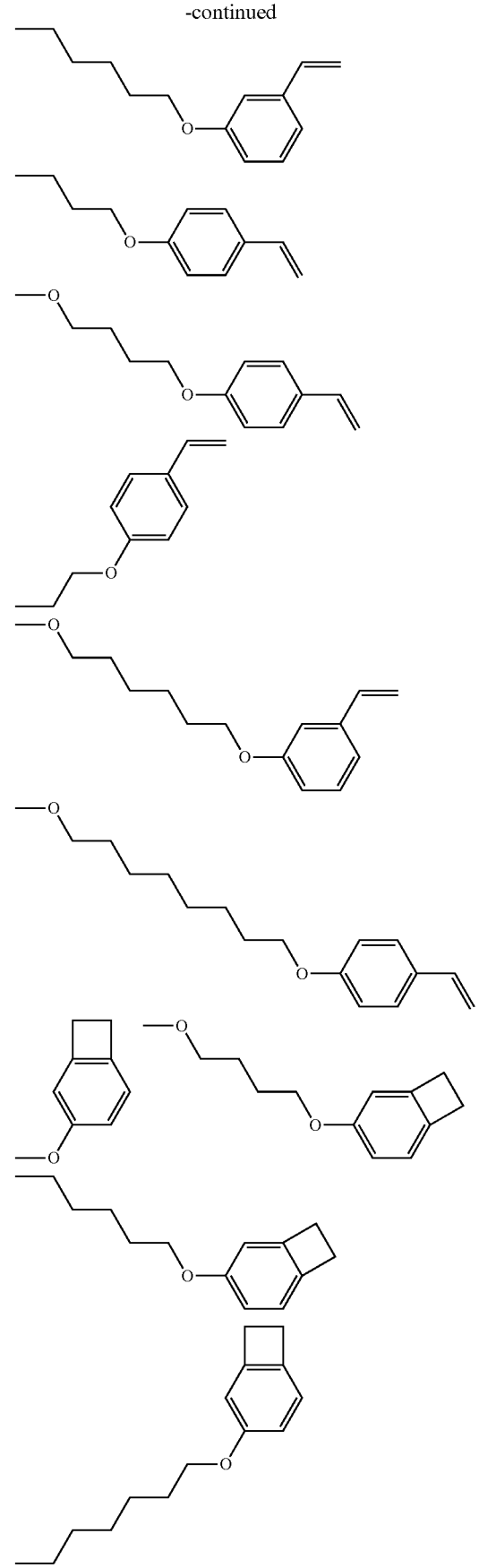

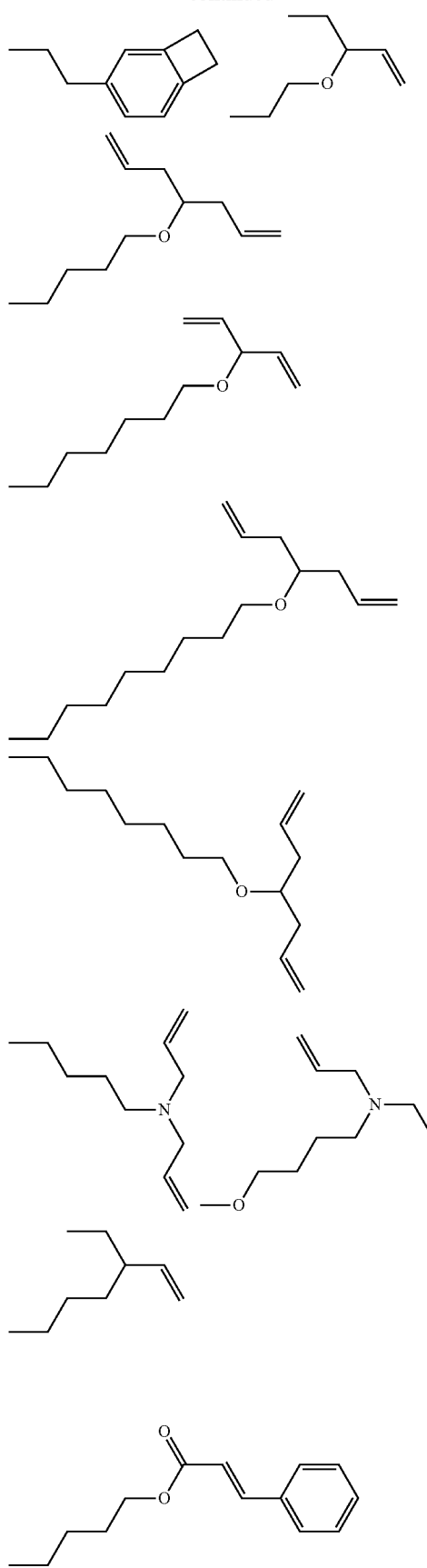
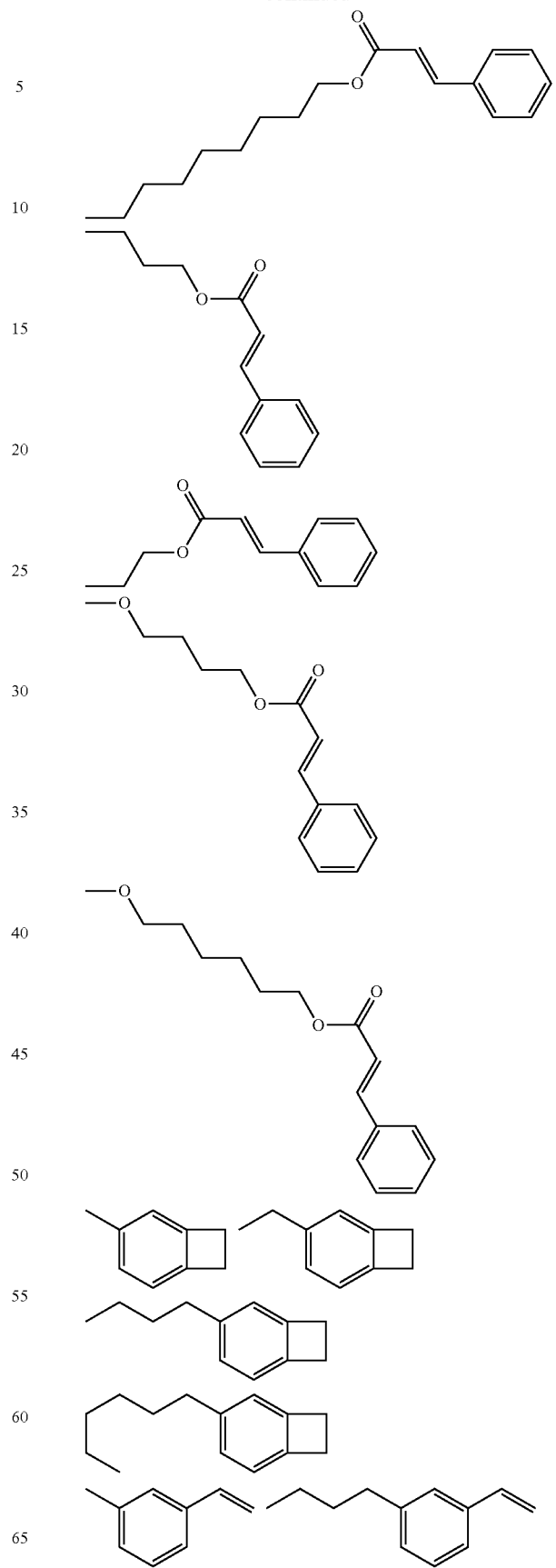

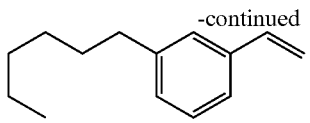

In an embodiment of the invention, the hole transporting material preferably comprises an electroconductive polymer or oligomer. The electroconductive polymer or oligomer is generally a mixture of an electron-donating compound, an electron-accepting compound, or an acidic compound. The mixture may be a solid or a liquid, preferably a solution, a dispersion, a colloid, an ink, or a varnish, because these are suitable for forming a solid layer by a coating method. The mixture may be contain an additive to improve the hole transporting ability and the film-forming properties.

Examples of the electroconductive polymer or oligomer usable in an embodiment of the invention will be described below.

Representative examples of the electron-donating compound include an aromatic amine derivative, a phthalocyanine derivative, a porphyrin derivative, a thiophene derivative, a benzylphenyl derivative, a compound wherein tertiary amines are linked via a fluorene group, a hydrazone derivative, a silazane derivative, a silanamine derivative, a phosphamine derivative, a quinacridone derivative, an aniline derivative, a pyrrole derivative, a phenylenevinylene derivative, a thienylenevinylene derivative, a quinoline derivative, a quinoxaline derivative, and carbon. These derivatives may be any of a low molecular compound having a molecular weight of less than 1,000, an oligomer or a dendrimer having a molecular weight of 1,000 to 10,000, and a macromolecular compound having a molecular weight of 10,000 or more. Of the above, an aromatic amine derivative, a polythiophene derivative, a polyaniline derivative, and an oligoaniline derivative are preferably used.

Representative example of the electron-accepting compound and the acidic compound may be at least one compound selected from the group consisting of a triarylboron compound, a metal halide, a Lewis acid, an organic acid, an onium salt, a salt between an arylamine and a metal halide, and a salt between an arylamine and a Lewis acid. More specifically, examples thereof include an onium salt having an organic group, such as 4-isopropyl-4'-methyldiphenyliodonium tetrakis(pentafluorophenyl)borate and triphenylsulfonium tetrafluoroborate; iron(III) chloride; a high valence inorganic compound, such as ammonium peroxodisulfate; a cyano compound, such as tetracyanoethylene; an aromatic boron compound, such as tris(pentafluorophenyl) borane; a fullerene derivative; iodine; and a sulfonate ion, such as polystyrenesulfonate ion, alkylbenzenesulfonate ion, and camphorsulfonate ion.

Like the electron-donating compound, these derivatives may be any of a low molecular compound having a molecular weight of less than 1,000, an oligomer or a dendrimer having a molecular weight of 1,000 to 10,000, and a polymer having a molecular weight of 10,000 or more.

These electron-accepting compounds increase the electroconductivity of the hole transporting layer by oxidizing the hole transporting material. The content of the electron-accepting compound in the hole transporting layer or the composition for hole transporting layer is generally 0.1 mol % or more, preferably 1 mol % or more, and generally 100 mol % or less, preferably 40 mol % or less.

The following materials (i) to (x) are representative examples of the hole transporting layer materials usable in an embodiment of the invention. These may be used alone or in combination, preferably in combination of a relatively electron-donating material and a relatively electron-accepting material. In addition, one or more third components may be added, for example, an additive for promoting the charge transport between the electron-donating compound and the electron-accepting compound and for improving the film-forming properties by coating may be added.

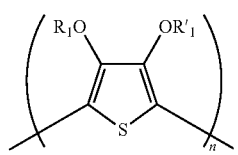

(i)

In formula (i), $R_1$ and $R_{1'}$ are each independently selected from a hydrogen atom and an alkyl group having 1 to 4 carbon atoms; $R^1$ and $R_{1'}$ may be bonded to each other to form an alkylene chain having 1 to 4 carbon atoms; the alkylene chain optionally has a substituent selected from an alkyl group having 1 to 12 carbon atoms, an aromatic group having 6 to 12 carbon atoms, and a 1,2-cyclohexylene group; and n represents a number larger than 6.

A polyaniline comprising a monomer unit represented by formula (ii) and/or (iii):

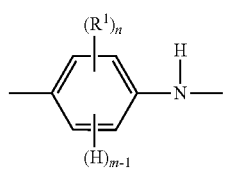

(ii)

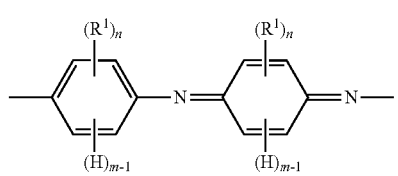

(iii)

wherein n represents an integer of 0 to 4;

m−1 represents an integer of 1 to 5, and n+(m−1)=5;

each $R^1$ may be the same or different and is independently selected from an alkyl group, an alkenyl group, an alkoxy group, a cycloalkyl group, a cycloalkenyl group, an alkanoyl group, an alkylthio group, an aryloxy group, an alkylthioalkyl group, an alkylaryl group, an arylalkyl group, an amino group, an alkylamino group, a dialkylamino group, an aryl group, an alkylsulfinyl group, an alkoxyalkyl group, an alkylsulfonyl group, an arylthio group, an arylsulfinyl group, an alkoxycarbonyl group, an arylsulfonyl group, a carboxyl group, a halogen atom, a cyano group, an alkyl group having one or more substituents selected from a sulfonic acid group, a carboxyl group, a halogen atom, a nitro group, a cyano group, and an epoxy group; and adjacent two group $R^1$ may be bonded to each other to form an alkylene chain or an alkenylene chain each completing a 3-, 4-, 5-, 6- or 7-membered aromatic or aliphatic ring which may include at least one of a nitrogen atom, a sulfur atom and an oxygen atom.

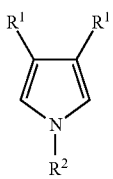

(iv)

In formula (iv), each $R^1$ is independently selected from a hydrogen atom, an alkyl group, an alkenyl group, an alkoxy group, an alkanoyl group, an alkylthio group, an aryloxy group, an alkylthioalkyl group, an alkylaryl group, an arylalkyl group, an amino group, an alkylamino group, a dialkylamino group, an aryl group, an alkylsufinyl group, an alkoxyalkyl group, an alkylsulfonyl group, an arylthio group, an arylsulfinyl group, an alkoxycarbonyl group, an arylsulfonyl group, an acrylic acid group, a phosphoric acid group, a phosphonic acid group, a halogen atom, a nitro group, a cyano group, a hydroxyl group, an epoxy group, a silyl group, a siloxane group, an alcohol group, a benzyl group, a carboxylate group, an ether group, an ether carboxylate group, an amide sulfonate group, an ether sulfonate group, and an urethane group;

adjacent two group $R^1$ may be bonded to each other to form an alkylene chain or an alkenylene chain each completing a 3-, 4-, 5-, 6- or 7-membered aromatic or aliphatic ring which may include at least one of a nitrogen atom, a sulfur atom and an oxygen atom; and $R^2$ is selected from a hydrogen atom, an alkyl group, an alkenyl group, an aryl group, an alkanoyl group, an alkylthioalkyl group, an alkylaryl group, an arylalkyl group, an amino group, an epoxy group, a silyl group, a siloxane group, an amide sulfonate group, an alcohol group, a benzyl group, a carboxylate group, an ether group, an ether carboxylate group, an amide sulfonate group, an ether sulfonate group, and an urethane group.

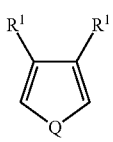

(v)

In formula (v), Q is selected from the group consisting of S, Se, and Te;

each $R^1$ is independently selected from a hydrogen atom, an alkyl group, an alkenyl group, an alkoxy group, an alkanoyl group, an alkylthio group, an aryloxy group, an alkylthioalkyl group, an alkylaryl group, an arylalkyl group, an amino group, an alkylamino group, a dialkylamino group, an aryl group, an alkylsulfinyl group, an alkoxyalkyl group, an alkylsulfonyl group, an arylthio group, an arylsulfinyl group, an alkoxycarbonyl group, an arylsulfonyl group, an acrylic acid group, a phosphoric acid group, a phosphonic acid group, a halogen atom, a nitro group, a cyano group, a hydroxyl group, an epoxy group, a silyl group, a siloxane group, an alcohol group, a benzyl group, a carboxylate group, an ether group, an ether carboxylate group, an amide sulfonate group, an ether sulfonate group, an ester sulfonate group, and an urethane group; and adjacent two group $R^1$ may be bonded to each other to form an alkylene chain or an alkenylene chain each completing a 3-, 4-, 5-, 6- or 7-membered aromatic or aliphatic ring which may include at least one of a nitrogen atom, a selenium atom, a tellurium atom, a sulfur atom, and an oxygen atom.

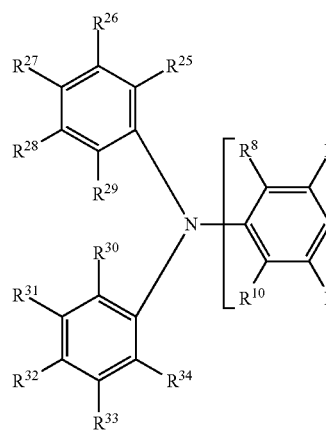

(vi)

In formula (vi), $R^1$ and $R^2$ each independently represent a hydrogen atom, a substituted or unsubstituted monovalent hydrocarbon group, a t-butoxycarbonyl group, or a benzyloxycarbonyl group;

$R^3$ to $R^{34}$ each independently represent a hydrogen atom, a hydroxyl group, a silanol group, a thiol group, a carboxyl group, a phosphoric acid group, a phosphoric ester group, an ester group, a thioester group, an amido group, a nitro group, a substituted or unsubstituted monovalent hydrocarbon group, an organooxy group, an organoamino group, an organosilyl group, an organothio group, an acyl group, a sulfone group, or a halogen atom; and m and n each independently represent an integer of 1 or more, which satisfy $m+n \leq 20$.

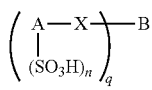

In formula (vii), X represents O, S or NH;

A represents a naphthalene ring or an anthracene ring which may have a substituent other than X and (SO₃H)n groups;

B represents a substituted or unsubstituted hydrocarbon group, a 1,3,5-triazine group, or a group represented by formula (vii-1) or (vii-2) which may have a substituent:

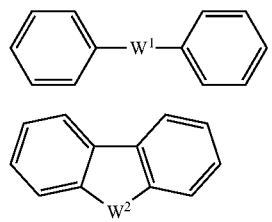

wherein $W^1$ and $W^2$ each independently represent O, S, S(O), or S(O$_2$), or represent N, Si, P, or P(O) which may have a substituent; and n represents an integer satisfying 1≤n≤4 and q is an integer satisfying 1≤q.

In view of improving the durability and increasing the charge transporting ability, B is preferably a substituted or unsubstituted di- or more valent hydrocarbon group comprising at least one aromatic ring, a di- or tri-valent 1,3,5-triazine group, or a substituted or unsubstituted di-valent diphenylsulfone group, and particularly preferably a substituted or unsubstituted di- or tri-valent benzyl group, a substituted or unsubstituted divalent p-xylylene group, a substituted or unsubstituted di- or tri-valent naphthyl group, a di- or tri-valent 1,3,5-triazine group, a substituted or unsubstituted divalent diphenylsulfone group, a di- to tetravalent perfluorobiphenyl group, a substituted or unsubstituted divalent 2,2-bis((hydroxypropoxy)phenyl)propyl group, or a substituted or unsubstituted polyvinylbenzyl group.

The compound represented by formula (vii) is particularly preferably represented by formula (vii-3):

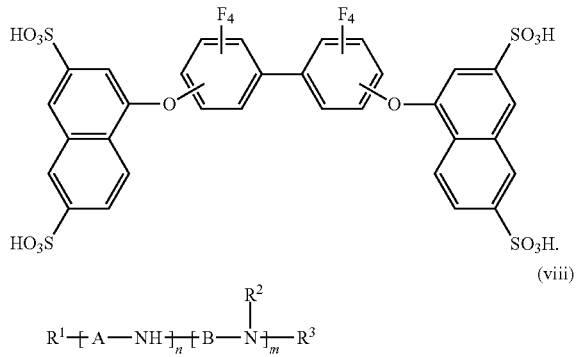

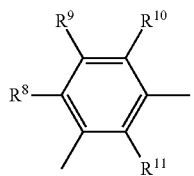

In formula (viii), $R^1$, $R^2$, and $R^3$ each independently represent a hydrogen atom, a halogen atom, a hydroxyl group, an amino group, a silanol group, a thiol group, a carboxyl group, a phosphoric acid group, a phosphoric ester group, an ester group, a thioester group, an amido group, a nitro group, a monovalent hydrocarbon group, an organooxy group, an organoamino group, an organosilyl group, an organothio group, an acyl group, or a sulfonic acid group; and A and B each independently represent a divalent group represented by formula (viii-1) or (viii-2):

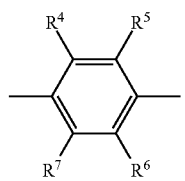

wherein $R^4$ to $R^{11}$ each independently represent a hydrogen atom, a halogen atom, a hydroxyl group, an amino group, a silanol group, a thiol group, a carboxyl group, a phosphoric acid group, a phosphoric ester group, an ester group, a thioester group, an amido group, a nitro group, a monovalent hydrocarbon group, an organooxy group, an organoamino group, an organosilyl group, an organothio group, an acyl group, or a sulfonic acid group; and m and n each independently represent an integer of 1 or more satisfying m+n≤20.

The material (ix) is a mixture of the following compounds:

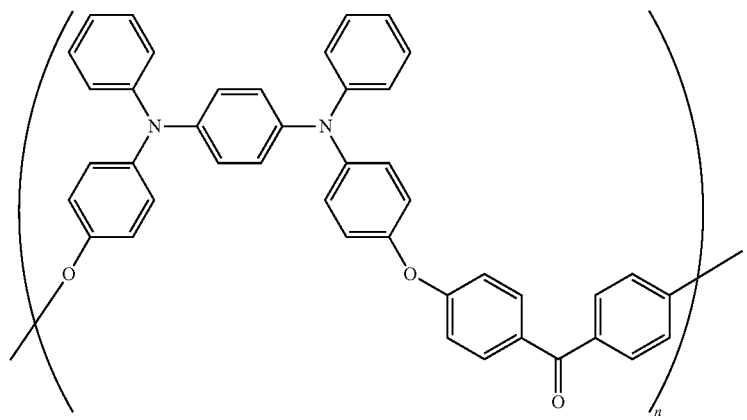
wherein n is an integer of 3 or more, and
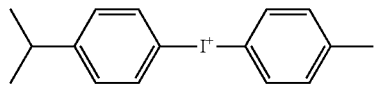
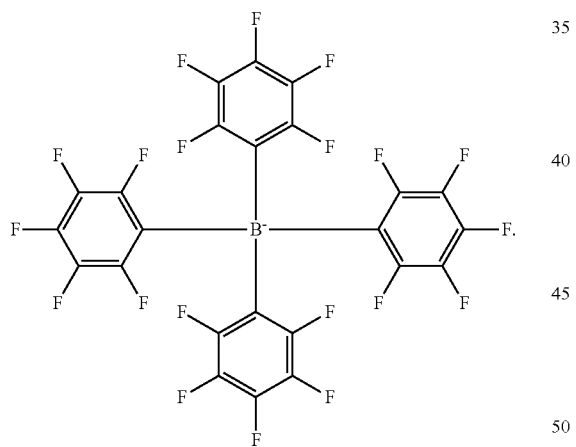
The material (x) is a mixture of the following compounds:
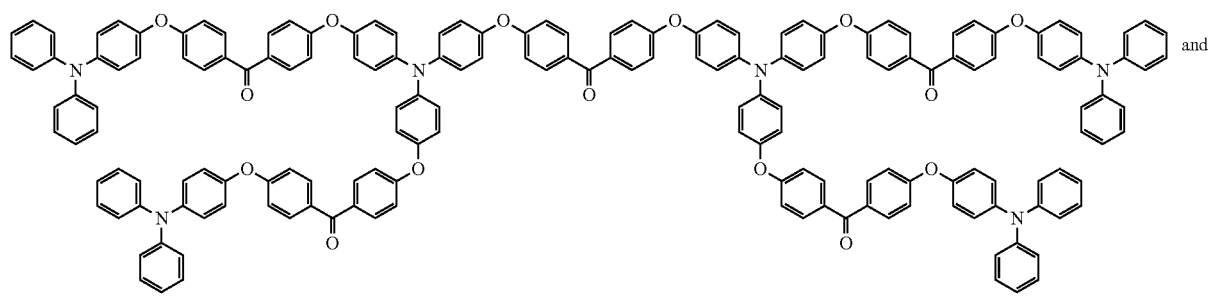

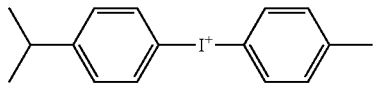
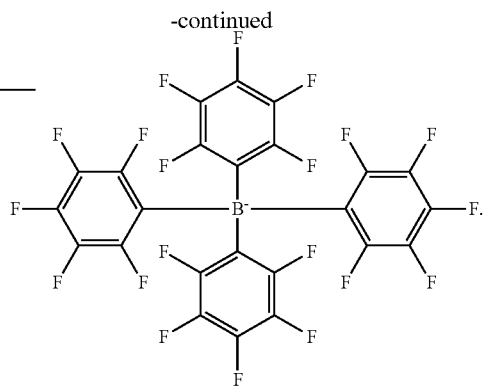

In an embodiment of the invention, a phenylamine-based polymer represented by formula (X) is also usable as the hole transporting material:

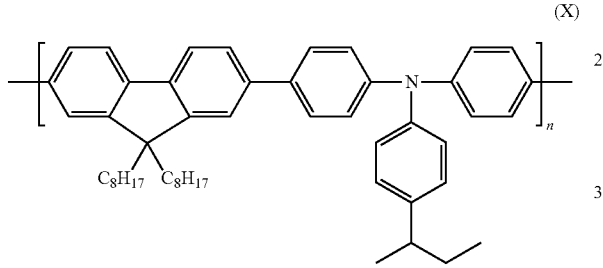
(X)

wherein n is an integer of 3 or more.

In an embodiment of the invention, the hole transporting layer may be made into a two-layered structure of a first hole transporting layer (anode side) and a second hole transporting layer (cathode side).

The thickness of the hole transporting layer is preferably 10 to 200 nm, although not particularly limited thereto.

In an embodiment of the invention, a layer comprising an acceptor material may be formed in contact with the anode side of the hole transporting layer or the first hole transporting layer. With such a layer, it is expected that the driving voltage is lowered and the production cost is reduced.

The acceptor material is preferably a compound represented by formula (K):

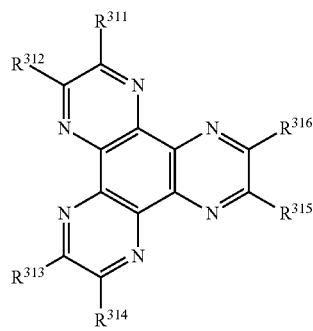
(K)

wherein $R^{311}$ to $R^{316}$ may be the same or different and each independently represent a cyano group, —$CONH_2$, a carboxyl group, or —$COOR^{317}$ wherein $R^{317}$ represents an alkyl group having 1 to 20 carbon atoms or a cycloalkyl group having 3 to 20 carbon atoms; and one or more pairs selected from $R^{311}$ and $R^{312}$, $R^{313}$ and $R^{314}$, and $R^{315}$ and $R^{316}$ may bond to each other to form a group represented by —CO—O—CO—.

Examples of $R^{317}$ include a methyl group, an ethyl group, a n-propyl group, an isopropyl group, a n-butyl group, an isobutyl group, a t-butyl group, a cyclopentyl group, and a cyclohexyl group.

The thickness of the layer comprising the acceptor material is preferably 5 to 20 nm, although not particularly limited thereto.

The following compounds may be used as the acceptor material.

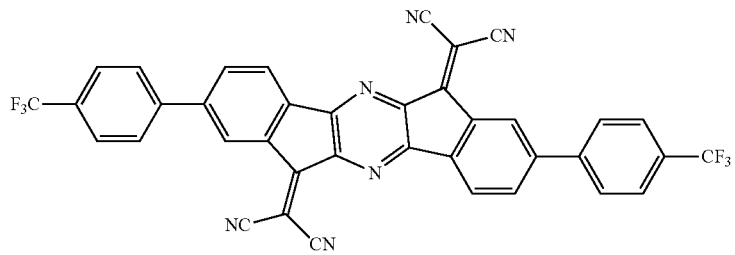
(A-1)

-continued
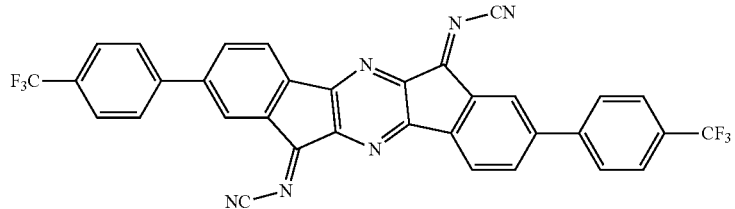
(A-2)
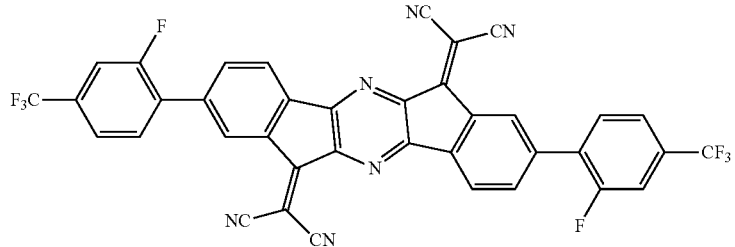
(A-3)
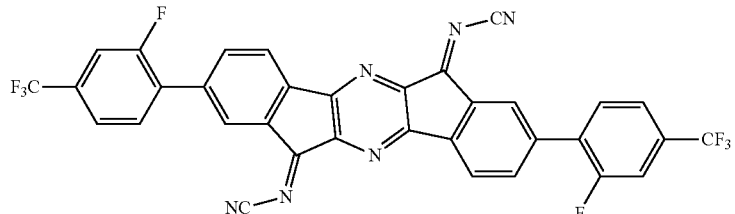
(A-4)
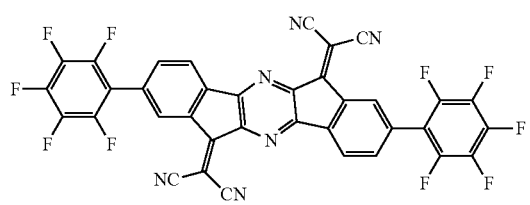
(A-5)
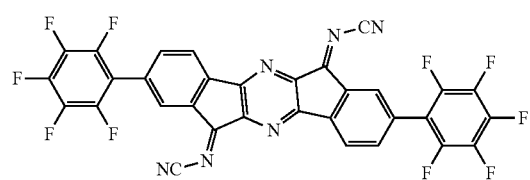
(A-6)
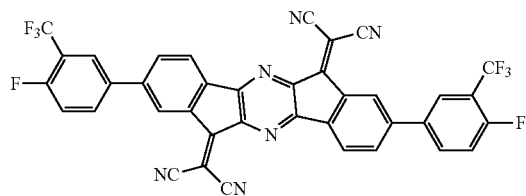
(A-7)
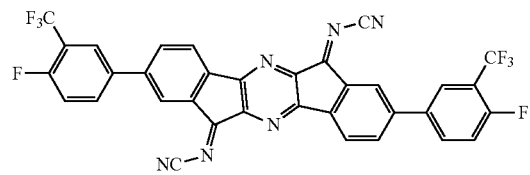
(A-8)
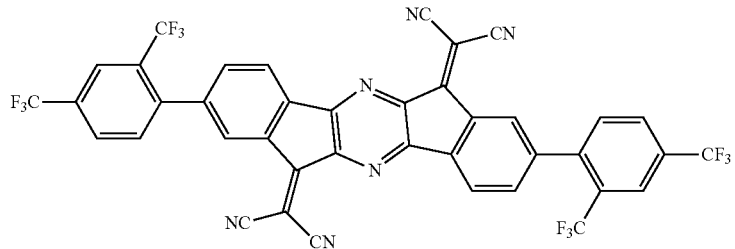
(A-9)

-continued
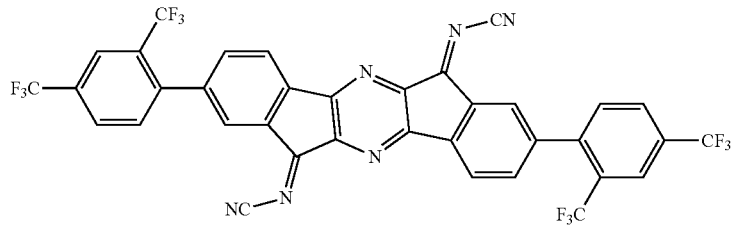
(A-10)
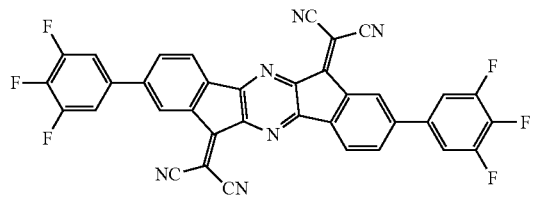
(A-11)
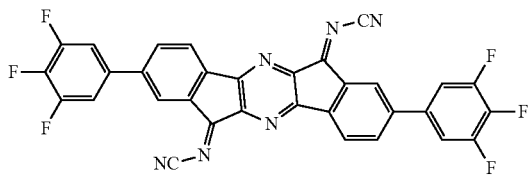
(A-12)
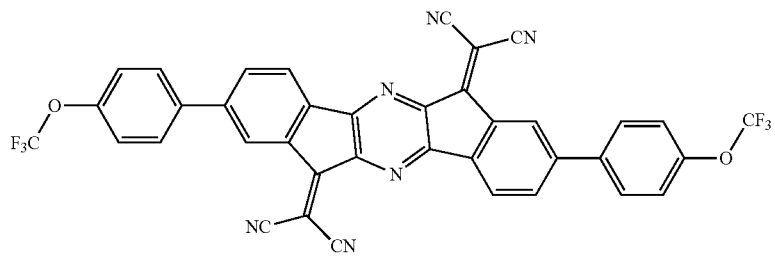
(A-13)
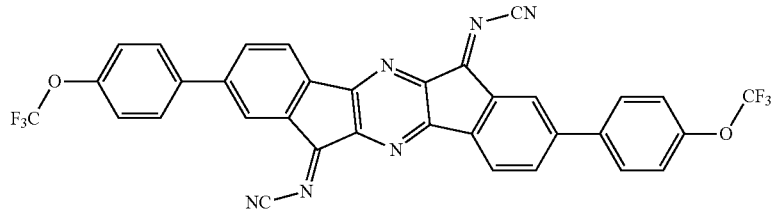
(A-14)
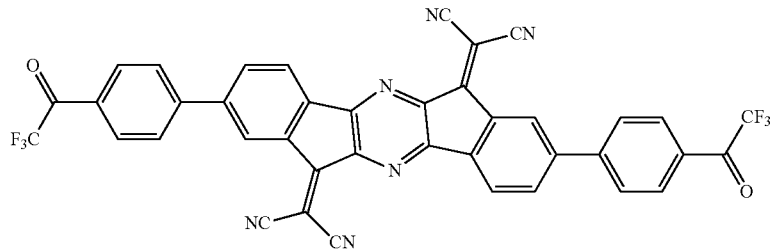
(A-15)
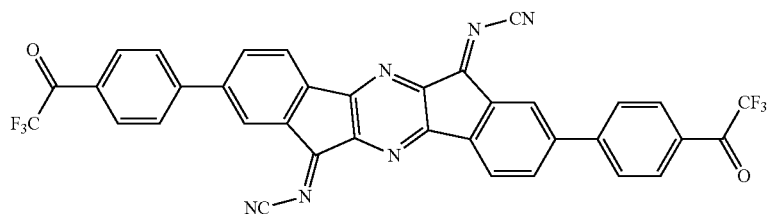
(A-16)

-continued
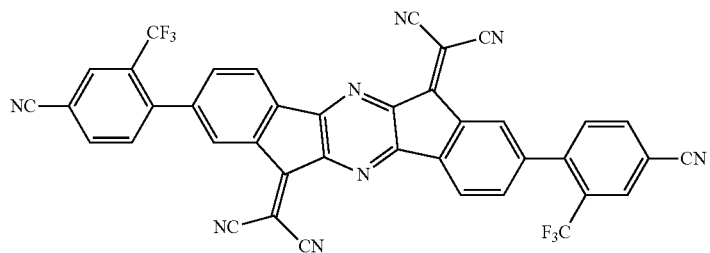
(A-17)
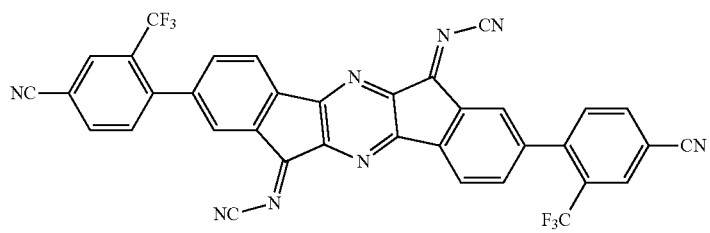
(A-18)
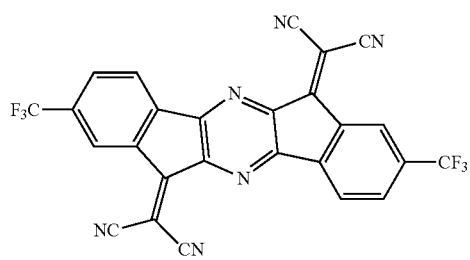
(A-19)
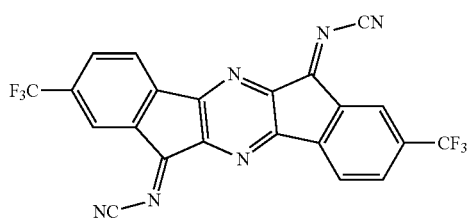
(A-20)
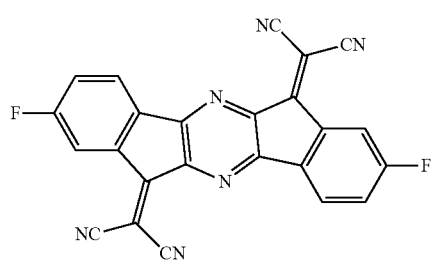
(A-21)
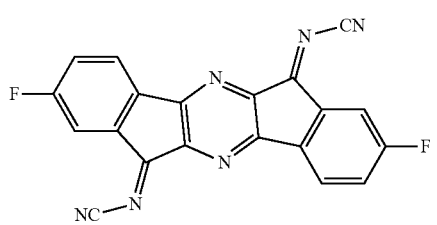
(A-22)
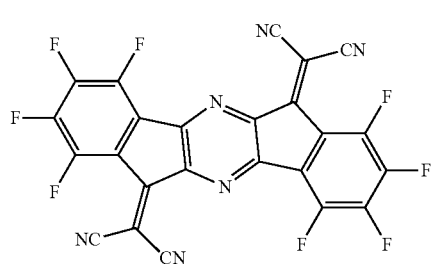
(A-23)
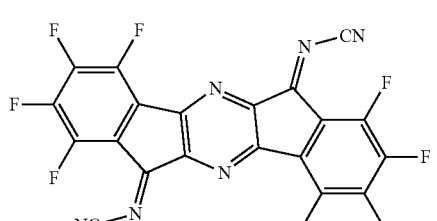
(A-24)
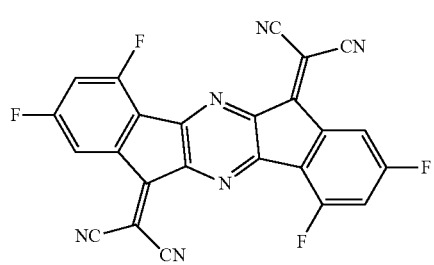
(A-25)
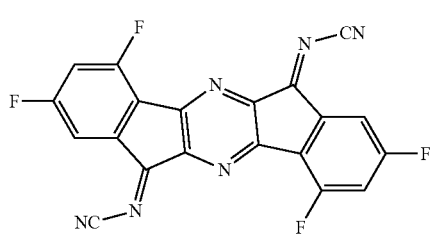
(A-26)

-continued
(A-27)
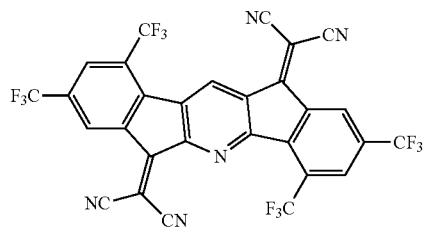
(A-28)
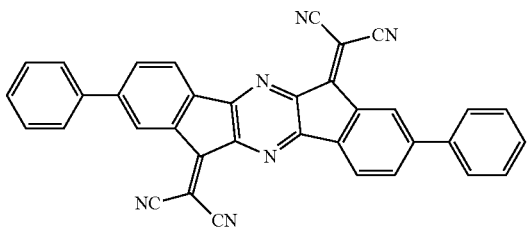
(A-29)
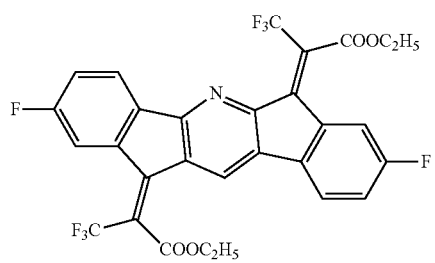
(A-30)
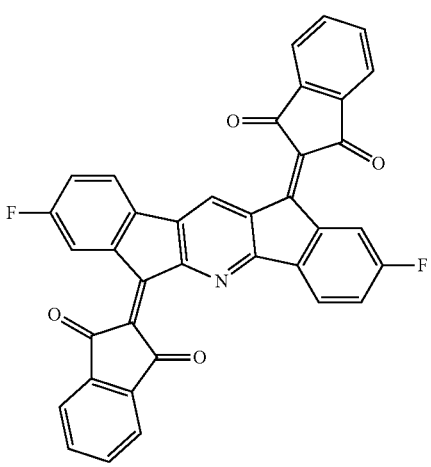
(A-31)
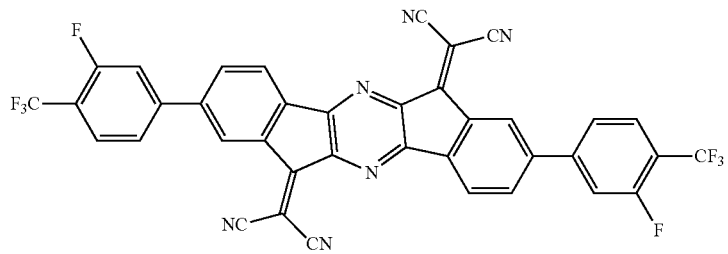
(A-32)
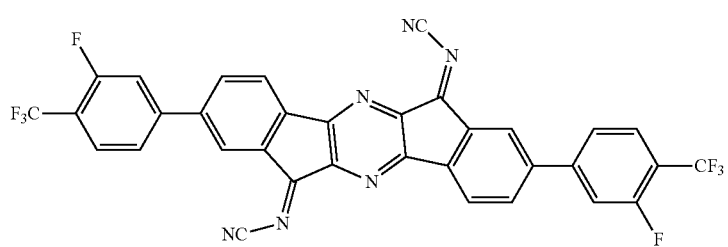
(A-33)
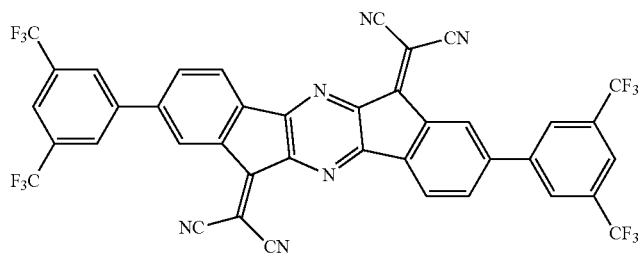

-continued
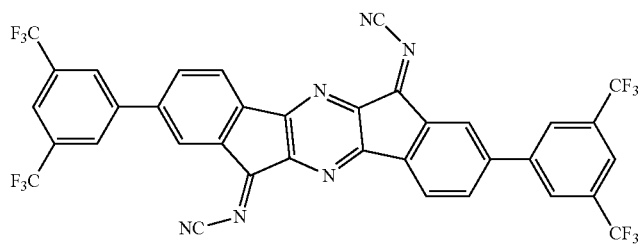
(A-34)
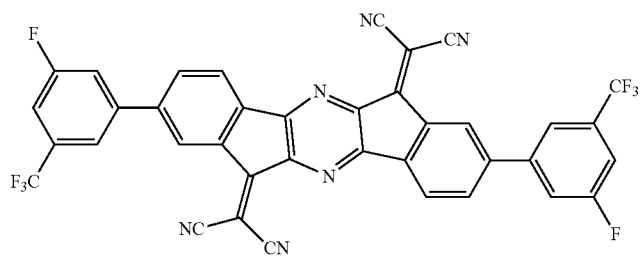
(A-35)
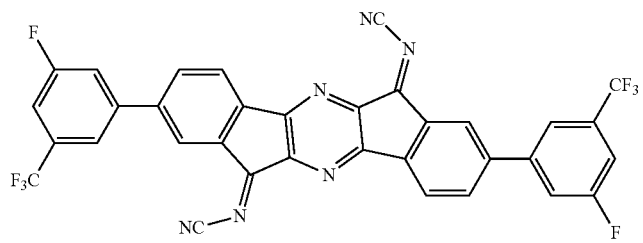
(A-36)
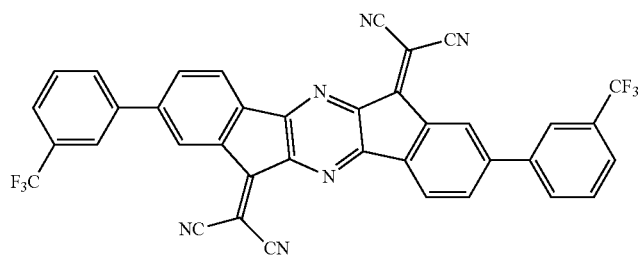
(A-37)
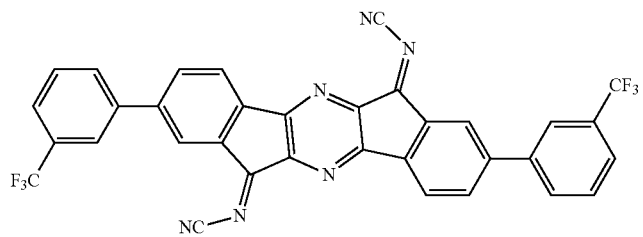
(A-38)
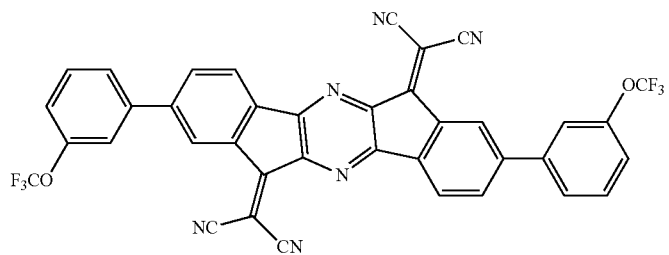
(A-39)

-continued
(A-40)
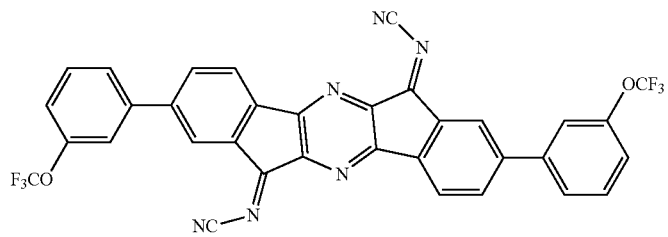
(A-41)
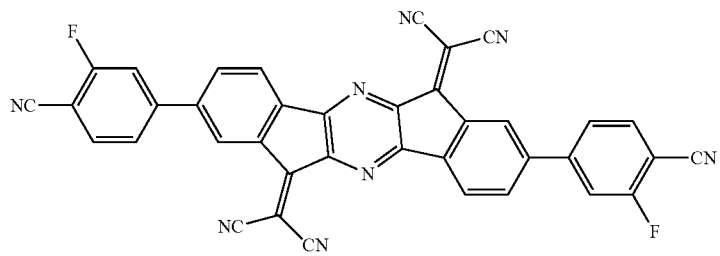
(A-42)
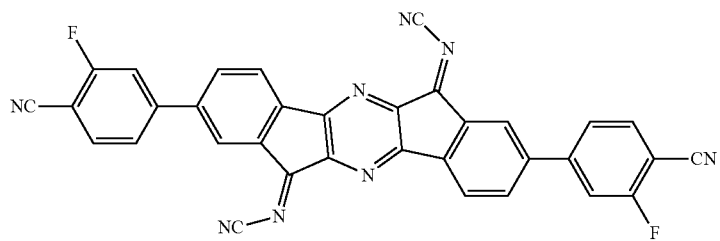
(A-43)
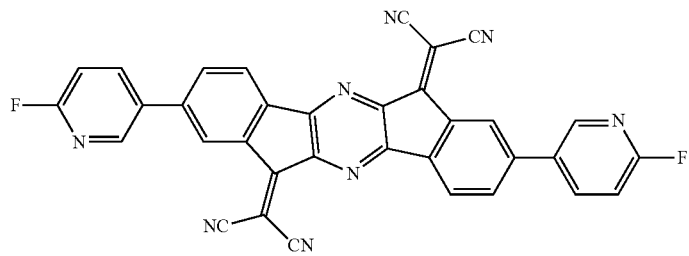
(A-44)
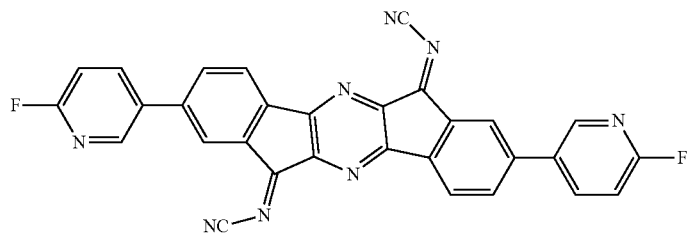
(A-45)
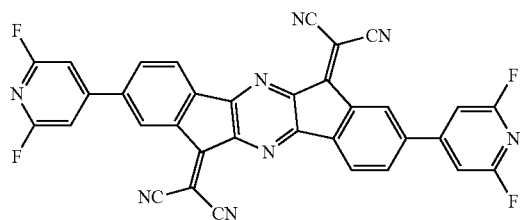
(A-46)
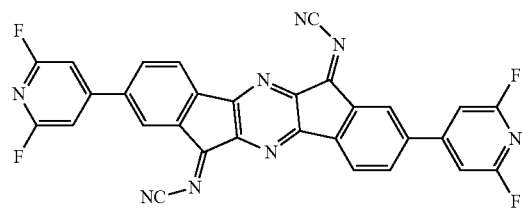

-continued
(A-47)
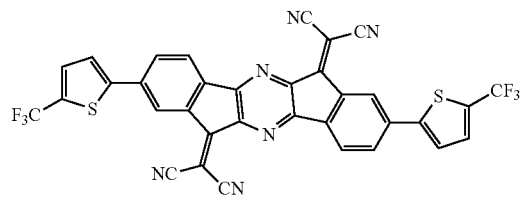
(A-48)
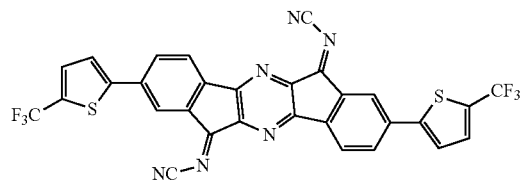
(A-49)
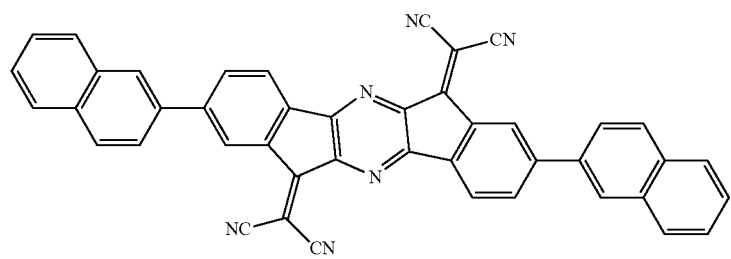
(A-50)
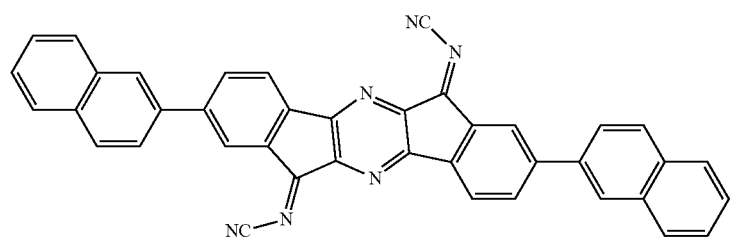
(A-51)
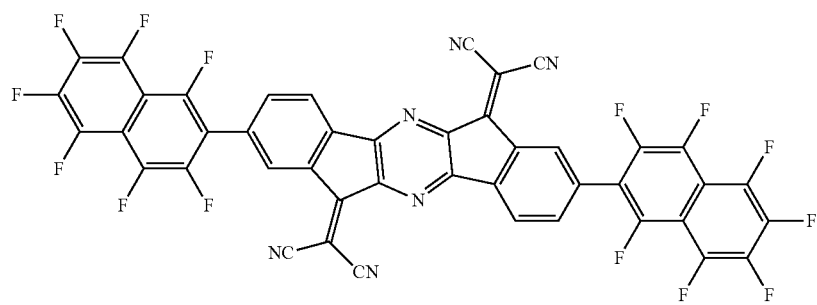
(A-52)
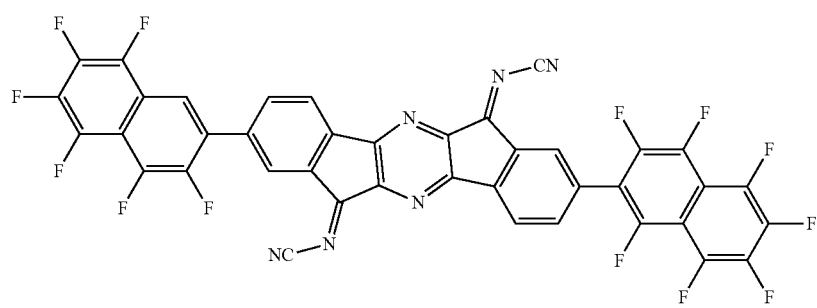

-continued
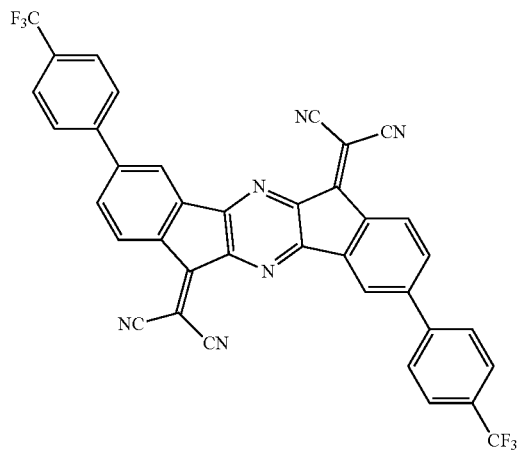
(A-53)
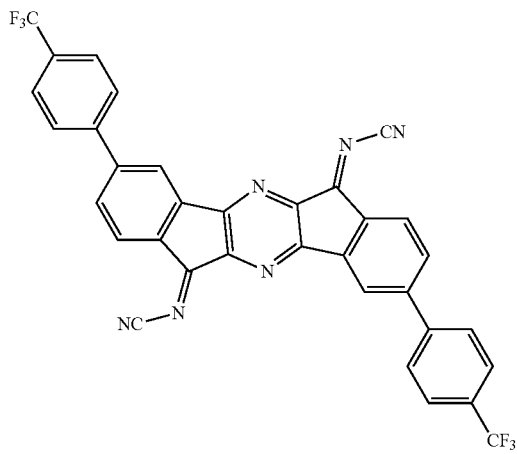
(A-54)
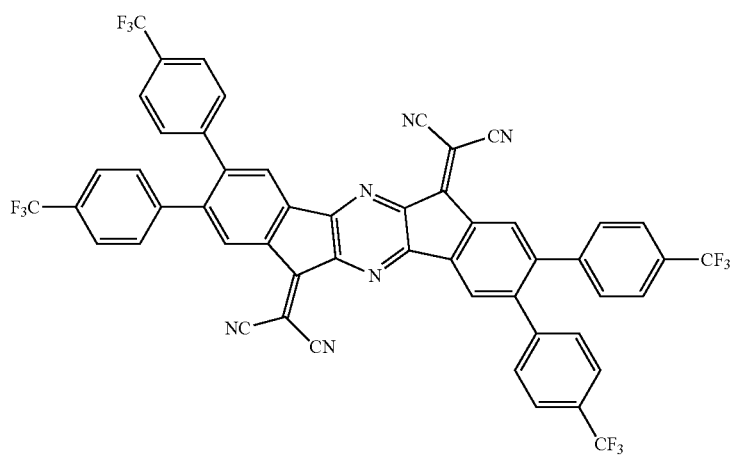
(A-55)
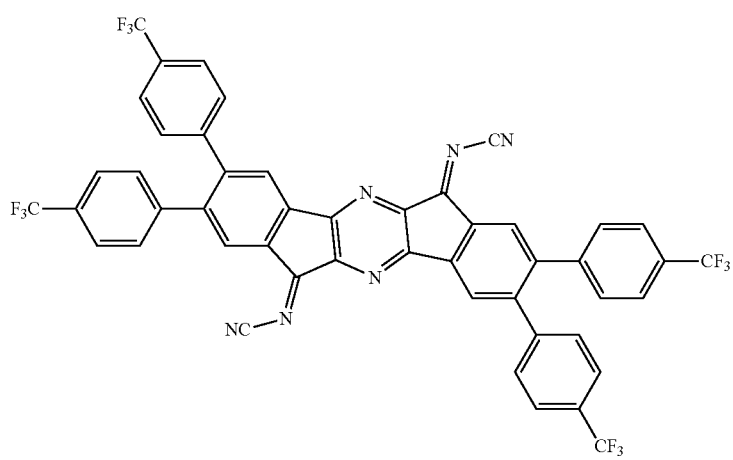
(A-56)

(A-57)
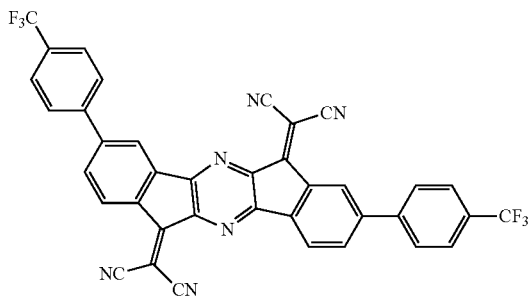
(A-58)
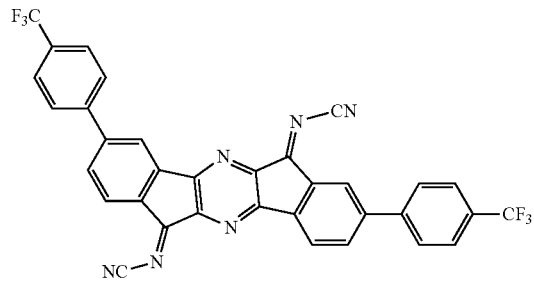
(A-59)
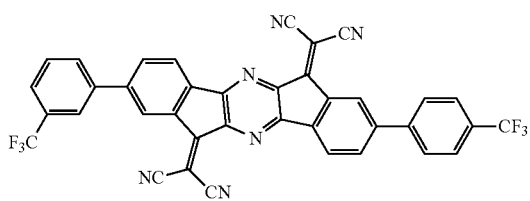
(A-60)
(A-61)
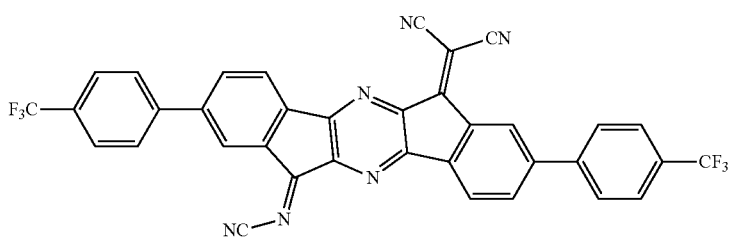
(B-1)
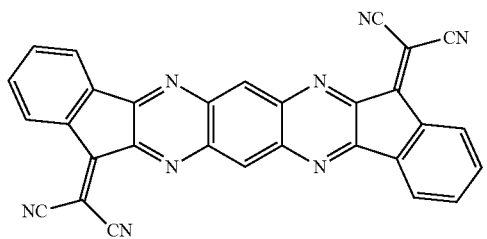
(B-2)
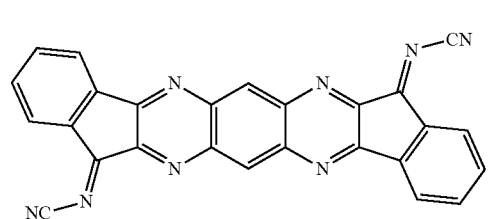
(B-3)
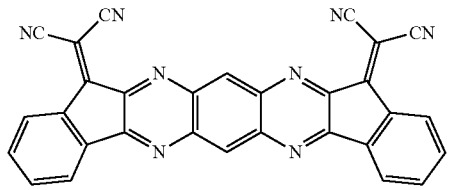
(B-4)
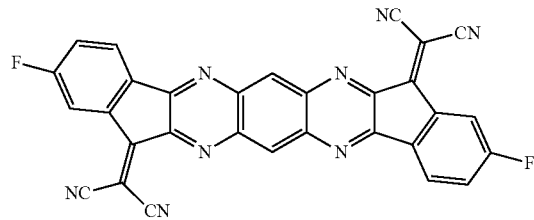
(B-5)
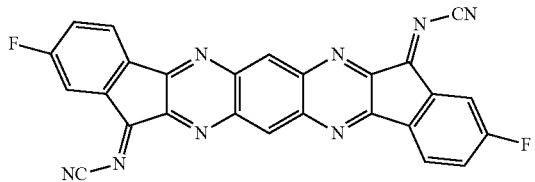
(B-6)
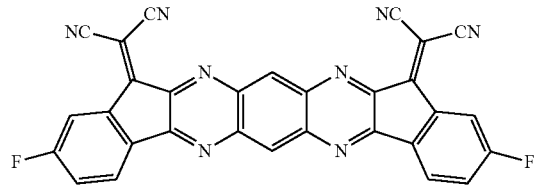

-continued
(B-7)
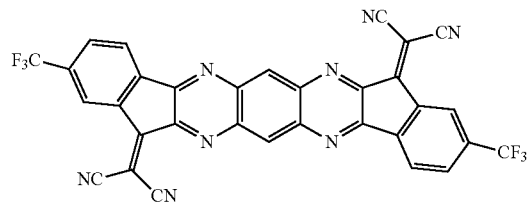
(B-8)
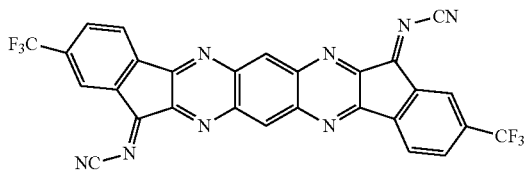
(B-9)
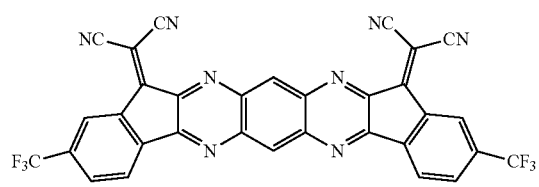
(B-10)
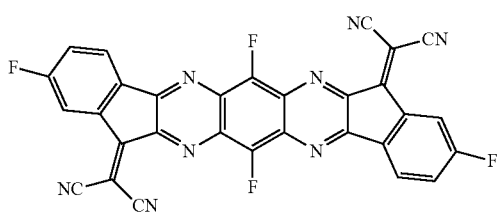
(B-11)
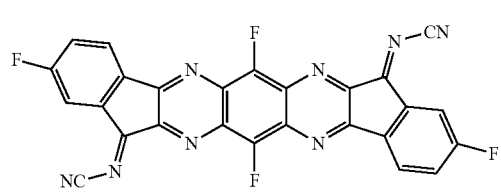
(B-12)
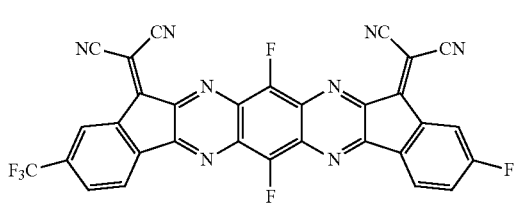
(B-13)
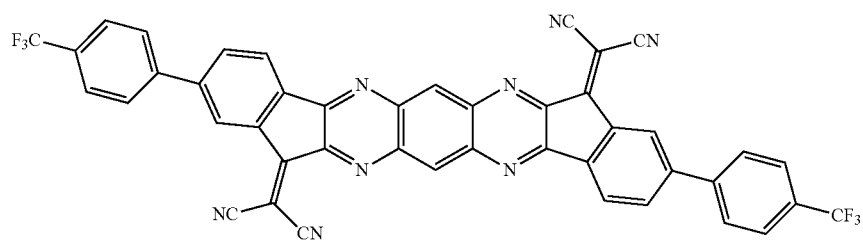
(B-14)
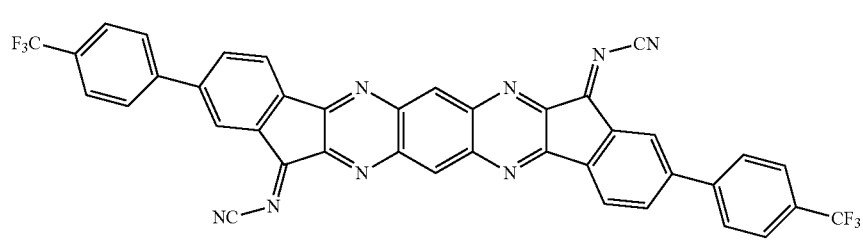
(B-15)
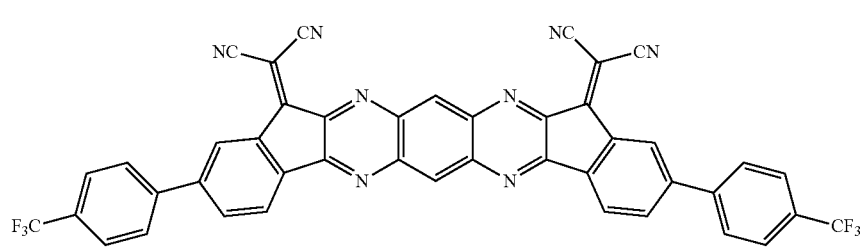

-continued
(B-16)
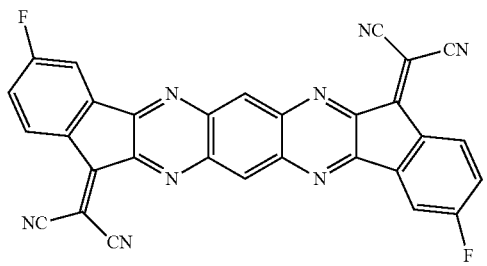
(B-17)
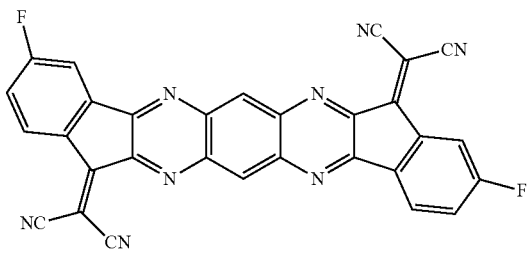
(B-18)
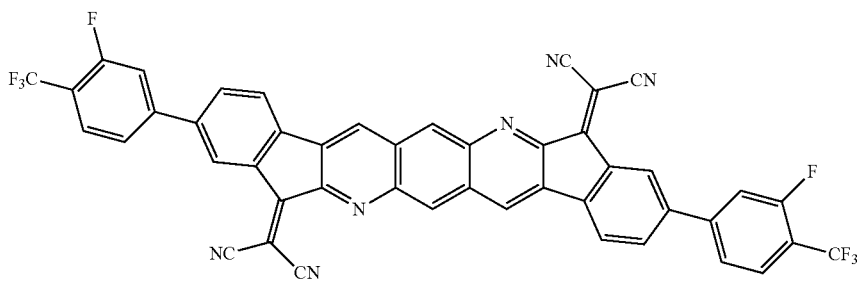
(B-19)
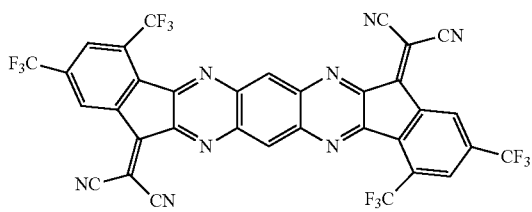
(B-20)
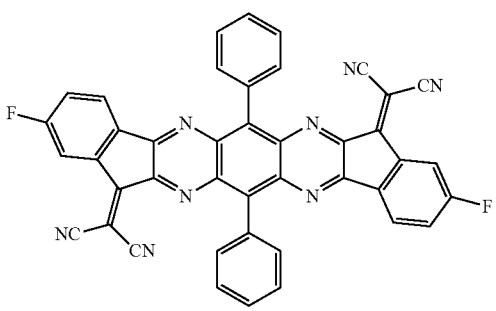
(A'-1)
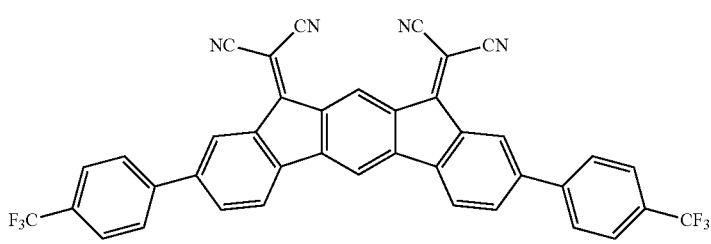
(A'-2)
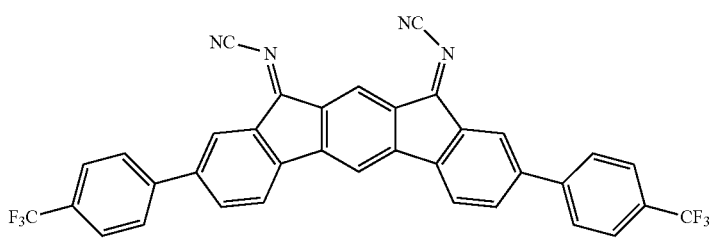
(A'-3)
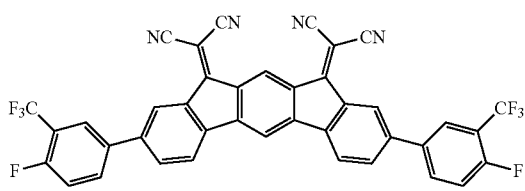
(A'-4)
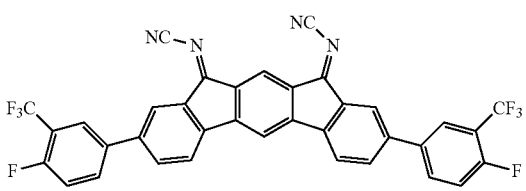

-continued
(A'-5)
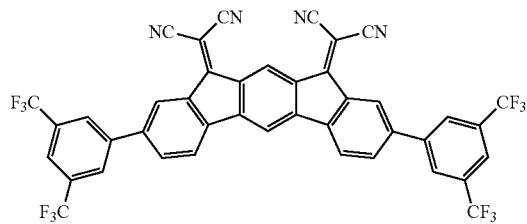
(A'-6)
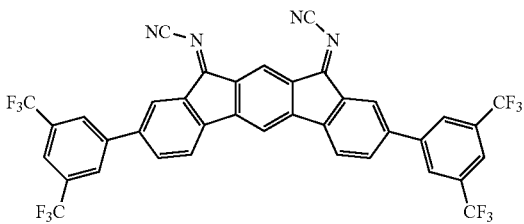
(A'-7)
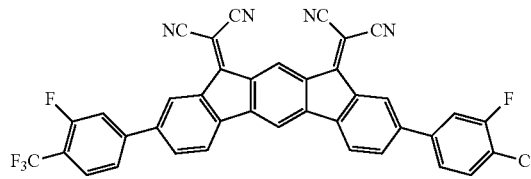
(A'-8)
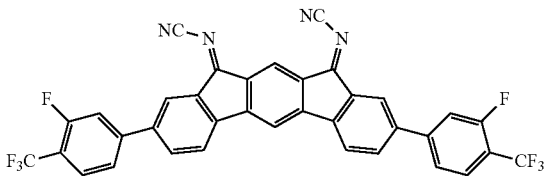
(A'-9)
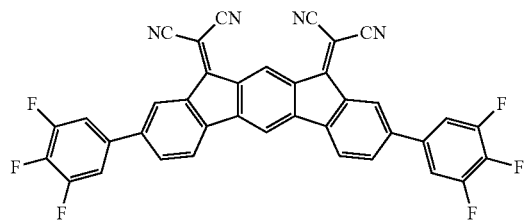
(A'-10)
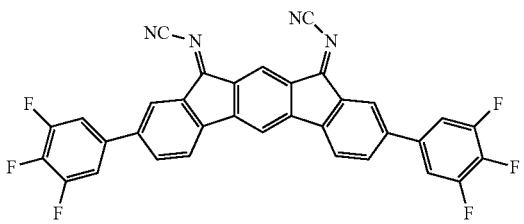
(A'-11)
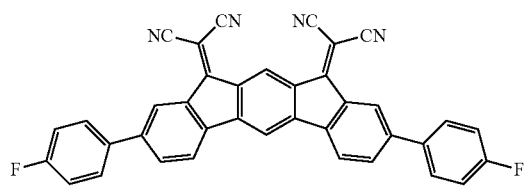
(A'-12)
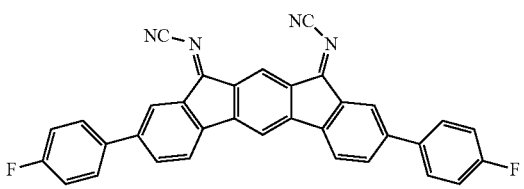
(A'-13)
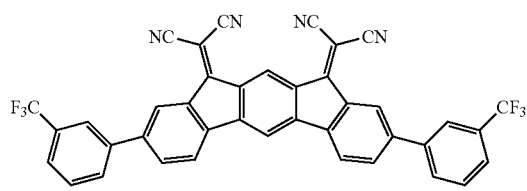
(A'-14)
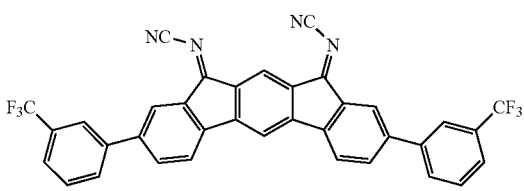
(A'-15)
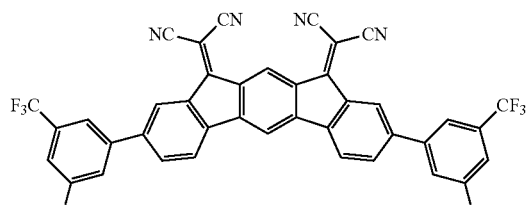
(A'-16)
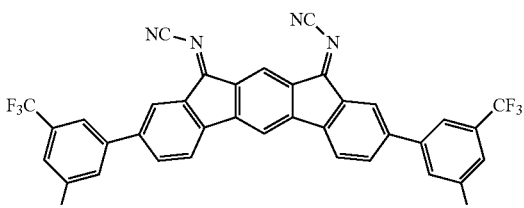
(A'-17)
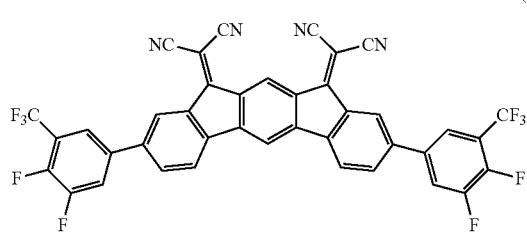

-continued
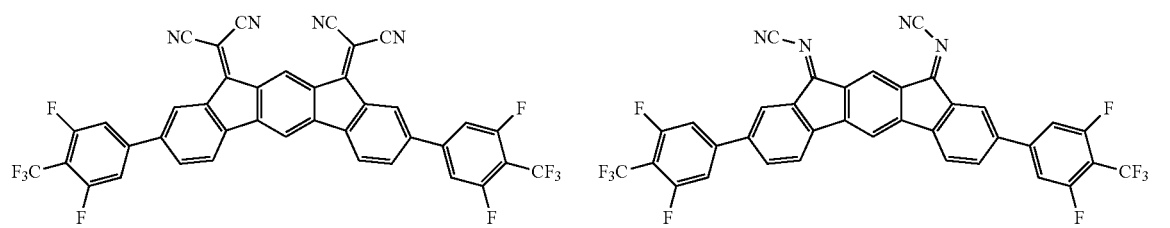
(A'-19) (A'-20)
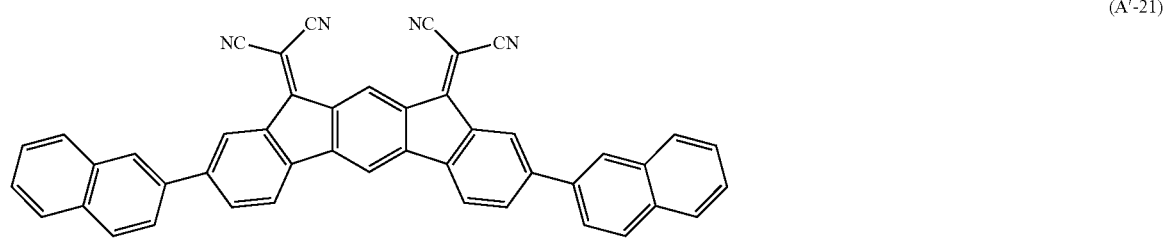
(A'-21) (A'-22)
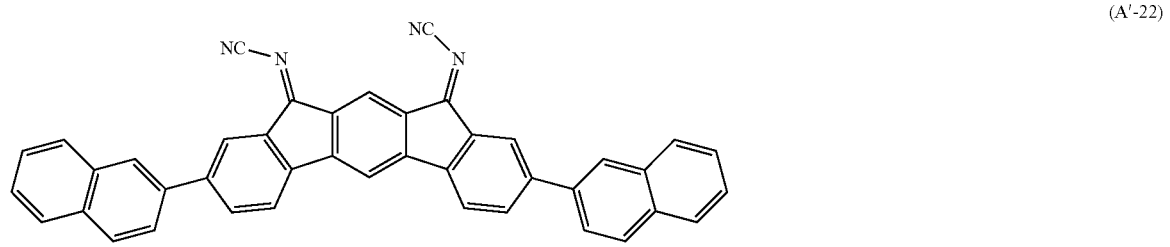
(A'-23) (A'-24)
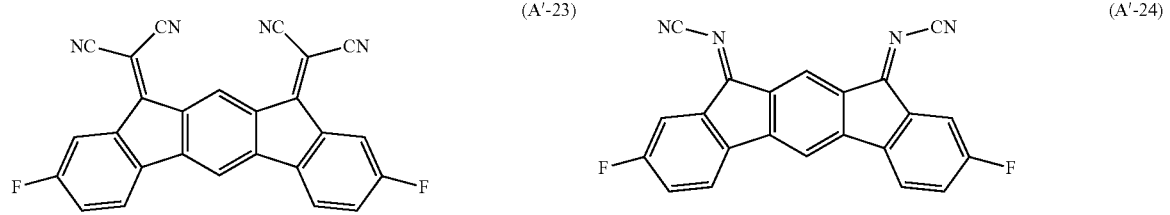
(A'-25) (A'-26)
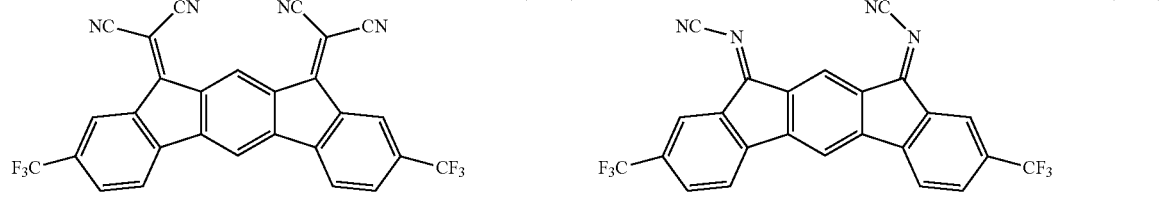
(A'-27) (A'-28)
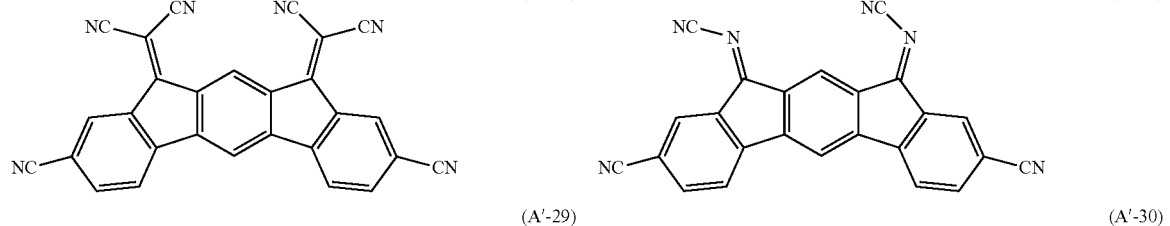
(A'-29) (A'-30)
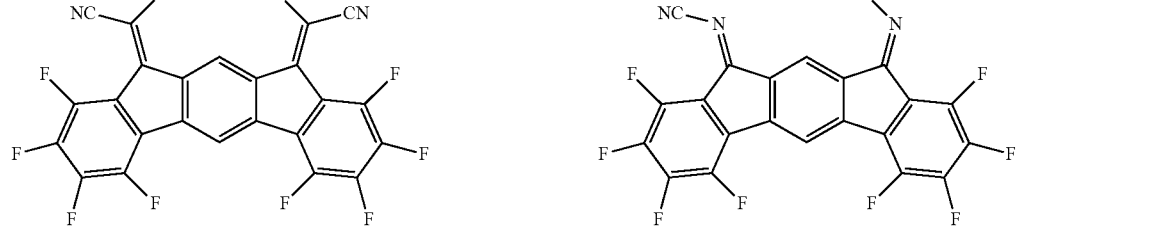

-continued
(A'-31)
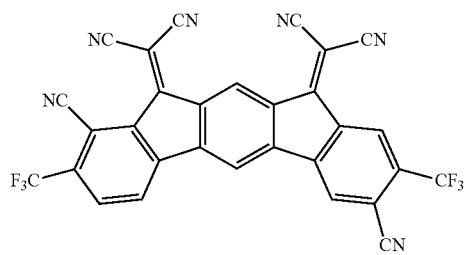
(A'-32)
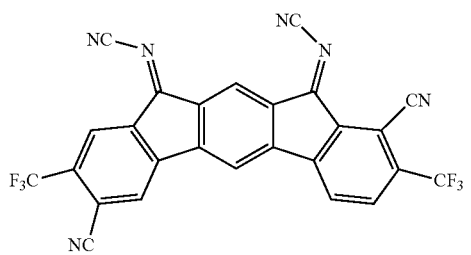
(A'-43)
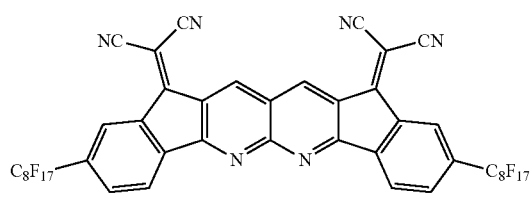
(A'-44)
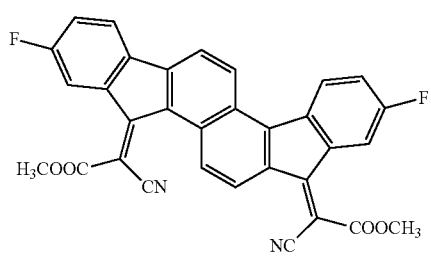
(A'-45)
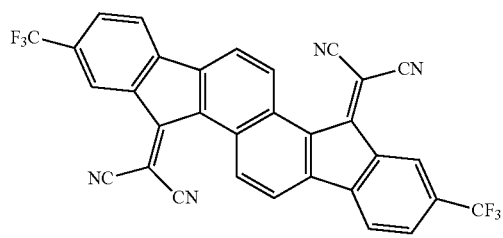
(A'-46)
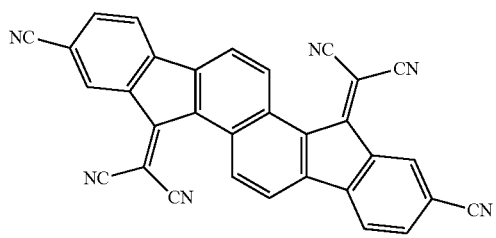
(A'-47)
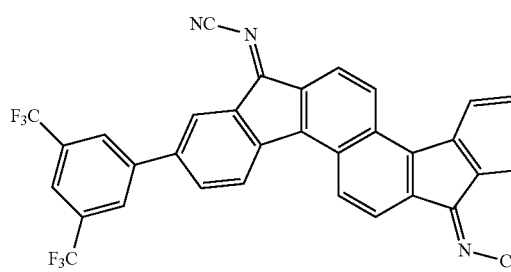
(A'-48)
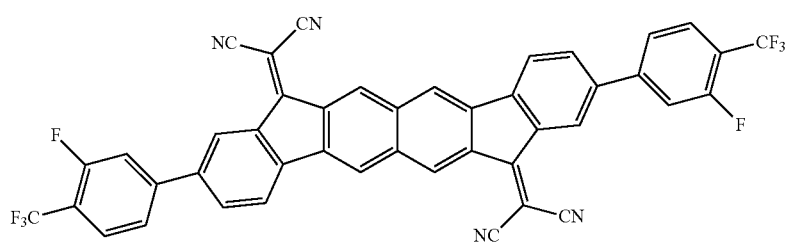
(A'-49)
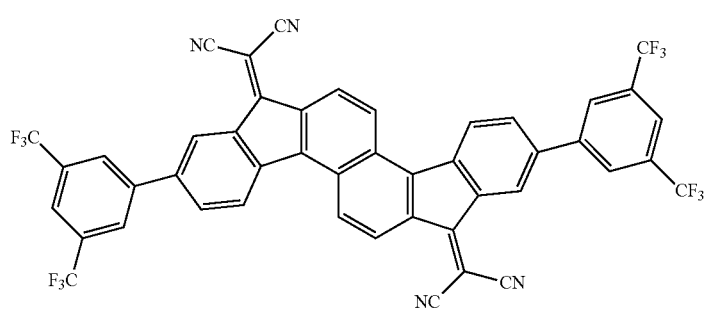

-continued
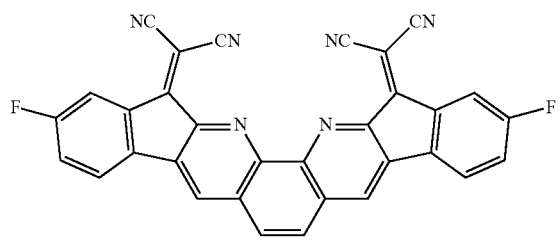
(A'-50)
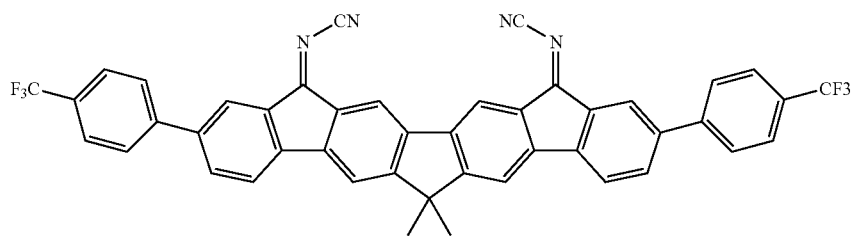
(A'-51)
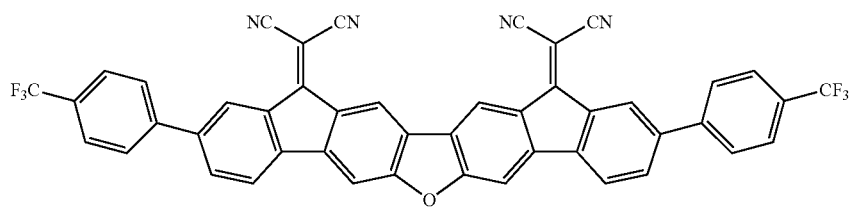
(A'-52)
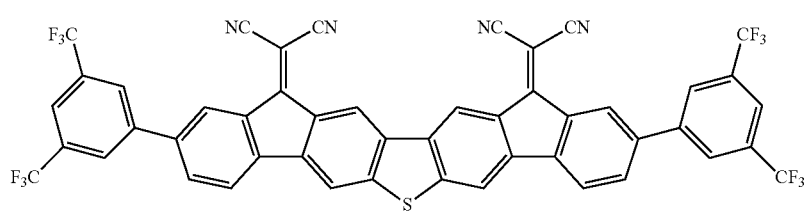
(A'-53)
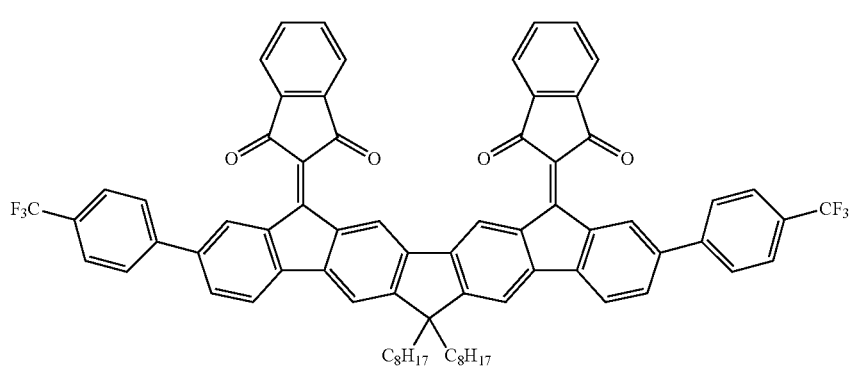
(A'-54)
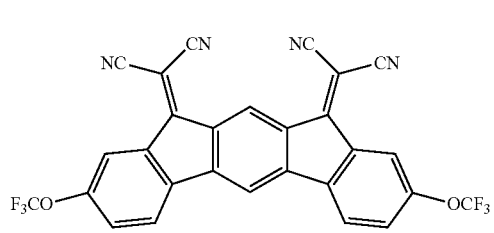
(A'-55)
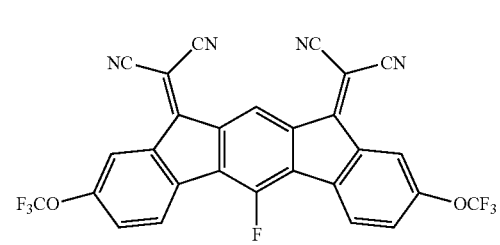
(A'-56)

-continued
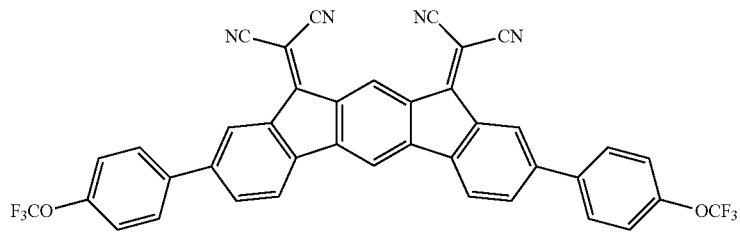
(A'-57)
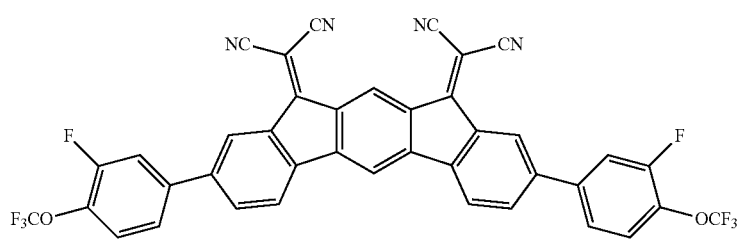
(A'-58)
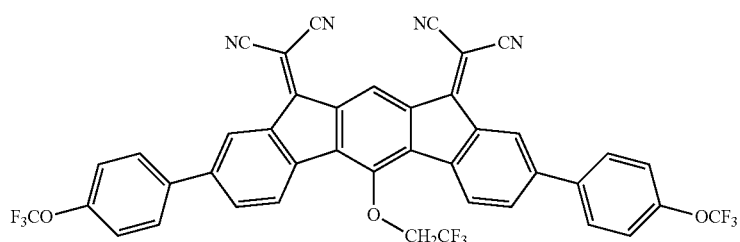
(A'-59)
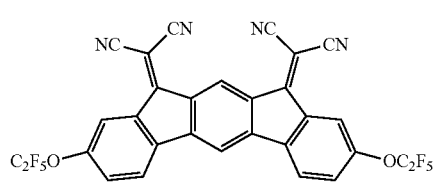
(A'-60)
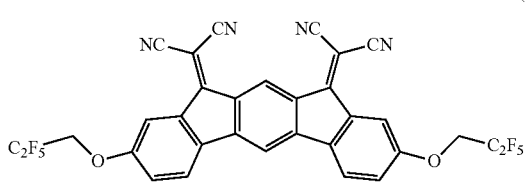
(A'-61)
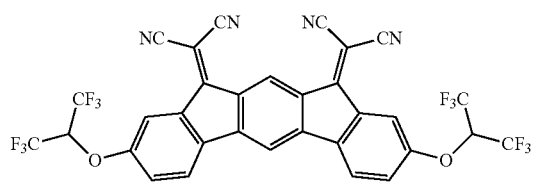
(A'-62)
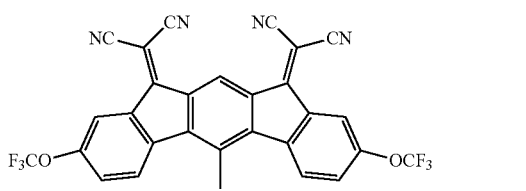
(A'-63)
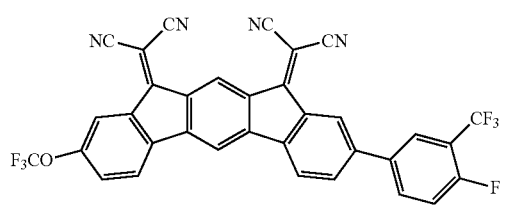
(A'-64)
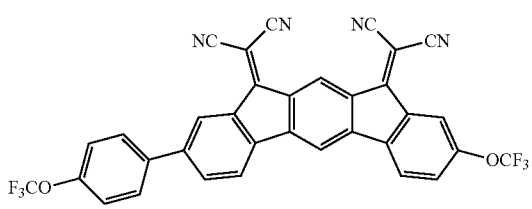
(A'-65)
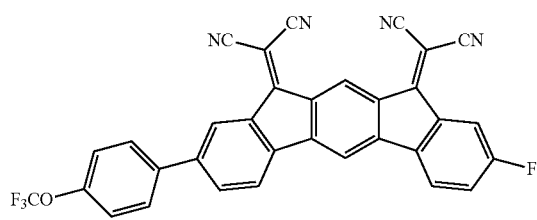
(A'-66)

N/P Doping

The carrier injecting properties of the hole transporting layer and the electron transporting layer can be controlled, as described in JP 3695714B, by the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$ (2,3,5,6-Tetrafluoro-7,7,8,8-tetracyanoquinodimethane).

Space Layer

The space layer is a layer, for example, disposed between a fluorescent emitting layer and a phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used as a material for the space layer. To prevent the diffusion of triplet energy in the adjacent phosphorescent emitting layer, the triplet energy of the material for the space layer is preferably 2.6 eV or more. The materials described above with respect to the hole transporting layer are usable as the material for the space layer. In an embodiment of the invention, the compound (1) and the material for organic EL devices may be used as the material for the space layer.

Blocking Layer

In an embodiment of the invention, a blocking layer, such as an electron blocking layer, a hole blocking layer, and a triplet blocking layer, is preferably formed adjacent to the light emitting layer. The electron blocking layer is a layer which prevents the diffusion of electrons from the light emitting layer to the hole transporting layer. In an embodiment of the invention, the compound (1) and the material for organic EL devices may be used as the material for hole blocking layer.

The triplet blocking layer prevents the diffusion of triplet excitons generated in a light emitting layer to adjacent layers and has a function of confining the triplet excitons within a light emitting layer, thereby preventing the deactivation of energy on a molecule other than the emitting dopant of triplet excitons, for example, on a molecule in an electron transporting layer.

If a phosphorescent device having a triplet blocking layer satisfies the following energy relationship:

$$E^T_d < E^T_{TB}$$

wherein $E^T_d$ is the triplet energy of a phosphorescent dopant in a light emitting layer and $E^T_{TB}$ is the triplet energy of a compound forming the triplet blocking layer,
the triplet excitons of phosphorescent dopant are energetically confined (not move into other molecules). Therefore, the energy deactivation process other than the emission on the phosphorescent dopant may be prevented, thereby enabling the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of the ambient heat energy when a device is operated at around room temperature as generally employed in practical operation. As compared with the fluorescent emission, the phosphorescent emission is likely to be affected by the endothermic diffusion of excitons because the lifetime of triplet excitons is longer. Therefore, as for the energy difference $\Delta E^T$, the larger as compared with the heat energy of room temperature, the better, i.e., the energy difference $\Delta E^T$ is more preferably 0.1 eV or more and particularly preferably 0.2 eV or more. In an embodiment of the invention, the compound (1) and the material for organic EL devices are usable as the material for triplet blocking layer of the TTF fluorescent device described in WO 2010/134350A1.

The electron mobility of the material for the triplet blocking layer is preferably $10^{-6}$ cm$^2$/Vs or more at an electric field strength of 0.04 to 0.5 MV/cm. There are several methods for measuring the electron mobility of organic material, for example, Time of Flight method. In the present invention, the electron mobility is determined by an impedance spectroscopy.

The electron mobility of the electron injecting layer is preferably $10^{-6}$ cm$^2$/Vs or more at an electric field strength of 0.04 to 0.5 MV/cm. Within the above range, the injection of electrons from the cathode to the electron transporting layer is promoted and the injection of electrons to the adjacent blocking layer and the light emitting layer is also promoted, thereby enabling to drive a device at lower voltage.

In an embodiment of the invention, each layer of the organic EL device may be formed by any of known methods, such as a vacuum vapor deposition method and a spin coating method, for example, by a vacuum vapor deposition method, a molecular beam epitaxy method (MBE method) and a coating method using a solution of the compound for each layer in a solvent, such as a dipping method, a spin coating method, a casting method, a bar coating method and a roll coating method.

The thickness of each organic thin film layer is not particularly limited and preferably several nanometers to 1 m because an excessively small thickness may cause defects, such as pin holes, and an excessively large thickness may require a high applied voltage to reduce the efficiency.

The layer comprising the compound (1) (light emitting layer, hole transporting layer, electron transporting layer) is preferably formed by forming a solution (ink composition) containing the compound (1) and another optional material, such as a dopant, into a film by the above coating method.

Examples of the film-forming method include known coating methods, and preferably a spin coating method, a casting method, a microgravure coating method, a gravure coating method, a bar coating method, a roll coating method, a slit coating method, a wire bar coating method, a dip coating method, a spray coating method, a screen printing method, a flexographic printing method, an off-set printing method, an ink-jet printing method, and a nozzle printing method. When a pattern is formed, a screen printing method, a flexographic printing method, an off-set printing method, and an ink-jet printing method are preferred. The film formation by these methods can be made under the conditions well known by a skilled person.

After coating, the solvent is removed by heating (250° C. or below) and drying under vacuum, and the irradiation of light and the high temperature heating exceeding 250° C. for polymerization reaction are not needed. Therefore, the deterioration of the device in its performance due to the irradiation of light and the high temperature heating exceeding 250° C. can be prevented.

The film-forming solution (ink composition) comprises at least one compound (1) and may further comprise another material, for example, a hole transporting material, an electron transporting material, a light emitting material, an acceptor material, and an additive, such as a stabilizer.

The film-forming solution may contain an additive for controlling the viscosity and/or surface tension, for example, a thickener (a high molecular weight compound, etc.), a viscosity depressant (a low molecular weight compound, etc.) and a surfactant. In addition, an antioxidant not adversely affecting the performance of the organic EL device, for example, a phenol antioxidant and a phosphorus antioxidant, may be included so as to improve the storage stability.

The content of the compound (1) in the film-forming solution (ink composition) is preferably 0.1 to 15% by mass and more preferably 0.5 to 10% by mass based on the total amount of the film-forming solution.

Examples of the high molecular weight compound usable as the thickener include an insulating resin, such as polystyrene, polycarbonate, polyarylate, polyester, polyamide, polyurethane, polysulfone, polymethyl methacrylate, polymethyl acrylate, cellulose, and a copolymer thereof, a photoconductive resin, such as poly-N-vinylcarbazole and polysilane; and an electroconductive resin, such as polythiophene and polypyrrole.

Examples of the solvent for the film-forming solution include a chlorine-containing solvent, such as chloroform, methylene chloride, 1,2-dichloroethane, 1,1,2-trichloroethane, chlorobenzene, and o-dichlorobenzene; an ether solvent, such as tetrahydrofuran, dioxane, dioxolane, and anisole; an aromatic hydrocarbon solvent, such as toluene and xylene; an aliphatic hydrocarbon solvent, such as cyclohexane, methylcyclohexane, n-pentane, n-hexane, n-heptane, n-octane, n-nonane, and n-decane; a ketone solvent, such as acetone, methyl ethyl ketone, cyclohexanone, benzophenone, and acetophenone; an ester solvent, such as ethyl acetate, butyl acetate, ethyl cellosolve acetate, methyl benzoate, and phenyl acetate; a polyhydric alcohol and its derivatives, such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, and 1,2-hexanediol; an alcoholic solvent, such as methanol, ethanol, propanol, isopropanol, and cyclohexanol; a sulfoxide solvent, such as dimethyl sulfoxide; and an amide solvent, such as N-methyl-2-pyrrolidone and N,N-dimethylformamide. These solvents may be used alone or in combination of two or more.

Of the above solvents, in view of solubility, uniform film formation, viscosity, etc., preferred are the aromatic hydrocarbon solvent, the ether solvent, the aliphatic hydrocarbon solvent, the ester solvent and the ketone solvent, and more preferred are toluene, xylene, ethylbenzene, diethylbenzene, trimethylbenzene, n-propylbenzene, isopropylbenzene, n-butylbenzene, isobutylbenzene, 5-butylbenzene, n-hexylbenzene, cyclohexylbenzene, 1-methylnaphthalene, tetralin, 1,3-dioxane, 1,4-dioxane, 1,3-dioxolane, anisole, ethoxybenzene, cyclohexane, bicyclohexyl, cyclohexenylcyclohexanone, n-heptylcyclohexane, n-hexylcyclohexane, decalin, methyl benzoate, cyclohexanone, 2-propylcyclohexanone, 2-heptanone, 3-heptanone, 4-heptanone, 2-octanone, 2-nonanone, 2-decanone, dicyclohexyl ketone, acetophenone, and benzophenone.

In an embodiment of the invention, the organic electroluminescence device is usable in electronic equipment, for example, as display parts, such as organic EL panel module; display devices of television sets, mobile phones, personal computer, etc.; and light emitting sources of lighting equipment and vehicle lighting equipment.

EXAMPLES

The present invention will be described in more detail with reference to the examples. However, it should be noted that the scope of the present invention is not limited thereto.

Synthesis Example 1: Synthesis of Compound H-1

Compound H-1 was synthesized according to the following synthetic route.

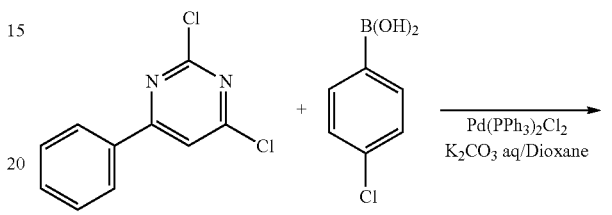

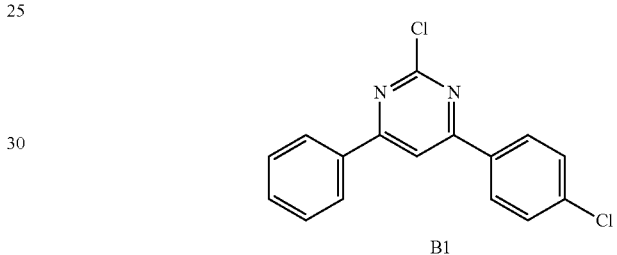

B1

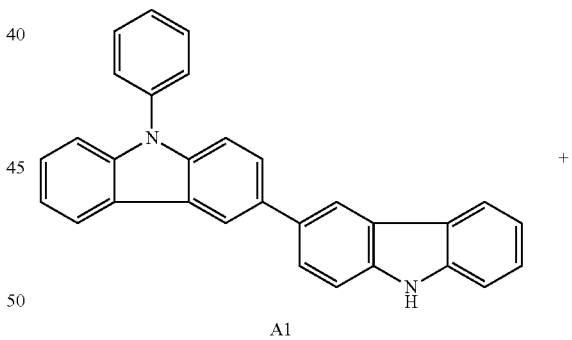

A1

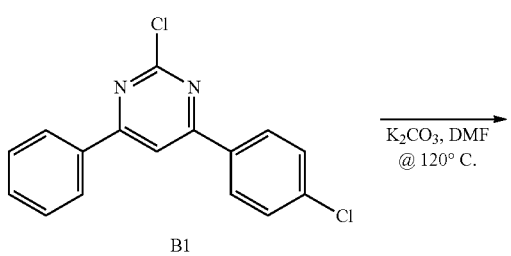

B1

-continued

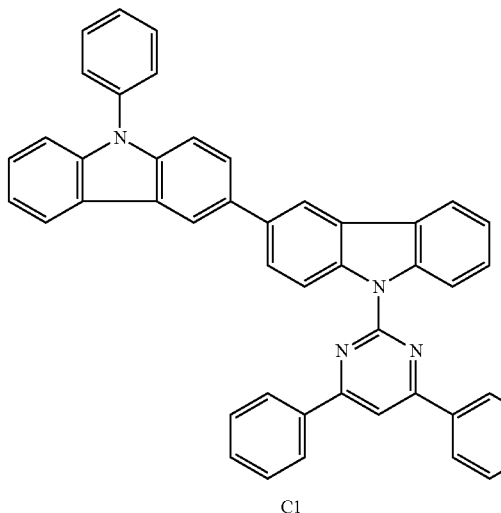

C1

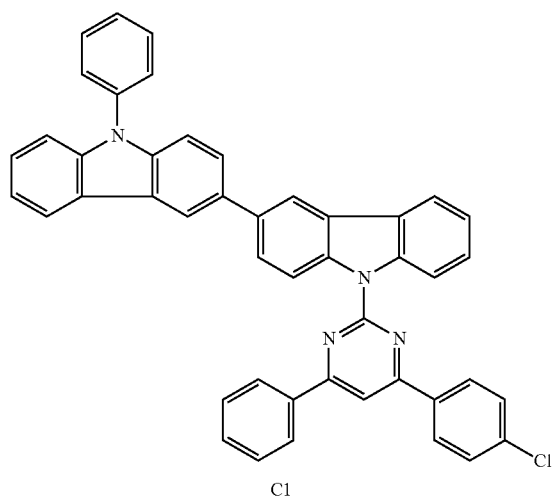

C1

+

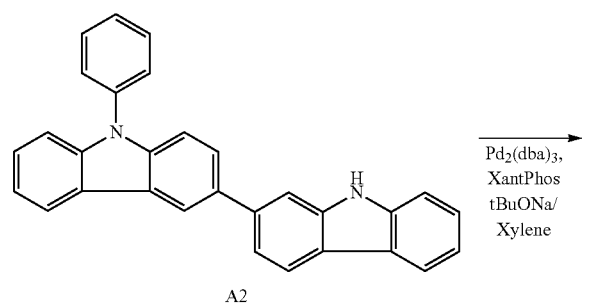

A2

→ Pd₂(dba)₃, XantPhos tBuONa/ Xylene

-continued

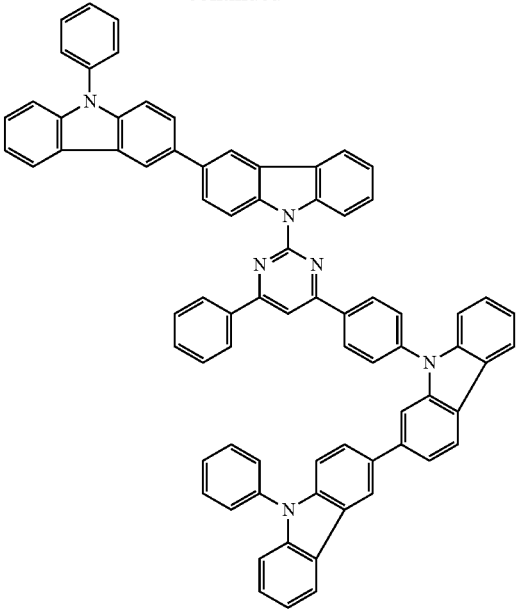

H-1

Under an argon atmosphere, 4-phenyl-2,6-dichloropyrimidine (9.00 g, 40 mmol), 4-chlorophenylboronic acid (6.26 g, 40 mmol), dichloro(bistriphenylphosphine)palladium complex (0.70 g, 1.0 mmol), 1,4-dioxane (160 mL), and a 2 M aqueous solution of potassium carbonate (80 mL) were successively mixed and the resultant mixture was refluxed for 8 h under heating. After cooling to room temperature, the reaction solution was diluted with toluene, washed with water, and dried under reduced pressure. The obtained residue was purified by silica gel column chromatography to obtain a pyrimidine intermediate B1 (9.76 g, yield: 81%).

Under an argon atmosphere, a bicarbazolyl intermediate A1 (12.26 g, 30 mmol), a pyrimidine intermediate B1 (9.04 g, 30 mmol), and potassium carbonate (4.35 g, 31.5 mmol) were added to 30 mL of dry DMF and the resultant mixture was stirred at 120° C. for 8 h under heating. After cooling the reaction solution to room temperature, 30 mL water was added, and the precipitated solid was collected by filtration, washed with water and then methanol, and dried under reduced pressure. The obtained residue was purified by silica gel column chromatography to obtain the target intermediate C1 (15.14 g, yield: 75%).

Under an argon atmosphere, the intermediate C1 (2.02 g, 3.0 mmol), a bicarbazolyl intermediate A2 (1.23 g, 3.0 mmol), tris(dibenzylideneacetone)dipalladium (0.055 g, 0.06 mmol), xantphos (4,5-bis(diphenylphosphino)-9,9-dimethylxanthene) (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-1 (2.86 g, yield: 91%).

HPLC purity: 99.1%

FD-MS: calcd for $C_{76}H_{48}N_6$=1045.

found m/z=1045 (M+, 100).

Synthesis Example 2: Synthesis of Compound H-2
Compound H-2 was synthesized according to the following synthetic route.
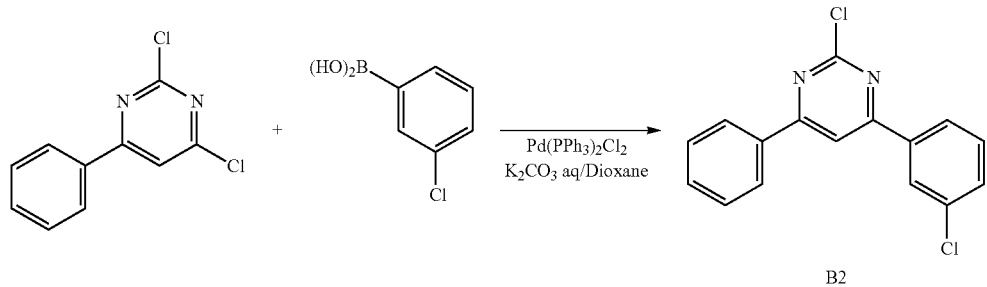
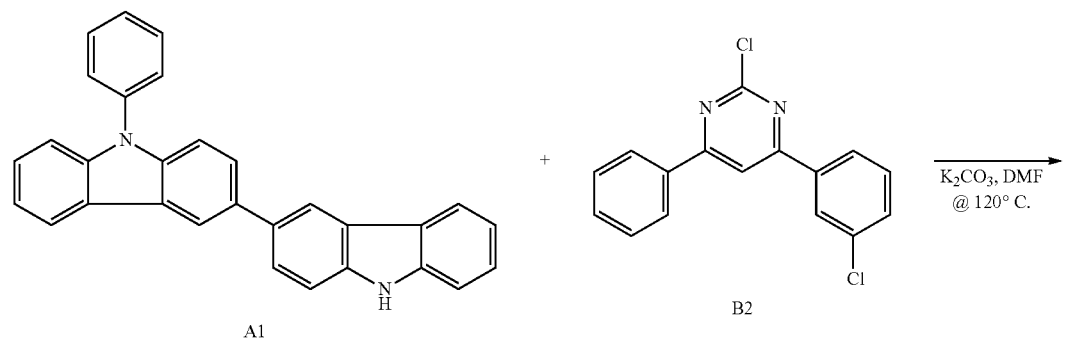
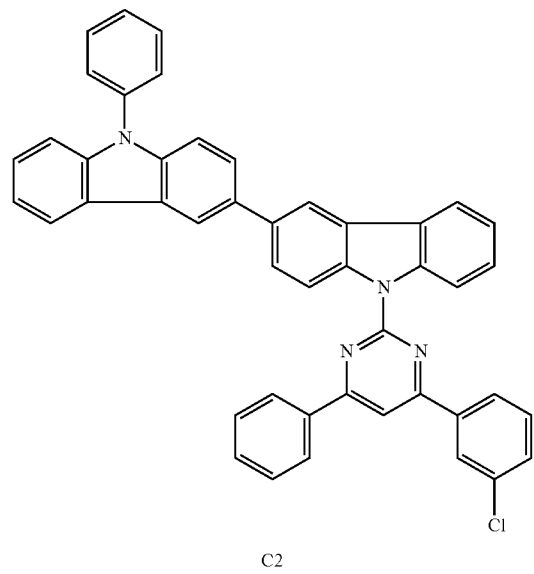

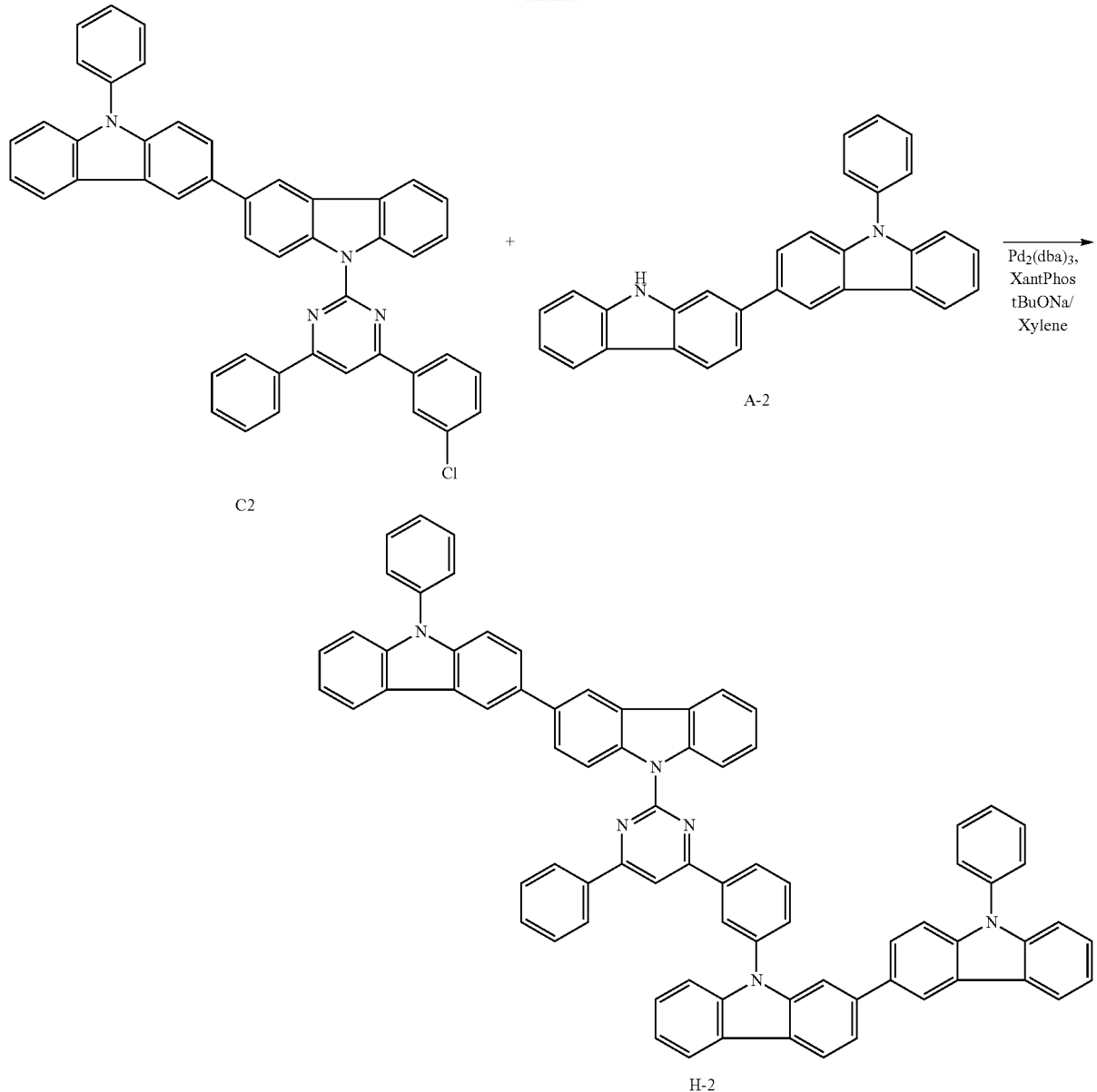

Under an argon atmosphere, 4-phenyl-2,6-dichloropyrimidine (9.00 g, 40 mmol), 3-chlorophenylboronic acid (6.26 g, 40 mmol), dichloro(bistriphenylphosphine)palladium complex (0.70 g, 1.0 mmol), 1,4-dioxane (160 mL), a 2 M aqueous solution of potassium carbonate (80 mL) were successively mixed and the resultant mixture was refluxed for 8 h under heating. After cooling to room temperature, the reaction solution was diluted with toluene, washed with water, and dried under reduced pressure. The obtained residue was purified by silica gel column chromatography to obtain a pyrimidine intermediate B2 (9.40 g, yield: 78%).

Under an argon atmosphere, a bicarbazolyl intermediate A1 (12.26 g, 30 mmol), a pyrimidine intermediate B2 (9.04 g, 30 mmol), potassium carbonate (4.35 g, 31.5 mmol) were added to 30 mL of dry DMF, and the resultant mixture was stirred at 120° C. for 8 h under heating. After cooling the reaction solution to room temperature, 30 mL water was added, and the precipitated solid was collected by filtration, washed with water and then methanol, and dried under reduced pressure. The obtained residue was purified by silica gel column chromatography to obtain the target intermediate C2 (14.74 g, yield: 73%).

Under an argon atmosphere, the intermediate C2 (2.02 g, 3.0 mmol), a bicarbazolyl intermediate A2 (1.23 g, 3.0 mmol), tris(dibenzylideneacetone)dipalladium (0.055 g, 0.06 mmol), xantphos (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-2 (2.76 g, yield: 88%).

HPLC purity: 99.6%

FD-MS: calcd for $C_{76}H_{48}N_6$=1045.

found m/z=1045 (M+, 100).

Synthesis Example 3: Synthesis of Compound H-3
Compound H-3 was synthesized according to the following synthetic route.
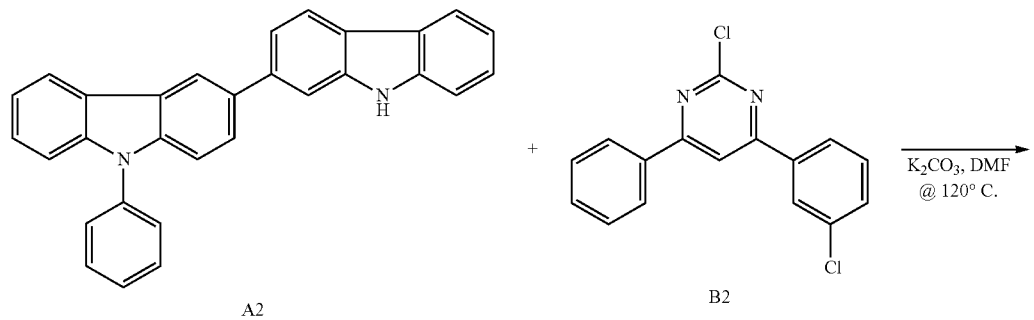
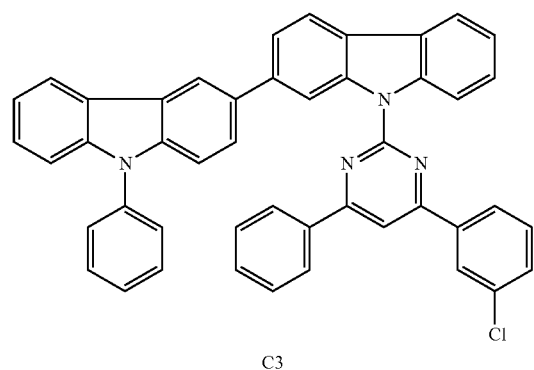
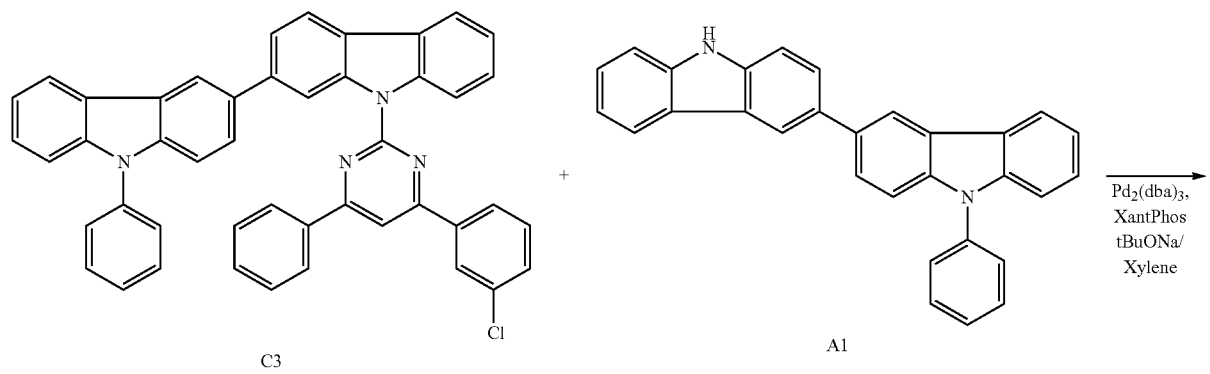

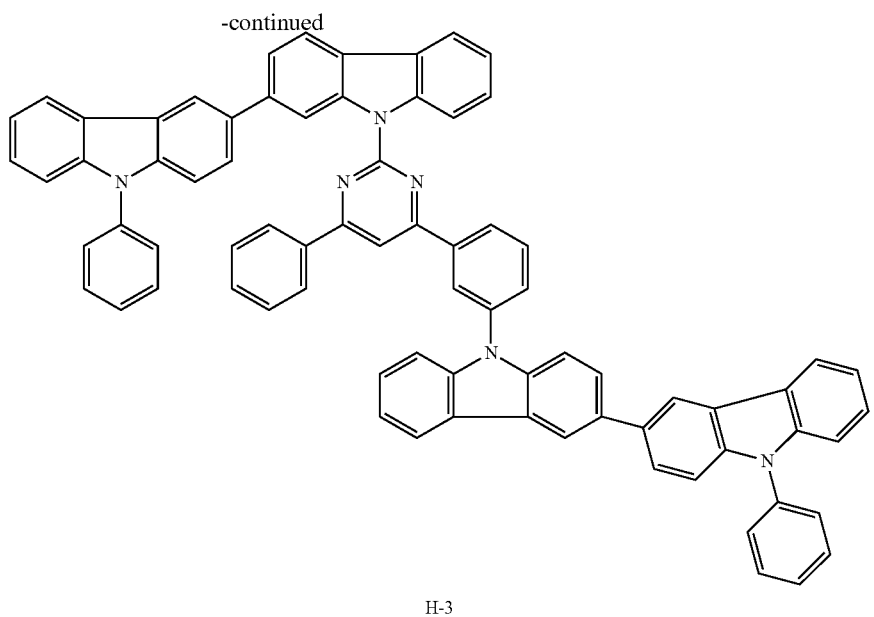

H-3

Under an argon atmosphere, a bicarbazolyl intermediate A2 (12.26 g, 30 mmol), a pyrimidine intermediate B2 (9.04 g, 30 mmol), and potassium carbonate (4.35 g, 31.5 mmol) were added to 30 mL of dry DMF and the resultant mixture was stirred at 120° C. for 8 h under heating. After cooling the reaction solution to room temperature, 30 mL water was added, and the precipitated solid was collected by filtration, washed with water and then methanol, and dried under reduced pressure. The obtained residue was purified by silica gel column chromatography to obtain the target intermediate C3 (13.13 g, yield: 65%).

Under an argon atmosphere, the intermediate C3 (2.02 g, 3.0 mmol), a bicarbazolyl intermediate A1 (1.23 g, 3.0 mmol), tris(dibenzylideneacetone)dipalladium (0.055 g, 0.06 mmol), xantphos (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-3 (2.70 g, yield: 86%).

HPLC purity: 99.8%
FD-MS: calcd for $C_{76}H_{48}N_6$=1045.
found m/z=1045 (M+, 100).

Synthesis Example 4: Synthesis of Compound H-4

Compound H-4 was synthesized according to the following synthetic route.

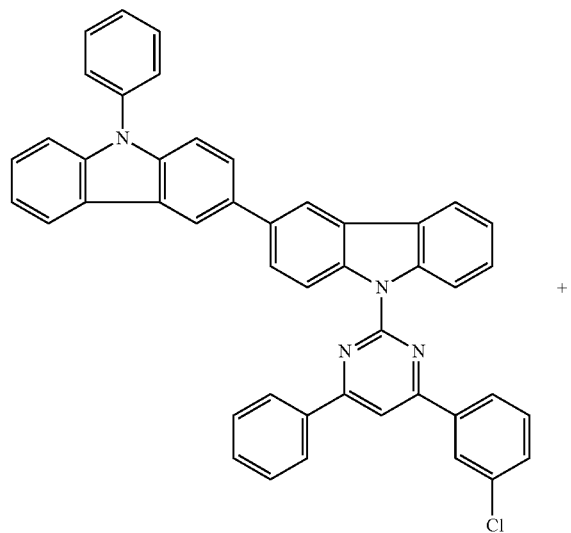

C2

-continued

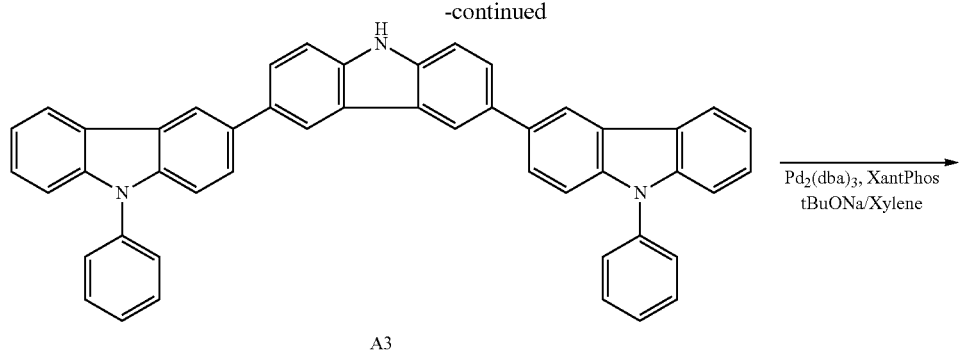

A3

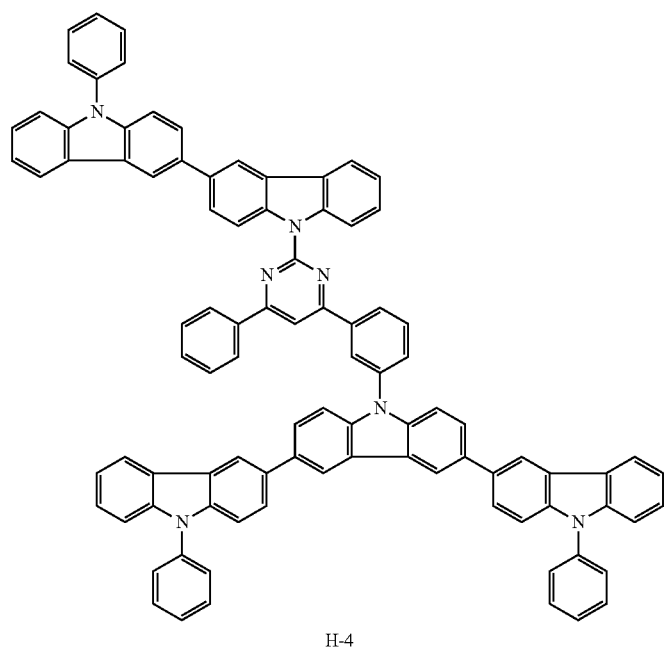

H-4

Under an argon atmosphere, the intermediate C2 (2.02 g, 3.0 mmol), a tricarbazolyl intermediate A3 (1.95 g, 3.0 mmol), tris(dibenzylideneacetone)dipalladium (0.055 g, 0.06 mmol), xantphos (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-4 (1.85 g, yield: 48%).

HPLC purity: 99.2%

FD-MS: calcd for $C_{94}H_{59}N_7$=1286.

found m/z=1286 (M+, 100).

Synthesis Example 5: Synthesis of Compound H-5

Compound H-5 was synthesized according to the following synthetic route.

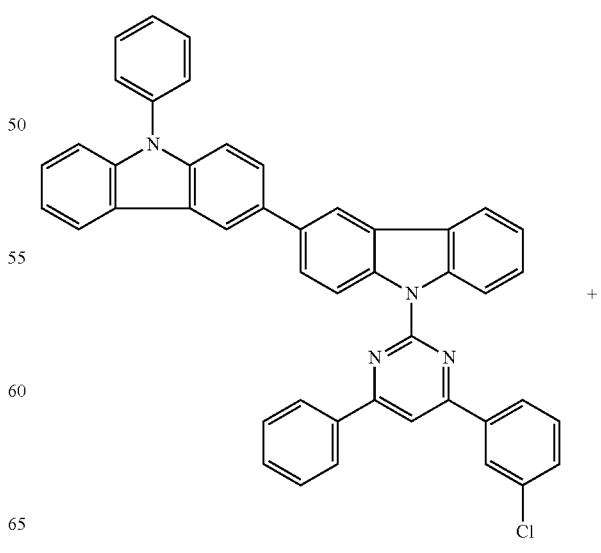

C2

-continued

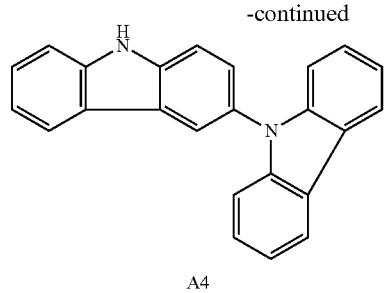

A4

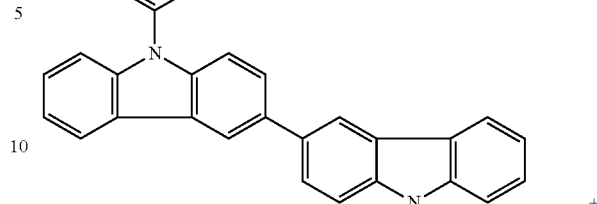

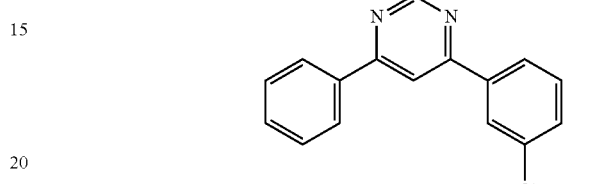

A5

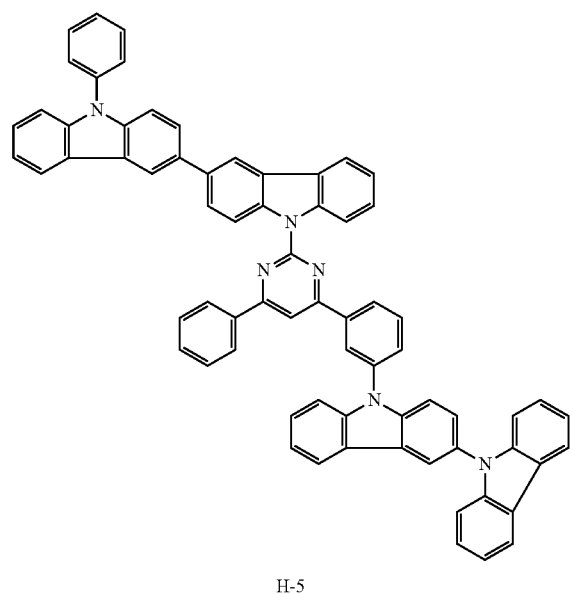

H-5

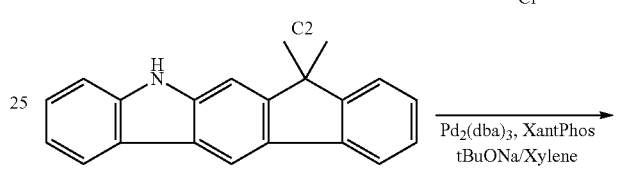

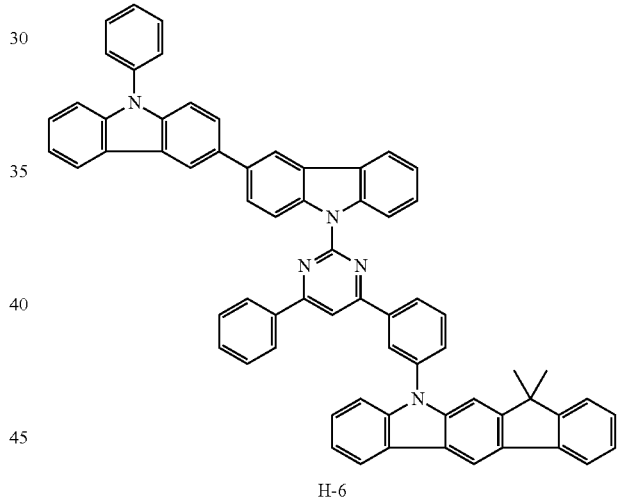

H-6

Under an argon atmosphere, the intermediate C2 (2.02 g, 3.0 mmol), a carbazole intermediate A4 (1.00 g, 3.0 mmol), tris(dibenzylideneacetone)dipalladium (0.055 g, 0.06 mmol), xantphos (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-5 (1.85 g, yield: 86%).

HPLC purity: 98.8%

FD-MS: calcd for $C_{70}H_{44}N_6$=969.

found m/z=969 (M+, 100).

Synthesis Example 6: Synthesis of Compound H-6

Compound H-6 was synthesized according to the following synthetic route.

Under an argon atmosphere, the intermediate C2 (2.02 g, 3.0 mmol), a carbazole intermediate A5 (0.85 g, 3.0 mmol), tris(dibenzylideneacetone)dipalladium (0.055 g, 0.06 mmol), xantphos (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-6 (1.69 g, yield: 61%).

HPLC purity: 98.9%

FD-MS: calcd for $C_{67}H_{45}N_5$=920.

found m/z=920 (M+, 100).

Synthesis Example 7: Synthesis of Compound H-7

Compound H-7 was synthesized according to the following synthetic route.

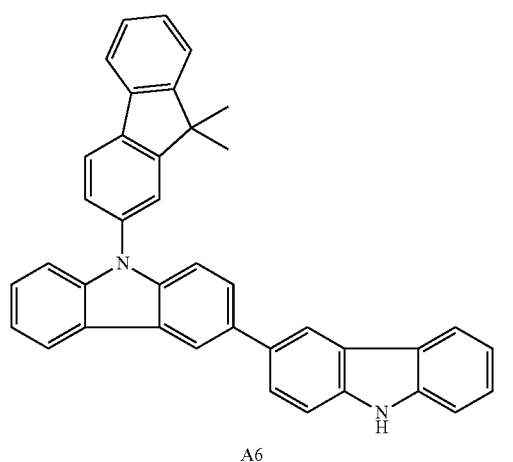
A6
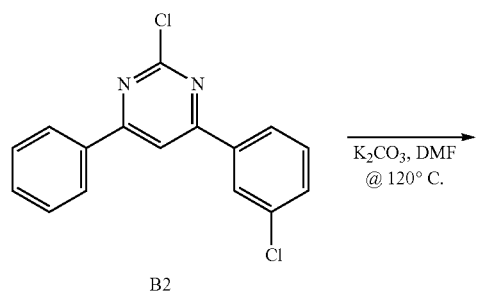
B2
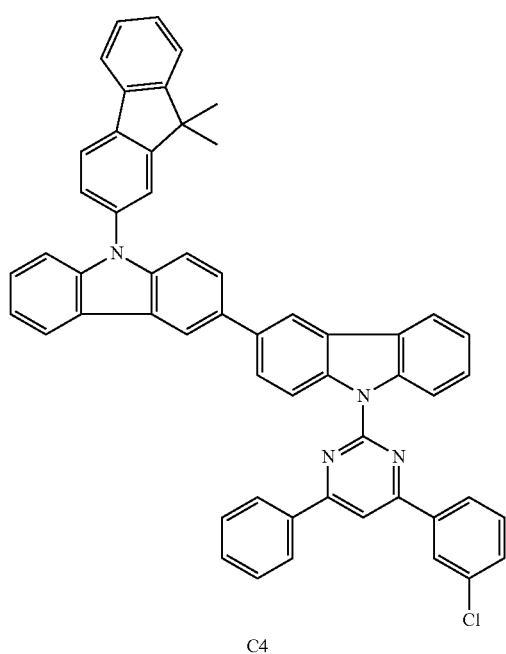
C4
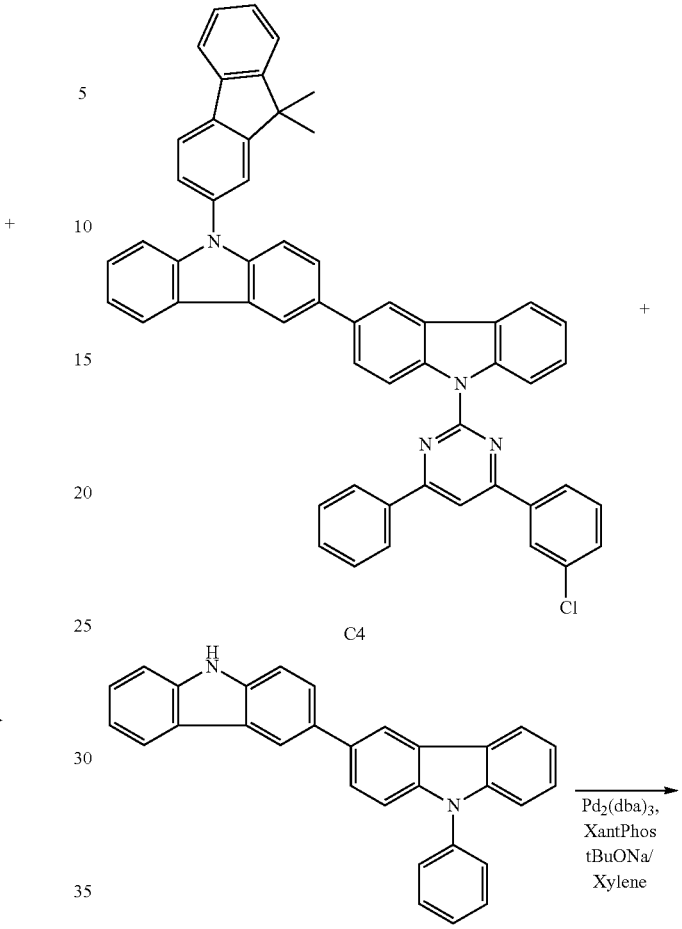
Under an argon atmosphere, a bicarbazolyl intermediate A6 (10.49 g, 20 mmol), a pyrimidine intermediate B2 (6.02 g, 20 mmol), and potassium carbonate (3.32 g, 24 mmol) were added to 20 mL of dry DMF, and the resultant mixture was stirred at 120° C. for 8 h under heating. After cooling the reaction solution to room temperature, 30 mL water was added, and the precipitated solid was collected by filtration, washed with water and then methanol, and dried under reduced pressure to obtain the target intermediate C4 (15.31 g, yield: 97%).

Under an argon atmosphere, the intermediate C4 (2.37 g, 3.0 mmol), a bicarbazolyl intermediate A1 (1.23 g, 3.0 mmol), tris(dibenzylideneacetone)dipalladium (0.055 g, 0.06 mmol), xantphos (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-7 (3.06 g, yield: 88%).

HPLC purity: 99.3%

FD-MS: calcd for $C_{85}H_{58}N_6$=1161.

found m/z=1161 (M+, 100).

Synthesis Example 8: Synthesis of Compound H-8

Compound H-8 was synthesized according to the following synthetic route.

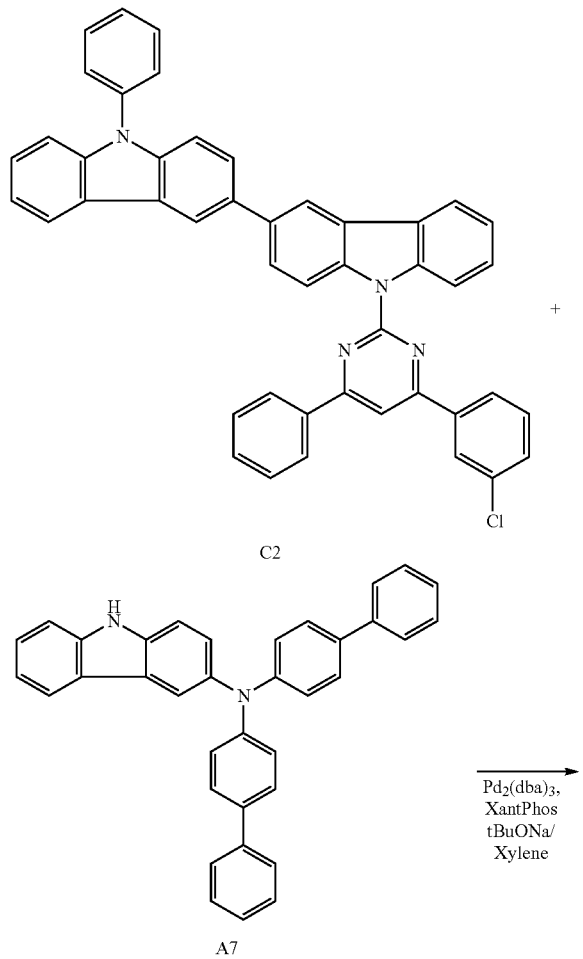

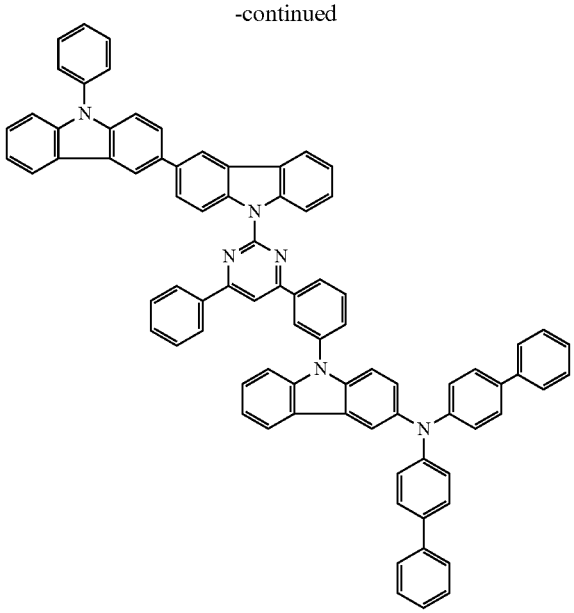

H-8

Under an argon atmosphere, the intermediate C2 (2.02 g, 3.0 mmol), a carbazole intermediate A7 (1.46 g, 3.0 mmol), tris(dibenzylideneacetone)dipalladium (0.055 g, 0.06 mmol), xantphos (0.069 g, 0.12 mmol), sodium t-butoxide (0.43 g, 4.5 mmol), and dehydrated xylene(60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-8 (2.81 g, yield: 83%).

HPLC purity: 98.9%

FD-MS: calcd for $C_{82}H_{54}N_6$=1123.

found m/z=1123 (M+, 100).

Synthesis Example 9: Synthesis of Compound H-9

Compound H-9 was synthesized according to the following synthetic route.

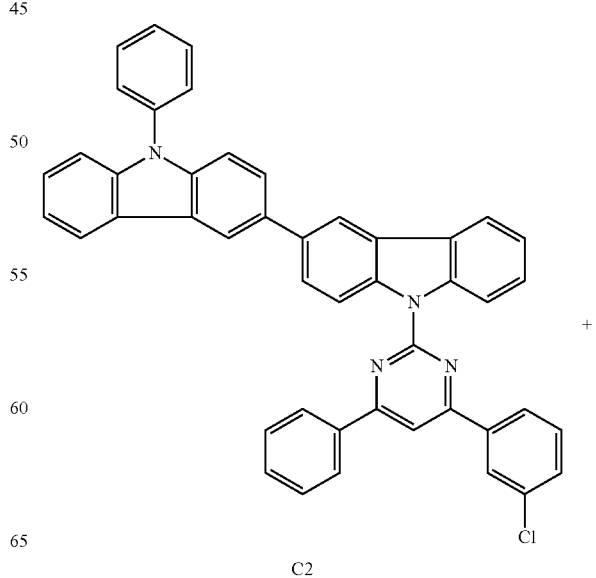

-continued

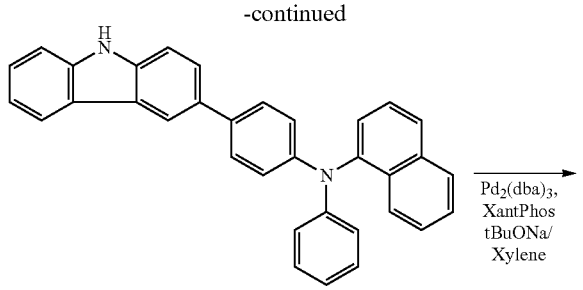

A8

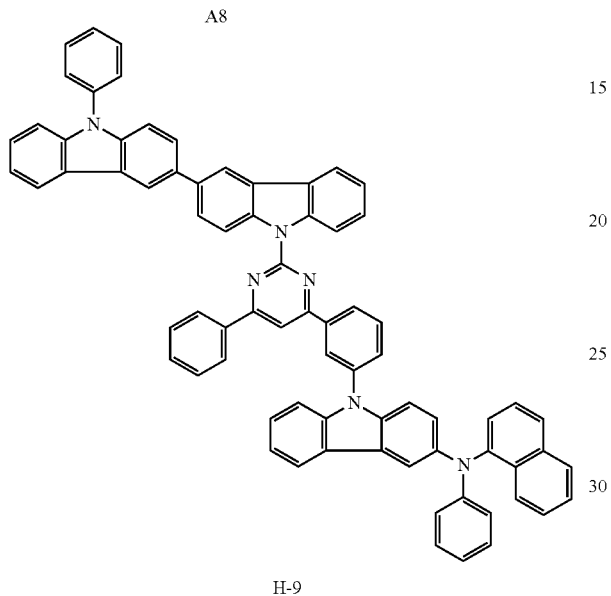

H-9

Under an argon atmosphere, the intermediate C2 (2.02 g, 3.0 mmol), a carbazole intermediate A8 (1.38 g, 3.0 mmol), tris(dibenzylideneacetone)dipalladium (0.055 g, 0.06 mmol), xantphos (0.069 g, 0.12 mmol), sodium t-butoxide (0.43 g, 4.5 mmol), and dehydrated xylene(60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-9 (2.44 g, yield: 74%).

HPLC purity: 99.2%

FD-MS: calcd for $C_{80}H_{52}N_6=1097$.

found m/z=1097 (M+, 100).

Synthesis Example 10: Synthesis of Compound H-10

Compound H-10 was synthesized according to the following synthetic route.

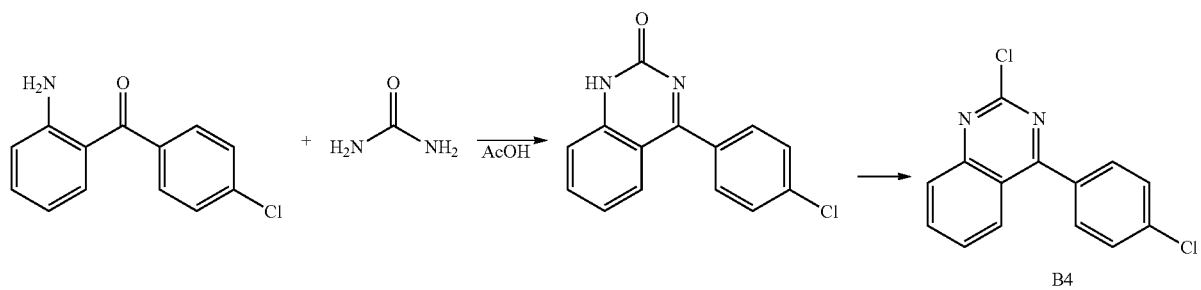

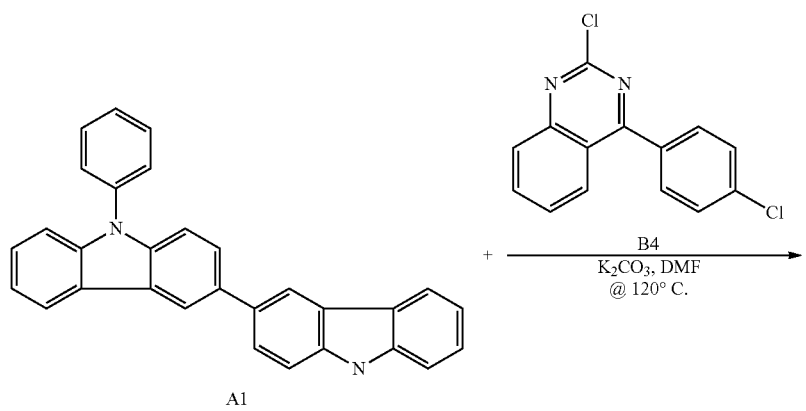

-continued
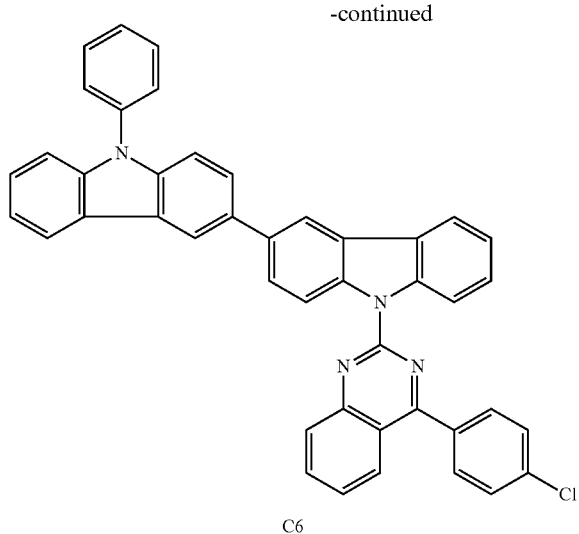
C6
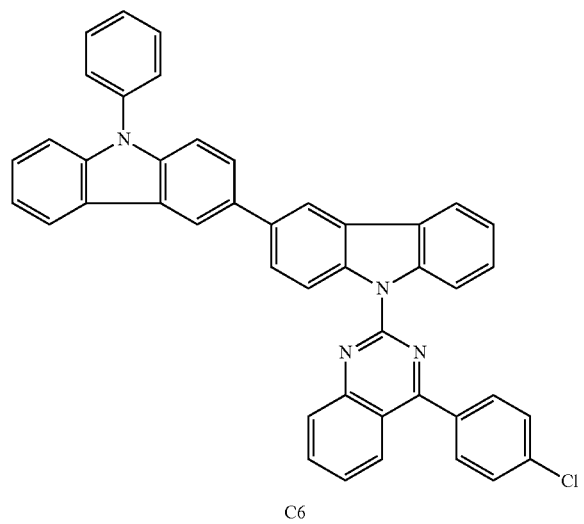
C6
+
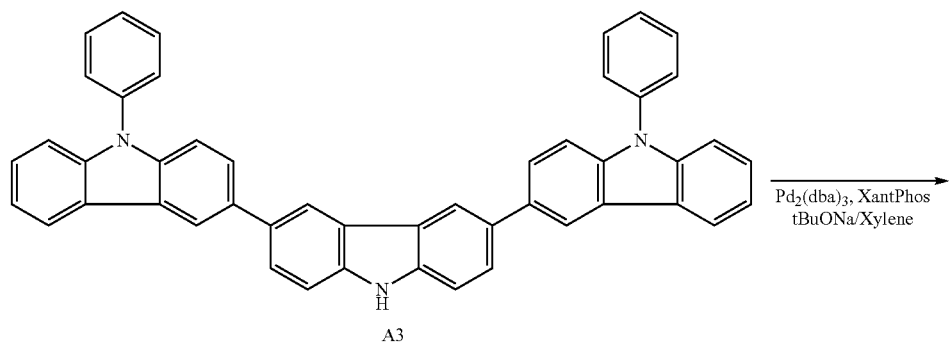
A3
$\xrightarrow{\text{Pd}_2(\text{dba})_3, \text{XantPhos}}_{\text{tBuONa/Xylene}}$

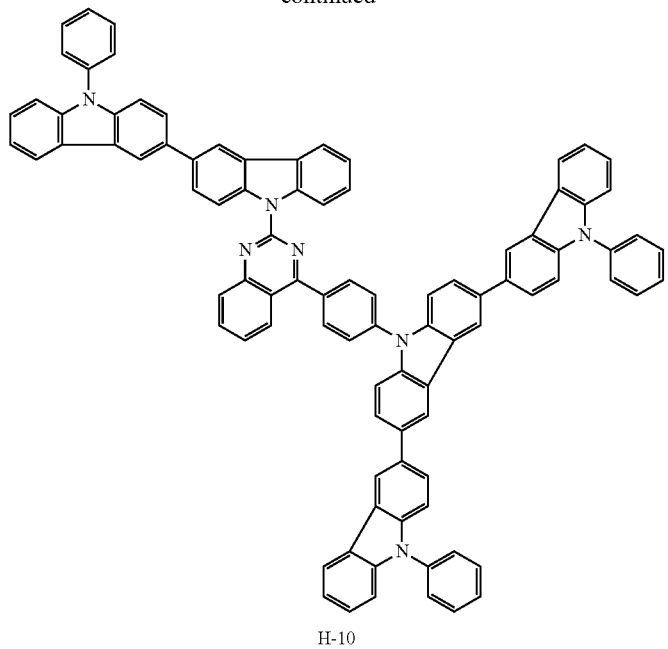

H-10

A solution of 2-amino-4'-chlorobenzophenone (23.17 g, 100 mmol) and urea (12.01 g, 200 mmol) in 100 mL of acetic acid was refluxed for 8 h under heating. After cooling the reaction solution to room temperature, 200 mL of water was added, and the precipitated solid was collected by filtration, washed with water and then methanol, and dried under reduced pressure. After adding 200 mL of phosphoryl chloride, the resultant solution was refluxed for 3 h under heating. After cooling to room temperature, the reaction solution was poured into iced water and extracted with methylene chloride. The organic layer was washed with water and dried over magnesium sulfate, and then the organic solvent was evaporated off under reduced pressure. The obtained residue was purified by silica gel column chromatography to obtain a quinazoline intermediate B4 (20.6 g, yield: 75%).

Under an argon atmosphere, a bicarbazolyl intermediate A1 (8.58 g, 21.0 mmol), the quinazoline intermediate B4 (5.50 g, 20.0 mmol), and potassium carbonate (2.76 g, 20.0 mmol) were added to 20 mL of dry DMF, and the resultant mixture was stirred at 120° C. for 8 h under heating. After cooling the reaction solution to room temperature, 10 mL of water was added, and the precipitated solid was collected by filtration, washed with water and then methanol, and dried under reduced pressure. The obtained residue was purified by silica gel column chromatography to obtain the target intermediate C6 (9.06 g, yield: 70%).

Under an argon atmosphere, the intermediate C6 (1.94 g, 3.0 mmol), a tricarbazolyl intermediate A3 (1.95 g, 3.0 mmol), tris(dibenzylideneacetone)dipalladium (0.055 g, 0.06 mmol), xantphos (4,5-bis(diphenylphosphino)-9,9-dimethylxanthene) (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-10 (2.76 g, yield: 73%).

HPLC purity: 99.4%

FD-MS: calcd for C92H57N7=1260.

found m/z=1260 (M+, 100).

Synthesis Example 11: Synthesis of Compound H-11

Compound H-11 was synthesized according to the following synthetic route.

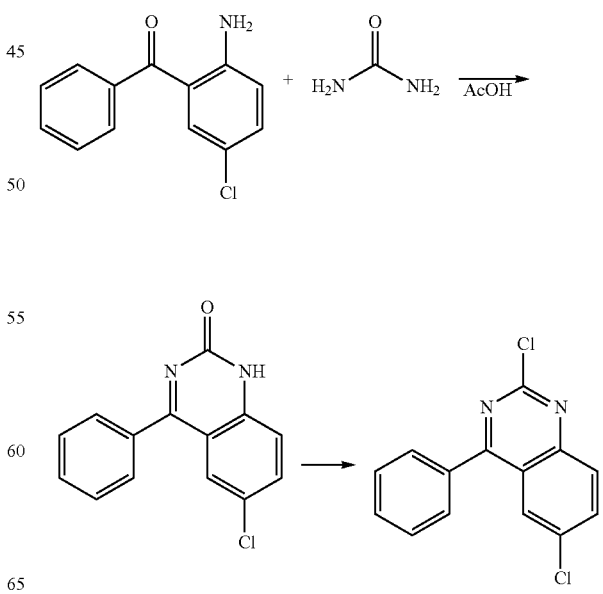

B5

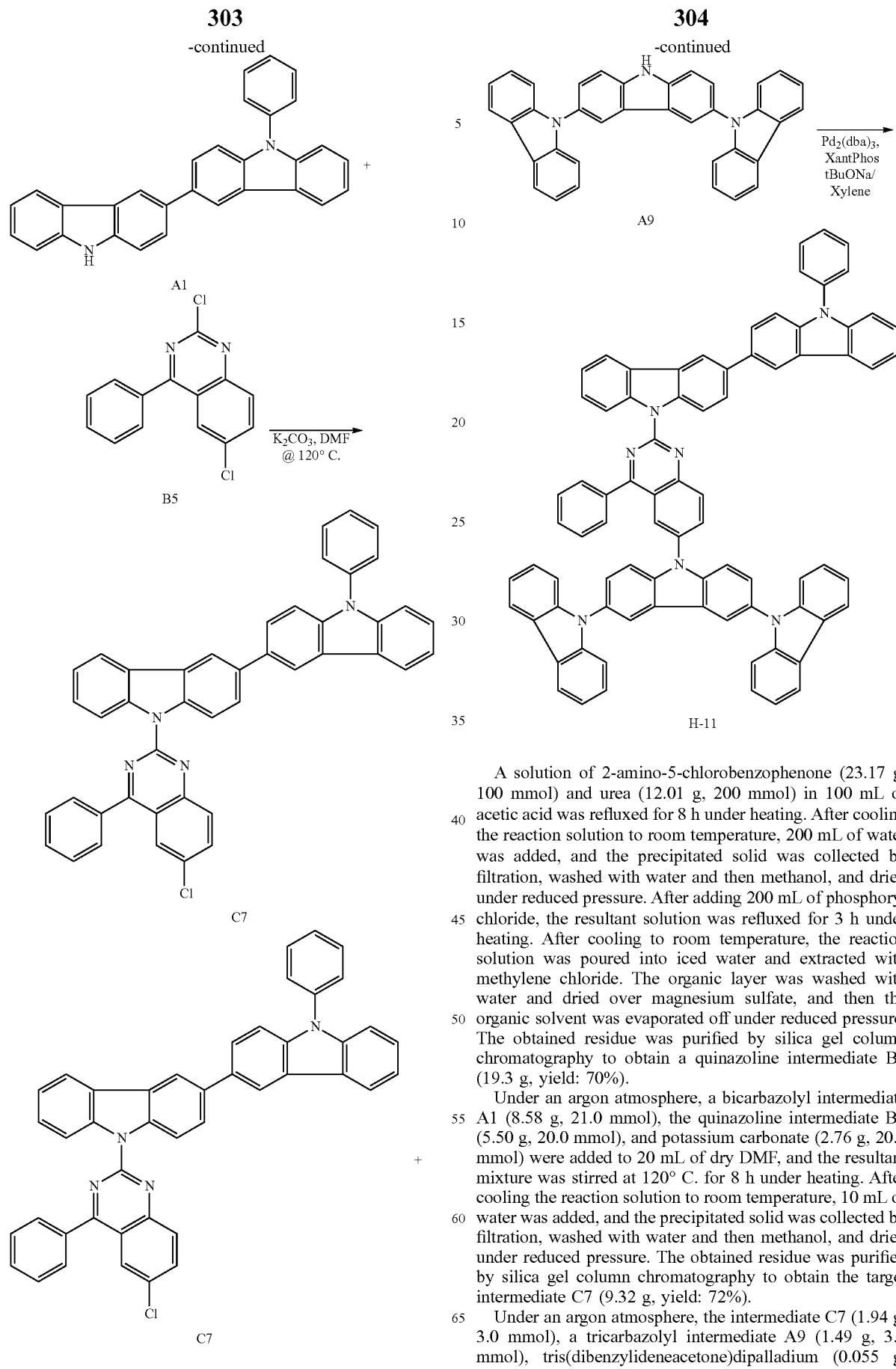

A solution of 2-amino-5-chlorobenzophenone (23.17 g, 100 mmol) and urea (12.01 g, 200 mmol) in 100 mL of acetic acid was refluxed for 8 h under heating. After cooling the reaction solution to room temperature, 200 mL of water was added, and the precipitated solid was collected by filtration, washed with water and then methanol, and dried under reduced pressure. After adding 200 mL of phosphoryl chloride, the resultant solution was refluxed for 3 h under heating. After cooling to room temperature, the reaction solution was poured into iced water and extracted with methylene chloride. The organic layer was washed with water and dried over magnesium sulfate, and then the organic solvent was evaporated off under reduced pressure. The obtained residue was purified by silica gel column chromatography to obtain a quinazoline intermediate B5 (19.3 g, yield: 70%).

Under an argon atmosphere, a bicarbazolyl intermediate A1 (8.58 g, 21.0 mmol), the quinazoline intermediate B5 (5.50 g, 20.0 mmol), and potassium carbonate (2.76 g, 20.0 mmol) were added to 20 mL of dry DMF, and the resultant mixture was stirred at 120° C. for 8 h under heating. After cooling the reaction solution to room temperature, 10 mL of water was added, and the precipitated solid was collected by filtration, washed with water and then methanol, and dried under reduced pressure. The obtained residue was purified by silica gel column chromatography to obtain the target intermediate C7 (9.32 g, yield: 72%).

Under an argon atmosphere, the intermediate C7 (1.94 g, 3.0 mmol), a tricarbazolyl intermediate A9 (1.49 g, 3.0 mmol), tris(dibenzylideneacetone)dipalladium (0.055 g, 0.06 mmol), xantphos (4,5-bis(diphenylphosphino)-9,9-dimethylxanthene) (0.069 g, 0.12 mmol), sodium t-butoxide (0.43 g, 4.5 mmol), and dehydrated xylene(60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-11 (2.74 g, yield: 82%).

HPLC purity: 99.5%
FD-MS: calcd for $C_{80}H_{49}N_7$=1108.
found m/z=1108 (M+, 100).

Synthesis Example 12: Synthesis of Compound H-12

Compound H-12 was synthesized according to the following synthetic route.

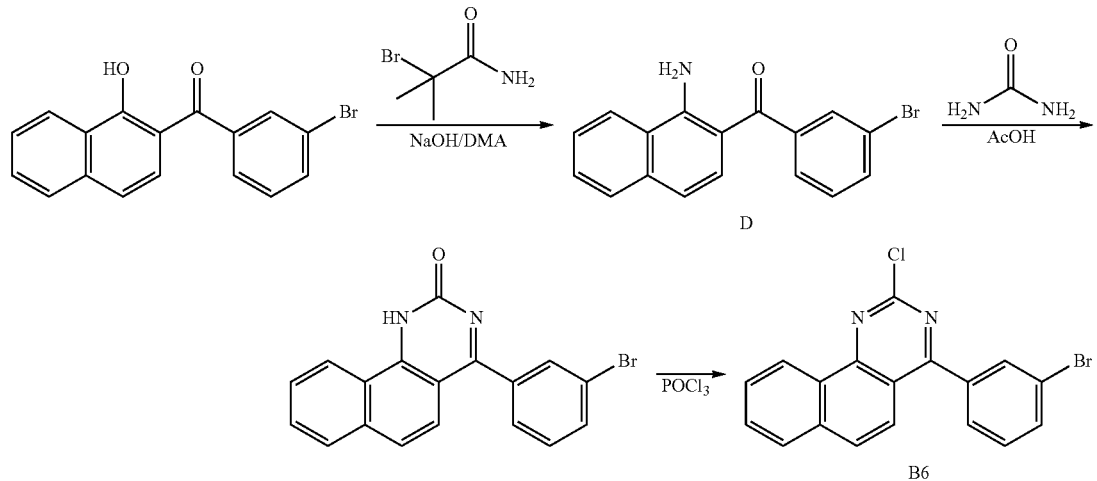

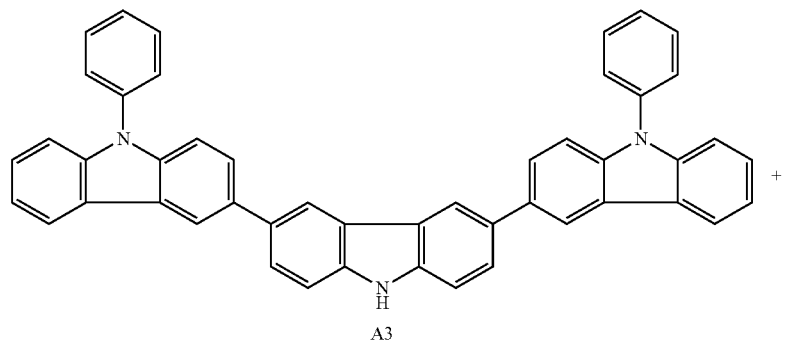

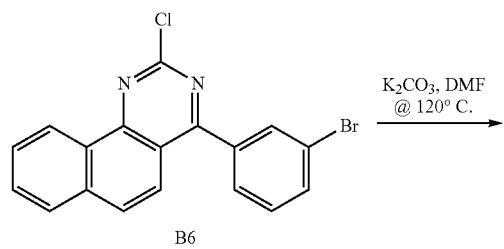

-continued
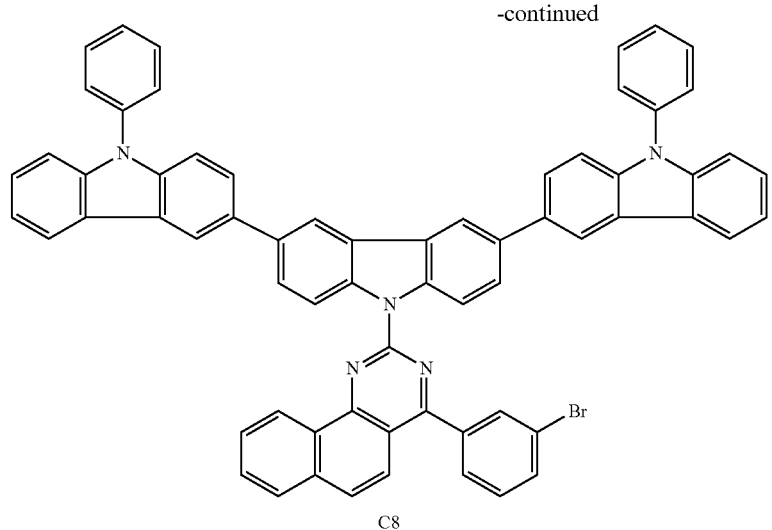
C8
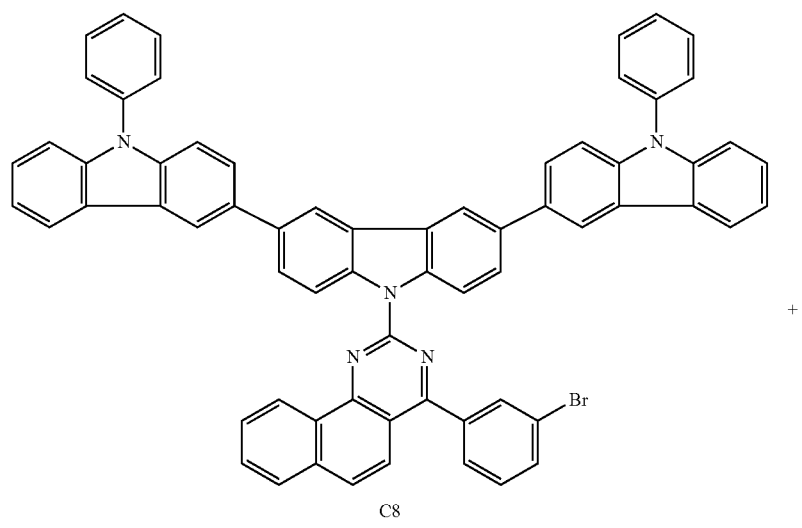
C8
+
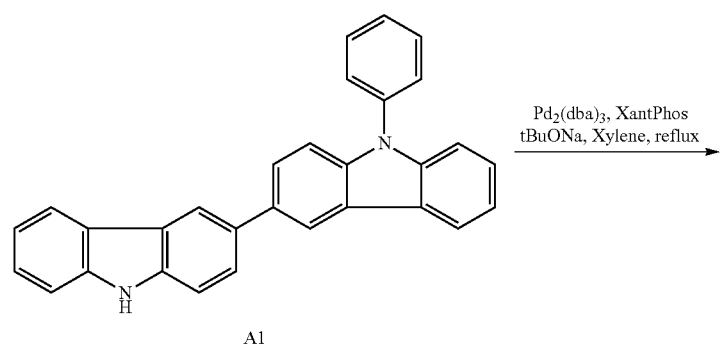
A1

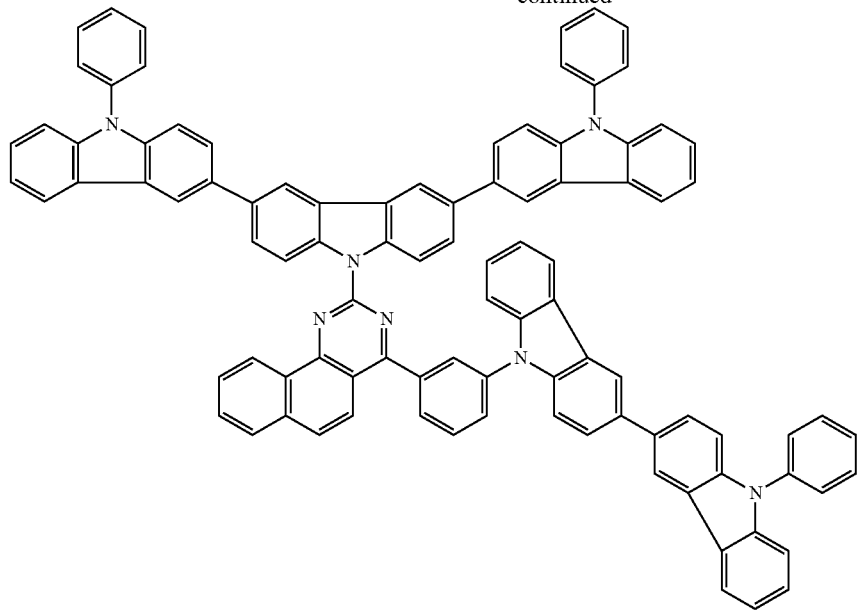

H-12

A solution of 2-(3-bromobenzoyl)-1-naphthol (12.44 g, 50 mmol) and sodium hydroxide (6.0 g, 150 mmol) in N,N-dimethylacetamide (DMA) (75 mL) was stirred at room temperature for one hour. After adding 2-bromoisobutylamide (24.9 g, 150 mmol), the solution was further stirred at room temperature for 5 h. After adding sodium hydroxide (18.0 g, 450 mmol), the solution was heated to 50° C. and allowed to react for one hour. After adding 75 mL of water, the temperature was raised and the solution was refluxed for one hour under heating. After cooling to room temperature, the reaction solution was extracted with ethyl acetate. The extract was dried over magnesium sulfate, the solvent was evaporated off, and the residue was purified by silica gel chromatography to obtain an intermediate D (13.86 g, yield: 85%). A solution of the intermediate D (13.05 g, 40 mmol) and urea (4.80 g, 40 mmol) in 20 mL of acetic acid was allowed to react for 5 h while refluxing under heating. After cooling to 100° C. or lower, 80 mL of water was added, and the powder formed was collected by filtration, washed with water, and vacuum-dried. The obtained powder was added to 20 mL of phosphorus oxychloride and allowed to react for 5 h while refluxing under heating. After cooling to room temperature, the reaction solution was poured into 200 mL of iced water, and the powder formed was washed with water and purified by silica gel column chromatography to obtain a benzoquinazoline intermediate B6 (9.31 g, yield: 63%).

Under an argon atmosphere, a tricarbazolyl intermediate A3 (3.41 g, 5.25 mmol), the quinazoline intermediate B6 (1.85 g, 5.00 mmol), and potassium carbonate (0.83 g, 6.0 mmol) were added to 5 mL of dry DMF, and the resultant mixture was stirred at 120° C. for 8 h under heating. After cooling the reaction solution to room temperature, 10 mL of water was added, and the precipitated solid was collected by filtration, washed with water and then methanol, and dried under reduced pressure to obtain the target intermediate C8 (3.98 g, yield: 81%).

Under an argon atmosphere, the intermediate C8 (2.95 g, 3.0 mmol), a bicarbazolyl intermediate A1 (1.23 g, 3.0 mmol), tris(dibenzylideneacetone)dipalladium (0.055 g, 0.06 mmol), xantphos (4,5-bis(diphenylphosphino)-9,9-dimethylxanthene) (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-12 (3.38 g, yield: 86%).

HPLC purity: 99.21%

FD-MS: calcd for $C_{96}H_{59}N_7$=1310.

found m/z=1310 (M+, 100).

Synthesis Example 13: Synthesis of Compound H-13

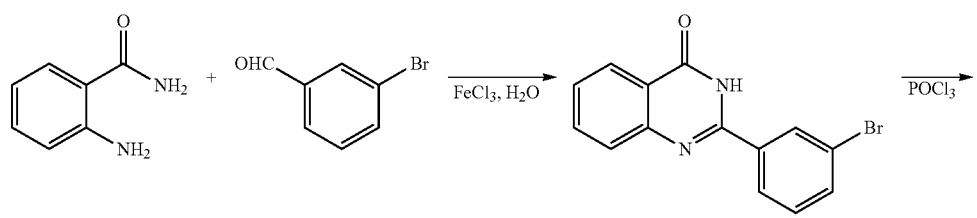

-continued
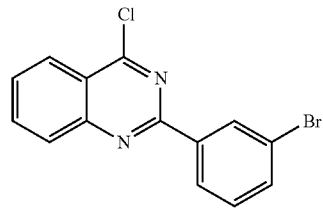
B7
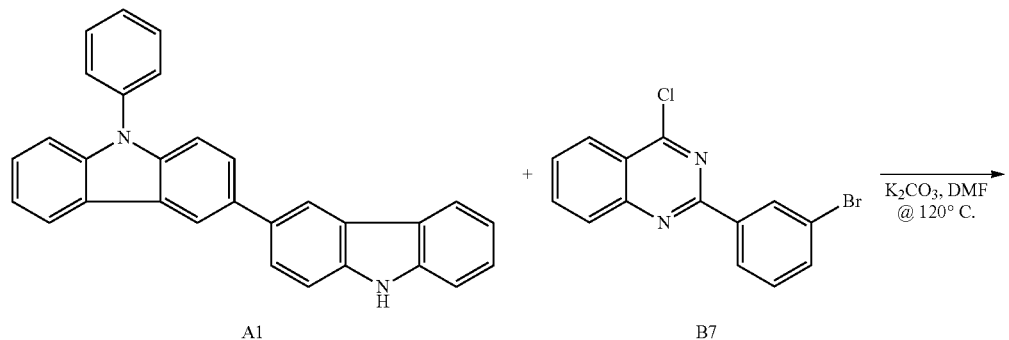
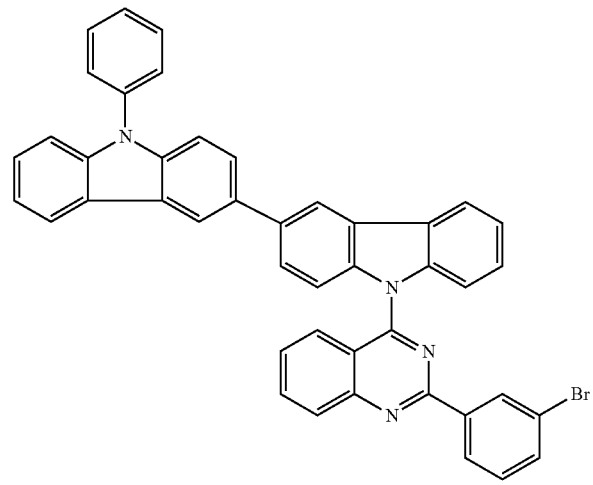
C9
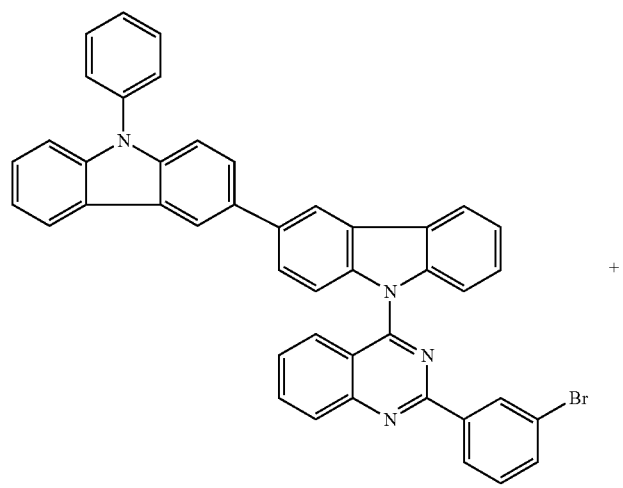
C9 +

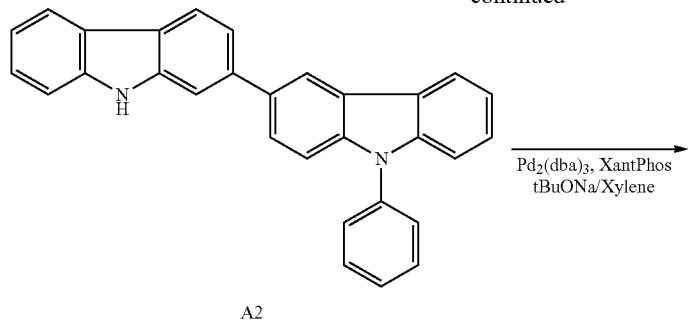

A2

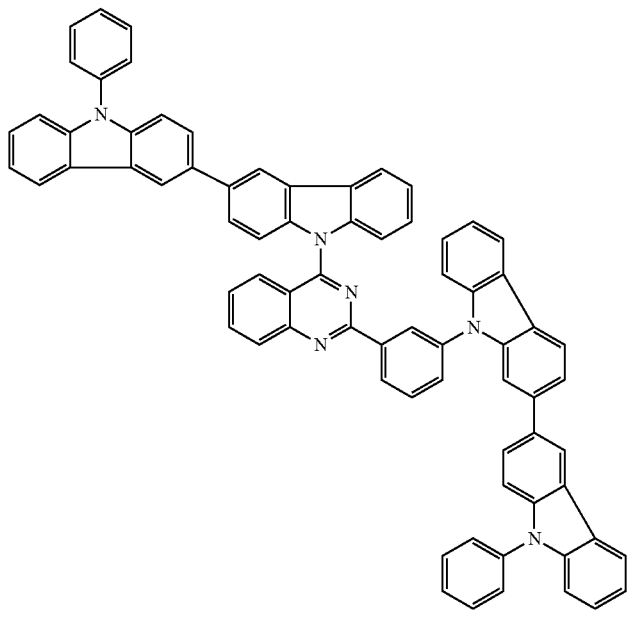

H-13

Into a solution of iron(III) chloride (6.45 g, 40 mmol) in 200 mL of water, 2-aminobenzamide (2.72 g, 20 mmol) and 3-bromobenzaldehyde (3.70 g, 20 mmol) were successively added and the resultant solution was refluxed for 3 h under heating. After cooling the reaction solution to room temperature, the precipitated solid was collected by filtration, washed with water and then acetone, and dried under reduced pressure. After adding 20 mL of phosphoryl chloride to the dried solid, the resultant solution was refluxed for 3 h under heating. After cooling to room temperature, the reaction solution was poured into iced water and extracted with methylene chloride. The organic layer was washed with water and dried over magnesium sulfate, and then the organic solvent was evaporated off under reduced pressure. The obtained residue was purified by silica gel column chromatography to obtain an intermediate B7 (2.88 g, yield: 45%).

Under an argon atmosphere, the intermediate A1 (2.14 g, 5.25 mmol), the intermediate B7 (1.60 g, 5.00 mmol), and potassium carbonate (0.83 g, 6.0 mmol) were added to 5 mL of dry DMF, and the resultant mixture was stirred at 120° C. for 8 h under heating. After cooling the reaction solution to room temperature, 10 mL of water was added, and the precipitated solid was collected by filtration, washed with water and then methanol, and dried under reduced pressure to obtain the target intermediate C9 (3.01 g, yield: 87%).

Under an argon atmosphere, the intermediate C9 (2.07 g, 3.0 mmol), the intermediate A2 (1.23 g, 3.0 mmol), tris (dibenzylideneacetone)dipalladium (0.055 g, 0.06 mmol), xantphos (4,5-bis(diphenylphosphino)-9,9-dimethylxanthene) (0.069 g, 0.12 mmol), sodium t-butoxide (0.43 g, 4.5 mmol), and dehydrated xylene(60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-13 (2.85 g, yield: 93%).

HPLC purity: 99.4%
FD-MS: calcd for $C_{74}H_{46}N_6$=1019.
found m/z=1019 (M+, 100).
HPLC: High performance liquid chromatography
FD-MS: Field Desorption Mass Spectrometry Synthesis Example 14: Synthesis of Compound H-14
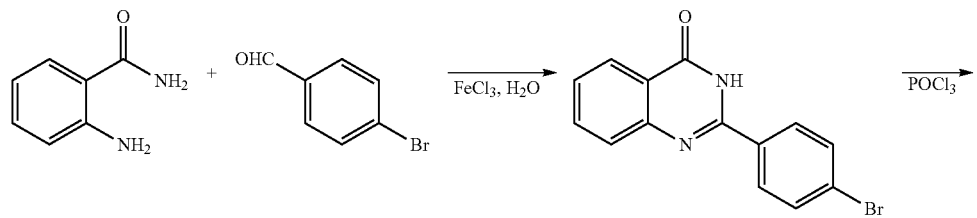
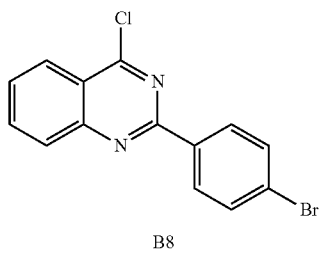
B8
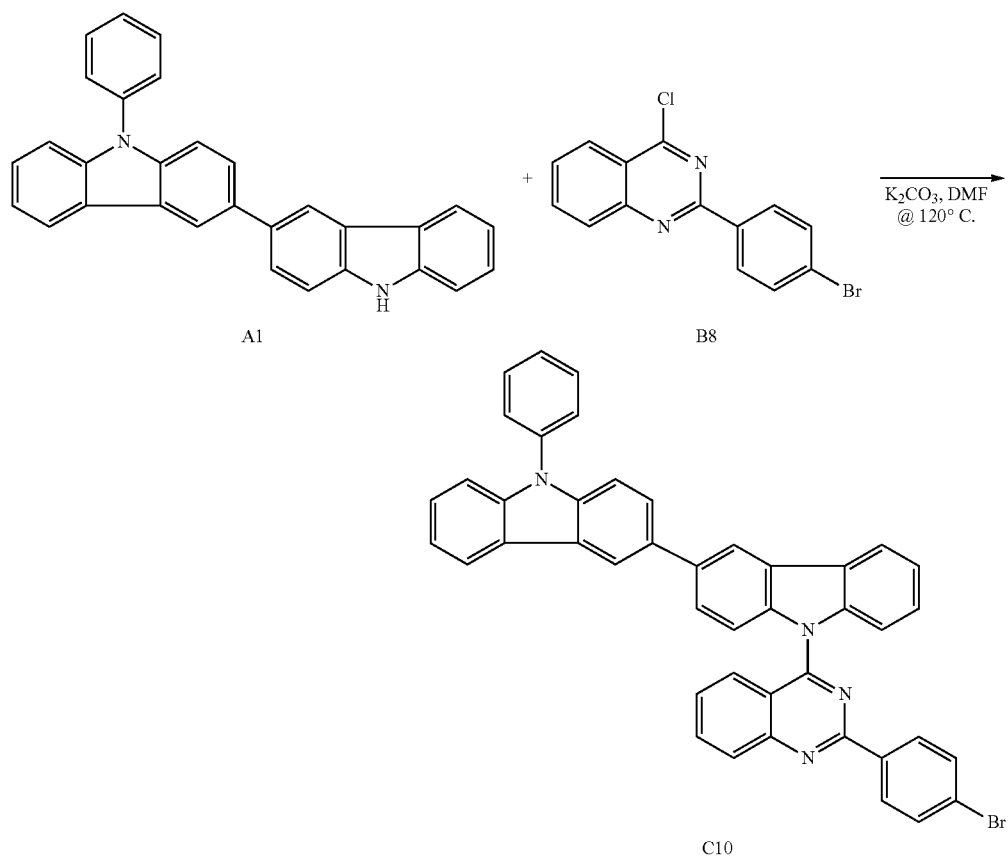

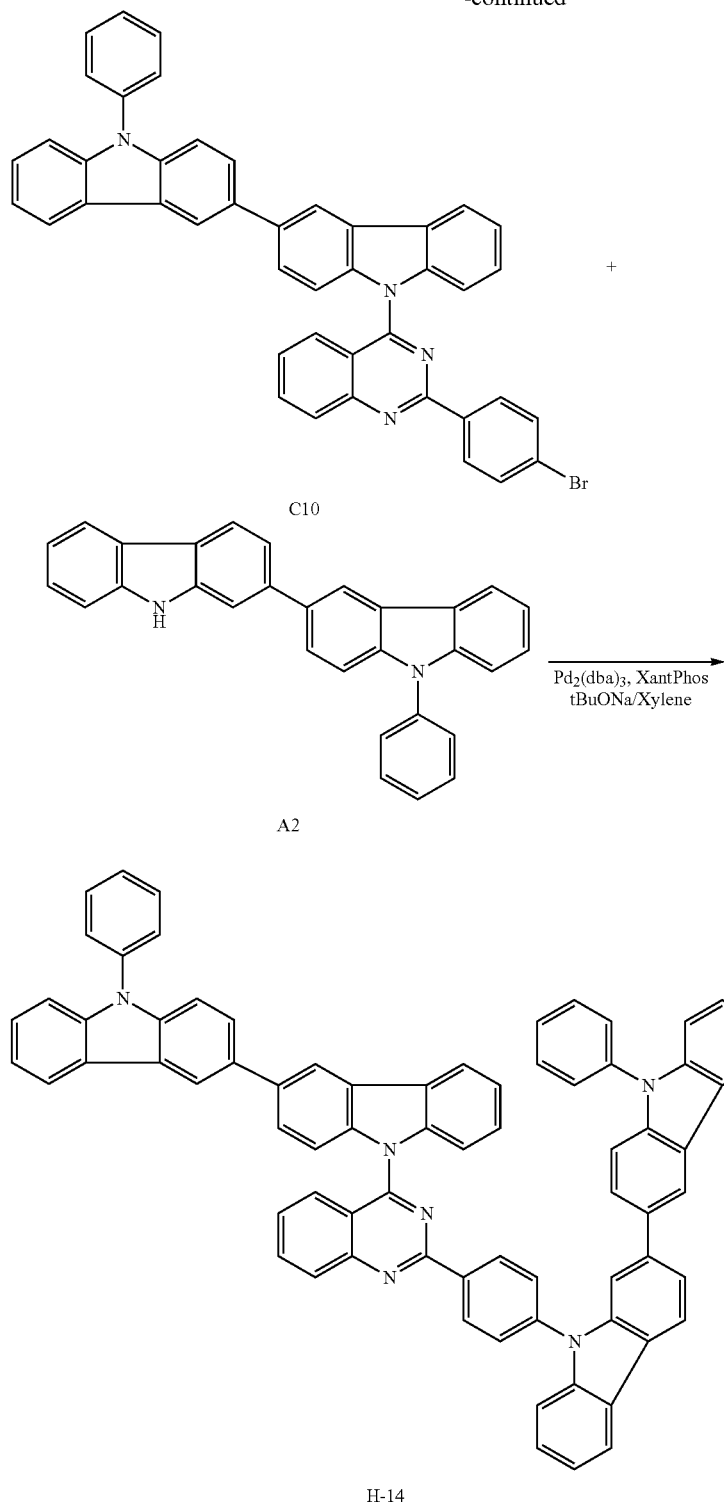

Into a solution of iron(III) chloride (6.45 g, 40 mmol) in 200 mL of water, 2-aminobenzamide (2.72 g, 20 mmol) and 4-bromobenzaldehyde (3.70 g, 20 mmol) were successively added and the resultant solution was refluxed for 3 h under heating. After cooling the reaction solution to room temperature, the precipitated solid was collected by filtration, washed with water and then acetone, and dried under reduced pressure. After adding 20 mL of phosphoryl chloride to the dried solid, the resultant solution was refluxed for 3 h under heating. After cooling to room temperature, the reaction solution was poured into iced water and extracted with methylene chloride. The organic layer was washed with water and dried over magnesium sulfate, and then the organic solvent was evaporated off under reduced pressure.

The obtained residue was purified by silica gel column chromatography to obtain an intermediate B8 (3.26 g, yield: 51%).

Under an argon atmosphere, the intermediate A1 (2.14 g, 5.25 mmol), the intermediate B8 (1.60 g, 5.00 mmol), and potassium carbonate (0.83 g, 6.0 mmol) were added to 5 mL of dry DMF and the resultant mixture was stirred at 120° C. for 8 h under heating. After cooling the reaction solution to room temperature, 10 mL of water was added, and the precipitated solid was collected by filtration, washed with water and then methanol, and dried under reduced pressure to obtain the target intermediate C10 (2.94 g, yield: 85%).

Under an argon atmosphere, the intermediate C2 (2.07 g, 3.0 mmol), the intermediate A2 (1.23 g, 3.0 mmol), tris(dibenzylideneacetone)dipalladium (0.055 g, 0.06 mmol), xantphos (4,5-bis(diphenylphosphino)-9,9-dimethylxanthene) (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-14 (2.90 g, yield: 95%).

HPLC purity: 99.3%

FD-MS: calcd for $C_{74}H_{46}N_6$=1019.

found m/z=1019 (M+, 100).

Synthesis Example 15: Synthesis of Compound 11-15

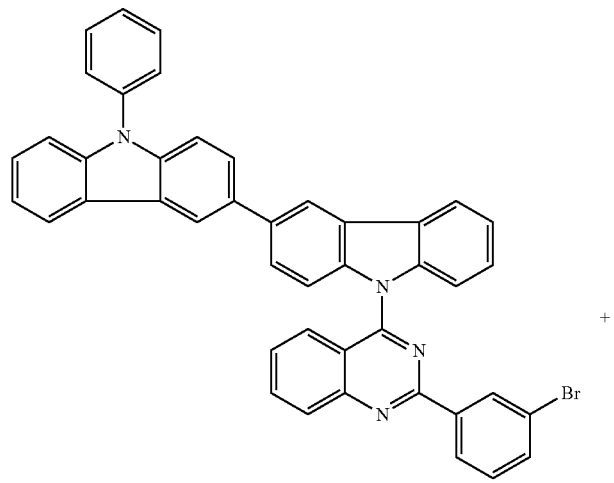

C9

+

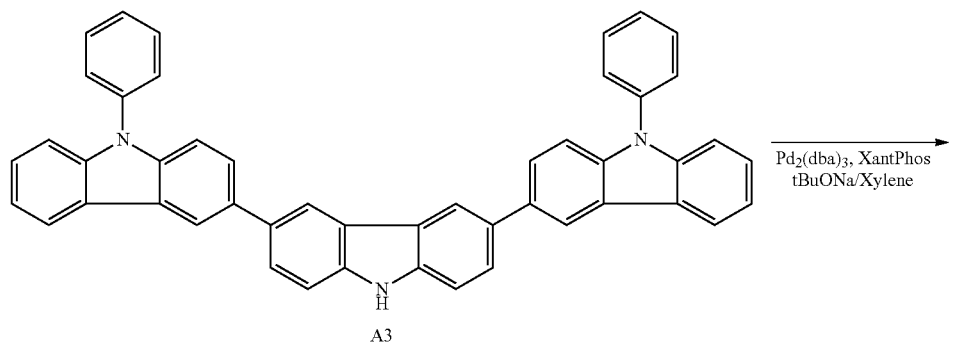

A3

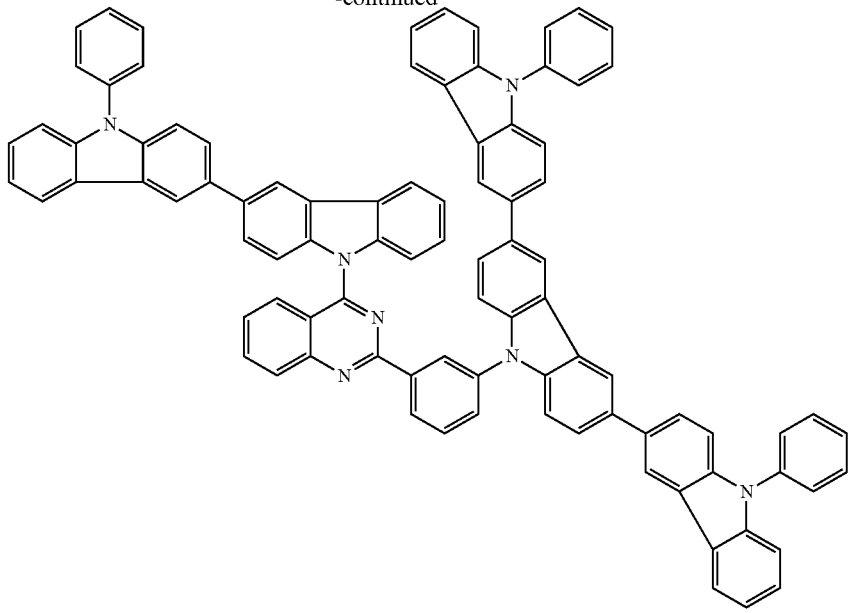

H-15

Under an argon atmosphere, the intermediate C9 (2.07 g, 3.0 mmol), the intermediate A3 (1.94 g, 3.0 mmol), tris(dibenzylideneacetone)dipalladium (0.055 g, 0.06 mmol), xantphos (4,5-bis(diphenylphosphino)-9,9-dimethylxanthene) (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-15 (3.37 g, yield: 89%).

HPLC purity: 99.4%

FD-MS: calcd for $C_{92}H_7N_7$=1260.

found m/z=1260 (M+, 100).

Synthesis Example 16: Synthesis of Compound H-16

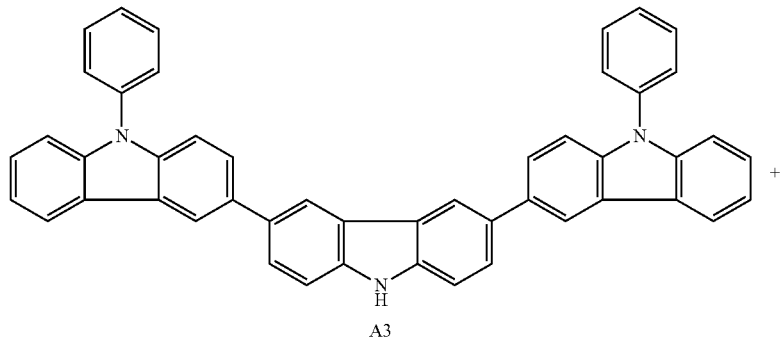

A3

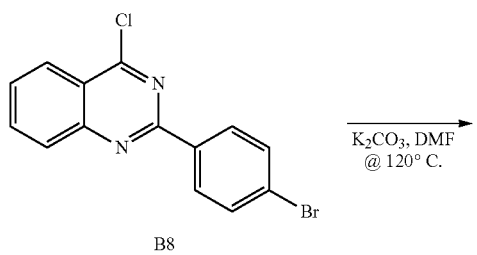

B8

-continued
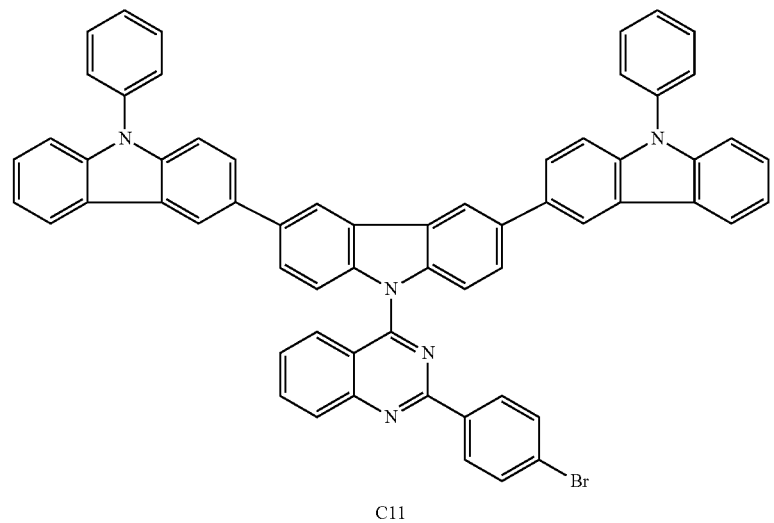
C11
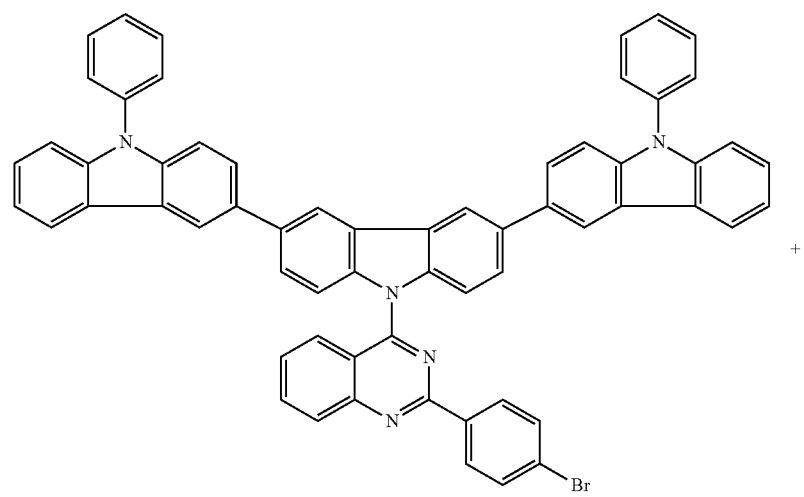
C11 +
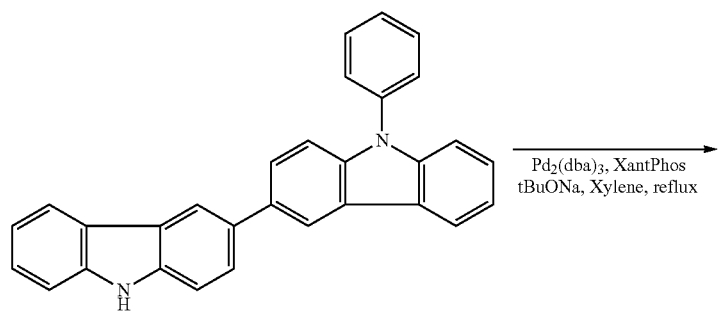
A1

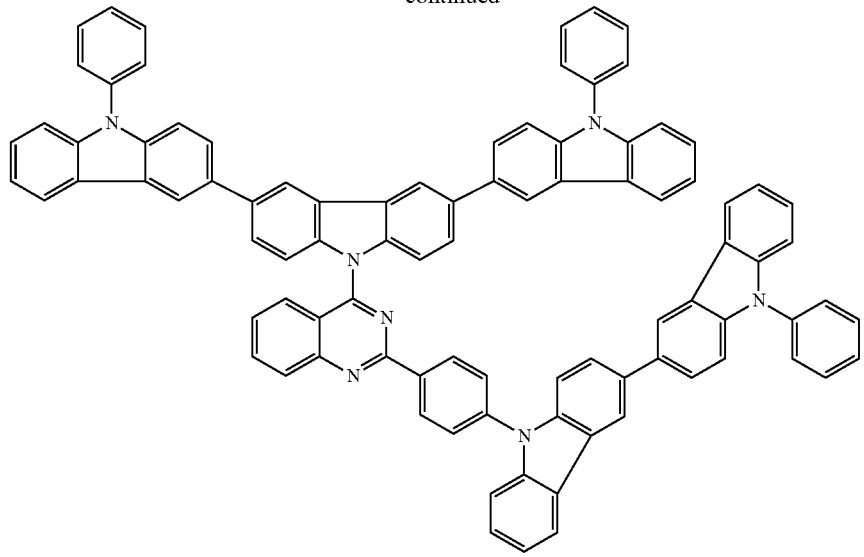

H-16

Under an argon atmosphere, the intermediate A3 (2.14 g, 5.25 mmol), the intermediate B8 (1.60 g, 5.00 mmol), and potassium carbonate (0.83 g, 6.0 mmol) were added to 5 mL of dry DMF and the resultant mixture was stirred at 120° C. for 8 h under heating. After cooling the reaction solution to room temperature, 10 mL of water was added, and the precipitated solid was collected by filtration, washed with water and then methanol, and dried under reduced pressure to obtain the target intermediate C011 (4.01 g, yield: 86%).

Under an argon atmosphere, the intermediate C11 (2.80 g, 3.0 mmol), the intermediate A1 (1.23 g, 3.0 mmol), tris(dibenzylideneacetone)dipalladium (0.055 g, 0.06 mmol), xantphos (4,5-bis(diphenylphosphino)-9,9-dimethylxanthene) (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-16 (3.40 g, yield: 90%).

HPLC purity: 99.5%
FD-MS: calcd for $C_{92}H_7N_7$=1260.
found m/z=1260 (M+, 100).

Synthesis Example 17: Synthesis of Compound H-17

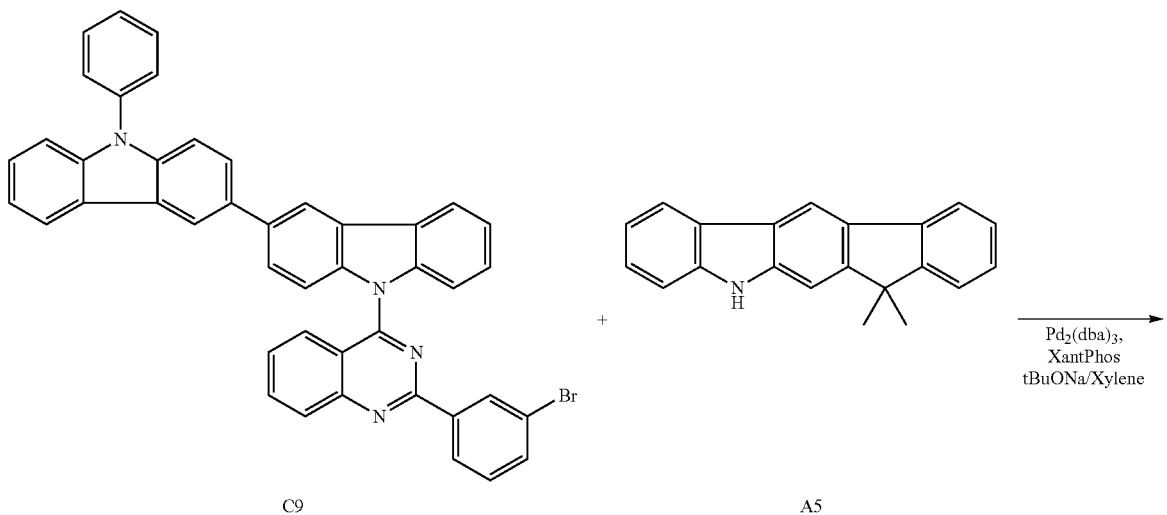

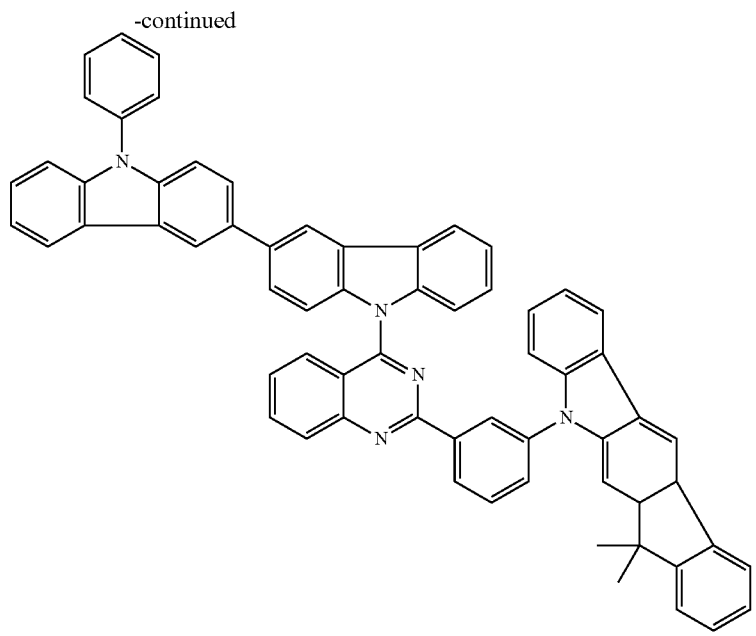

H-17

Under an argon atmosphere, the intermediate C9 (2.07 g, 3.0 mmol), the intermediate A5 (0.85 g, 3.0 mmol), tris(dibenzylideneacetone)dipalladium (0.055 g, 0.06 mmol), xantphos (4,5-bis(diphenylphosphino)-9,9-dimethylxanthene) (0.069 g, 0.12 mmol), sodium t-butoxide (0.43 g, 4.5 mmol), and dehydrated xylene (60 mL) were successively mixed and the resultant mixture was refluxed for 8 h under heating.

After cooling the reaction solution to room temperature, the insolubles were removed by filtration, and the organic solvent was evaporated off under reduced pressure. The obtained residue was purified by silica gel column chromatography to obtain the compound H-17 (2.33 g, yield: 87%).

HPLC purity: 99.1%
FD-MS: calcd for $C_{65}H_{43}N_5$=894.
found m/z=894 (M+, 100).

Example 1

Cleaning of Substrate

A glass substrate of 25 mm×25 mm×1.1 mm thickness having an ITO transparent electrode (product of Geomatec Company) was cleaned by ultrasonic cleaning in isopropyl alcohol for 5 min and then UV ozone cleaning for 5 min.

Formation of Underlayers

Clevious AI4083 (tradename) manufactured by Heraeus as a hole transporting material was spin-coated on the ITO substrate to form a hole transporting layer with a thickness of 30 nm. Thereafter, unnecessary portion was removed by acetone and then a base substrate was produced by baking in air for 10 min on a hot plate at 200° C.

Formation of Light Emitting Layer

Separately, a 1.6% by mass toluene solution containing the compound H-4 obtained in Synthesis Example 4 as a host material and the following compound D-1 as a dopant material was prepared in a mixing ratio of compound H-4:compound D-1=90:10 by mass. The toluene solution was spin-coated on the base substrate into a thickness of 50 nm. Thereafter, unnecessary portion was removed by toluene and then a coat-laminated substrate with a light emitting layer was obtained by drying under heating at 150° C. on a hot plate. The film-forming operations for forming the light emitting layer were all conducted in a glove box under a nitrogen atmosphere.

Vapor Deposition and Sealing

The coat-laminated substrate was conveyed into a vapor deposition chamber and the following compound ET-1 as an electron transporting material was vapor-deposited into a thickness of 50 nm to form an electron transporting layer. Then, lithium fluoride was vapor-deposited into a thickness of 1 nm and aluminum was vapor-deposited into a thickness of 80 nm. After completing all the vapor deposition processes, the substrate with laminated films was sealed with a bored glass in a glove box under a nitrogen atmosphere to produce an organic EL device.

By driving on a direct current, the obtained organic EL device was allowed to emit light to measure the external quantum efficiency (EQE) at a current density of 10 mA/cm². The result was shown in Table 1.

Example 2

An organic EL device was produced in the same manner as in Example 1 except for using the compound D-2 as the dopant material. The result of measurement is shown in Table 1.

Comparative Example 1

An organic EL device was produced in the same manner as in Example 1 except for using the following comparative compound H-a as the host material. The result of measurement is shown in Table 1.

Comparative Example 2

An organic EL device was produced in the same manner as in Example 2 except for using the following comparative compound H-a as the host material. The result of measurement is shown in Table 1.

Example 3

An organic EL device was produced in the same manner as in Example 1 except for preparing a 1.6% by mass toluene solution using the compound H-13 obtained in Synthesis Example 13 as the host material and the following compound D-1 as the dopant material in a mixing ratio of compound H-13:compound D-1=95:5 by mass. The result of measurement is shown in Table 1.

Examples 4 to 7

Each organic EL device was produced in the same manner as in Example 3 except for using each of the compounds obtained in Synthesis Examples, i.e., the compound H-14 (Examples 4), the compound H-15 (Example 5), the compound H-16 (Example 6), and compound H-17 (Example 7) as the host material. The result of measurement is shown in Table 1.

Comparative Example 3

An organic EL device was produced in the same manner as in Example 3 except for using the compound Q-1 disclosed in WO 2012/086170 as the host material. The result of measurement is shown in Table 1.

Comparative Example 4

An organic EL device was produced in the same manner as in Example 3 except for using the compound Q-2 disclosed in WO 2012/086170 as the host material. The result of measurement is shown in Table 1.

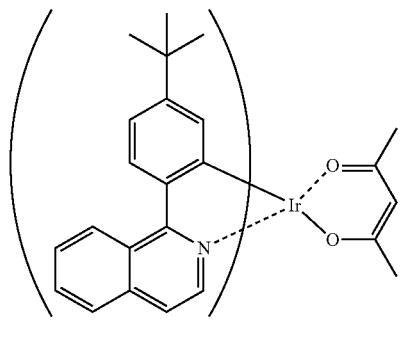

D-1

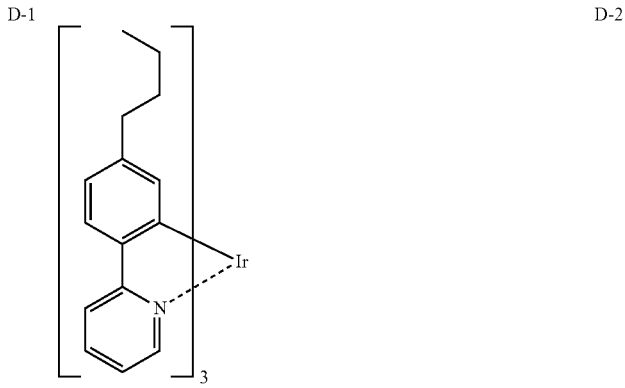

D-2

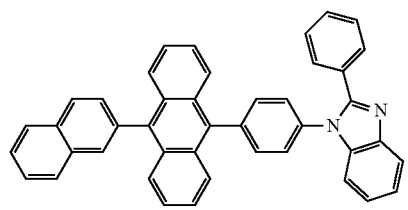

ET-1

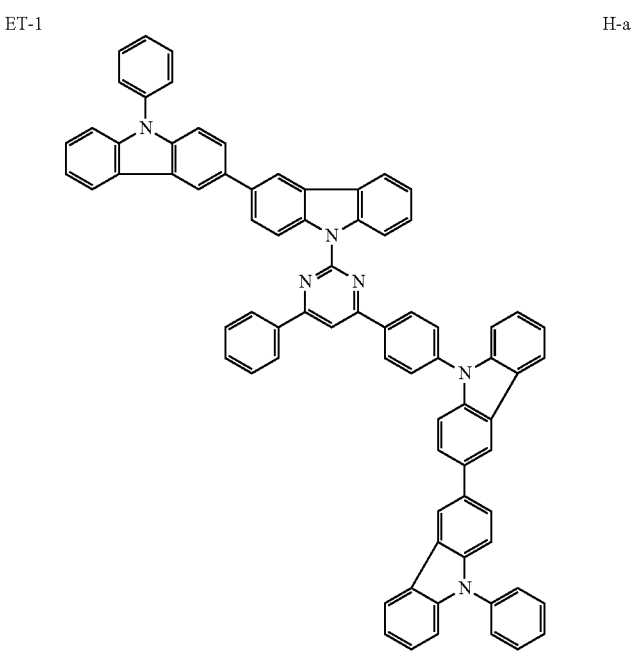

H-a

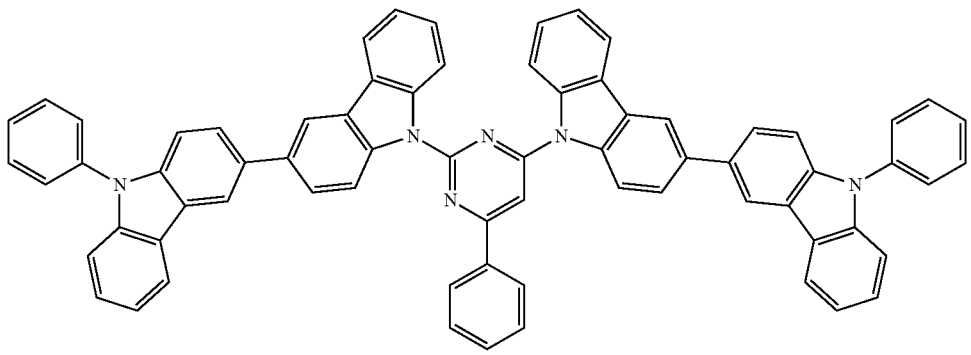

Q-1

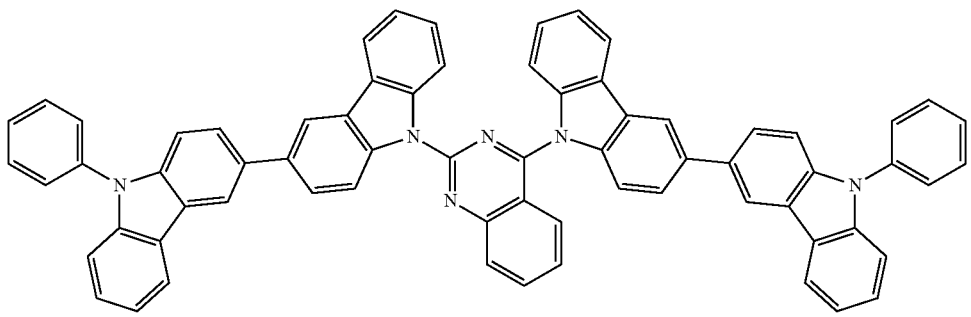

Q-2

TABLE 1

| | Host material | Dopant material | Host/Dopant | External quantum efficiency (%) |
|---|---|---|---|---|
| Example 1 | H-4 | D-1 | 90/10 | 4.5 |
| Comparative example 1 | H-a | D-1 | 90/10 | 2.2 |
| Example 2 | H-4 | D-2 | 90/10 | 7.2 |
| Comparative example 2 | H-a | D-2 | 90/10 | 7.1 |
| Example 3 | H-13 | D-1 | 95/5 | 5.1 |
| Example 4 | H-14 | D-1 | 95/5 | 5.0 |
| Example 5 | H-15 | D-1 | 95/5 | 6.2 |
| Example 6 | H-16 | D-1 | 95/5 | 6.7 |
| Example 7 | H-17 | D-1 | 95/5 | 4.9 |
| Comparative example 3 | Q-1 | D-1 | 95/5 | 1.2 |
| Comparative example 4 | Q-2 | D-1 | 95/5 | 3.0 |

In accordance with the production method in an aspect of the invention, the compound of formula (1) wherein $A^1$ and $A^2$ are different from each other, i.e., the compounds having a variety of skeletons can be easily produced in a high yield. Therefore, as shown above, various compounds usable in the production of organic EL devices which comprises different dopants, i.e., organic EL devices having different emission properties, are easily obtained. This advantageous effect is difficult to obtain by a compound wherein the groups corresponding to $A^1$ and $A^2$ of formula (1) are the same, namely, by a compound wherein a nitrogen-containing heterocyclic ring has two or more same biscarbazole-containing groups, for example, the comparative compounds H-a, Q-1, and Q-2.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

What is claimed is:
1. A compound represented by formula (1):

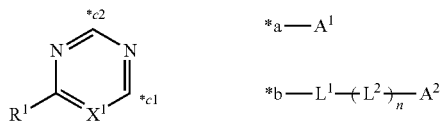

(1)

wherein one of *a and *b is bonded to a carbon atom *c1, and the other is bonded to a carbon atom *c2;
$R^1$ represents a hydrogen atom or a substituent;
$X^1$ represents N or $CR^2$, $R^2$ represents a hydrogen atom or a substituent, and $R^2$ may be bonded to $R^1$ to form a ring;
when *b is bonded to the carbon atom *c2, $X^1$ represents $CR^2$, and $R^2$ is bonded to $R^1$ to form a ring, —$R^1R^2$— represents $X^a$=$X^b$—$X^c$=$X^d$—;
$X^a$ to $X^d$ each independently represent N or $CR^a$, $R^a$ represents a hydrogen atom or a substituent, and adjacent two groups $R^a$ may be bonded to each other to form a ring;
$L^1$ represents a linking group;
$L^2$ represents a divalent linking group;
n represents an integer of 0 to 3 and when n is 0, $L^2$ represents a single bond;
$A^1$ and $A^2$ are different from each other and each represent a group represented by any of formulae (2), (2'), (3), (3'), (3"), and (4):

(2)

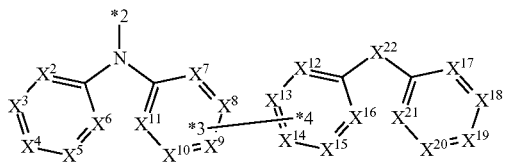

wherein *2 is bonded to the carbon atom *c1, the carbon atom *c2, $L^1$ when n is 0, or $L^2$ when n is an integer of 1 to 3, each described in formula (1);
one of $X^7$ to $X^{11}$ is a carbon atom bonded to *3;
one of $X^{12}$ to $X^{16}$ is a carbon atom bonded to *4;
a rest of $X^7$ to $X^{11}$, a rest of $X^{12}$ to $X^{16}$, $X^2$ to $X^6$, and $X^{17}$ to $X^{21}$ each independently represent N or $CR^3$;
$R^3$ represents a hydrogen atom or a substituent and groups $R^3$ may be bonded to each other to form a ring;
$X^6$ and $X^{11}$ may be carbon atoms which are bonded to each other, and $X^{16}$ and $X^{21}$ may be carbon atoms which are bonded to each other;
$X^{22}$ represents $NR^4$, $CR^5R^6$, O, S, Se, or $SiR^7R^8$; and
$R^4$ to $R^8$ each independently represent a hydrogen atom or a substituent, and $R^5$ and $R^6$, and $R^7$ and $R^8$ may be bonded to each other to form a ring;

(2')

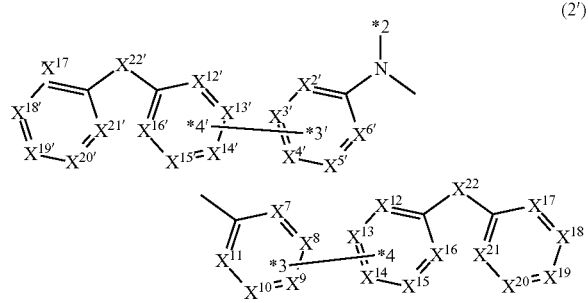

wherein *2, $X^7$ to $X^{11}$, $X^{12}$ to $X^{16}$, $X^{17}$ to $X^{21}$, and $X^{22}$ are as defined above;
one of $X^{2'}$ to $X^{6'}$ represents a carbon atom bonded to *3';
one of $X^{12'}$ to $X^{16'}$ represents a carbon atom bonded to *4';
a rest of $X^{2'}$ to $X^{6'}$, a rest of $X^{12'}$ to $X^{16'}$, and $X^{17'}$ to $X^{21'}$ each independently represent N or $CR^3$;
$R^3$ is as defined above;
$X^{6'}$ and $X^{11}$ may be carbon atoms which are bonded to each other, $X^{16}$ and $X^{21}$ may be carbon atoms which are bonded to each other, and $X^{16'}$ and $X^{21'}$ may be carbon atoms which are bonded to each other;
$X^{22'}$ represents $NR^4$, $CR^5R^6$, O, S, Se, or $SiR^7R^8$; and
$R^4$ to $R^8$ are as defined above;

(3)

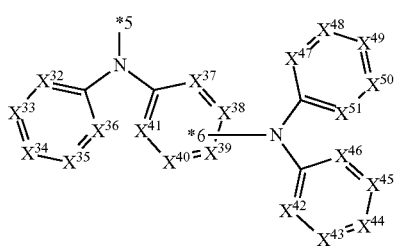

wherein *5 is bonded to the carbon atom *c1, the carbon atom *c2, $L^1$ when n is 0, or $L^2$ when n is an integer of 1 to 3, each described in formula (1);
one of $X^{37}$ to $X^{41}$ represents a carbon atom bonded to *6;
a rest of $X^{37}$ to $X^{41}$, $X^{32}$ to $X^{36}$, and $X^{42}$ to $X^{51}$ each independently represent N or $CR^9$;
$R^9$ represents a hydrogen atom or a substituent and groups $R^9$ may be bonded to each other to form a ring; and
$X^{36}$ and $X^{41}$ may be carbon atoms which are bonded to each other and $X^{46}$ and $X^{51}$ may be carbon atoms which are bonded to each other;

(3')

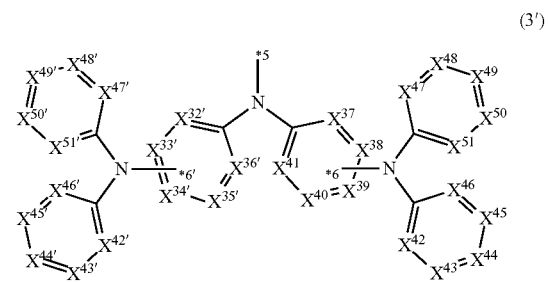

wherein *5, $X^{37}$ to $X^{41}$, and $X^{42}$ to $X^{51}$ are as defined above;
one of $X^{32'}$ to $X^{36'}$ represents a carbon atom bonded to *6'
a rest of $X^{32'}$ to $X^{36'}$ and $X^{42'}$ to $X^{51'}$ each independently represent N or $CR^9$;
$R^9$ is as defined above; and
$X^{36'}$ and $X^{41}$ may be carbon atoms which are bonded to each other, $X^{46}$ and $X^{51}$ may be carbon atoms which are bonded to each other, and $X^{46'}$ and $X^{51'}$ may be carbon atoms which are bonded to each other;

(3")

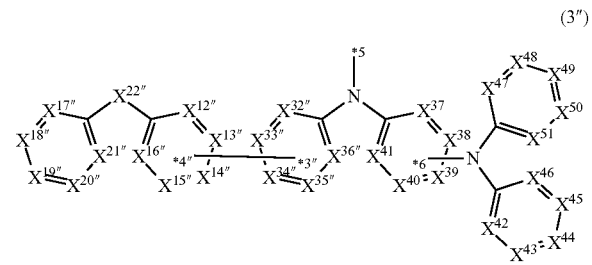

wherein *5, $X^{37}$ to $X^{41}$, and $X^{42}$ to $X^{51}$ are as defined above;
one of $X^{32''}$ to $X^{36''}$ represents a carbon atom bonded to 3";
one of $X^{12''}$ to $X^{16''}$ represents a carbon atom bonded to *4";
a rest of $X^{32''}$ to $X^{36''}$, a rest of $X^{12''}$ to $X^{16''}$, and $X^{17''}$ to $X^{21''}$ each independently represent N or $CR^3$;
$R^3$ is as defined above;
$X^{36''}$ and $X^{41}$ may be carbon atoms which are bonded to each other, $X^{46}$ and $X^{51}$ may be carbon atoms which are bonded to each other, $X^{16''}$ and $X^{21''}$ may be carbon atoms which are bonded to each other;
$X^{22''}$ represents $NR^4$, $CR^5R^6$, O, S, Se, or $SiR^7R^8$; and
$R^4$ to $R^8$ are as defined above;

(4)

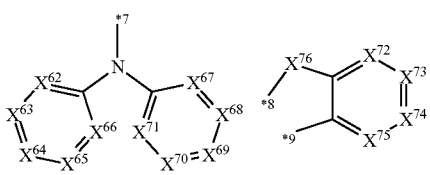

wherein *7 is bonded to the carbon atom *c1, the carbon atom *c2, $L^1$ when n is 0, or $L^2$ when n is an integer of 1 to 3, each described in formula (1);

one of adjacent two selected from $X^{67}$ to $X^{71}$ represents a carbon atom bonded to *8 and the other represents a carbon atom bonded to *9;

a rest of $X^{67}$ to $X^{71}$, $X^{62}$ to $X^{66}$, and $X^{72}$ to $X^{75}$ each independently represent N or $CR^{10}$;

$R^{10}$ represents a hydrogen atom or a substituent, and groups $R^{10}$ may be bonded to each other to form a ring;

$X^{66}$ and $X^{71}$ may be carbon atoms which are bonded to each other;

$X^{76}$ represents $NR^{11}$, $CR^{12}R^{13}$, O, S, Se, or $SiR^{14}R^{15}$; and $R^{11}$ to $R^{15}$ each independently represent a hydrogen atom or a substituent, and $R^{11}$ and $R^{12}$, and $R^{13}$ and $R^{14}$ may be bonded to each other to form a ring.

2. The compound according to claim 1, wherein when *b is bonded to the carbon atom *c1, $L^1$ represents a substituted or unsubstituted arylene group having 6 to 50 ring carbon atoms or a group of atoms which completes a ring together with $R^2$;

when $L^1$ represents a substituted or unsubstituted arylene group having 6 to 50 ring carbon atoms and n is 1, $L^1$ and $L^2$ may be the same or different and may be crosslinked together; and when $L^1$ represents a substituted or unsubstituted arylene group having 6 to 50 ring carbon atoms and n is 2 or 3, $L^1$ and two or three groups $L^2$ may be the same or different, and $L^1$ and $L^2$, and two groups $L^2$ may be crosslinked together.

3. The compound according to claim 1, wherein when *b is bonded to the carbon atom *c2 and n is 1, $L^1$ and $L^2$ may be the same or different and may be crosslinked together; and when *b is bonded to the carbon atom *c2 and n is 2 or 3, $L^1$ and two or three groups $L^2$ may be the same or different, and $L^1$ and $L^2$, and two groups $L^2$ may be crosslinked together.

4. The compound according to claim 1, wherein the compound is represented by formula (1a):

(1a)

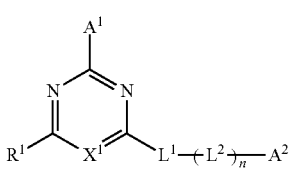

wherein $R^1$, $X^1$, $L^1$, $L^2$, n, $A^1$, and $A^2$ are as defined above.

5. The compound according to claim 1, wherein the compound is represented by formula (1b):

(1b)

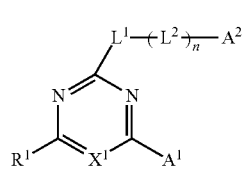

wherein $R^1$, $X^1$, $L^1$, $L^2$, n, $A^1$, and $A^2$ are as defined above.

6. The compound according to claim 1, wherein the compound is represented by formula (1c):

(1c)

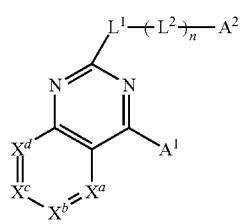

wherein $X^a$ to $X^d$, $L^1$, $L^2$, n, $A^1$, and $A^2$ are as defined above.

7. The compound according to claim 1, wherein $A^1$ and $A^2$ each represent a group represented by any of the following formulae:

(2a)

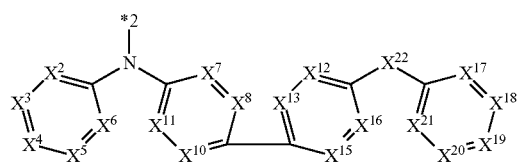

(2b)

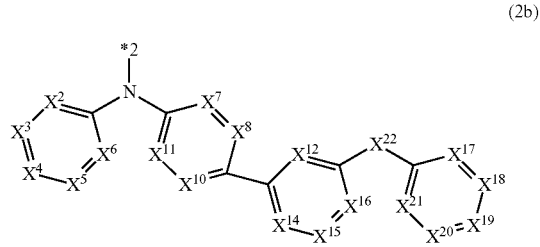

(2c)

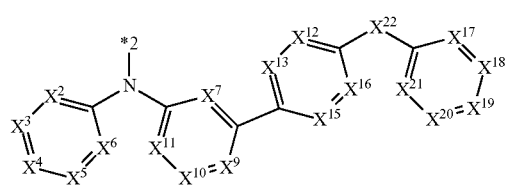

in formulae (2a) to (2c), *2 and $X^2$ to $X^{22}$ are as defined above;

(2'a)
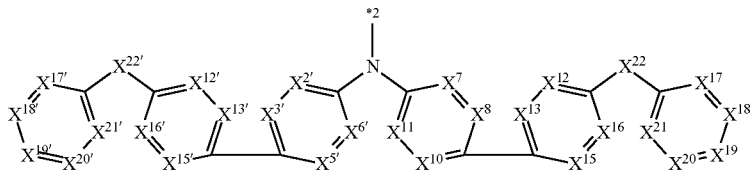
(2'b)
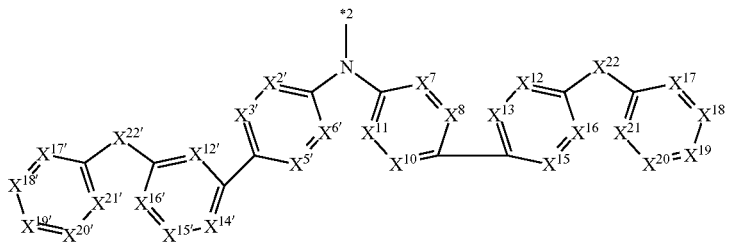
(2'c)
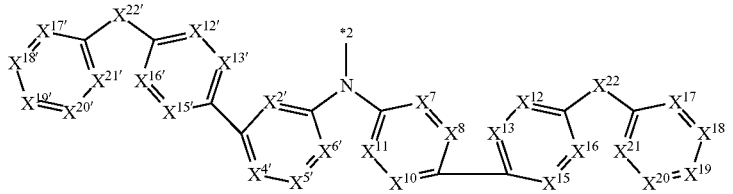
(2'd)
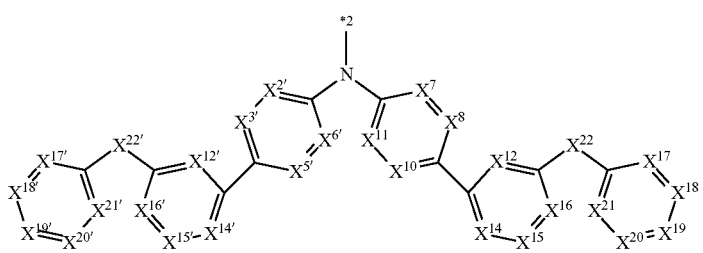
(2'e)
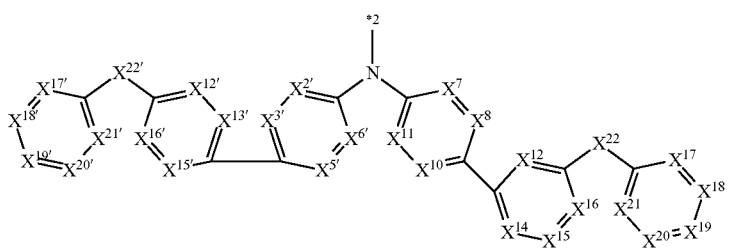
(2'f)
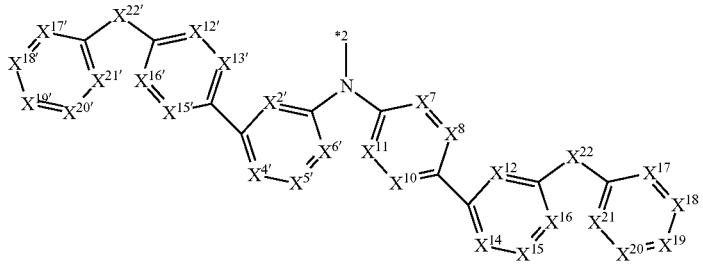

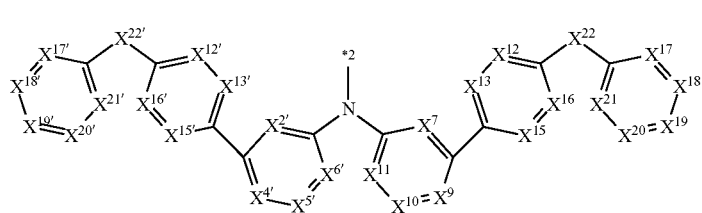
(2'g)
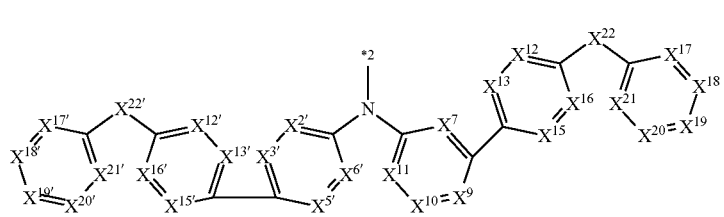
(2'h)
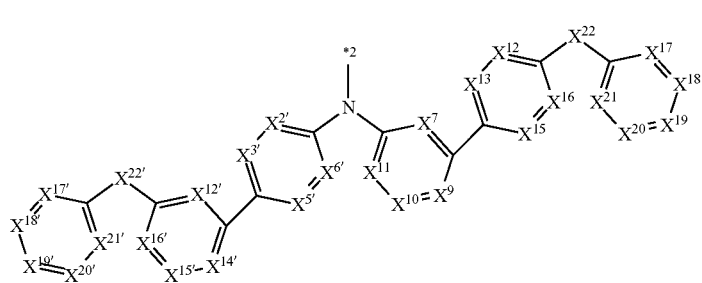
(2'i)
in formulae (2'a) to (2'i), *2, $X^7$ and $X^{22}$, $X^{2'}$ to $X^{6'}$, and $X^{12'}$ to $X^{22'}$ are as defined above;
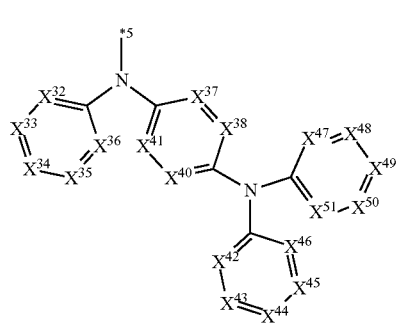
(3a)
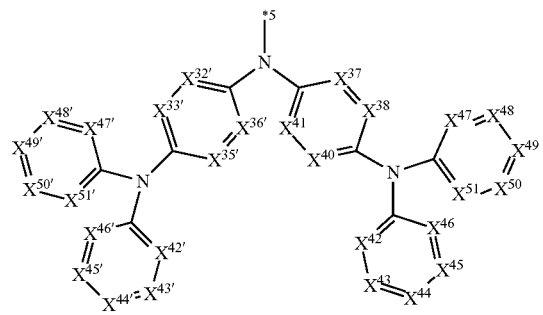
(3'a)
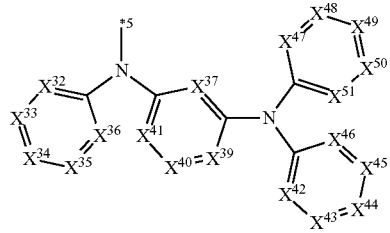
(3b)
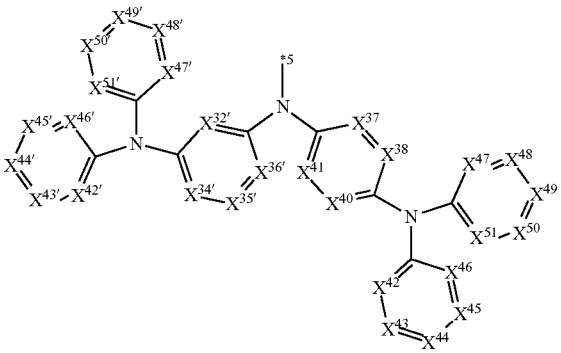
(3'b)
in formulae (3a) and (3b), and $X^{32}$ to $X^{51}$ are as defined above;

(3'c)
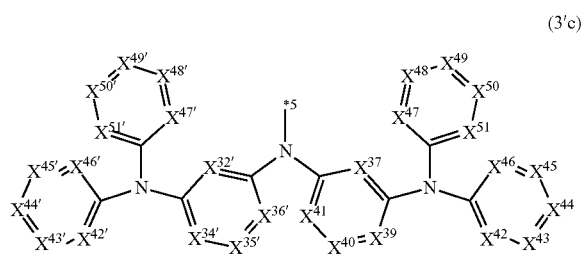
in formulae (3'a) and (3'b), $X^{37}$ to $X^{51}$, $X^{32'}$ to $X^{36'}$, and $X^{42'}$ to $X^{51'}$ are as defined above;
(3"a)
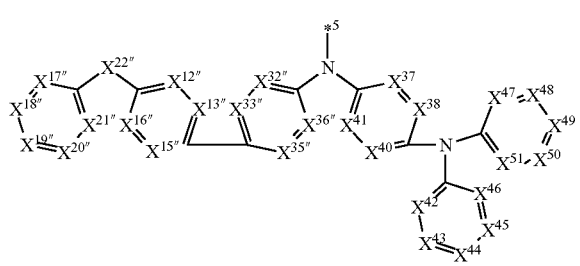
(3"b)
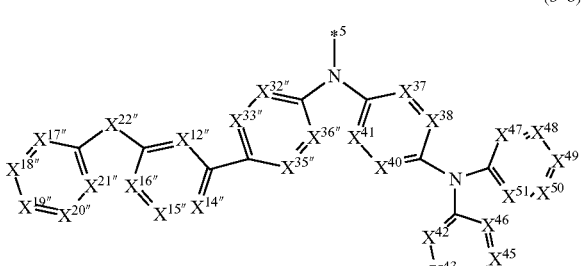
(3"c)
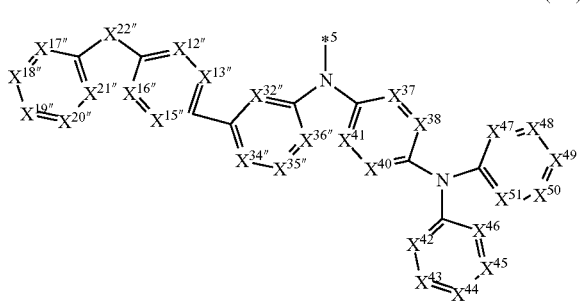
(3"d)
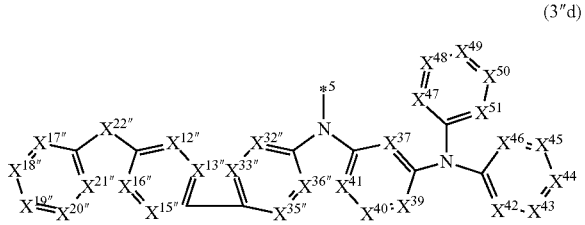
(3"e)
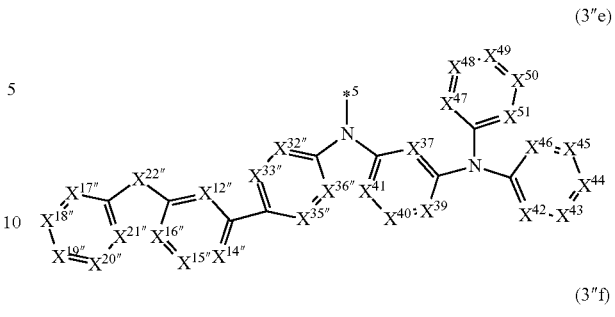
(3"f)
in formulae (3"a) to (3"f), 5*, $X^{37}$ to $X^{51}$, $X^{32'}$ to $X^{36''}$, and $X^{12''}$ to $X^{22''}$ are as defined above;
(4a)
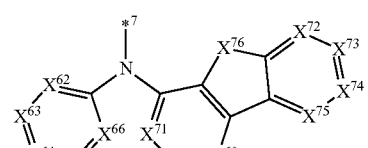
(4b)
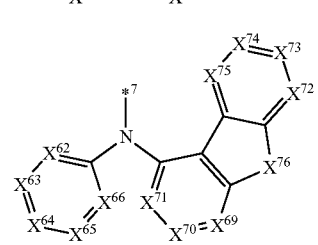
(4c)
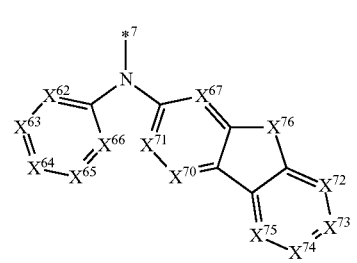
(4d)
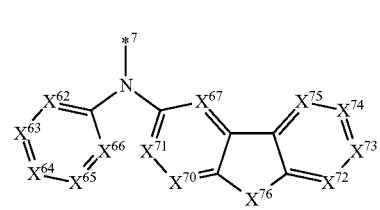

-continued
(4e)
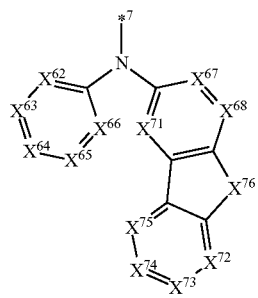
(4f)
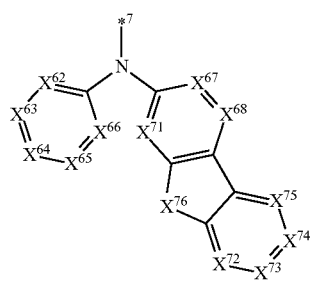
in formulae (4a) to (4f), *7 and $X^{62}$ to $X^{76}$ are as defined above.
8. The compound according to claim 1, wherein $A^1$ and $A^2$ each represent a group represented by any of the following formulae:
(2a-1)
(2a-2)
(2a-3)
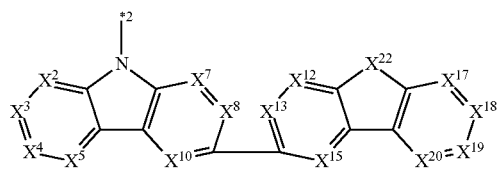
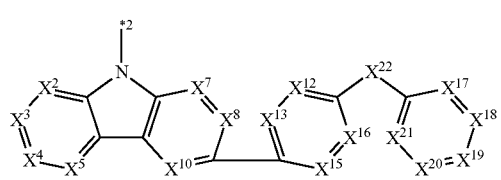
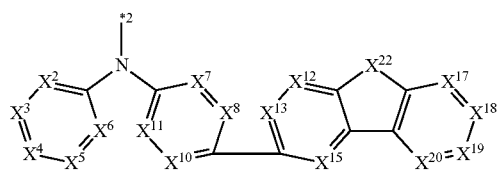
in formulae (2a-1) to (2a-3), *2 and each X are as defined above;
(2b-1)
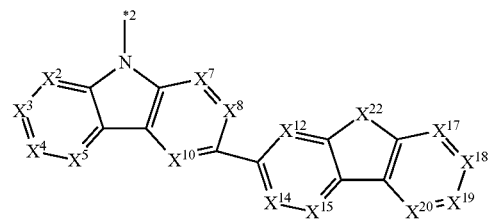
(2b-2)
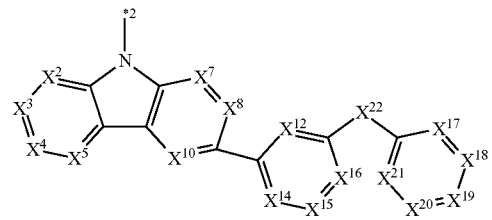
(2b-3)
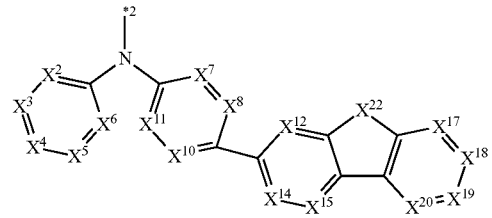
in formulae (2b-1) to (2b-3), *2 and each X are as defined above;
(2c-1)
(2c-2)
(2c-3)
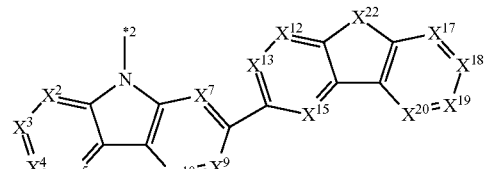
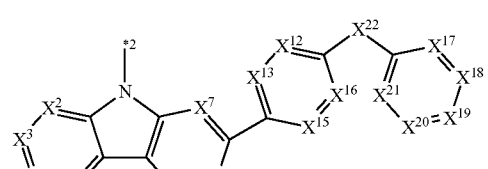
in formulae (2c-1) to (2c-3), *2 and each X are as defined above;

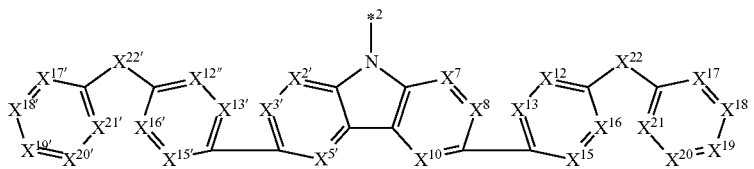 (2'a-1)
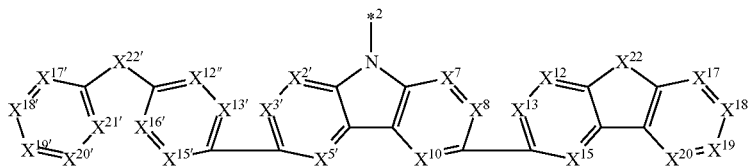 (2'a-2)
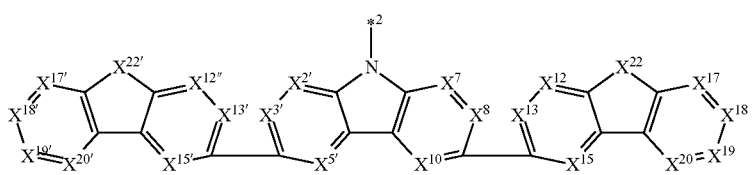 (2'a-3)
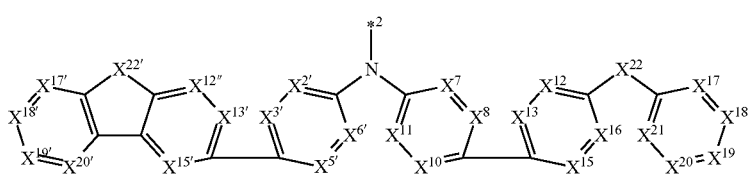 (2'a-4)
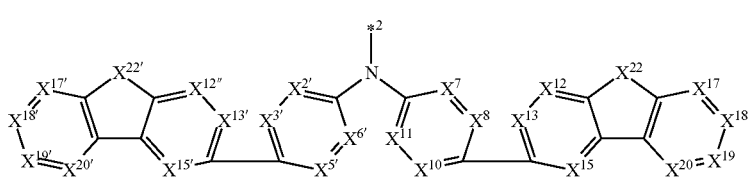 (2'a-5)
in formulae (2'a-1) to (2'a-5), *2 and each X are as defined above;
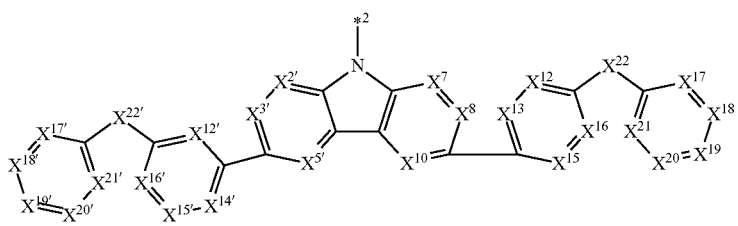 (2'b-1)
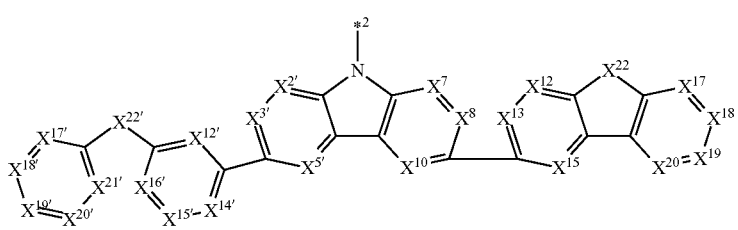 (2'b-2)

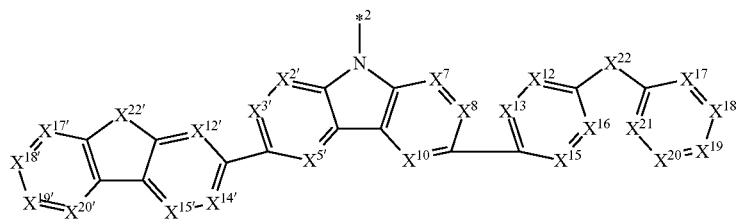
(2'b-3)
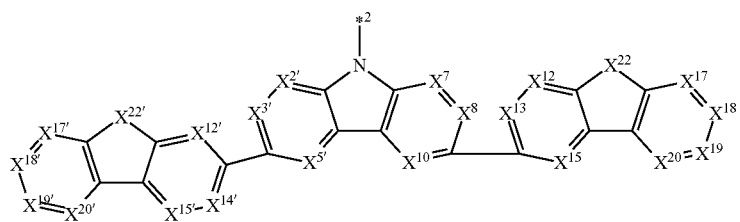
(2'b-4)
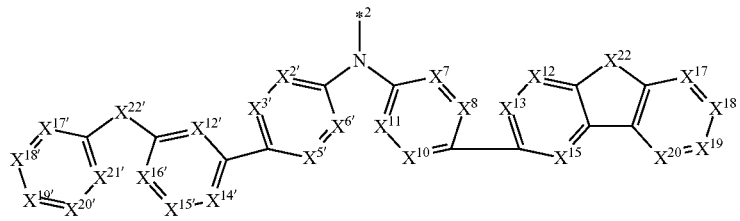
(2'b-5)
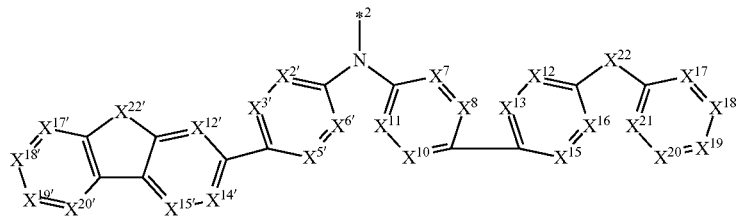
(2'b-6)
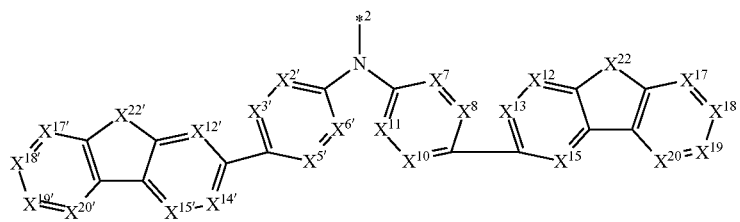
(2'b-7)
in formulae (2'b-1) to (2'b-7), *2 and each X are as defined above;
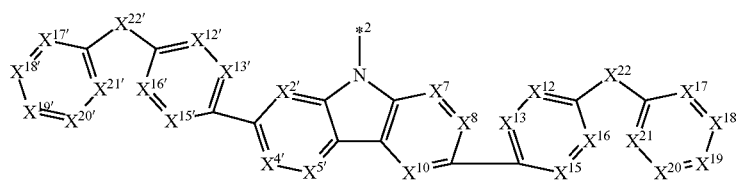
(2'c-1)

-continued
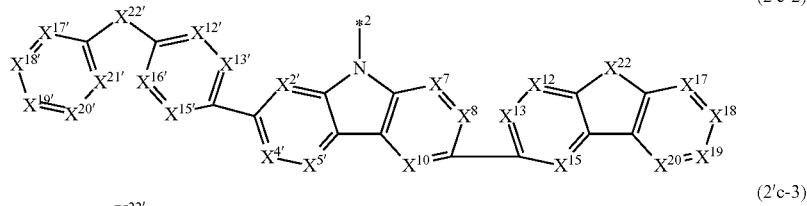
(2'c-2)
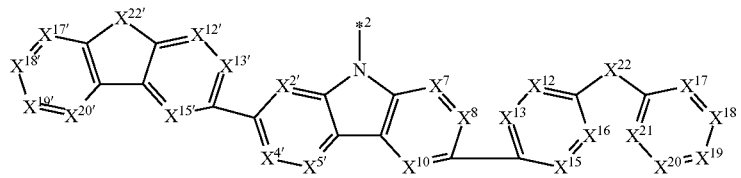
(2'c-3)
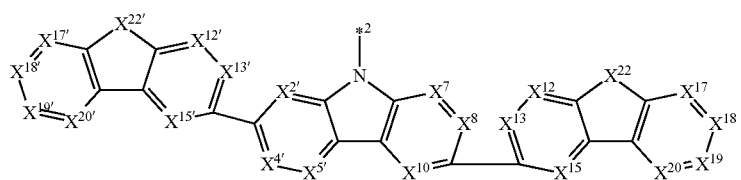
(2'c-4)
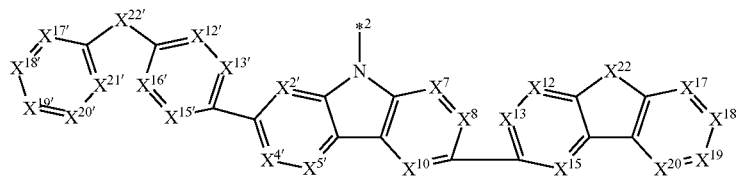
(2'c-5)
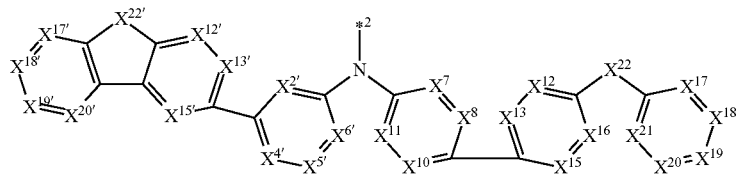
(2'c-6)
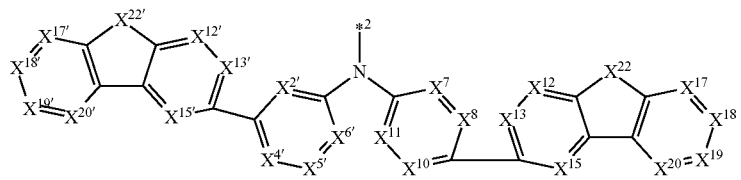
(2'c-7)
in formulae (2'c-1) to (2'c-7), *2 and each X are as defined above;
-continued
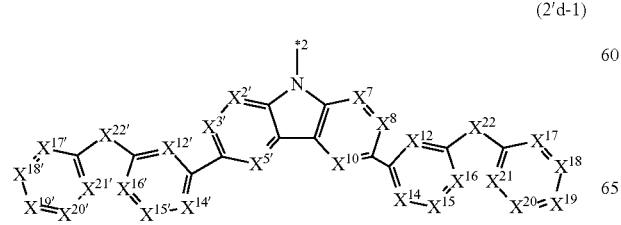
(2'd-1)
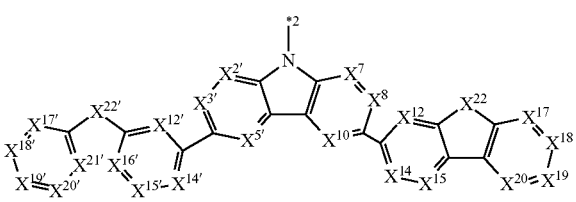
(2'd-2)

(2'd-3)
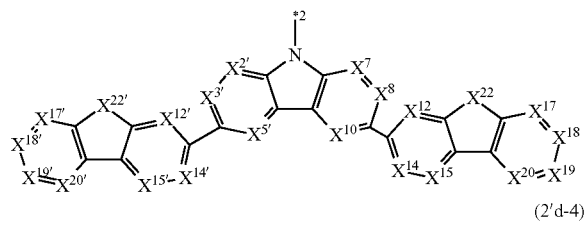
(2'd-4)
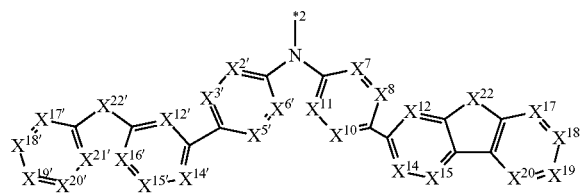
(2'd-5)
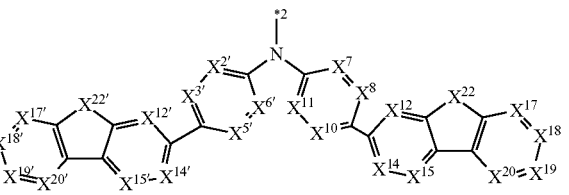
in formulae (2'd-1) to (2'd-5), *2 and each X are as defined above;
(2'e-1)
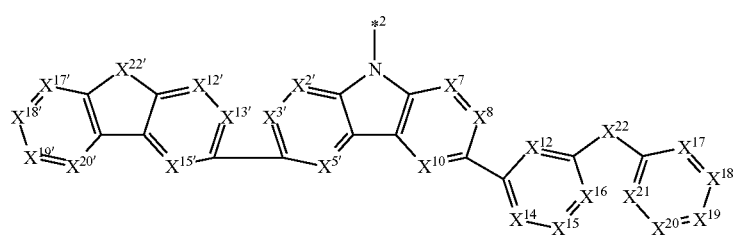
(2'e-2)
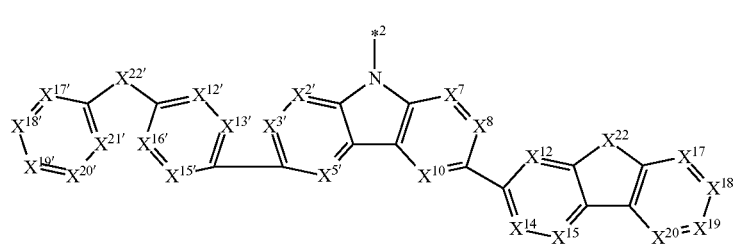
(2'e-3)
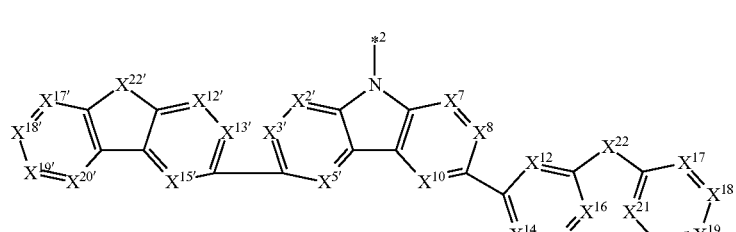
(2'e-4)
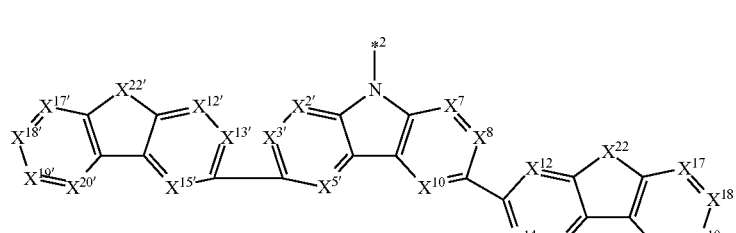

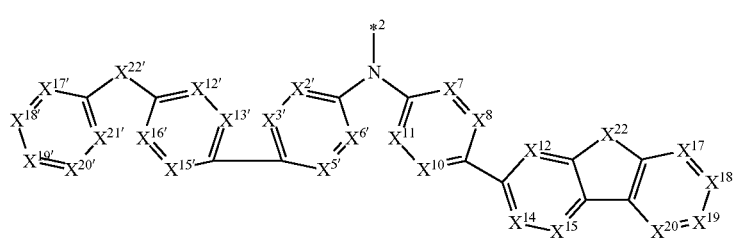
in formulae (2'e-1) to (2'e-7), *2 and each X are as defined above;

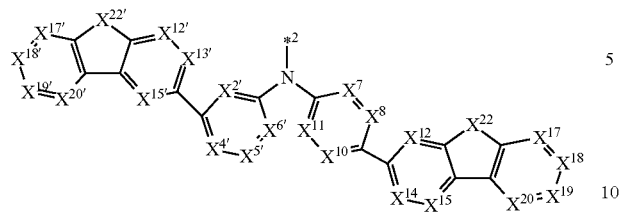
(2'f-7)
in formulae (2'f-1) to (2'f-7), *2 and each X are as defined above;
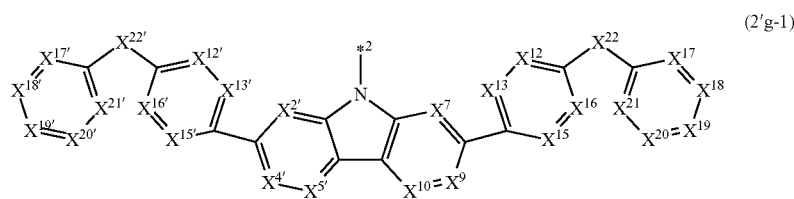
(2'g-1)
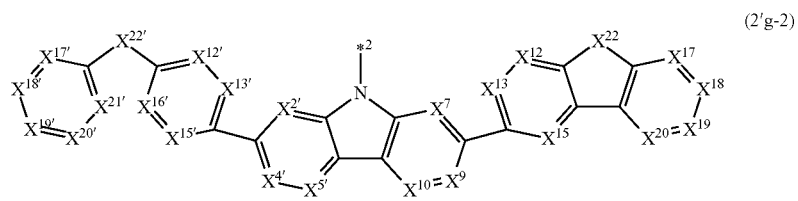
(2'g-2)
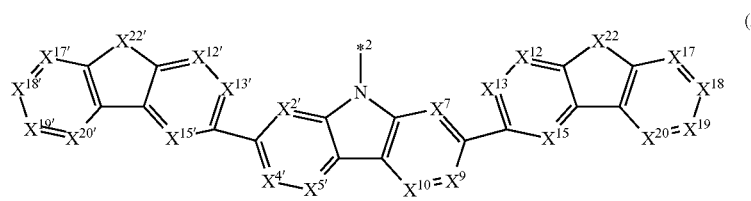
(2'g-3)
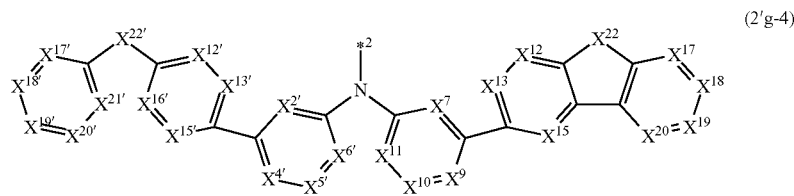
(2'g-4)
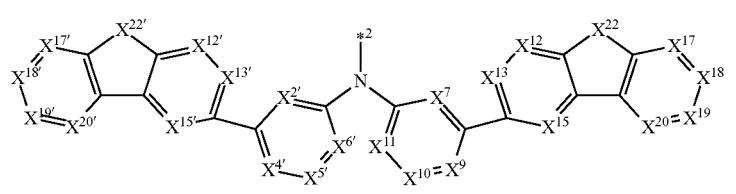
(2'g-5)
in formulae (2'g-1) to (2'g-5), *2 and each X are as defined above;

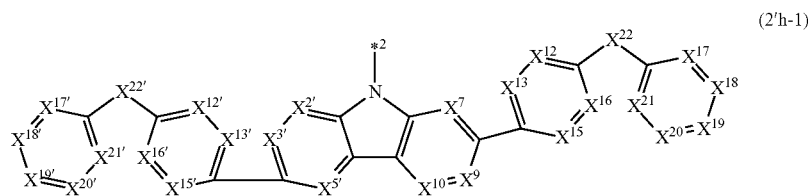
(2'h-1)
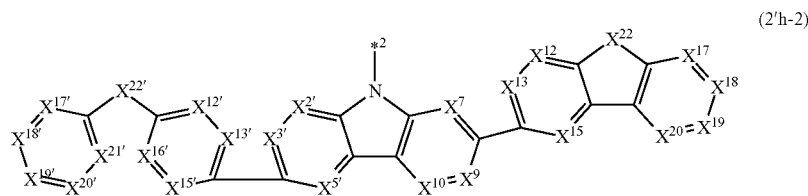
(2'h-2)
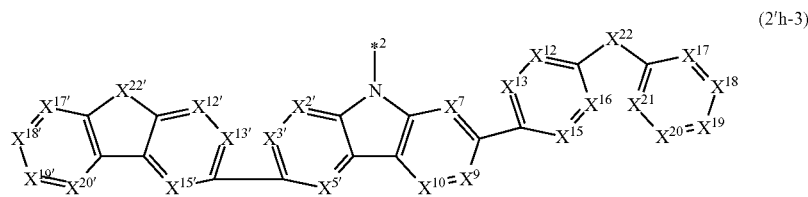
(2'h-3)
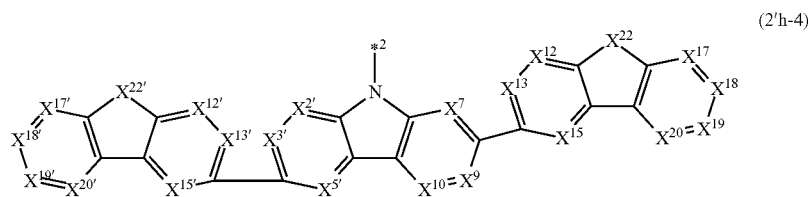
(2'h-4)
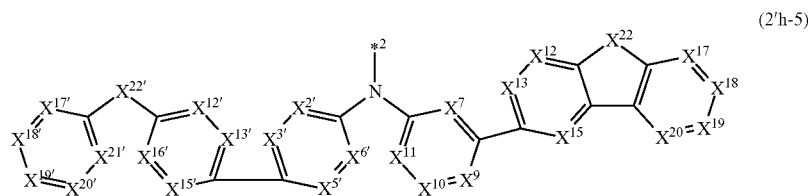
(2'h-5)
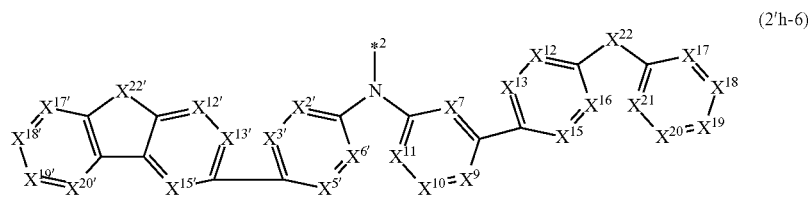
(2'h-6)
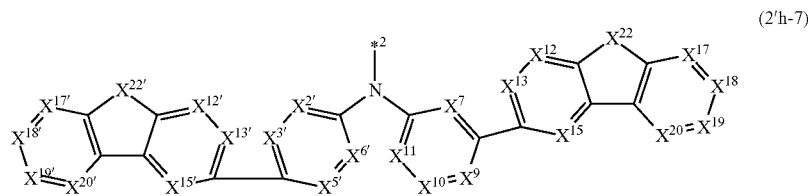
(2'h-7)
in formulae (2'h-1) to (2'h-7), *2 and each X are as defined above;

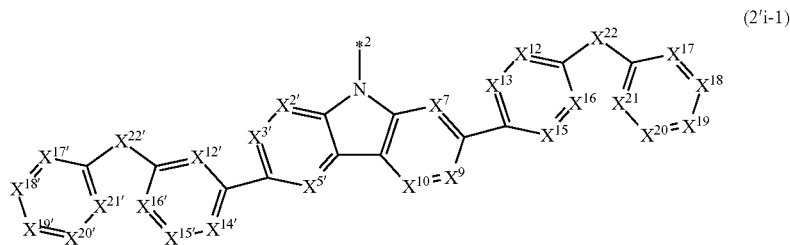
(2'i-1)
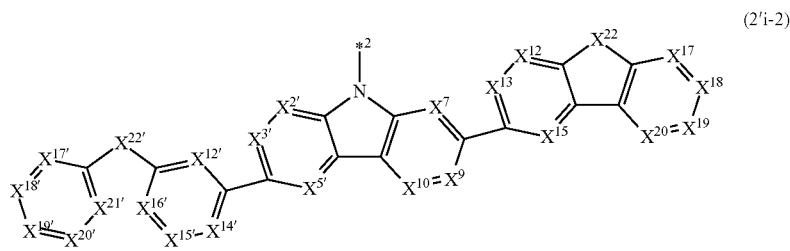
(2'i-2)
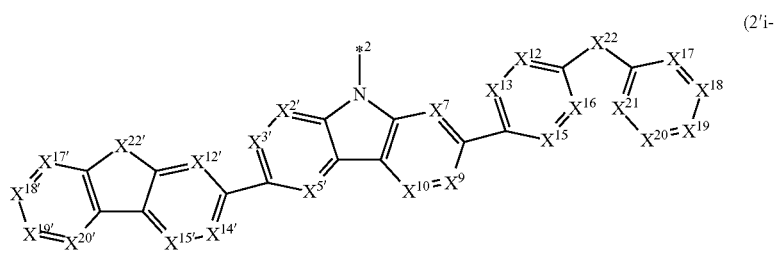
(2'i-3)
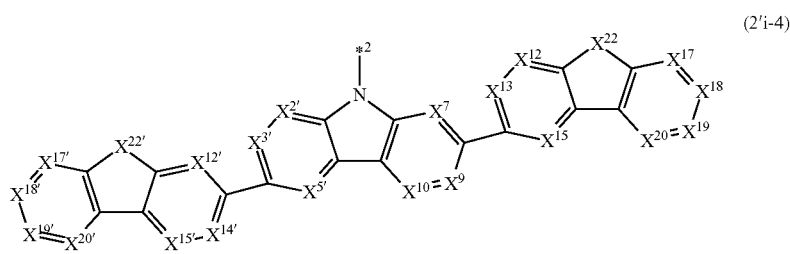
(2'i-4)
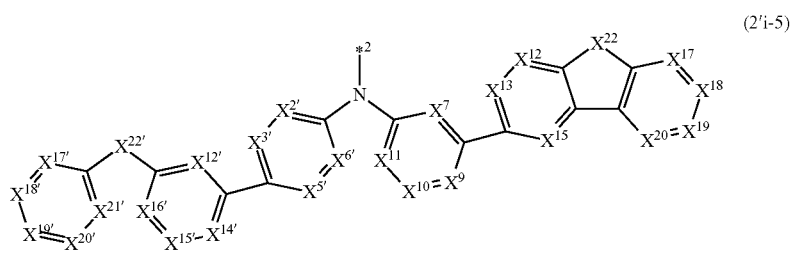
(2'i-5)
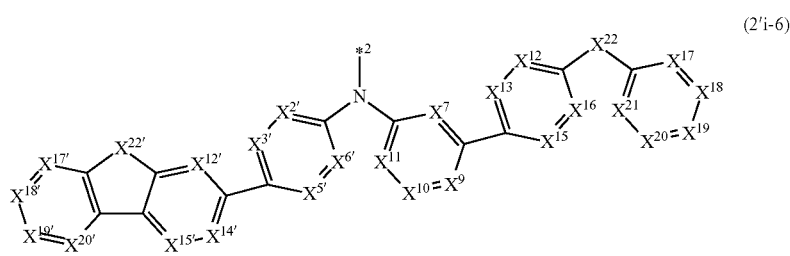
(2'i-6)

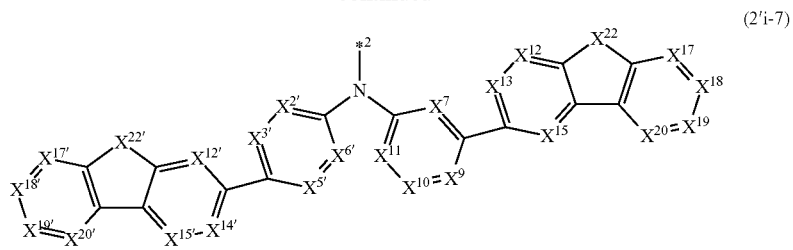
(2'i-7)
in formulae (2'i-1) to (2'i-7), *2 and each X are as defined above;
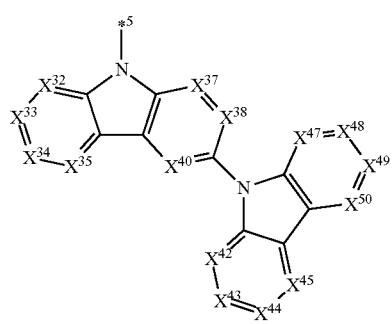
(3a-1)
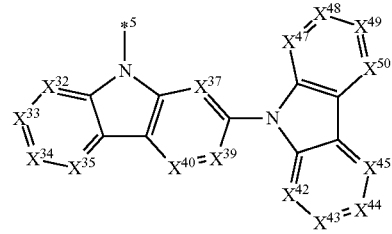
(3b-1)
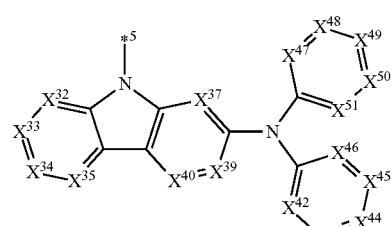
(3b-2)
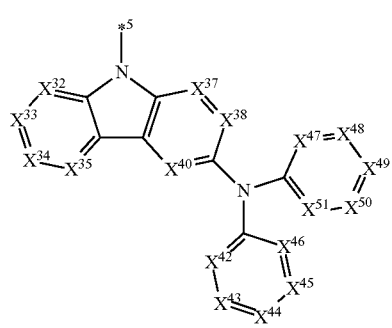
(3a-2)
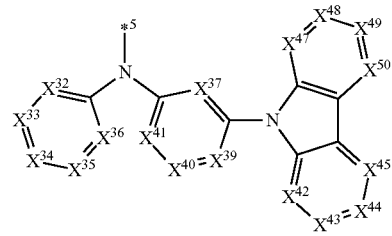
(3b-3)
in formulae (3b-1) to (3b-3), *5 and each X are as defined above;
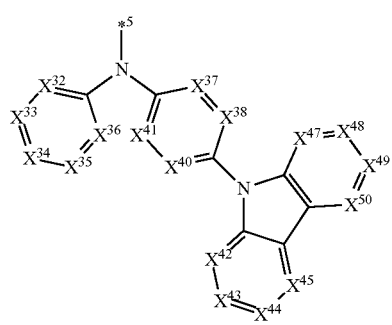
(3a-3)
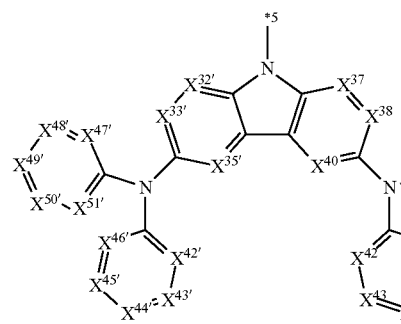
(3'a-1)
in formulae (3a-1) to (3a-3), *5 and each X are as defined above;

(3'a-2)
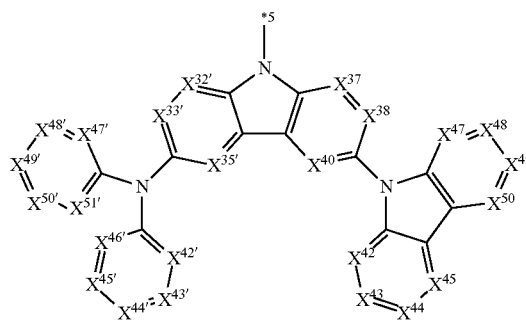
(3'a-3)
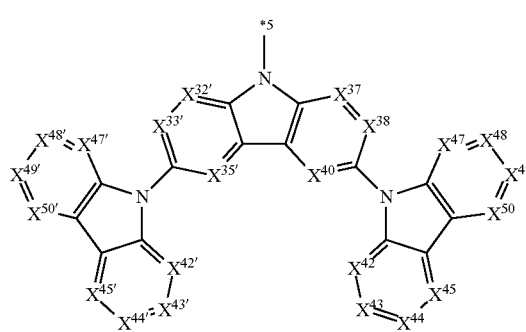
(3'a-4)
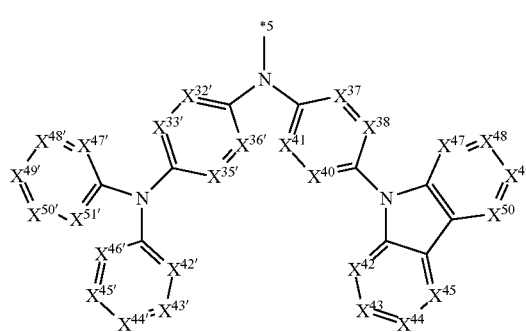
(3'a-5)
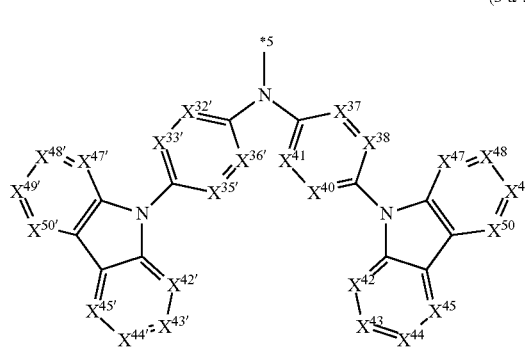
in formulae (3'a-1) to (3'a-5), *5 and each X are as defined above;
(3'b-1)
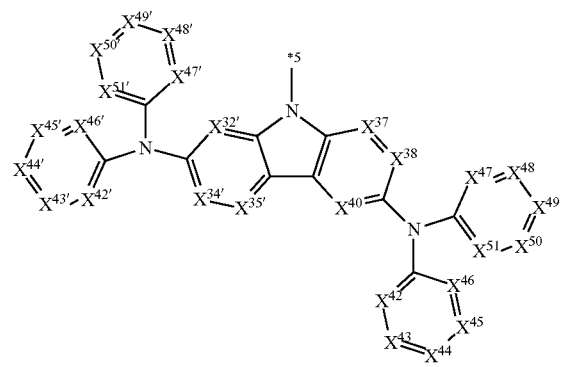
(3'b-2)
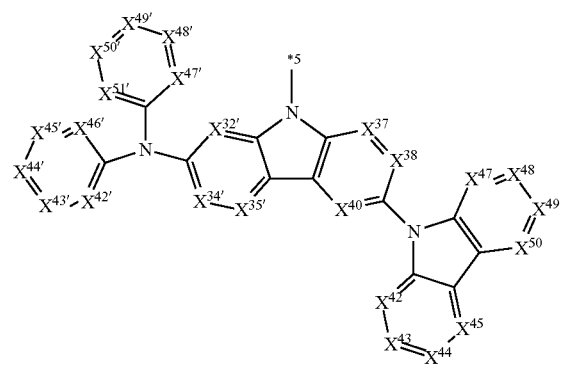
(3'b-3)
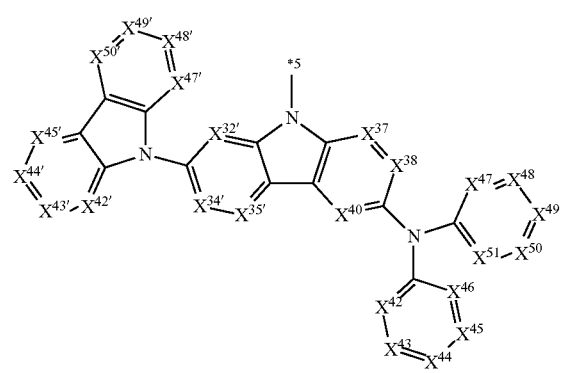
(3'b-4)
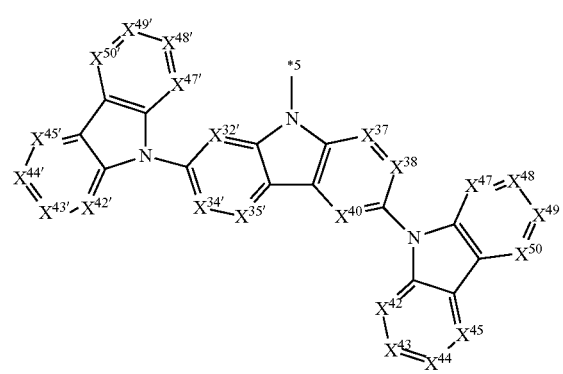

(3'b-5)
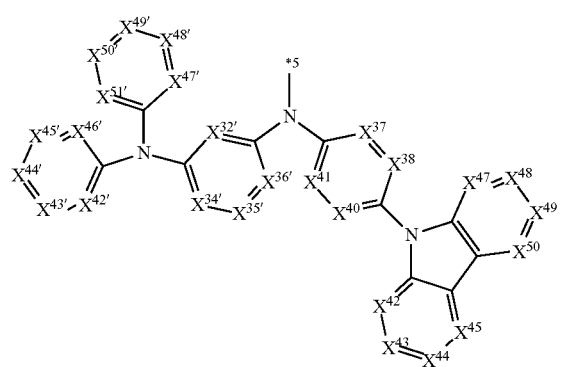
(3'b-6)
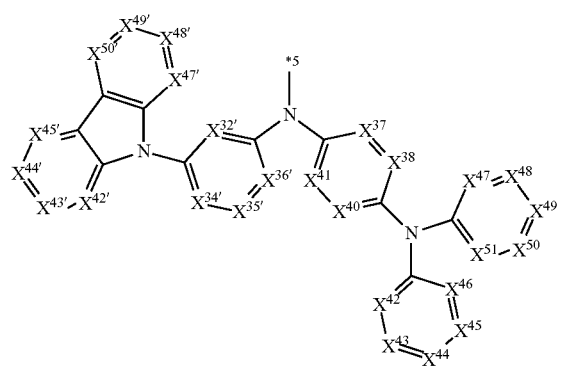
(3'b-7)
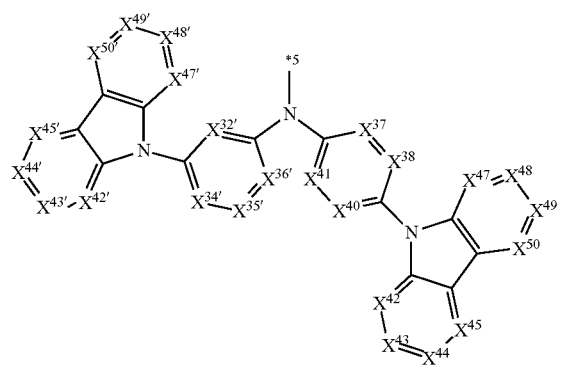
in formulae (3'b-1) to (3'b-7), *5 and each X are as defined above;
(3'c-1)
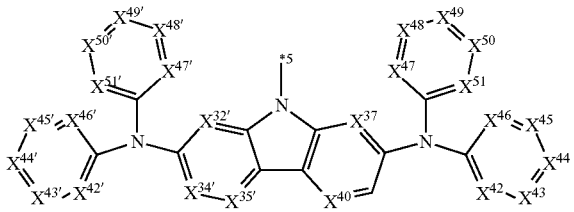
(3'c-2)
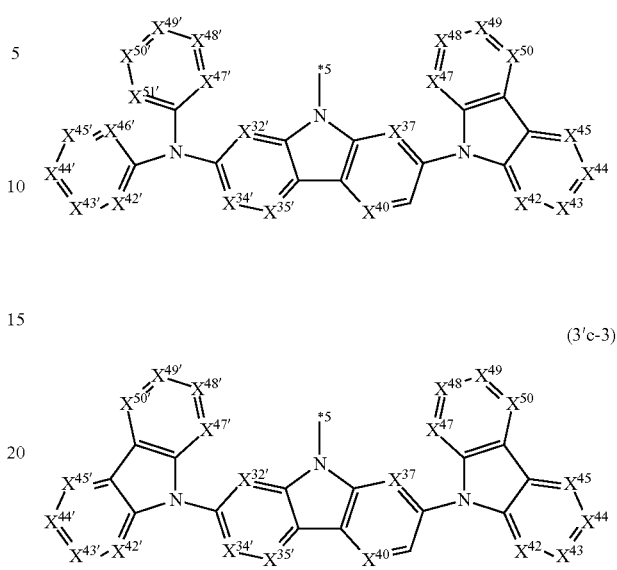
(3'c-3)
(3'c-4)
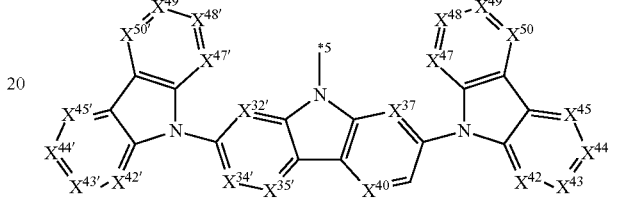
(3'c-5)
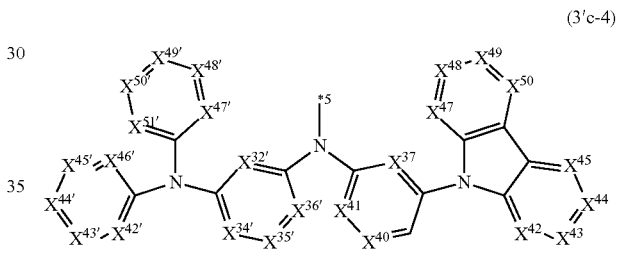
in formulae (3'c-1) to (3'c-5), *5 and each X are as defined above;
(3"a-1)
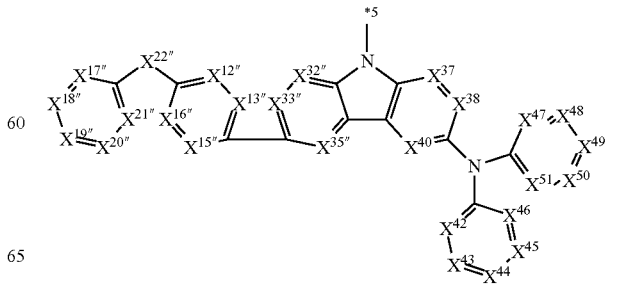

-continued
(3″a-2)
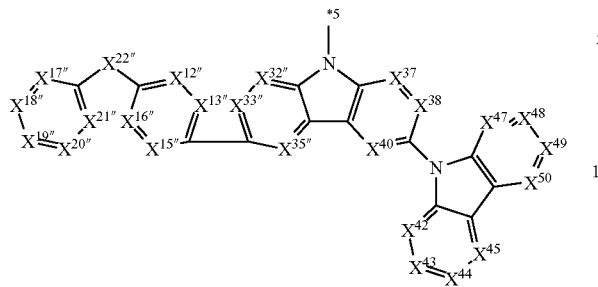
(3″a-3)
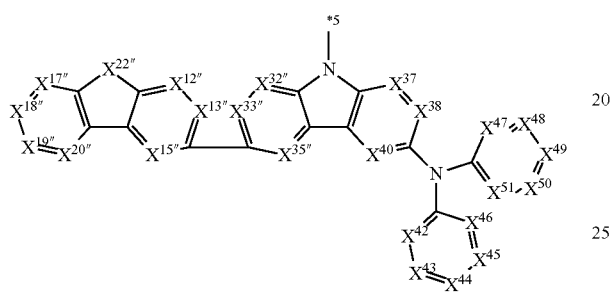
(3″a-4)
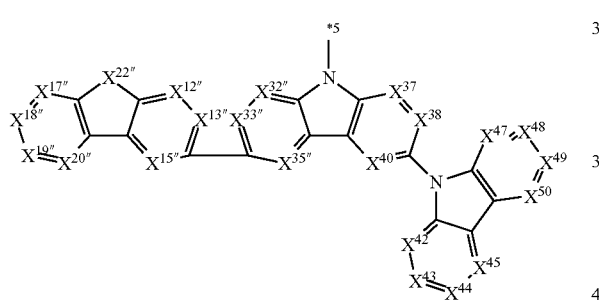
(3″a-5)
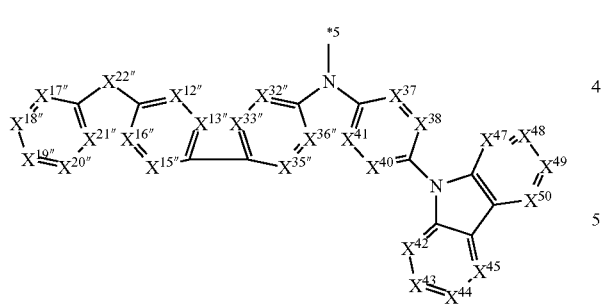
(3″a-6)
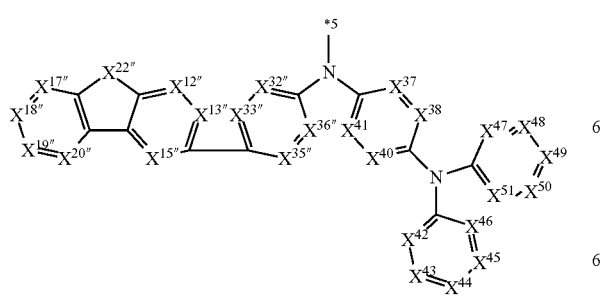
-continued
(3″a-7)
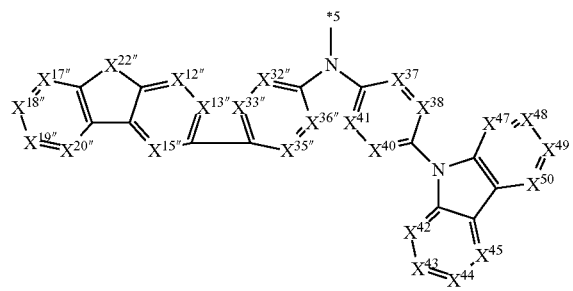
in formulae (3″a-1) to (3″a-7), *5 and each X are as defined above;
(3″b-1)
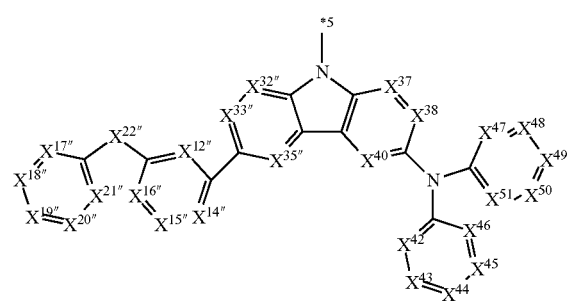
(3″b-2)
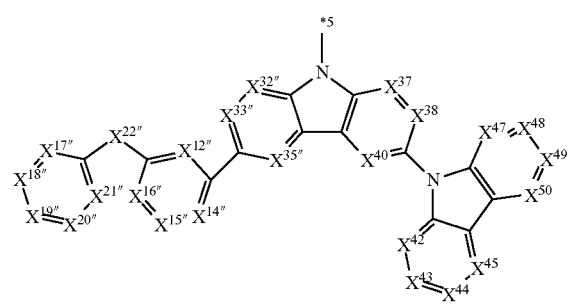
(3″b-3)
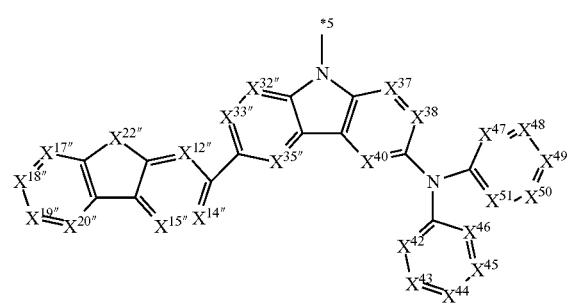

(3″b-4)
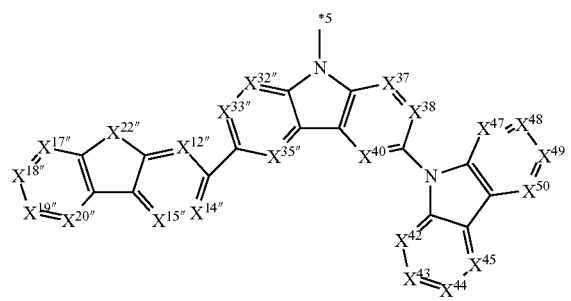
(3″b-5)
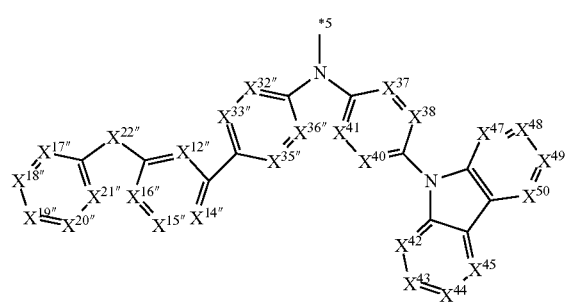
(3″b-6)
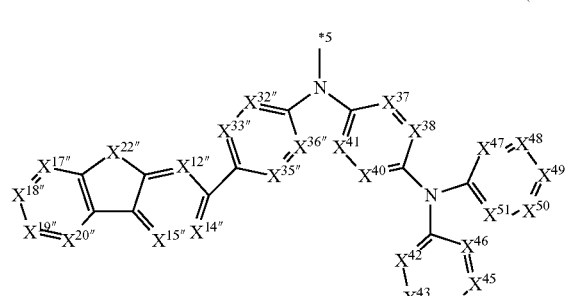
(3″b-7)
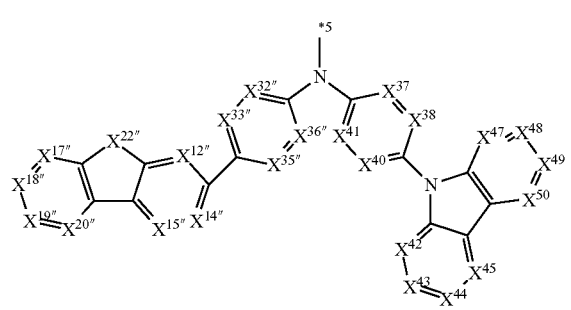
in formulae (3″b-1) to (3″b-7), *5 and each X are as defined above;
(3″c-1)
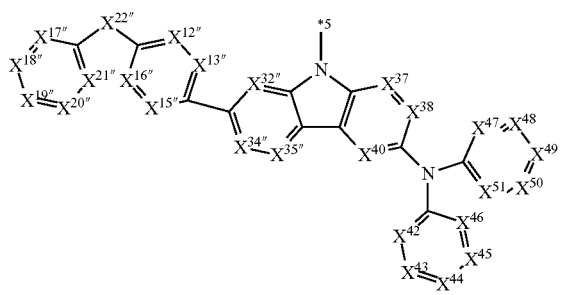
(3″c-2)
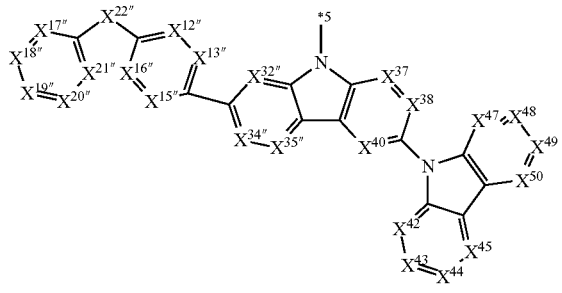
(3″c-3)
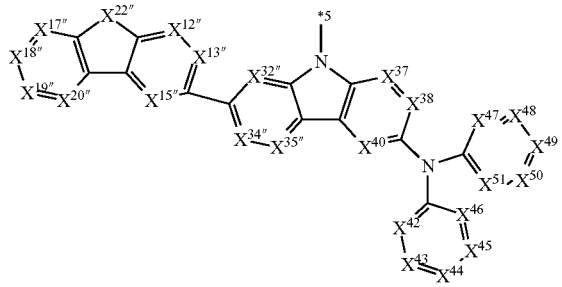
(3″c-4)
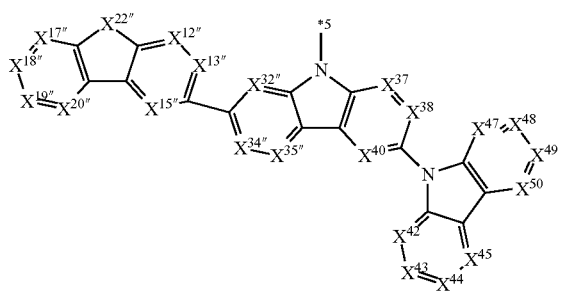
(3″c-5)
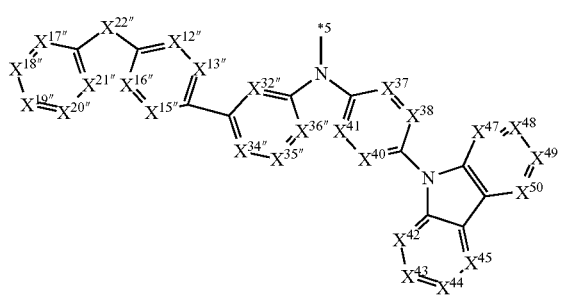

-continued
(3″c-6)
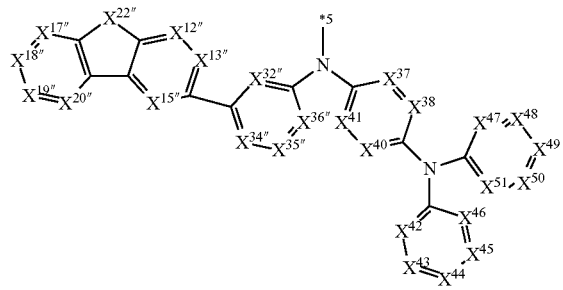
(3″c-7)
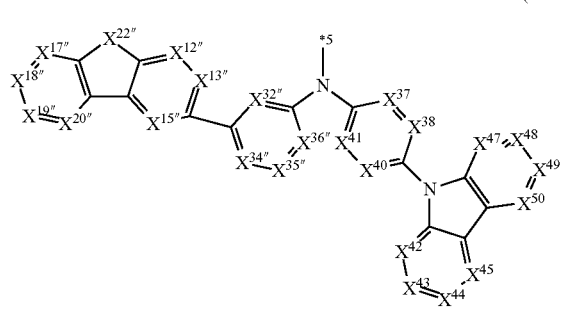
in formulae (3″c-1) to (3″c-7), *5 and each X are as defined above;
(3″d-1)
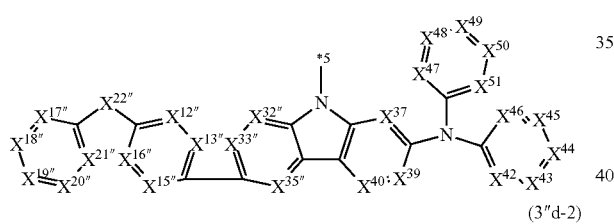
(3″d-2)
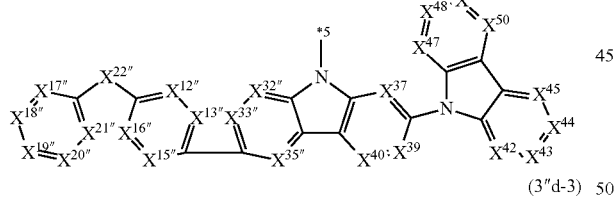
(3″d-3)
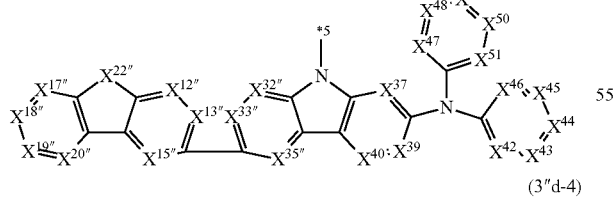
(3″d-4)
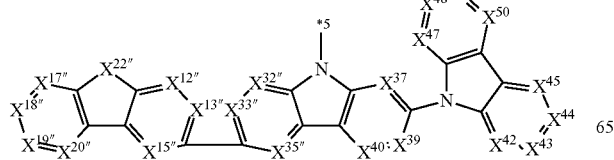
-continued
(3″d-5)
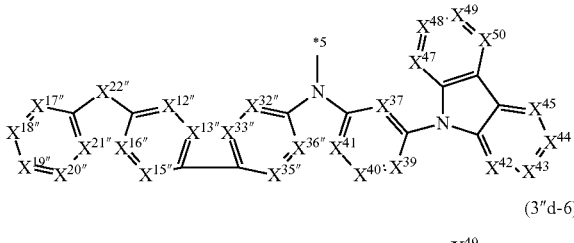
(3″d-6)
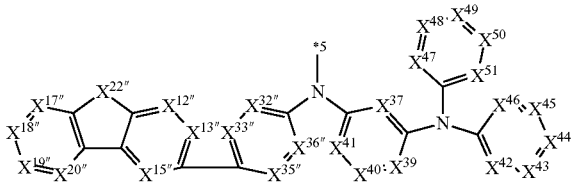
(3″d-7)
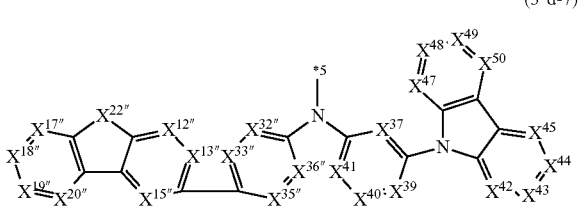
in formulae (3″d-1) to (3″d-7), and each X are as defined above;
(3″e-1)
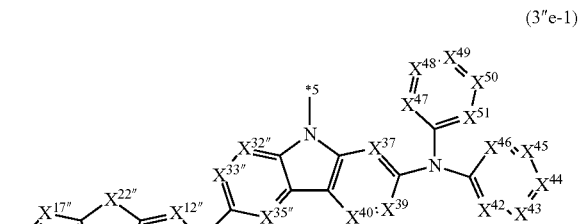
(3″e-2)
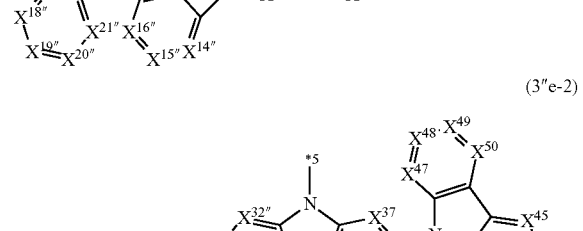
(3″e-3)
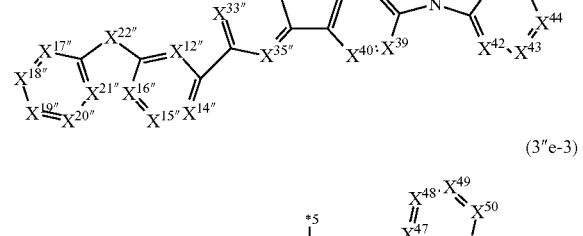
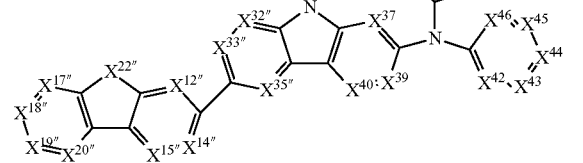

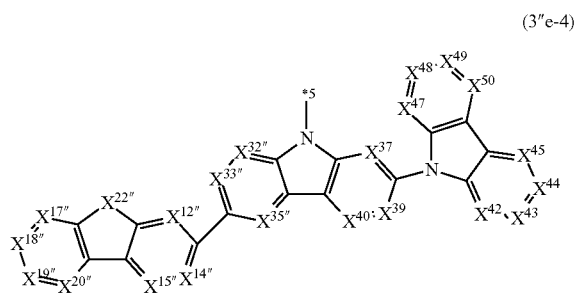
(3″e-4)
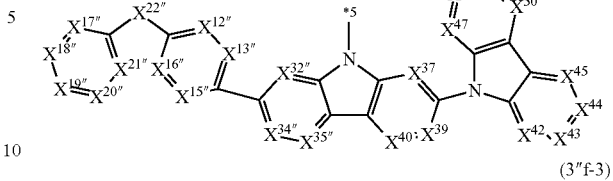
(3″f-2)
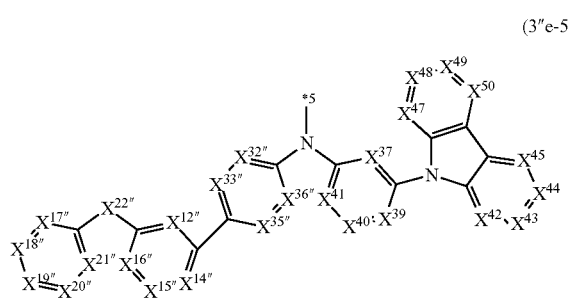
(3″e-5)
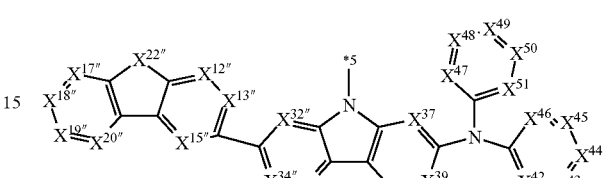
(3″f-3)
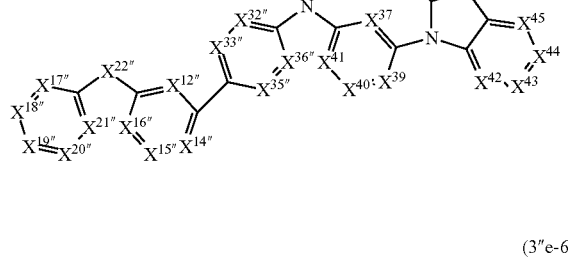
(3″e-6)
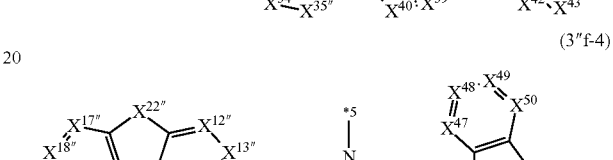
(3″f-4)
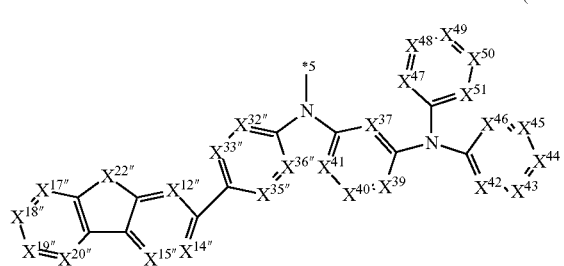
(3″e-7)
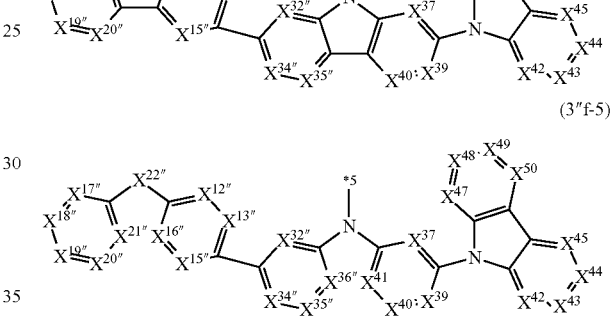
(3″f-5)
(3″f-6)
(3″f-7)
in formulae (3″e-1) to (3″e-7), *5 and each X are as defined above;
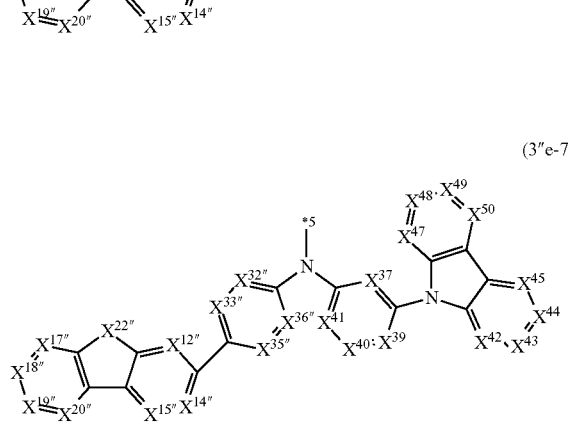
in formulae (3″f-1) to (3″f-7), and each X are as defined above; and
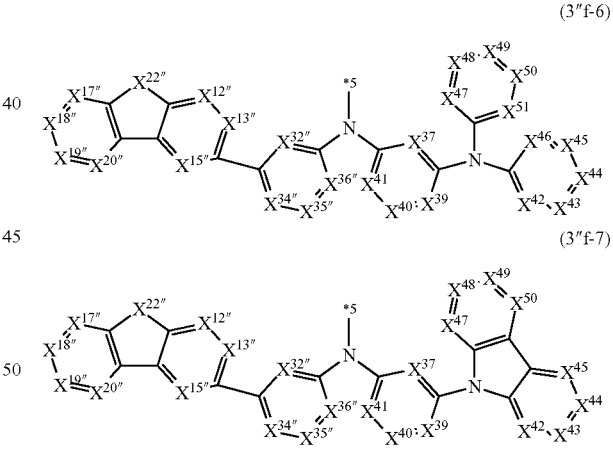
(3″f-1)
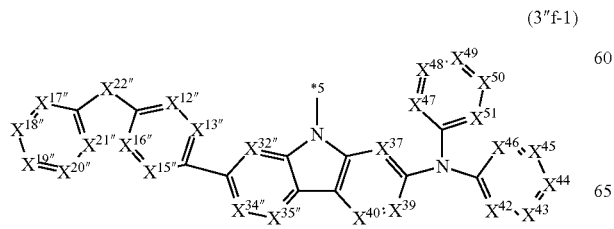
(4a-1)
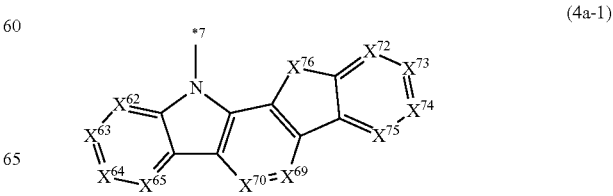

-continued

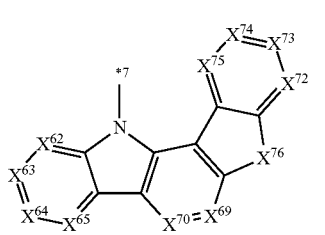
(4b-1)

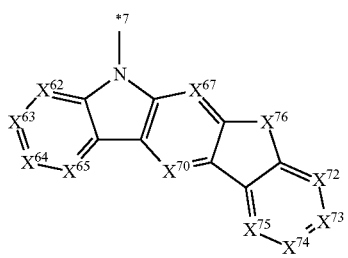
(4c-1)

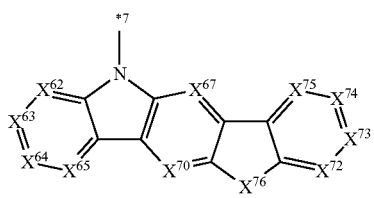
(4d-1)

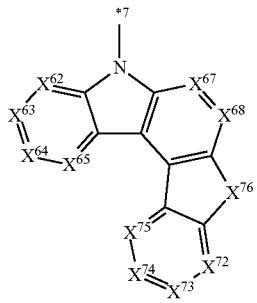
(4e-1)

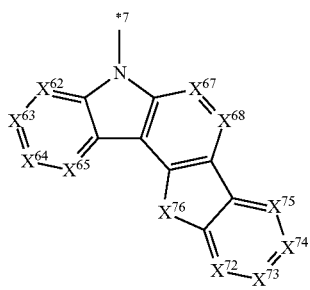
(4f-1)

in formulae (4a-1) to (4f-1), *7 and each X are as defined above.

9. The compound according to claim 1, wherein the substituent represented by $R^1$ is selected from the group consisting of a halogen atom, a cyano group, a nitro group, a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, an aralkyl group having 7 to 51 carbon atoms which includes an aryl group having 6 to 60 ring carbon atoms, an amino group, a mono- or di-substituted amino group wherein the substituent is selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted cycloalkoxy group having 3 to 50 ring carbon atoms, a substituted or unsubstituted aryloxy group having 6 to 60 ring carbon atoms, a substituted or unsubstituted alkylthio group having 1 to 50 carbon atoms, a substituted or unsubstituted arylthio group having 6 to 60 ring carbon atoms, a silyl group, a mono-, di- or tri-substituted silyl group wherein the substituent is selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, and a substituted or unsubstituted haloalkyl group having 1 to 50 carbon atoms.

10. The compound according to claim 1, wherein the substituent represented by $R^a$ is selected from the group consisting of a halogen atom, a cyano group, a nitro group, a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, an aralkyl group having 7 to 51 carbon atoms which includes an aryl group having 6 to 60 ring carbon atoms, an amino group, a mono- or di-substituted amino group wherein the substituent is selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted cycloalkoxy group having 3 to 50 ring carbon atoms, a substituted or unsubstituted aryloxy group having 6 to 60 ring carbon atoms, a substituted or unsubstituted alkylthio group having 1 to 50 carbon atoms, a substituted or unsubstituted arylthio group having 6 to 60 ring carbon atoms, a silyl group, a mono-, di- or tri-substituted silyl group wherein the substituent is selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, and a substituted or unsubstituted haloalkyl group having 1 to 50 carbon atoms.

11. The compound according to claim 1, wherein the substituent represented by any of $R^2$, $R^3$, $R^9$, and $R^{10}$ is selected from the group consisting of a halogen atom, a cyano group, a nitro group, a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, an aralkyl group having 7 to 51 carbon atoms which includes an aryl group having 6 to 60 ring carbon atoms, an amino group, a mono- or di-substituted amino group wherein the substituent is selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted cycloalkoxy group having 3 to 50 ring carbon atoms, a substituted or unsubstituted aryloxy group having 6 to 60 ring carbon atoms, a substituted or unsubstituted alkylthio group having 1 to 50 carbon atoms, a substituted or unsubstituted arylthio group having 6 to 60 ring carbon atoms, a silyl group, a mono-, di- or tri-substituted silyl group wherein the substituent is selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, and a substituted or unsubstituted haloalkyl group having 1 to 50 carbon atoms.

12. The compound according to claim 1, wherein the substituent represented by any of $R^4$ to $R^8$ and $R^{11}$ to $R^{15}$ is selected from the group consisting of a halogen atom, a cyano group, a nitro group, a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, an aralkyl group having 7 to 51 carbon atoms which includes an aryl group having 6 to 60 ring carbon atoms, an amino group, a mono- or di-substituted amino group wherein the substituent is selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted cycloalkoxy group having 3 to 50 ring carbon atoms, a substituted or unsubstituted aryloxy group having 6 to 60 ring carbon atoms, a substituted or unsubstituted alkylthio group having 1 to 50 carbon atoms, a substituted or unsubstituted arylthio group having 6 to 60 ring carbon atoms, a silyl group, a mono-, di- or tri-substituted silyl group wherein the substituent is selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, and a substituted or unsubstituted haloalkyl group having 1 to 50 carbon atoms.

13. The compound according to claim 1, wherein $L^1$ represents a m-phenylene group or a p-phenylene group.

14. The compound according to claim 2, wherein the ring formed when $L^1$ and $R^2$ are bonded to each other is selected from the group consisting of a fused or non-fused aromatic ring having 6 to 50 ring carbon atoms, a partially hydrogenated fused or non-fused aromatic ring having 6 to 50 ring carbon atoms, a fused or non-fused aromatic heterocyclic ring having 5 to 50 ring atoms, and a partially hydrogenated fused or non-fused aromatic heterocyclic ring having 5 to 50 ring atoms.

15. The compound according to claim 1, wherein the ring formed when $R^2$ and $R^1$ are bonded to each other is selected from the group consisting of a fused or non-fused aromatic ring having 6 to 50 ring carbon atoms, a partially hydrogenated fused or non-fused aromatic ring having 6 to 50 ring carbon atoms, a fused or non-fused aromatic heterocyclic ring having 5 to 50 ring atoms, and a partially hydrogenated fused or non-fused aromatic heterocyclic ring having 5 to 50 ring atoms.

16. The compound according to claim 1, wherein the ring formed when adjacent two groups $R^a$ are bonded to each other is selected from the group consisting of a fused or non-fused aromatic ring having 6 to 50 ring carbon atoms, a partially hydrogenated fused or non-fused aromatic ring having 6 to 50 ring carbon atoms, a fused or non-fused aromatic heterocyclic ring having 5 to 50 ring atoms, and a partially hydrogenated fused or non-fused aromatic heterocyclic ring having 5 to 50 ring atoms.

17. The compound according to claim 1, wherein $X^a$ to $X^d$ each represent $CR^a$ wherein $R^a$ represents a hydrogen atom.

18. A material comprising the compound according to claim 1.

19. An ink composition comprising a solvent and the compound according to claim 1.

20. An organic electroluminescence device which comprises a cathode, an anode, and at least one organic thin film layer which is disposed between the cathode and the anode, wherein the at least one organic thin film layer comprises a light emitting layer and at least one layer of the at least one organic thin film layer comprises the compound according to claim 1.

21. The organic electroluminescence device according to claim 20, wherein the light emitting layer comprises the compound as a host material.

22. The organic electroluminescence device according to claim 20, wherein the light emitting layer comprises a phosphorescent emitting material.

23. The organic electroluminescence device according to claim 22, wherein the phosphorescent emitting material is an ortho-metallated complex of a metal selected from the group consisting of iridium (Ir), osmium (Os) and platinum (Pt).

24. The organic electroluminescence device according to claim 20, wherein the organic electroluminescence device comprises an electron transporting layer between the cathode and the light emitting layer and the electron transporting layer comprises the compound.

25. The organic electroluminescence device according to claim 20, wherein the organic electroluminescence device comprises a hole transporting layer between the anode and the light emitting layer and the hole transporting layer comprises the compound.

26. The organic electroluminescence device according to claim 20, wherein an interfacial region between the cathode and the organic thin film layer comprises an electron-donating dopant.

27. An electronic equipment comprising the organic electroluminescence device according to claim 20.

28. A method of producing the compound according to claim 1, which comprises a coupling reaction 1 and a coupling reaction 2:

(1) the coupling reaction 1, wherein a compound represented by formula (I):

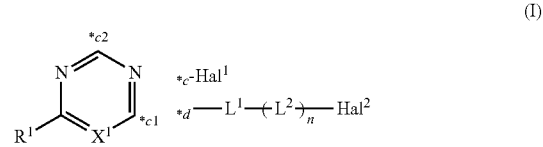

wherein $R^1$, $X^1$, $L^1$, $L^2$, and n are as defined in formula (1);

one of *c and *d is bonded to the carbon atom *c1 and the other is bonded to the carbon atom *c2; and $Hal^1$ and $Hal^2$ represent the same or different halogen atoms;

is allowed to react with an amine compound represented by any of formulae (II), (II'), (III), (III'), (III''), and (IV):

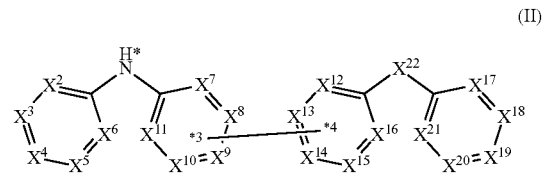

-continued (II')

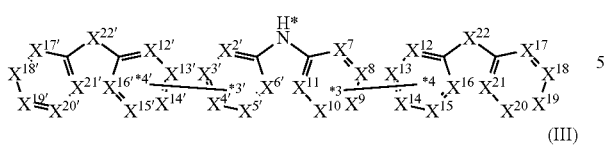

(III)

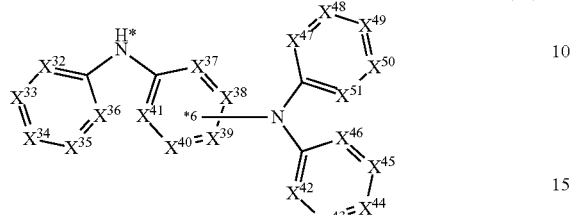

(III')

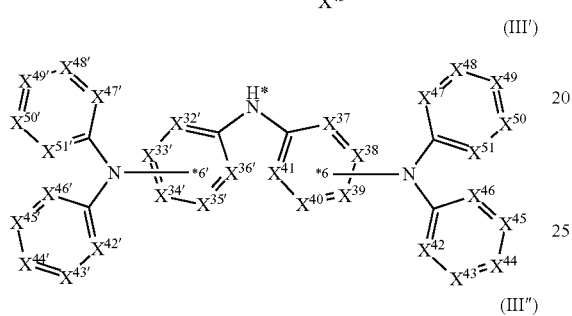

(III'')

(IV)

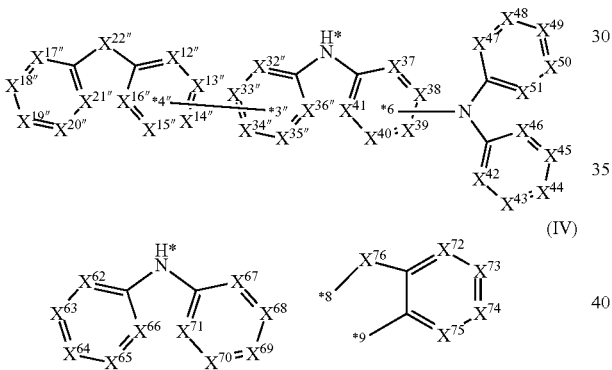

wherein $X^2$ to $X^{22}$, $X^{32}$ to $X^{51}$, $X^{62}$ to $X^{76}$, $X^{2'}$ to $X^{6'}$, $X^{12'}$ to $X^{22'}$, $X^{32'}$ to $X^{36'}$, $X^{42'}$ to $X^{51'}$, $X^{32''}$ to $X^{36''}$, and $X^{12''}$ to $X^{22''}$ are as defined in formula (1), and H* represents a hydrogen atom to be reacted with $Hal^1$ of formula (I), in an organic solvent in the presence of a basic catalyst and in the absence of a transition metal catalyst, thereby obtaining a compound represented by formula (V):

(V)

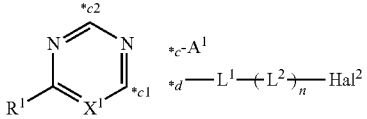

wherein *c, *d, $A^1$, $R^1$, $X^1$, $L^1$, $L^2$, and n are as defined in formula (1) and $Hal^2$ is as defined above, and (2) the coupling reaction 2, wherein the compound represented by formula (V) and an amine compound represented by any of formulae (II), (II'), (III), (III'), (III''), and (IV) which is different from the amine compound used in the coupling reaction 1 are subject to a coupling reaction by eliminating $Hal^2$ of the compound represented by formula (V) and the hydrogen atom H* of the amine compound in an organic solvent in the presence of a transition metal catalyst and a ligand and in the presence or absence of a base, thereby synthesizing the compound represented by formula (1).

29. The method according to claim 28, wherein the basic catalyst is at least one selected from the group consisting of an alkali metal carbonate, an alkali metal hydrogencarbonate, an alkaline earth metal carbonate, a metal phosphate, an alkali metal hydride, and a metal amide.

30. The method according to claim 28, wherein the transition metal catalyst comprises at least one transition metal selected from the group consisting of palladium, copper, platinum, rhodium, ruthenium, nickel, and iron.

31. The method according to claim 28, wherein the base is at least one selected from the group consisting of an alkoxide, a carbonate salt, and a phosphate salt.

\* \* \* \* \*